United States Patent
Seyda et al.

(10) Patent No.: US 9,592,258 B2
(45) Date of Patent: *Mar. 14, 2017

(54) TREATMENT OF NEUROLOGICAL INJURY BY ADMINISTRATION OF HUMAN UMBILICAL CORD TISSUE-DERIVED CELLS

(71) Applicant: DePuy Synthes Products, Inc., Raynham, MA (US)

(72) Inventors: Agnieszka Seyda, Edison, NJ (US); Anna Gosiewska, Skillman, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,680

(22) Filed: May 6, 2015

(65) Prior Publication Data

US 2015/0231185 A1  Aug. 20, 2015

Related U.S. Application Data

(60) Continuation-in-part of application No. 12/642,773, filed on Dec. 19, 2009, now abandoned, and a continuation-in-part of application No. 14/152,649, filed on Jan. 10, 2014, which is a continuation of application No. 13/605,716, filed on Sep. 6, 2012, now Pat. No. 8,658,152, which is a division of application No. 12/429,849, filed on Apr. 24, 2009, now Pat. No. 8,277,796, which is a continuation of application No. 10/877,269, filed on Jun. 25, 2004, now Pat. No. 7,524,489.

(60) Provisional application No. 61/139,305, filed on Dec. 19, 2008, provisional application No. 60/483,264, filed on Jun. 27, 2003.

(51) Int. Cl.
*A61K 45/06* (2006.01)
*C12N 5/071* (2010.01)
*A61K 35/51* (2015.01)

(52) U.S. Cl.
CPC .............. *A61K 35/51* (2013.01); *A61K 45/06* (2013.01); *C12N 5/0682* (2013.01)

(58) Field of Classification Search
None
See application file for complete search history.

(56) References Cited

U.S. PATENT DOCUMENTS

| | | |
|---|---|---|
| 3,665,061 A | 5/1972 | Eberly, Jr. |
| 3,930,954 A | 1/1976 | Irie |
| 4,193,992 A | 3/1980 | Fontaine |
| 4,290,962 A | 9/1981 | Tachi et al. |
| 4,352,883 A | 10/1982 | Lim |
| 4,487,865 A | 12/1984 | Balazs et al. |
| 4,657,866 A | 4/1987 | Kumar |
| 4,882,162 A | 11/1989 | Ikada et al. |
| 4,925,677 A | 5/1990 | Feijen |
| 4,963,489 A | 10/1990 | Naughton et al. |
| 5,004,681 A | 4/1991 | Boyse et al. |
| 5,192,553 A | 3/1993 | Boyse et al. |
| 5,248,608 A | 9/1993 | Van Dooren et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,486,359 A | 1/1996 | Caplan et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,684,032 A | 11/1997 | Elliott et al. |
| 5,698,518 A | 12/1997 | Carson et al. |
| 5,707,643 A | 1/1998 | Ogura et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,855,619 A | 1/1999 | Caplan et al. |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,928,214 A | 7/1999 | Rubinstein et al. |
| 5,942,225 A | 8/1999 | Bruder et al. |
| 5,955,343 A | 9/1999 | Holmes et al. |
| 5,962,325 A | 10/1999 | Naughton et al. |

(Continued)

FOREIGN PATENT DOCUMENTS

CN  1407088  2/2003
JP  2003-235549  8/2003

(Continued)

OTHER PUBLICATIONS

In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.

(Continued)

*Primary Examiner* — Christina Borgeest
(74) *Attorney, Agent, or Firm* — Johnson & Johnson

(57) ABSTRACT

Methods, pharmaceutical compositions and kits for regenerating or repairing neural tissue, decreasing apoptosis and improving neurological function following injury using human umbilical cord tissue-derived cells are disclosed.

17 Claims, 63 Drawing Sheets

(56) References Cited

U.S. PATENT DOCUMENTS

| | | |
|---|---|---|
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,261,841 B1 | 7/2001 | Cohen et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,444,205 B2 | 9/2002 | Dinsmore |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,699,837 B2 | 3/2004 | Nakamura |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 8,491,883 B2 | 7/2013 | Gosiewska et al. |
| 8,518,390 B2 | 8/2013 | Kramer et al. |
| 8,658,152 B2 | 2/2014 | Messina et al. |
| 8,703,121 B2 | 4/2014 | Harris et al. |
| 8,722,034 B2 | 5/2014 | Kihm et al. |
| 8,815,587 B2 | 8/2014 | Harris et al. |
| 9,125,906 B2 | 9/2015 | Buensuceso et al. |
| 9,175,261 B2 | 11/2015 | Harmon et al. |
| 9,234,172 B2 | 1/2016 | Mistry et al. |
| 2001/0024824 A1 | 9/2001 | Moss et al. |
| 2001/0031256 A1 | 10/2001 | Edge |
| 2001/0046489 A1 | 11/2001 | Habener et al. |
| 2001/0055587 A1 | 12/2001 | Dinsmore et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0232752 A1 | 12/2003 | Freeman et al. |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0204387 A1 | 10/2004 | McLaurin |
| 2004/0224401 A1 | 11/2004 | Ludwig et al. |
| 2004/0224409 A1 | 11/2004 | Pradier et al. |
| 2004/0230309 A1 | 11/2004 | DiMauro et al. |
| 2004/0235159 A1 | 11/2004 | Mandalam et al. |
| 2004/0265283 A1 | 12/2004 | Morishita |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0089513 A1 | 4/2005 | Sakuragawa et al. |
| 2005/0124003 A1 | 6/2005 | Atala et al. |
| 2005/0148074 A1 | 7/2005 | Davies et al. |
| 2005/0249731 A1 | 11/2005 | Aslan et al. |
| 2006/0128014 A1 | 6/2006 | Haggblad et al. |
| 2006/0147415 A1 | 7/2006 | Mousa et al. |

(56) References Cited

U.S. PATENT DOCUMENTS

| | | |
|---|---|---|
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0210544 A1 | 9/2006 | Honmou et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0025973 A1 | 2/2007 | Fitzsimmons et al. |
| 2007/0036767 A1 | 2/2007 | Mistry et al. |
| 2007/0042437 A1 | 2/2007 | Wands et al. |
| 2007/0053888 A1 | 3/2007 | Hariri et al. |
| 2007/0141700 A1 | 6/2007 | Harmon |
| 2007/0160588 A1 | 7/2007 | Kihm |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2008/0057053 A1 | 3/2008 | Stolen |
| 2008/0112939 A1 | 5/2008 | Colter et al. |
| 2008/0131409 A1 | 6/2008 | Cataldo et al. |
| 2008/0145934 A1 | 6/2008 | Harris et al. |
| 2008/0166328 A1 | 7/2008 | Harmon et al. |
| 2008/0226595 A1 | 9/2008 | Edinger et al. |
| 2008/0260699 A1 | 10/2008 | Parman |
| 2008/0274087 A1 | 11/2008 | Li et al. |
| 2008/0305148 A1 | 12/2008 | Fu |
| 2009/0074731 A1 | 3/2009 | Librach et al. |
| 2009/0092653 A1 | 4/2009 | Colter et al. |
| 2009/0166178 A1 | 7/2009 | Harmon et al. |
| 2009/0169597 A1 | 7/2009 | Brown et al. |
| 2010/0158877 A1 | 6/2010 | Colter et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0247499 A1 | 9/2010 | Kihm et al. |
| 2010/0260843 A1 | 10/2010 | Messina et al. |
| 2010/0272803 A1 | 10/2010 | Mistry et al. |
| 2011/0223205 A1 | 9/2011 | Gosiewska et al. |
| 2012/0014921 A1 | 1/2012 | Kramer et al. |
| 2012/0315251 A1 | 12/2012 | Harris et al. |
| 2013/0022585 A1 | 1/2013 | Messina et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |
| 2015/0374758 A1 | 12/2015 | Buensuceso et al. |

FOREIGN PATENT DOCUMENTS

| | | |
|---|---|---|
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |
| WO | WO 00/09666 | 2/2000 |
| WO | WO 00/18413 | 4/2000 |
| WO | WO 00/53795 A1 | 9/2000 |
| WO | WO 00/53795 A1 | 9/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/46373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/002140 | 1/2003 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2007/047468 | 4/2004 |
| WO | WO 2004/072273 | 8/2004 |
| WO | WO 2005/001076 | 1/2005 |
| WO | WO 2005/001076 A3 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/007176 | 1/2005 |
| WO | WO 2005/021738 | 3/2005 |
| WO | WO 2005/038012 | 4/2005 |
| WO | WO 2005/042703 | 5/2005 |
| WO | WO 2005/085421 | 9/2005 |
| WO | WO 2005/001078 R | 12/2005 |
| WO | WO 2006/055685 | 5/2006 |
| WO | WO 2006/057003 | 6/2006 |
| WO | WO 2006/071773 | 7/2006 |
| WO | WO 2006/071777 | 7/2006 |
| WO | WO 2006/071778 | 7/2006 |
| WO | WO 2006/071794 | 7/2006 |
| WO | WO 2006/071802 | 7/2006 |
| WO | WO 2006/083394 | 8/2006 |
| WO | WO 2006/105152 | 10/2006 |
| WO | WO 2006/117237 | 11/2006 |
| WO | WO 2007/051625 | 5/2007 |
| WO | WO 2007/070870 | 6/2007 |
| WO | WO 2007/073552 | 6/2007 |
| WO | WO 2007/076522 | 7/2007 |
| WO | WO 2007/079184 | 7/2007 |
| WO | WO 2007/084957 | 7/2007 |
| WO | WO 2007/089063 | 8/2007 |
| WO | WO 2007/108003 | 9/2007 |
| WO | WO 2007/142651 | 12/2007 |
| WO | WO 2008/036447 | 3/2008 |
| WO | WO 2008/045498 | 4/2008 |
| WO | WO 2008/060541 | 5/2008 |
| WO | WO 2008/085221 | 7/2008 |
| WO | WO 2009/046335 | 4/2009 |
| WO | WO 2009/085860 | 7/2009 |
| WO | WO 2010/071862 | 6/2010 |
| WO | WO 2010/071863 A1 | 6/2010 |
| WO | WO 2010/071864 | 6/2010 |

(56) References Cited

FOREIGN PATENT DOCUMENTS

| WO | WO 2010/080364 | 7/2010 |
|---|---|---|
| WO | WO 2010/111663 | 9/2010 |
| WO | WO-2011/017915 A1 | 2/2011 |
| WO | WO 2010/071863 R | 6/2011 |
| WO | WO 2012/112576 | 8/2012 |

OTHER PUBLICATIONS

In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action, in re: U.S. Appl. No. 11/297,156, dated Oct. 10, 2008, 11 pages.
In the U. S. Patent and Trademark Office, Non-Final Office Action in re: U.S. Appl. No. 11/317,574, dated Sep. 30, 2008, 23 pages.
In the U. S. Patent and Trademark Office, Non-Final Office Action in re: U.S. Appl. No. 11/315,969, dated Dec. 23, 2008, 11 pages.
In the U. S. Patent and Trademark Office, Non-Final Office Action in re: U.S. Appl. No. 10/951,357, dated Nov. 26, 2008, 19 pages.
In the U. S. Patent and Trademark Office, Non-Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action in re: U.S. Appl. No. 11/315,943, dated Feb. 20, 2009, 9 pages.
In the U. S. Patent and Trademark Office, Non-Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003 dated Feb. 13, 2009, 17 pages.
In the U. S. Patent and Trademark Office, Final Office Action in re: U.S. Appl. No. 10/876,998 dated Feb. 13, 2009, 10 pages.
In the U. S. Patent and Trademark Office, Final Office Action in re: U.S. Appl. No. 11/322,372 dated Feb. 13, 2009, 14 pages.
In the U. S. Patent and Trademark Office, Non-Final Office Action in re: U.S. Appl. No. 11/315,898 dated Feb. 18, 2009, 10 pages.
In the U. S. Patent and Trademark Office, Non-Final Office Action in re: U.S. Appl. No. 11/304,091 dated Feb. 27, 2009, 11 pages.
In the U. S. Patent and Trademark Office, Non-Final Office Action in re: U.S. Appl. No. 11/481,456 dated Apr. 16, 2009, 14 pages.
In the U. S. Patent and Trademark Office, Non-Final Office Action in re: U.S. Appl. No. 11/317,574 dated Apr. 29, 2009, 21 pages.
In the U. S. Patent and Trademark Office, Advisory Action in re: U.S. Appl. No. 11/315,969 dated Sep. 29, 2009, 8 pages.
In the U. S. Patent and Trademark Office, Advisory Action in re: U.S. Appl. No. 11/322,372 dated May 12, 2009, 10 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/617,346 dated Aug. 11, 2009,12 pages.
In the U. S. Patent and Trademark Office, Final Office Action in re: U.S. Appl. No. 11/481,456 dated Oct. 9, 2009, 11 pages.
In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.

(56) References Cited

OTHER PUBLICATIONS

In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 10/877,445 dated Jul. 8, 2010, 20 pages.
In the U. S. Patent and Trademark Office, Final Office Action in re: U.S. Appl. No. 10/876,998 dated Aug. 3, 2010, 14 pages.
In the U. S. Patent and Trademark Office, Non-Final Office Action in re: U.S. Appl. No. 11/321,863 dated Aug. 17, 2010, 15 pages.
In the U. S. Patent and Trademark Office, Final Office Action in re: U.S. Appl. No. 11/617,346 dated Aug. 20, 2010, 12 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 12/245,571 dated Sep. 15, 2010, 8 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Final Action in re: U.S. Appl. No. 11/617,346 dated Apr. 15, 2010, 7 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
In the U. S. Patent and Trademark Office, Non-Final Office Action in re: U.S. Appl. No. 12/337,439 dated Jan. 6, 2011, 11 pages.
In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Non-Final Office Action in re: U.S. Appl. No. 12/748,170 dated May 21, 2012, 7 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U. S. Patent and Trademark Office, Final Office Action in re: U.S. Appl. No. 11/481,456 dated Oct. 11, 2011, 6 pages.
In the U. S. Patent and Trademark Office, Final Office Action in re: U.S. Appl. No. 10/877,446 dated Nov. 2, 2011, 12 pages.
In the U.S. Patent and Trademark Office, Non-Final Office Action in re: U.S. Appl. No. 12/697,081 dated Apr. 2, 2012, 8 pages.
In the U.S. Patent and Trademark Office, Final Office Action in re: U.S. Appl. No. 12/642,774 dated Nov. 6, 2012, 10 pages.
In the U.S. Patent and Trademark Office, Non-Final Office Action in re: U.S. Appl. No. 12/642,775 dated Nov. 21, 2012, 16 pages.
In the U.S. Patent and Trademark Office, Non-Final Office Action in re: U.S. Appl. No. 13/605,716 dated Feb. 13, 2013, 13 pages.
In the U.S. Patent and Trademark Office, Final Office Action in re: U.S. Appl. No. 12/642,775 dated Jun. 21, 2013, 17 pages.
In the U.S. Patent and Trademark Office, Non-Final Office Action in re: U.S. Appl. No. 11/317,574 dated Jul. 11, 2013, 29 pages.
In the U.S. Patent and Trademark Office, Non-Final Office Action in re: U.S. Appl. No. 11/322,372 dated Jan. 16, 2014, 17 pages.
In the U.S. Patent and Trademark Office, Non-Final Office Action in re: U.S. Appl. No. 11/321,864 dated Jan. 29, 2014, 9 pages.
In the U.S. Patent and Trademark Office, Non-Final Office Action in re: U.S. Appl. No. 11/321,863 dated Jan. 31, 2014, 17 pages.
In the U.S. Patent and Trademark Office, Final Office Action in re: U.S. Appl. No. 11/317,574 dated Feb. 3, 2014, 16 pages.
In the U. S. Patent and Trademark Office, Non-Final Office Action in re: U.S. Appl. No. 10/876,998 dated Feb. 11, 2014, 14 pages.
In the U.S. Patent and Trademark Office, Non-Final Office Action in re: U.S. Appl. No. 12/389,305 dated Mar. 6, 2014, 37 pages.
In the U. S. Patent and Trademark Office, Non-Final Office Action in re: U.S. Appl. No. 11/316,104 dated Mar. 14, 2014, 11 pages.
In the U.S. Patent and Trademark Office, Non-Final Office Action in re: U.S. Appl. No. 12/642,775 dated Mar. 18, 2014, 33 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 21 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 15 pages.
In the U.S. Patent and Trademark Office, Non-Final Office Action in re: U.S. Appl. No. 12/642,773 dated Mar. 29, 2012, 28 pages.
In the U.S Patent and Trademark Office, Final Office Action in re: U.S. Appl. No. 12/642,773 dated Sep. 13, 2012, 21 pages.
In the U.S. Patent and Trademark Office, Non-Final Office Action in re: U.S. Appl. No. 12/642,773 dated Nov. 14, 2013, 28 pages.
In the U.S. Patent and Trademark Office, Final Office Action in re: U.S. Appl. No. 12/642,773 dated Aug. 6, 2014, 19 pages.
In the U.S. Patent and Trademark Office, Final Office Action in re: U.S. Appl. No. 12/389,305 dated Aug. 6, 2014, 57 pages.
In the U.S. Patent and Trademark Office, Final Office Action in re: U.S. Appl. No. 10/877,446 dated Aug. 6, 2014, 35 pages.
In the U.S. Patent and Trademark Office, Non-Final Office Action in re: U.S. Appl. No. 11/611,602 dated Oct. 9, 2014, 15 pages.
In the U.S. Patent and Trademark Office, Final Office Action in re: U.S. Appl. No. 11/317,574 dated Feb. 3, 2014, 12 pages.
In the U.S. Patent and Trademark Office, Final Office Action in re: U.S. Appl. No. 11/321,864 dated Nov. 3, 2014, 10 pages.

(56) References Cited

OTHER PUBLICATIONS

In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/321,863 dated Jan. 31, 2014, 17 pages.
In the U.S. Patent and Trademark Office, Non-Final Office Action in re: U.S. Appl. No. 14/152,649 dated Feb. 26, 2015, 9 pages.
In the U.S. Patent and Trademark Office, Non-Final Office Action in re: U.S. Appl. No. 14/444,689 dated Mar. 24, 2015, 9 pages.
In the U.S. Patent and Trademark Office, Final Office Action in re: U.S. Appl. No. 11/317,574 dated Apr. 1, 2015, 12 pages.
In the U.S. Patent and Trademark Office, Final Office Action in re: U.S. Appl. No. 11/617,346 dated Apr. 15, 2015, 21 pages.
"Cell Lysis, p. 2", available online at <http://www.piercenet.com/objects/view.cfm?type=Page&ID=1904ED25-8FA4-475C-8068-C2EB13D5F4E7>; accessed Aug. 7, 2008.
"CSL Behring Wound Healing", available online at <http://www.cslbehring.com/s1/cs/enco/1255923358067/page/1255923357834/TabsLandingpage.htm>; accessed Mar. 4, 2014.
"Dulbecco's Modified Eagle's Medium (DME) Formulation." Sigma-Aldrich, available online at <http://www.sigmaaldrich.com/life-science/cell-culture/learning-center/media-formulations/dme.printerview.html>; accessed Mar. 17, 2014.
"Unigene Entry for Hs.522632, *Homo sapiens* TMP Metallopeptidase Inhibitor 1 (TIMP1)," printed from http://www.ncbi.nlm.nih.gov/UniGene on Oct. 12, 2006.
Abbas, A.K. et al., *Cellular and Molecular Immunology*, 5th Ed. (2003) Saunders, Philadelphia, p. 171.
Aboody, K.S. et al., "Neural Stem Cells Display Extensive Tropism for Pathology in Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch Ophthalmol.*, 2001; 119(10): 1417-1436.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Alini, M. et al., "A Biological Approach to Treating Disc Degeneration: Not for Today, But Maybe for Tomorrow," Eur. Spine J., 2002; 11 (Supp. 2 ): S215-220.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.
Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.

Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.
Bai, M., et al., "Dimerization of the Extracellular Calcium-sensing Receptor (CaR) on the Cell Surface of CaR-Transfected HEK293 Cells," *J. Biol Chem.*, 1998; 273(36): 23605-23610.
Baker, K.A. et al., "Intrastriatal and Intranigral Grafting of hNT Neurons in the 6-OHDA Rat Model of Parkinson's Disease," *Exper. Neurol.*, 2000; 162:350-360.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Baksh, D. et al., "Comparison of proliferative and multilineage differentiation potential of human mesenchymal stem cells derived from umbilical cord and bone marrow." *Stem Cells*, 2007; 25: 1384-1392.
Balis, F. et al., "Central Nervous System Pharmacology of Antileukemic Drugs," *Am. J. of Pediatric Hematol. Oncol.*, 1989; 11(1):74-86.
Balkema, G.W. et al., "Impaired Visual Thresholds in Hypopigmented Animals," *Visual Neuroscience*, 1991; 6:577-585.
Bao, Z.Z. et al., "Regulation of Chamber-Specific Gene Expression in the Developing Heart by IrX 4," *Science*, 1999; 283(5405):1161-1164.
Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.
Basso, DM et al., "A sensitive and reliable locomotor rating scale for open field testing in rats," *J Neurotrauma*, 1995; 12(1):1-21.
Basso, DM et al., "Graded histological and locomotor outcomes after spinal cord confusion using the NYU weight-drop device versus transection," *Exp. Neurol.*, 1996; 139:244-256.
Beck, R.W. et al., "A Clinical Comparison of Visual Field Testing With a New Automated Perimeter, the Humphrey Field Analyzer, and the Goldmann Perimeter," *Ophthalmology*, 1985; 92(1):77-82.
Beeres, S.L. et al., "Sustained effect of autologous bone marrow mononuclear cell injection in patients with refractory angina pectoris and chronic myocardial ischemia: twelve-month follow-up results." Am Heart J., 2006; 152:684.e11-6.
Bennett et al., "A Peripheral Mononeuropathy in Rate that Produces Disorders of Pain Sensation Like Those Seen in Man," Pain, 1988; 33:87-107.
Bergers, G. et al., "The Role of Pericytes in Blood-Vessel Formation and Maintenance," *Neuro-Oncology*, 2005; 7:452-464.
Bhatia, R. et al., "A clinically suitable ex vivo expansion culture system for LTC-IC and CFC using stroma-conditioned medium," *Exp Hematol.*, 1997;25(9):980-91 (Abstract only).
Bhindi, R. et al., "Rat Models of Mycocardial Infarction," *Thromb Haemost*, 2006; 96:602-610.
Björklund, L.M. et al., "Embryonic Stem Cells Develop Into Functional Dopaminergic Neurons After Transplantation in a Parkinson Rat Model," *PNAS*, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Borlongan, C.V. et al., "Upregulation of CNS trophic factors by human umbilical cord transplant is essential for neuroprotection against acute stroke," *Society for Neuroscience Abstract*, 2003, Presentation No. 789.17.
Bradley, B.A., "The Role of HLA Matching in Transplantation," *Immunol. Lett.*, 1991; 29:55-59.
Brodsky, S.V., "Coagulation, Fibrinolysis and Angiogenesis: New Insights From Knockout Mice," *Exp. Nephrol.*, 2002; 10:299-306.
Brooks, P., "Inflammation as an Important Feature of Osteoarthritis," *Bull. World Health Org.*, 2003; 81(9):689-690.
Brown, J.A. et al., "Blockade of Programmed Death-1 Ligands on Dendritic Cells Enhances T Cell Activation and Cytokine Production," *J. Immunology*, 2003; 170:1257-1266.
Bruder et al., "Mesenchymal Stem Cell Surface Antigen SB-10 Corresponds to Activated Leukocyte Cell Adhesion Molecule and Is

(56) References Cited

OTHER PUBLICATIONS

Involved in Osteogenic Differentiation," *Journal of Bone and Mineral Research*, 1998; 13(4):655-663.

Bunge et al., "The Role of the Schwann Cell in Trophic Support and Regeneration," Journal of Neurology, 1994; 241:536.

Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.

Bussolati et al., "Isolation of Renal Progenitor Cells from Adult Human Kidney," *American Journal of Pathology*, 2005; 166(2):545-555.

Caballero, S. et al., "The Many Possible Roles of Stem Cells in Age-Related Macular Degeneration," *Graefe's Arch. Clin. Exp. Ophthalmol.*, 2004; 242:85-90.

Cai, J. et al., "Stem cell and precursor cell therapy," *NeuroMolecular Medicine*, 2002; 3:233-249.

Campbell, I.K. et al., "Human Articular Cartilage and Chondrocytes Produce Hematopoietic Colony-Stimulating Factors in Culture in Response to IL-1," *J. of Immun.*, 1991; 147(4):1238-1246.

Can et al., "Concise Review: Human Umbilical Cord Stroma with Regard to the Source of Fetus-Derived Stem Cells," Stem Cells, 2007; 25:2886-2895.

Cao, Q. et al., "Stem Cell Repair of Central Nervous System Injury," *J. of Neuroscience Res.*, 2002; 68:501-510.

Caplan, A.I. et al., "Mesenchymal Stem Cells: Building Blocks for Molecular Medicine in the 21st Century," *Trends in Molecular Med.*, 2001; 7(6):259-264.

Carter, D. et al., "Characterization of MSC Potential to Treat GVHD Using Molecular Markers Linked to MSC-Mediated Immunosuppression In Vitro," *Blood*, 2005; 106(11) part 2, Abstract No. 4322, 160B.

Chagraoui, J. et al., "Fetal Liver Stroma Consists of Cells in Epithelial-To-Mesenchymal Transition," *Blood*, 2003; 101(8):2973-2982.

Chen J. et al., "Combination therapy of stroke in rats with a nitric oxide donor and human bone marrow stromal cells enhances angiogenesis and neurogenesis," *Brain Res.* 2004; 105:21-28.

Chen J. et al., "Statins induce angiogenesis, neurogenesis, and synaptogenesis after stroke," Ann. Neurol., 2003; 53:743-751.

Chen K. et al., "Human umbilical cord mesenchymal stem cells hUC-MSCs exert immunosuppressive activities through a PGE2-dependent mechanism," Clinical Immunology, 2010, 135; 448-458.

Chen, D. et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.

Chen, H. et al., "The Effect of Hypothermia on Transient Middle Cerebral Artery Occlusion in the Rat," *J. Cereb. Blood Flow Metab.*, 1992; 12(4):621-628.

Chen, J. et al., "Intravenous Administration of Human Umbilical cord Blood Reduces Behavioral Deficits After Stroke in Rats," *Stroke*, 2001; 32:2682-2688.

Chen, J. et al., "Therapeutic Benefit of Intravenous Administration of Bone Marrow Stromal Cells after Cerebral Ischemia in Rats," *Stroke*, 2001; 32(4):1005-1011.

Chen, ST. et al., "A model of focal ischemic stroke in the rat: reproducible extensive cortical infarction," *Stroke*, 1986; 17: 738-743.

Cheng, A. et al. "Nitric Oxide Acts in a Positive Feedback Loop With BDNF to Regulate Neural Progenitor Cell Proliferation and Differentiation in the Mammalian Brain," *Dev. Biol.*, 2003; 258:319-333.

Chujo, T. et al., "Effects of Growth Differentiation Factor-5 on the Intervertebral Disc—In Vitro Bovine Study and In Vivo Rabbit Disc Degeneration Model Study," Spine, 2006; 31: 2909-2917.

Ciavarella, S. et al., "Umbilical Cord Mesenchymal Stem Cells: Role of Regulatory Genes in Their Differentiation to Osteoblasts," Stem Cells and Development, 2009; 18:1211-1220.

Constantini, S. et al., "The Effects of Methylprednisolone and the Ganglioside GM1 on Acute Spinal Cord Injury in Rats," *J. Neurosurg.*, 1994; 80(1):97-111.

Coumans, B. et al., "Lymphoid Cell Apoptosis Induced by Trophoblastic Cells: A Model of Active Foeto-Placental Tolerance," *J. of Immunological Methods*, 1999; 224:185-196.

Covas, D.T. et al., "Isolation and culture of umbilical vein mesenchymal stem cells." *Brazilian Journal of Medical and Biological Research*, 2003; 36: 1179-1183.

D'Cruz, P.M. et al., "Mutation of the Receptor Tyrosine Kinase Gene Mertk in the Retinal Dystrophic RCS Rat," *Hum. Mol. Genet.*, 2000; 9(4):645-651.

Daley, G.Q. et al., "Realistic Prospects for Stem Cell Therapeutics," *Hematol.*, 2003; 398-418.

Danon, D. et al., "Macrophage Treatment of Pressure Sores in Paraplegia," *J. Wound Care*, 1998; 7(6):281-283.

Danon, D. et al., "Treatment of Human Ulcers by Application of Macrophages Prepared From a Blood Unit," *Exp. Gerontol.*, 1997; 32(6):633-641.

Dawson, T.M. et al., "Neuroprotective and Neurorestorative Strategies for Parkinson's Disease," *Nat. Neurosci.*, 2002; 5 Suppl.:1058-1061.

Deans, R.J. et al., "Mesenchymal stem cells: Biology and potential clinical uses," *Experimental Hematology*, 2000; 28: 875-884.

del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.

Diao et al, "Human Umbilical Cord Mesenchymal Stem Cells: Osteogenesis In Vivo as Seed Cells for Bone Tissue Engineering," *J. BioMed Mater Res.*, 2009; 91A:123-131.

Dickinson, A.M. et al., "Non-HLA Immunogenetics in Hematopoietic Stem Cell Transplantation," *Curr. Opin. Immunol.*, 2005; 17(5):517-525.

Dimri, G.P. et al., "A Biomarker That Identifies Senescent Human Cells in Culture and in Aging Skin In Vivo," *Proc. Natl. Acad. Sci. USA*, 1995; 92:9363-9367.

Domb, A. et al., "Degradable Polymers for Site-Specific Drug Delivery," *Polymers for Advanced Technologies*, 1992; 3:279-292.

Doshi, S.N. et al., "Evolving Role of Tissue Factor and Its Pathway Inhibitor," *Critical Care Med.*, 2002; 30(5):S241-S250.

Doyle, J., "Spiraling Complexity, Robustness, and Fragility in Biology," http://www.cds.caltech.edu/~doyle/CmplxNets/Bio1.pdf, available online Feb. 28, 2004.

Draper et al., "Surface Antigens of Human Embryonic Stem Cells: Changes Upon Differentiation in Culture," J. Anat., 2002; 200:249-258.

Du, Y. et al., "Functional Reconstruction of Rabbit Corneal Epithelium by Human Limbal Cells Cultured on Amniotic Membrane," *Molecular Vision*, 2003; 9:635-643.

Dutton, R, et al., "Precursor Cells in the Subventricular Zone of the Adult Mouse Are Actively Inhibited from Differentiating into Neurons," *Dev Neurosci*, 2000; 22:96-105.

Dykens, J. et al., "Photoreceptor Preservation in the S334ter Model of Retinitis Pigmentosa by a Novel Estradiol Analog", *Biochemical Pharmacology*, 2004; 68: 1971-1984.

Eagle, H., "The Specific Amino Acid Requirements of a Mammalian Cell (Strain L) in Tissue Culture," *J. Biol. Chem.*, 1955; 214:839-852.

Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).

Edelstein, M. L. et al., "Gene Therapy Clinical Trials Worldwide 1989-2004—An Overview," *J. Gene Med.*, 2004; 6(6):597-602.

Edlund, H., "Pancreatic Organogenesis—Developmental Mechanisms and Implications for Therapy," *Nat. Rev. Genet.*, 2002; 3:524-532.

Efrat, S. et al., "Cell Replacement Therapy for Type 1 Diabetes," *Trends in Molecular Medicine*, 2002; 8(7):334-339.

Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.

(56) References Cited

OTHER PUBLICATIONS

Ehtesham, M. et al., "The Use of Interleukin 12-Secreting Neural Stem Cells for the Treatment of Intracranial Glioma," *Cancer Res.*, 2002; 5657-5663.

Eisenhofer, G.E. et al., "Tyrosinase: A Developmentally Specific Major Determinant of Peripheral Dopamine," *FASEB J.*, 2003; 17:1248-1255.

Ende, N. et al., "Parkinson's Disease Mice and Human Umbilical Cord Blood," *J. Med.*, 2002; 33(1-4):173-180.

Engstad, C.S. et al., "The Effect of Soluble β-1,3-Glucan and Lipopolysaccharide on Cytokine Production and Coagulation Activation in Whole Blood," *Int. Immunopharmacol.*, 2002; 2:1585-1597.

Enzmann, V. et al., "Enhanced Induction of RPE Lineage Markers in Pluripotent Neural Stem Cells Engrafted Into the Adult Rat Subretinal Space," *Investig. Ophthalmol. Visual Sci.*, 2003; 44:5417-5422.

Erices et al., "Mesenchymal Progenitor Cells in Human Umbilical Cord Blood," *Br. J. Haematol.*, 2000; 109:235-242.

Evers, B.M., et al., "Stem Cells in Clinical Practice," *J Am Coll Surg.* 2003; 197(3):458-478.

Fazleabas, A.T. et al., "Endometrial Function: Cell Specific Changes in the Uterine Environment," *Mol. & Cellular. Endo.*, 2002; 186:143-147.

Fernandes, A.M. et al., "Mouse Embryonic Stem Cell Expansion in a Microcarrier-based Stirred Culture System," *Journal of Biotechnology*, 2007; 132:227-236.

Fiegel, H.C. et al., "Liver-Specific Gene Expression in Cultured Human Hematopoietic Stem Cells," *Stem Cells*, 2003; 21:98-104.

Fields, G.B., "Induction of Protein-Like Molecular Architecture by Self-Assembly Processes," *Bioorg. Med. Chem.*, 1999; 7:75-81.

Fischer, D. et al., "Counteracting the Nogo Receptor Enhances Optic Nerve Regeneration If Retinal Ganglion Cells Are in an Active Growth State," *J. Neurosci.*,2004; 24:1646-1651.

Fischer, D. et al., "Lens-Injury-Stimulated Axonal Regeneration Throughout the Optic Pathway of Adult Rats," *Exp. Neurol.*, 2001; 172:257-272.

Foley, A. et al., "Heart Induction: Embryology to Cardiomyocyte Regeneration," *Trends Cardiovasc. Med.*, 2004; 14(3):121-125.

Franc, S. et al., "Microfibrillar Composition of Umbilical Cord Matrix : Characterization of Fibrillin, Collagen VI and Intact Collagen V," *Placenta*, 1988; 19:95-104.

Freed, C.R. et al., "Transplantation of Embryonic Dopamine Neurons for Severe Parkinson's Disease," *N. Engl. J. Med.*, 2001; 344(10):710-719.

Frenkel, O. et al., "Activated Macrophages for Treating Skin Ulceration: Gene Expression in Human Monocytes After Hypo-Osmotic Shock," *Clin. Exp. Immunol.*, 2002; 128:59-66.

Friedman, J.A. et al., "Biodegradable Polymer Grafts for Surgical Repair of the Injured Spinal Cord," *Neurosurgery*, 2002; 51(3):742-751.

Fukuchi, Y. et al., "Human Placenta-Derived Cells Have Mesenchymal Stem/Progenitor Cell Potential," *Stem Cells*, 2004; 22:649-658.

Fukuda, K., "Reprogramming of Bone Marrow Mesenchymal Stem Cells Into Cardiomyocytes," *C.R. Biol.*, 2002; 325:1027-1038.

Galán, L. et al., "Cell therapy in amyotrophic lateral sclerosis: science and controversy," *Neurologia*, 2010: 25(8): 467-469.

Garbuzova-Davis, S. et al., "Human Umbilical Cord Blood Treatment in a Model of ALS: Optimization of Cell Dose," *PLoS One*, 2008; 3(6): e2494.

Garbuzova-Davis, S. et al., "Intravenous Administration of Human Umbilical Cord Blood Cells in a Mouse Model of Amyotrophic Lateral Sclerosis: Distribution, Migration, and Differentiation," *Journal of Hematotherapy & Stem Cell Research*, 2003; 12:255-270.

Garbuzova-Davis, S. et al., "Multiple Intravenous Administrations of Human Umbilical Cord Blood Cells Benefit in a Mouse Model of ALS," *PLoS One*, 2012, 7(2): e31254.

Gellersen, B. et al., "Cyclic AMP and Progesterone Receptor Cross-Talk in Human Endometrium: A Decidualizing Affair," *J. Endocrinol.*, 2003; 178(3):357-372.

Gennarelli, T.A. et al., "Axonal injury in the optic nerve: a model stimulating diffuse axonal injury in the brain," *J. Neurosurg*, 1989; 71:244-253.

Gerdes, D. et al., "Cloning and Tissue Expression of Two Putative Steroid Membrane Receptors," *Biol. Chem.*, 1998; 379:907-911.

Germano, A.F. et al., "Behavioral deficits following experimental subarachnoid hemorrhage in the rat," *J Neurotrauma*, 1994; 11:345-352.

Giunta et al., "Inflammaging as a Prodrome to Alzheimer's Disease," *Journal of Neuroinflammation*, 2008; 5(1):51.

Gökhan, S. et al., "Basic and Clinical Neuroscience Applications of Embryonic Stem Cells," *Anat. Rec. (New Anat)*, 2001; 265:142-156.

Gong, C., et al., "Acute Inflammatory Reaction Following Experimental Intracerebral Hemorrhage in Rat," *Brain Res*, 2000; 871:57-65.

Gong, C., et al., "Intracerebral Hemorrhage-Induced Neuronal Death," *Neurosurgery*, 2001; 48(4):875-883.

Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7:581-588.

Gosiewska, A. et al., "Development of a Three-Dimensional Transmigration Assay for Testing Cell-Polymer Interactions for Tissue Engineering Applications," *Tissue Eng.*, 2001; 7(3):267-277.

Gottleib, D.I. "Large-Scale Sources of Neural Stem Cells," *Annu. Rev. Neurosci.*, 2002; 25:381-407.

Gröhn, P. et al., "Collagen-Coated $BA^{2+}$-Alginate Microcarriers for the Culture of Anchorage-Dependent Mammalian Cells," *BioTechniques*, 1997; 22(5): 970-975.

Gros-Louis, F. et al.,"Intracerebroventricular infusion of monoclonal antibody or its derived Fab fragment against misfolded forms of SOD1 mutant delays mortality in a mouse model of ALS," *J Neurochem.*, 2010; 113(5) 1188-1189.

Gupta, S. et al., "Isolation and Characterization of Kidney-Derived Stem Cells," *J. of Am. Soci. of Nephrol.*, 2006; 17(11):3028-3040.

Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.

Hanahan, D. "Heritable Formation of Pancreatic β-Cell Tumours in Transgenic Mice Expressing Recombinant Insulin/Simian Virus 40 Oncogenes," *Nature*, 1985; 315:115-122.

Hartgerink, J.D. et al., "Peptide-Amphiphile Nanofibers: A Versatile Scaffold for the Preparation of Self-Assembling Materials," *PNAS*, 2002; 99(8):5133-5138.

Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-1025.

Hass, R. et al., "Different populations and sources of human mesenchymal stem cells (MSC): A comparison of adult and neonatal tissue-derived MSC," *Cell Communication and Signaling*, 2011; 9:12, p. 1-14.

Hayflick, L., "The Longevity of Cultured Human Cells," *J. Am. Geriatr. Soc.*, 1974; 22(1):1-12.

Hayflick, L., "The Strategy of Senescence," *Gerontologist*, 1974; 14(1):37-45.

Haynesworth et al., "Cell Surface Antigens on Human Marrow-Derived Mesenchymal Cells are Detected by Monoclonal Antibodies," Bone, 1992; 13:69-80.

Henderson, GI, et al., "Inhibition of Placental Valine Uptake after Acute and Chronic Maternal Ethanol Consumption", *J Pharmacol Exp Therap*, 1981; 216:465-472.

Herrera, M.B. et al., "Mesenchymal Stem Cells Contribute to the Renal Repair of Acute Tubular Epithelial Injury," *Int. J. Mol. Med.*, 2004; 14(6):1035-1041.

Hill, D.P. et al., "Screening for Novel Pattern Formation Genes Using Gene Trap Approaches," *Methods in Enzymology*, 1993; 225:664-681.

Hill, M. et al., "Treatment for Swallowing Difficulties (Dysphagia) in Chronic Muscle Disease," *The Cochrane Library Cochrane Database Syst Rev.*, 2004; 2:1-12.

(56) References Cited

OTHER PUBLICATIONS

Hishikawa, K. et al., "Musculin/MyoR is Expressed in Kidney Side Population Cells and Can Regulate Their Function," *Journal of Cell Biology*, 2005; 169(6):921-928.

Ho, A.D. et al., "Heterogeneity of mesenchymal stromal cell preparations," *Cytotherapy*, 2008;10(4):320-30.

Holz, F.G. et al., "Intraocular Microablation of Choroidal Tissue by a 308 nm AIDA Excimer Laser for RPE-Transplantation in Patients With Age-Related Macular Degeneration," *Biomed. Technik*, 2003; 48:82-85.

Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.

Hoynowski, S.M. et al., "Characterization and Differentiation of Equine Umbilical Cord-Derived Matrix Cells," *Biochemical and Biophysical Research Communications*, 2007; 362:347-353.

Hu, A. et al., "Hepatic Differentiation From Embryonic Stem Cells In Vitro," *Chin. Med. J.*, 2003; 116(12):1893-1897.

Hua, Y., et al., "Behavioral Tests After Intracerebral Hemorrhage in the Rat," *Stroke*, 2002; 33:2478-2484.

Hua, Y., et al., "Plasminogen Activator Inhibitor-1 Induction after Experimental Intracerebral Hemorrhage," *J. Cereb Blood Flow Metab*, 2002; 22:55-61.

Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.

Hutmacher, D.W., "Scaffold Design and Fabrication Technologies for Engineering Tissues—State of the Art and Future Perspectives," *J. Biomater. Sci. Polymer Edn.*, 2001;12(1):107-124.

Igura et al. "Human Placental Derived Stem Cells Differentiate into Neural Cells," *Blood*, 2002; 100(11): 517A (Abstract 2021).

Ilieva, H. et al., "Non-cell autonomous toxicity in neurodegenerative disorders: ALS and beyond," *J. Cell Biol.*, 2009; 187:761-772.

In't Anker, P., et al., "Isolation of Mesenchymal Stem Cells of Fetal or Maternal Origin from Human Placenta," *Stem Cells*, 2004; 22:1338-1345.

Isacson, O., "The Production and Use of Cells As Therapeutic Agents in Neurodegenerative Diseases," *The Lancet (Neurology)*, 2003; 2:417-424.

Isacson, O., et al., "Specific Axon Guidance Factors Persist in the Adult Brain as Demonstrated by Pig Neuroblasts Transplanted to the Rat," *Neurosci.*, 1996; 75(3):827-837.

Ishii, M. et al., "Molecular Markers Distinguish Bone Marrow Mesenchymal Stem Cells From Fibroblasts," *Biochemical and Biophysical Research Communications*, 2005; 332:297-303.

Israelson, A. et al., "Misfolded Mutant SOD1 Directly Inhibits VDAC1 Conductance in a Mouse Model if Inherited ALS," *Neuron*, Aug. 26, 2010; 67(4):575-587.

Ito, Y. et al., "A Quantitative Assay Using Basement Membrane Extracts to Study Tumor Angiogenesis In Vivo," *Int. J. Cancer*, 1996; 67:148-152.

Jackson, K.A. et al., "Regeneration of Ischemic Cardiac Muscle and Vascular Endothelium by Adult Stem Cells," *J. Clin. Invest.*, 2001; 107:1395-1402.

Jaffe, E.A. et al., "Culture of Human Endothelial Cells Derived From Umbilical Veins; Identification by Morphologic and Immunologic Criteria" *J Clin Invest*, 1973; 52:2745-2756.

Janderová, L. et al., "Human Mesenchymal Stem Cells as an In Vitro Model for Human Adipogenesis," *Obes. Res.*, 2003; 11(1):65-74.

Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75:573-584.

Jikuhara, T. et al., "Left Atrial Function as a Reliable Predictor of Exercise Capacity in Patients With Recent Myocardial Infarction," *Chest*, 1997; 111(4):922-928.

Jin et al., "Neurogenesis in Dentate Subgranular Zone and Rostral Subventricular Zone After Focal Cerebral Ischemia in the Rat," *PNAS*, 2001; 98(8):4710-4715.

Johe, K.K. et al., "Single Factors Direct the Differentiation of Stem Cells From the Fetal and Adult Central Nervous System," *Genes & Devel.*, 1996; 10:3129-3140.

Johnstone, B. et al., "In Vitro Chondrogenesis of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," *Stem Cells*, 2006, AlphaMed Press, Downloaded from www.StemCells.com at Ethicon, Inc. on Sep. 11, 2006 and Supplemental Data: 2.

Jones, J. et al., "Insulin-Like Growth Factors and their Binding Proteins: Biological Actions," Endocrine Review, 1995; 16(1):3-34.

Jones-Villeneuve, E.M. et al., "Retinoic Acid-Induced Neural Differentiation of Embryonal Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, 2002; 277(9):7574-7580.

Joussen, A.M. "Cell Transplantation in Age Related Macular Degeneration: Current Concepts and Future Hopes," *Graefe's Arch. Clin. Exp. Ophthalmol.*, 2004; 242:1-2.

Jubran, et al.,"Repair of peripheral nerve transections with fibrin sealant containing neurotrophic factors." *Exp. Neurol*, 2002: 181: 204-212.

Kadiyala, S. et al., "Culture Expanded Canine Mesenchymal Stem Cells Possess Osteochondrogenic Potential In Vivo and In Vitro," *Cell Transplant.*, 1997; 6(2):125-134.

Karussis, D. et al., "Safety and immunological effects of mesenchymal stem cell transplantation in patients with Multiple sclerosis and amyotrophic lateral sclerosis," *Arch Neuorol.*, 2010;67(10):1187-1194.

Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, 1984; 160:633-651.

Kern, S. et al., "Comparative analysis of mesenchymal stem cells from bone marrow, umbilical cord blood, or adipose tissue," *Stem Cells*, 2006; 24(5):1294-301.

Kestendjieva, S. et al., "Characterization of mesenchymal stem cells isolated from the human umbilical cord." *Cell Biology International*, 2008; 32: 724-732.

Keyvani et al., "Plasticity-Associated Molecular and Structural Events in the Injured Brain," *Journal of Neuropathology Experimental Neurology*, 2002; 61(10):831-840.

Kicic, A. et al., "Differentiation of Marrow Stromal Cells Into Photoreceptors in the Rat Eye," *J. of Neurosci.*, 2003; 23(21):7742-7749.

Kim, H. et al., "Dose-dependent efficacy of ALS-human mesenchymal stem cells transplantation into cisterna magna in SOD1-G93A ALS mice," *Neurosci Lett.*, 2010; 468(3) 190-194.

Kim, J. et al., "Dopamine Neurons Derived From Embryonic Stem Cells Function in an Animal Model of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, K.J., et al., "Comparison of Three Rodent Neuropathic Pain Models," *Exp. Brain Res.*, 1997; 113:200-206.

Kim, S.H. et al., "An experimental model for peripheral neuropathy produced by segmental spinal nerve ligation in the rat," *Pain*, 1992; 50:355-363.

Kim, S.K. et al., "Intercellular Signals Regulating Pancreas Development and Function," *Genes Dev.*, 2001; 15:111-127.

Kirschstein, R. et al., "Can Stem Cells Repair a Damaged Heart?" *Stem Cells: Scientific Progress and Future Research Directions*, 2001; 87-92.

Kitamura, S. et al., "Establishment and Characterization of Renal Progenitor Like Cells from S3 Segment of Nephron in Rat Adult Kidney," *The FASEB Journal*, 2005; 19:1789-1797.

Klass et al., "Intravenous Mononuclear Marrow Cells Reverse Neuropathic Pain from Experimental Mononeuropathy," *International Anesthesia Research Society*, 2007; 104:944-949.

(56) References Cited

OTHER PUBLICATIONS

Klassen, H. et al., "Stem Cells and Retinal Repair," *Prog. Retin. Eye Res.*, 2004; 23:149-181.
Kolb, B, "Synaptic Plasticity and the Organization of Behaviour after Early and Late Brain Injury," *Canadian Journal of Experimental Psychology*, 1999; 53(1):62-76.
Kollmar, R. et al., "Neuroprotective effect of delayed moderate hypothermia after focal cerebral ischemia: an MRI study," *Stroke*, 2002; 33:1899-I904.
Komitova, M.; "Enriched environment increases neural stem/progenitor cell proliferation and neurogenesis in the subventricular zone of stroke-lesioned adult rats," *Stroke*, 2005: 36:1278-82.
Kopen, G. et al., "Marrow stromal cells migrate throughout forebrain and cerebellum, and they differentiate into astrocytes after injection into neonatal mouse brains", *PNAS*, 1999; 96:10711-6.
Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76:1643-1648.
Kusama, V. et al., "Growth and morphogenesis of mouse prostate epithelial cells in collagen gel matrix culture" *Cell Biol Int Rep*, 1989; 13:569-575.
Laface, D. et al., "Gene Transfer Into Hematopoietic Progenitor Cells Mediated by an Adeno-Associated Virus Vector," *Virology*, 1988; 162:483-486.
Lang, K.J.D. et al., "Differentiation of Embryonic Stem Cells to a Neural Fate: A Route to Re-Building the Nervous System?" *J. of Neurosci. Res.*, 2004; 76:184-192.
Langeggen, H. et al., "HUVEC Take Up Opsonized Zymosan Particles and Secrete Cytokines IL-6 and IL-8 In Vitro," *FEMS Immunol. Med. Microbiol.*, 2003; 36:55-61.
Le Belle, J.E. et al., "Stem Cells for Neurodegenerative Disorders: Where Can We Go From Here?," *Biodrugs*, 2002; 16(6):389-401.
Le Bouteiller, P. et al., "Soluble HLA-G1 at the Materno-Foetal Interface—A Review," *Placenta*, 2003; 24(Suppl. A):S10-S15.
Lee H.J. et al., "Brain transplantation of immortalized human neural stem cells promotes functional recovery in mouse intracerebral hemorrhage stroke model." *Stem Cells*, 2007;25:1204-12.
Lee, O. et al., "Isolation of Multipotent Mesenchymal Stem Cells from Umbilical Cord Blood," *Blood*, 2004; 103:1669-1675.
Lee, S-T. et al., "Quantification of human neural stem cell engraftments in rat brains using ERV-3 real-time PCR," *Journal of Neuroscience Methods*, 2006; 157:225-229.
Lepore, AC et al., "Neural precursor cells can be delivered into the injured cervical spinal cord by intrathecal injection at the lumbar cord," *Brain Res.*, 2005; 1045(1-2):206-216.
Leventhal, C. et al. "Endothelial trophic support for neuronal production and recruitment from the adult mammalian subependyma," *Molecular and Cellular Neuroscience*, 1999; 13; 450-464.
Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.
Li, C.D. et al., "Mesenchymal Stem Cells Derived From Human Placenta Suppress Allogeneic Umbilical Cord Blood Lymphocyte Proliferation," *Cell Research*, 2005; 15(7):539-547.
Li, L.X. et al., "Inherited Retinal Dystrophy in the RCS Rat: Prevention of Photoreceptor Degeneration by Pigment Epithelial Cell Transplantation," *Exp. Eye Res.*, 1988; 47:911-917.
Li, Y. et al., "Human Marrow Stromal Cell Therapy for Stroke in Rat Neurotrophins and Functional Recovery," *Neurology*, 2002; 59:514-523.
Li, Y. et al., "Intact, Injured, Necrotic and Apoptotic Cells after Focal Cerebral Ischemia in the Rat," *J. Neurol. Sci.*, 1998; 156:119-132.
Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.
Li, Y. et al., "Transplanted Olfactory Ensheathing Cells Promote Regeneration of Cut Adult at Optic Nerve Axons," *J. of Neuro.*, 2003; 23(21):7783-7788.
Li, Y. et al., "Ultrastructural and Light Microscopic Evidence of Apoptosis after Middle Cerebral Artery Occlusion in the Rat," *Am. J. Pathol.*, 1995; 146(5):1045-1051.
Liddiard, et al., "An Improved Method for the Preparation of Human Fetal and Adult Hepatocytes," *Arch. Toxicol.*, 1980; 44:107-112.
Lindenlaub, T. et al., "Partial Sciatic Nerve Transection as a Model of Neuropathic Pain: A Qualitative and Quantitative Study," *Pain*, 2000; 89: 97-106.
Lindvall, O. et al., "Stem Cell Therapy for Human Neurodegenerative Disorders—How to Make It Work," *Nature Medicine*, 2004;10(Suppl.):S42-S50.
Liu, Y. et al., "Molecular and Genetic Mechanisms of Obesity: Implications for Future Management," *Curr. Mol. Med.*, 2003; 3(4):325-340.
Liu. K. et al, "Constitutive and Regulated Expression of Telomerase Reverse Transcriptase (hTERT) in Human Lymphocytes," Proc. Natl. Acad. Sci., 1999; 96:5147-5152.
Lockhart, D.J. et al., "Expression Monitoring by Hybridization to High-Density Oligonucleotide Arrays," *Nat. Biotechnol.*, 1996; 14:1675-1680.
Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.
Lois, C. et al., "Chain Migration of Neuronal Precursors," *Science*, 1996; 271:978-981.
Lonza (Cambrex), hMSC Human Mesenchymal Stem Cells, Lonza, 2014, http://www.lonza.com/products-services/bio-research/primary-and-stem-cells/adult-stem-cells-and-media/hmsc-mesenchymal-stem-cells.aspx; accessed Jan. 31, 2014.
Lu, F-Z et al. "Characterization and gene transfer in mesenchymal stem cells derived from human umbilical-cord blood," *J. Lab Clin. Med.*, 2005; 146:271-278.
Lund, R.D. et al., "Cell Transplantation As a Treatment for Retinal Disease," *Progress in Retinal and Eye Research*, 2001; 20(4):415-449.
Lund, R.D. et al., "Retinal Transplantation: Progress and Problems in Clinical Application," *J. Leukocyte Biol.*, 2003; 74:151-160.
Lund, R.D. et al., "Subretinal Transplantation of Genetically Modified Human Cell Lines Attenuates Loss of Visual Function in Dystrophic Rats," *PNAS*, 2001; 98(17):9942-9997.
Luo, D. et al., "Synthetic DNA Delivery Systems," *Nat. Biotechnol.*, 2000; 18(1):33-36.
Luyten, F.P. et al., "Skeletal Tissue Engineering: Opportunities and Challenges," *Best Pract. Res. Clin. Rheumatol.*, 2001; 15(5):759-769.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.
MacDonald, R.J. "Expression of the Pancreatic Elastase I Gene in Transgenic Mice," *Hepatology*, 1987; 7(1):42S-51S.
Mackay, A.M. et al., "Chondrogenic Differentiation of Cultured Human Mesenchymal Stem Cells From Marrow," *Tissue Engineering*, 1998; 4(4):415-428.
Macrae, W., "Chronic post-surgical pain: 10 years on," *British Journal of Anaesthesia*, 2008; 101:77-86.
Makino, S. et al., "Cardiomyocytes can be generated from marrow stromal cells in vitro," J. Clin. Invest., 1999; 103:697-705.
Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.
Mason, A.J. et al., "The Hypogonadal Mouse: Reproductive Functions Restored by Gene Therapy," *Science*, 1986; 234:1372-1378.
Matsuo, Y. et al., "Protective effect of endothelin type A receptor antagonist on brain edema and injury after transient middle cerebral artery occlusion in rats," *Stroke*, 2001; 32:2143-2148.

(56) References Cited

OTHER PUBLICATIONS

Matsushita et al., "Evidence for Apoptosis After Intracerebral Hemorrhage in Rat Striatum," *Journal of Cerebral Blood Flow & Metabolism*, 2000; 20:396-404.
Mayer-Proschel, M. et al., "Isolation of Lineage-Restricted Neuronal Precursors From Multipotent Neuroepithelial Stem Cells," *Neuron.*, 1997; 19:773-785.
Medicetty, S. et al., "Transplantation of Human Umbilical Cord Matrix Stem Cells Alleviates Apomorphine-Induced Rotations in Parkinsonian Rats", Society for Neuorscience, 2003; XP-002383776, Abstract (Presentation No. 300.14), 1 page.
Meier et al., "Spastic Paresis After Perinatal Brain Damage in Rats is Reduced by Human Cord Blood Monomuclear Cells," Pediatric Research, 2006; 59(2):244-249.
Melero-Martin, J. et al., "Optimal In-Vitro Expansion of Chondroprogenitor Cells in Monolayer Culture," *Biotechnology and Bioengineering*, 2006; 93(3):519-533.
Mendelow, A. et al., "Early surgery vs conservative treatment in patients with spontaneous supratentorial intracerebral hematomas," Lancet, 2005; 365:387-397.
Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.
Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.
Miñambres et al., "Cerebral Apoptosis in Severe Traumatic Brain Injury Patients: An In Vitro, In Vivo, and Postmortem Study," *Journal of Neurotrauma*, 2008; 25:581-591.
Mitchell, K.E. et al., "Matrix Cells From Wharton's Jelly Form Neurons and Glia," *Stem Cells*, 2003; 21:50-60.
Mokudai, T. et al., "Delayed treatment with nicotinamide (Vitamin B3) improves neurological outcome and reduces infarct volume after transient focal cerebral ischemia in Wi star rats," *Stroke*, 2000; 31:1679-1685.
Moll, S. et al., "Monitoring Warfarin Therapy in Patients With Lupus Anticoagulants," *Ann. Intern. Med.*, 1997; 127(3):177-185.
Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.
Moore, A.E. et al., "Parkinsonian Motor Deficits are Reflected by Proportional A9/A10 Dopamine Neuron Degeneration in the Rat," *Exp. Neurol.*, 2001; 172(2):363-376.
Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-3596.
Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.
Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.
Moulder, J.E., "Pharmacological Intervention to Prevent or Ameliorate Chronic Radiation Injuries," *Semin. Radiat. Oncol.*, 2003; 13(1):73-84.
Nakamura, T. et al., "Ocular Surface Reconstruction Using Cultivated Mucosal Epithelial Stem Cells," *Cornea*, 2003; 22(Supp. 1):S75-S80.
Naughton, B.A. et al., "Cells isolated from Wharton's jelly of the human umbilical cord develop a cartilage phenotype when treated with TGF-b in vitro," 1997; *FASEB J* 11:A19 (Abstract 108).
Nehlin et al., "Immunogenicity and Immune-Modulating Properties of Human Stem Cells", *Stem Cells in Clinical Research*, 2011, pp. 105-143.
Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.
Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70(1):121-129.
Nishishita, T. et al., "A Potential Pro-Angiogenic Cell Therapy With Human Placenta-Derived Mesenchymal Cells," *Biochemical and Biophysical Research Communications*, 2004; 325:24-31.
Nixon, P.J. et al., "The Contribution of Cone Responses to Rat Electroretinograms," *Clin. Experiment Ophthalmol.*, 2001; 29(3):193-196.
Nork, T.M. et al., "Swelling and Loss of Photoreceptors in Chronic Human and Experimental Glaucomas," *Arch. Ophthalmol.*, 2000; 118:235-245.
Oaklander, A. et al., "The Pathology of Chronic Pain," *The Transverse Myeletis Association Newsletter*, 2001; 2:12-16.
Ochs, G. et al.,"Epi-arachnoidal drug deposit: A rare complication of intrathecal drug therapy," *J Pain Symptom Manage*, 1999; 18:229-232.
Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279(2):500-504.
Okuda-Ashitaka et al., "Molecular mechanisms of pain and new approaches for pain management," *Experimental Medicine*, 2000, 18: 2332-2337 (with English Abstract).
Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.
Orlic, D. et al., "Stem Cells for Myocardial Regeneration," *Circ. Res.*, 2002; 91:1092-1102.
Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.
Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.
Palù, G. et al., "In Pursuit of New Developments for Gene Therapy of Human Diseases," *J. Biotechnol.*, 1999; 68:1-13.
Pan, Y. et al., "Acute Treatment of Focal Cerebral Ischemia in Rats with Intracarotid Administration of Human Umbilical Cord Blood Cells," *Neurology*, 2003; 60(Suppl 1.): A63-A64 (Abstract P01.127).
Panepucci, R.A. et al., "Comparison of Gene Expression of Umbilical Cord Vein and Bone Marrow-Derived Mesenchymal Stem Cells," *Stem Cells*, 2004; 22:1263-1278.
Parent et al., "Rat Forebrain Neurogenesis and Striatal Neuron Replacement After Focal Stroke," *Ann. Neurol.*, 2002; 52:802-813.
Park, B-G et al., "Development of high density mammalian cell culture system for the production of tissue-type plasminogen activator," *Biotechnology and Bioprocess Engineering*, 2000; 5:123-129.
Pera, M.F. et al., "Human Embryonic Stem Cells", *J. Cell Science*, 2000; 113:5-10.
Pesce et al., "Myoendothelial Differentiation of Human Umbilical Cord Blood-Derived Stem Cells in Ischemic Limb Tissues," *Circulation Research*, 2003; 93:e51-e62.
Petersdorf, E.W., "HLA Matching in Allogeneic Stem Cell Transplantation," *Curr. Op. Hematol*, 2004; 11:386-391.
Peterson, D.A., "Umbilical cord blood cells and brain stroke injury: bringing in fresh blood to address an old problem," *J Clin Invest.*, 2004; 114:312-314.
Pfefferkorn T, and Rosenberg GA. "Closure of the blood-brain barrier by matrix metalloproteinase inhibition reduces rtP A-mediated mortality in cerebral ischemia with delayed reperfusion," *Stroke*, 2003; 34:2025-2030.
Phillips, A., "The challenge of gene therapy and DNA delivery," *J Pharmacology*, 2001; 53:1169-1174.

(56) References Cited

OTHER PUBLICATIONS

Phipps, J.A. et al., "Paired-Flash Identification of Rod and Cone Dysfunction in the Diabetic Rat," *Investigative Ophthalmology & Visual Science*, 2004; 45:4592-4600.
Piscaglia, A.C. et al., "Human Cordonal Stem Cell Intraperitoneal Injection Can Represent a Rescue Therapy After an Acute Hepatic Damage in Immunocompetent Rats." *Transplantation Proceedings*, 2005; 37, 2711-2714.
Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Mesenchymal Stem Cells and Their Potential as Cardiac Therapeutics," *Circ. Res.*, 2004; 95:9-20.
Pittenger, M.F. et al., "Multilineage Potential of Adult Human Mesenchymal Stem Cells," *Science*, 1999; 284:143-47 and seven pages of online supplementary material.
Pittenger, M.F. et al.; "Human mesenchymal stem cells: progenitor cells for cartilage, bone, fat and stroma," *Current Topics in Microbiology and Immunology*, 2000; 251:3-11.
Plaia, T., et al., "Characterization of a New NIH-Registered Variant Human Embryonic Stem Cell Line, BG01V: A Tool for Human Embryonic Stem Cell Research," *Stem Cells*, 2006: 24: 531-546.
Plate, KH, "Mechanisms of Angiogenesis in the Brain," *Journal of Neuropathology Experimental Neurology*, 1999; 58(4):313-320.
Pountos, I. et al., "Mesenchymal Stem Cell Tissue Engineering: Techniques for Isolation, Expansion and Application," *Injury, Int. J. Care Injured*, 2007; 38:S23-S33.
Rabbany, S.Y. et al., "Molecular Pathways Regulating Mobilization of Marrow-Derived Stem Cells for Tissue Revascularization," *Trends in Molecular Med.*, 2003; 9(3):109-117.
Rafii, S. et al., "Therapeutic Stem and Progenitor Cell Transplantation for Organ Vascularization and Regeneration," *Nature Med.*, 2003; 9(6):702-712.
Rahman, Z. et al., "Isolation and Primary Culture Urothelial Cells from Normal Human Bladder," *Urol. Research*, 1987; 15:315-320.
Ramon-Cueto, A. et al., "Functional Recovery of Paraplegic Rats and Motor Axon Regeneration in Their Spinal Cords by Olfactory Ensheathing Glia," *Neuron*, 2000; 25:425-435.
Readhead, C. et al., "Expression of a Myelin Basic Protein Gene in Transgenic Shiverer Mice: Correction of the Dysmyelinating Phenotype," *Cell*, 1987; 48:703-712.
Refaie, A. et al., "Experimental Islet Cell Transplantation in Rats: Optimization of the Transplantation Site," *Trans. Proc.*, 1998; 30:400-403.
Rehman, J. et al., "Secretion of Angiogenic and Antiapoptotic Factors by Human Adipose Stromal Cells," *Circulation*, 2004; 109:1292-1298.
Reubinoff, B.E. et al., "Neural Progenitors From Human Embryonic Stem Cells," *Nature Biotechnology*, 2001; 19:1134-1140.
Reyes, M. et al., "Purification and Ex Vivo Expansion of Postnatal Human Marrow Mesodermal Progenitor Cells," *Blood*, 2001; 98(9):2615-2625.
Rezai, K.A. et al., "Iris Pigment Epithelium Transplantation," *Graefe's Arch. Clin. Ophthalmol.*, 1997; 235:558-562.
Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.
Rios, M. et al., "Catecholamine Synthesis is Mediated by Tyrosinase in the Absence of Tyrosine Hydroxylase," *J. Neurosci.*, 1999, 19(9):3519-3526.
Rivlin, AS et al., "Objective clinical assessment of motor function after experimental spinal cord injury in the rat," *J Neurosurg*, 1977; 47:577-581.
Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.
Rosen, E.M. et al., "HGF/SF in Angiogenesis," *Ciba Found. Symp.*, 1997; 212:215-229.

Roskams, A.J. et al., "Directing Stem Cells and Progenitor Cells on the Stage of Spinal Cord Injury," *Exp. Neurol.*, 2005; 193:267-272.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2001; 7(1):11.
Ryadnov, M.G. et al., "Engineering the Morphology of a Self-Assembling Protein Fibre," *Nat. Mater.*, 2003; 2:329-332.
Sagrinati, C. et al., "Isolation and Characterization of Multipotent Progenitor Cells from the Bowman's Capsule of Adult Human Kidney," *Journal of American Society of Nephrology*, 2006; 17:2443-2456.
Sahn, D.J. et al., "Recommendations Regarding Quantitation in M-Mode Echocardiography: Results of a Survey of Echocardiographic Measurements," *Circulation*, 1978; 58(6):1072-1083.
Sakariassen, K.S. et al., "Methods and Models to Evaluate Shear-Dependent and Surface Reactivity-Dependent Antithrombotic Efficacy," *Thromb. Res.*, 2001; 104:149-174.
Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, 2004; 4:743-765.
Sauvé, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Schraermeyer, U. et al., "Subretinally Transplanted Embryonic Stem Cells Rescue Photoreceptor Cells From Degeneration in the RCS Rats," *Cell Transplantation*, 2001; 10:673-680.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54:409-437.
Schwartz, R.E. et al., "Multipotent Adult Progenitor Cells From Bone Marrow Differentiate Into Functional Hepatocyte-Like Cells," *J. of Clin. Invest.*, 2002; 109:1291-1302.
Seaver, S.S. et al. "The chick oviduct in tissue culture. I. Initial characterization of growing primary oviduct tissue cultures," *Exp. Cell Res.*, 1984; 155: 241-251.
Sébire, G. et al., "In Vitro Production of IL-6, IL-1β, and Tumor Necrosis Factor-α by Human Embryonic Microglial and Neural Cells," *J. Immunol.*, 1993; 150(4):1517-1523.
Secco, M. et al., "Multipotent Stem Cells from Umbilical Cord: Cord is Richer than Blood!" *Stem Cells*, 2008; 26:146-150.
Seiji, T. et al., Possibility of Regenerative Medicine Using Human Amniotic Cells, *Regenerative Medicine*, 2002; 1(2):79-85.
Sethe, S. et al., "Aging of Mesenchymal Stem Cells," *Ageing Research Reviews*, 2006; 5:91-116.
Seyfried DM et al., "Mannitol enhances delivery of marrow stromal cells to the brain after experimental intracerebral hemorrhage," *Brain Res.*, 2008; 1224:12-19.
Seyfried, D. et al., "Effects of Intravenous Administration of Human Bone Marrow Stromal Cells After Intracerebral Hemorrhage in Rats," *J Neurosurg*, 2006; 104:313-318.
Seyfried, D. et al., "Improvement in Neurological Outcome after Administration of Atorvastatin Following Experimental Intracerebral Hemorrhage in Rats," *J Neurosurg*, 2004; 101:104-107.
Shake et al., "Mesenchymal stem cell implantation in a swine myocardial infarct model: engraftment and functional effects," Ann Thorac Surg, 2002; 73:1919-1926.
Shani, M., "Tissue-Specific Expression of Rat Myosin Light-Chain 2 Gene in Transgenic Mice," *Nature*, 1985; 314:283-286.

(56) References Cited

OTHER PUBLICATIONS

Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.
Shimizu, T. et al., "Cell Sheet Engineering for Myocardial Tissue Reconstruction," *Biomaterials*, 2003; 24:2309-2316.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.
Simard, A.R., "Bone marrow-derived microglia play a critical role in restricting senile plaque formation in Alzheimer's disease," *Neuron*, 2006; 49:549-502.
Siminoff, R. et al., "Properties of Reptilian Cutaneous Mechanoreceptors," *Exp. Neurol.*, 1968; 20:403-414.
Solomon, D. E., "An in vitro examination of extracellular matrix scaffold for use in wound healing," *Int. J. Path*, 2002, 93: 209-216.
Song, H. et al., "Astroglia Induce Neurogenesis From Adult Neural Stem Cells," *Nature*, 2002; 417:39-44.
Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5):354-365.
Street, C.N. et al., "Stem Cells: A Promising Source of Pancreatic Islets for Transplantation in Type 1 Diabetes," *Curr. Top Dev. Biol.*, 2003; 58:111-136.
Stroemer et al., "Enhanced Neocortical Neural Sprouting, Synaptogenesis, and Behavioral Recovery with D-Amphetamine Therapy after Neocortical Infarction in Rats," *Stroke*, 1998; 29:2381-2395.
Stroemer et al., "Neocortical Neural Sprouting, Synaptogenesis, and Behavioral Recovery After Neocortical Infarction in Rats," *Stroke*, 1995; 26:2135-2144.
Sun, S. et al., "Physical manipulation of calcium oscillations facilitates osteodifferentiation of human mesenchymal stem cells," *FASEB J.*, 2007; 1472-1480.
Svendsen, C.N. "The Amazing Astrocyte," *Nature*, 2002; 417:29-32.
Svendsen, C.N. et al., "Long-Term Survival of Human Central Nervous System Progenitor Cells Transplanted Into a Rat Model of Parkinson's Disease," *Experim. Neurol.*, 1997; 148:135-146.
Swanson, R.A. et al., "A Semiautomated Method for Measuring Brain Infarct Volume," *J. Cereb. Blood Flow Metab.*, 1990; 10:290-293.
Swift, G.H. et al., "Tissue-Specific Expression of the Rat Pancreatic Elastase I Gene in Transgenic Mice," *Cell*, 1984; 38:639-646.
Szpak et al., "Border Zone Neovascularization in Cerebral Ischemic Infarct," *Folia Neuropathol*, 1999; 37(4):264-268. (Abstract only).
Tamura, A. et al., "Focal cerebral ischemia in the rat: 1. Description of technique and early neuropathological consequences following middle cerebral artery occlusion," *J Cereb Blood Flow Met*, 1981; 1:53-60.
Tao, W., "Application of Encapsulated Cell Technology for Retinal Degenerative Disease," *Expert. Opin. Biol. Ther.*, 2006; 6(7): 717-726.
Taylor, D.A. et al., "Cardiac Chimerism as a Mechanism for Self-Repair: Does It Happen and If So to What Degree?" *Circulation*, 2002; 106:2-4.
Taylor, D.A. et al., "Regenerating Functional Myocardium: Improved Performance After Skeletal Myoblast Transplantation," *Nature Medicine*, 1998; 4(8):929-1200.
Thorsby, E. et al., "Role of HLA Molecules in the Induction of Alloimmune Responses: Clinical Significance in the Cyclosporine Era," *Transplant Proc.*, 2004; 36(Suppl 2S):16S-21S.
Timmermans, F. et al., "Stem Cells for the Heart, Are We There Yet?" *Cardiology*, 2003; 100(4):176-185.
Toma, C. et al., "Human Mesenchymal Stem Cells Differentiate to a Cardiomyocyte Phenotype in the Adult Murine Heart," *Circulation*, 2002; 105:93-98.
Tomita, M. et al., "Bone Marrow-Derived Stem Cells Can Differentiate Into Retinal Cells in Injured Rat Retina," *Stem Cells*, 2002; 20:279-283.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," Stem Cells, 2001; 19:408-418.
Tresco, P.A. et al., "Cellular Transplants as Sources for Therapeutic Agents," *Advanced Drug Delivery Reviews*, 2000; 42:3-27.
Troyer, D. L. et al., "Concise Review: Wharton's Jelly-Derived Cells Are a Primitive Stromal Cell Population," *Stem Cells*, 2008; 26:591-599.
Turner, D., "The Human Leucocyte Antigen (HLA) System," *Vox Sang.*, 2004; 87(Suppl 1):S87-S90.
Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-917.
Tusher, V.G. et al., "Significance Analysis of Microarrays Applied to the Ionizing Radiation Response," *PNAS*, 2001; 98(9):5116-5121.
Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
Urbich, C. et al., "Endothelial Progenitor Cells Characterization and Role in Vascular Biology," *Circ. Res.*, 2004; 95:343-353.
Vajsar, J. et al., "Walker-Warburg Syndrome," *Orphanet Journal of Rare Diseases*, 2006; 1:29.
Van Hoffelen, S.J. et al., "Incorporation of Murine Brain Progenitor Cells Into the Developing Mammalian Retina," *Invest. Ophthalmol. Vis. Sci.*, 2003; 44(1):426-434.
Vassliopoulos, G. et al., "Transplanted Bone Marrow Regenerates Liver by Cell Fusion," *Nature*, 2003; 422:901-904.
Vendrame, M. et al., "Infusion of human umbilical cord blood cells in a rat model of stroke dose-dependently rescues behavioral deficits and reduces infarct volume," *Stroke*, 2004; 35:2390-2395.
Vendrame, M. et al., "Intravenous administration of human umbilical cord blood (HUCB) cells in a rat model of stroke: a dose dependent study," *Society for Neuroscience Abstract*, 2003; Presentation No. 844.11.
Verma, I. M. et al., "Gene Therapy—Promises, Problems and Prospects," *Nature*, 1997; 389:239-242.
Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
Voeglin, et al., "Effects of local continuous release of brain derived neurotrophic factor (BDNF) on peripheral nerve regeneration in a rat model." *Exp. Neurol*, 2006: 199:348-353.
Voet D and Voet JG, Biochemistry (2d Ed., John Wiley & Sons), 1995; Chapter 4. Amino Acids: B. The Fischer Convention, p. 64.
von Koskull, H. et al., "Induction of Cytokeratin Expression in Human Mesenchymal Cells," *J. Cell Physiol.*, 1987; 133:321-329.
Walboomers, X .F. et al., "Cell and Tissue Behavior on Micro-Grooved Surfaces," *Odontology*, 2001; 89:2-11.
Walter, D. H. et al., "Statin Therapy Accelerates Reendothelialization a Novel Effect Involving Mobilization and Incorporation of Bone Marrow-Derived Endothelial Progenitor Cells," *Circulation*, 2002; 105:3017-3024.
Wang, D. et al., "Synthesis and Characterization of a Novel Degradable Phosphate-Containing Hydrogel," *Biomaterials*, 2003; 24:3969-3980.
Wang, X . et al., "Cell Fusion Is the Principal Source of Bone-Marrow-Derived Hepatocytes," *Nature*, 2003; 422:897-900.

(56) References Cited

OTHER PUBLICATIONS

Wang, Y. et al., "Enhanced Recovery of Hematopoietic Progenitor and Stem Cells from Cultivated, Postpartum Human Placenta," *Blood*, 2001; 98(11): 183a (Abstract 769).
Wegman, A. et al., "Nonsteroidal Anti-Inflammatory Drugs or Acetaminophen for Osteoarthritis of the Hip or Knee? A Synstematic Review of Evidence and Guidelines," *J. Rheumatol.*, 2004; 31(2):344-354.
Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.
Weiss, M.L. et al., "Transplantation of Porcine Umbilical Cord Matrix Cells Into the Rat Brain," *Exp. Neur.*, 2003; 182:288-299.
Wenning, G.K. et al., "Neural Transplantation in Animal Models of Multiple System Atrophy: A Review," *J. Neural Transm.*, 1999; Suppl.(55):103-113.
Williams, J.T. et al., "Cells Isolated From Adult Human Skeletal Muscle Capable of Differentiating Into Multiple Mesodermal Phenotypes," *Am. Surg.* 1999; 65(I):22-6.
Winkler et al., "Lack of Long-Term Effects After Beta-Amyloid Protein Injections in Rat Brain," *Neurobiolo. Aging*, 1994; 15(5):601-607.
Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29:1525-1539.
Wolford, L.M. et al., "Considerations in Nerve Repair," *BUMC Proceedings*, 2003; 16(2):152-156.
Woodbury, D., et al., "Adult Rat and Human Bone Marrow Stromal Cells Differentiate Into Neurons," *J. Neurosci. Res.*, 2000; 61:364-370.
Wulf, G.G. et al., "Mesengenic Progenitor Cells Derived From Human Placenta," *Tissue Engineering*, 2004; 10(7/8):1136-1147.
Xi, G, et al., "Mechanisms of Edema Formation After Intracerebral Hemorrhage Effects of Extravasated Red Blood Cells on Blood Flow and Blood-Brain Barrier Integrity," *Stroke*, 2001; 32:2932-2938.
Xu, C. et al., "Characterization and Enrichment of Cardiomyocytes Derived From Human Embryonic Stem Cells," *Circ. Res.*, 2002; 91:501-508.
Xu, Y. et al., "Dopamine, in the Presence of Tyrosinase, Covalently Modifies and Inactivates Tyrosine Hydroxylase," *J. Neurosci. Res.*, 1998; 54:691-697.
Yamashima, T., "Implication of Cysteine Proteases Calpain, Cathepsin and Caspase in Ischemic Neuronal Death of Primates," *Progress in Neurobiology*, 2000; 62:273-295.
Yang, C. et al., "Enhancement of Neovascularization With Cord Blood CD133+ Cell-Derived Endothelial Progenitor Cell Transplantation," *Thrombosis and Haemostasis*, 2004; 91:1202-1212.
Yang, D. et al., "Therapeutic effect of human umbilical tissue-derived cell treated in Rats in experimental intracereberal hemorrhage", Brain Research, 2012; 1444:1-10.
Yang, H. et al., "Region-Specific Differentiation of Neural Tube-Derived Neuronal Restricted Progenitor Cells After Heterotopic Transplantation," *PNAS*, 2000; 97(24):13366-13371.
Ye Q. et al., "Recovery of Placental-Derived Adherent Cells With Mesenchymal Stem Cell Characteristics", *Blood*, 2001; 98(11 Part 2):147B (Abstract No. 4260).
Yip, H.K., et al., "Axonal Regeneration of Retinal Ganglion Cells: Effect of Trophic Factors," *Prog. Retin Eye Res.*, 2000; 19(5):559-575.
Yokoo, T. et al., "Stem Cell Gene Therapy for Chronic Renal Failure," *Curr Gene Ther.*, 2003; 3:387-394.
Yu, M. et al., "Mid-Trimester Fetal Blood-Derived Adherent Cells Share Characteristics Similar to Mesenchymal Stem Cells But Full-Term Umbilical Cord Blood Does Not," *British J. of Haematology*, 2004; 124:666-675.
Zangani, D. et al., "Multiple Differentiation Pathways of Rat Mammary Stromal Cells In Vitro: Acquisition of a Fibroblast, Adipocyte or Endothelial Phenotype Is Dependent on Hormonal and Extracellular Matrix Stimulation," *Differentiation*, 1999; 64:91-101.
Zhang ZG et al., "Magnetic resonance imaging and neurosphere therapy of stroke in rat," *Ann Neurol.*, 2003; 53(2):259-263.
Zhang, L. et al., "A Test for Detecting Long-Term Sensorimotor Dysfunction in the Mouse after Focal Cerebral Ischemia," *J. Neurosci. Methods*, 2002; 117:207-214.
Zhang, S. et al., "In Vitro Differentiation of Transplantable Neural Precursors From Human Embryonic Stem Cells," *Nature Biotechnology*, 2001; 19:1129-1133.
Zhang, X. et al., "Efficient Adeno-Associated Virus-Mediated Gene Expression in Human Placenta-Derived Mesenchymal Cells," *Microbiol. Immunol.*, 2003; 47(1):109-116.
Zhang, Y. et al., "Comparison of Mesenchymal Stem Cells from Human Placenta and Bone Marrow," *Chinese Medical Journal*, 2004; 117(6):882-887.
Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-392.
Zimmerman, S. et al., "Lack of Telomerase Activity in Human Mesenchymal Stem Cells," *Leukemia*, 2003; 17:1146-1149.
Zuloff-Shani, A. et al., "Macrophage Suspensions Prepared From a Blood Unit for Treatment of Refractory Human Ulcers," *Transfus. Apheresis Sci.*, 2004; 30:163-167.
In the U.S. Patent and Trademark Office Final Office Action in re: U.S. Appl. No. 14/152,649 dated Jul. 10, 2015, 7 pages.
In the U.S. Patent and Trademark Office, Non-Final Office Action in re: U.S. Appl. No. 12/642,775 dated Aug. 24, 2015, 38 pages.
In the U.S. Patent and Trademark Office, Non-Final Office Action in re: U.S. Appl. No. 11/321,864 dated Sep. 2, 2015, 11 pages.
In the U.S. Patent and Trademark Office, Non-Final Office Action in re: U.S. Appl. No. 12/389,305 dated Sep. 4, 2015, 63 pages.
In the U.S. Patent and Trademark Office, Non-Final Office Action in re: U.S. Appl. No. 11/316,104 dated Sep. 8, 2015, 63 pages.
In the U.S. Patent and Trademark Office, Non-Final Office Action in re: U.S. Appl. No. 14/152,649 dated Oct. 27, 2015, 7 pages.
In the U.S. Patent and Trademark Office, Final Office Action in re: U.S. Appl. No. 10/876,998 dated Dec. 22, 2015, 21 pages.
In the U.S. Patent and Trademark Office, Final Office Action in re: U.S. Appl. No. 11/321,864 dated Dec. 22, 2015, 15 pages.
In the U.S. Patent and Trademark Office, Non-Final Office Action in re: U.S. Appl. No. 11/317,574 dated Jan. 6, 2015, 11 pages.
In the U.S. Patent and Trademark Office, Final Office Action in re: U.S. Appl. No. 11/322,372 dated Jan. 6, 2015, 27 pages.
Broxmeyer, H.E. et al., "Growth characteristics and expansion of human umbilical cord blood and estimation of its potential for transplantation in adults," *PNAS*, 1992; 89(9): 4109-4113.
Caplan, A. I. et al., "Mesenchymal Stem Cells as Trophic Mediators," *J Cell Biochem.*, 2006; 98:1076-84.
Cho, S. et al, "Enhancement of Angiogenic Efficacy of Human Cord Blood Cell Transplantation," *Tissue Engineering*, 2006; 12:6 1651-1661.
Kroeber, M.W. et al., "New in vivo animal model to create intervertebral disc degeneration and to investigate the effects of therapeutic strategies to stimulate disc regeneration." *Spine* (Phila PA 1976), 2002; 27(23):2684-90.
Mankikar, S.D., "Stem Cells: A New Paradigm in Medical Therapeutics," *Journal of Long-Term Effects of Medical Implants*, 2010; 20:219-250.
Mendell, J. et al., "Painful Sensory Neuropathy," *New England Journal of Medicine*, 2003; 348: 1243-1255.
Xu, Y et al., "Umbilical Cord-Derived Mesenchymal Stem Cells Isolated by a Novel Explantation Technique Can Differentiate into Functional Endothelial Cells and Promote Revascularization,"*Stem Cells and Development*, 2010, 19(10): 1511-1522.
Zhao, Q.H. et al., "Biological characteristics of human umbilical cord-derived mesenchymal stem cells and their differentiation into chondrogenic and osteogenic cells," *Zhonghua Yi Xue Za Zhi.*, 2011;91(5):317-21 (Abstract only).
In the U.S. Patent and Trademark Office, Non-Final Office Action in re: U.S. Appl. No. 13/471,095 dated Mar. 22, 2016, 17 pages.

(56) References Cited

OTHER PUBLICATIONS

In the U. S. Patent and Trademark Office, Final Office Action in re: U.S. Appl. No. 12/337,439 dated Mar. 17, 2016 29 pages.
In the U. S. Patent and Trademark Office, Final Office Action in re: U.S. Appl. No. 11/315,969 dated Apr. 21, 2016 20 pages.
In the U. S. Patent and Trademark Office, Final Rejection in re: U.S. Appl. No. 10/876,998 dated May 20, 2016 21 pages.
In the U. S. Patent and Trademark Office, Final Office Action in re: U.S. Appl. No. 12/389,305 dated May 24, 2016 21 pages.
In the U. S. Patent and Trademark Office, Final Office Action in re: U.S. Appl. No. 11/316,104 dated May 24, 2016 24 pages.
In the U. S. Patent and Trademark Office, Non-Final Office Action in re: U.S. Appl. No. 10/877,446 dated May 24, 2016 36 pages.
In the U.S. Patent and Trademark Office, Non-Final Office Action in re: U.S. Appl. No. 11/322,372 dated May 31, 2016, 29 pages.
In the U.S. Patent and Trademark Office, Final Office Action in re: U.S. Appl. No. 11/317,574 dated May 31, 2016, 18 pages.
In the U.S. Patent and Trademark Office, Final Office Action in re: U.S. Appl. No. 14/152,649 dated Jun. 14, 2016, 6 pages.
In the U.S. Patent and Trademark Office, Final Office Action in re: U.S. Appl. No. 13/111,933 dated Jul. 6, 2016, 26 pages.
In the U.S. Patent and Trademark Office, Final Office Action in re: U.S. Appl. No. 11/317,574 dated Jul. 7, 2016, 9 pages.
In the U.S. Patent and Trademark Office, Non-Final Office Action in re: U.S. Appl. No. 14/244,426 dated Jul. 26, 2016, 29 pages.
Baksh, D. et al., "Adult mesenchymal stem cells: characterization, differentiation, and application in cell and gene therapy", *J Cell Mol Med.*, 2004; 8(3):301-16.
Kim, N.W. et al., "Specific association of human telomerase activity with immortal cells and cancer," *Science*, 1994; 266:2011-2015.
Li L.Y. et al., "Transplantation of NGF-gene-modified bone marrow stromal cells into a rat model of Alzheimer' disease," *J Mol Neurosci.* 2008; 34(2):157-63.
Lu, L.L. et al., "Isolation and characterization of human umbilical cord mesenchymal stem cells with hematopoiesis-supportive function and other potentials," *Haematologica*, 2006; 91(8):1017-26.
Naughton, B.A. et al., "Hematopoiesis on nylon mesh templates. I. Long-term culture of rat bone marrow cells," *Journal of Medicine*, 1987; 18(3-4):219-50.
Wakitani, S. et al., "Mesenchymal cell-based repair of large, full-thickness defects of articular cartilage", *J Bone Joint Surg Am*, 1994; 76(4): 579-592.
Weiss, M.L. et al., "Stem Cells in the Umbilical Cord," *Stem Cell Rev.*, 2006; 2(2):155-162.
Yamada, M. et al., "Electrical stimulation modulates fate determination of differentiating embryonic stem cells," *Stem Cells*, 2007; 25(3):562-70.

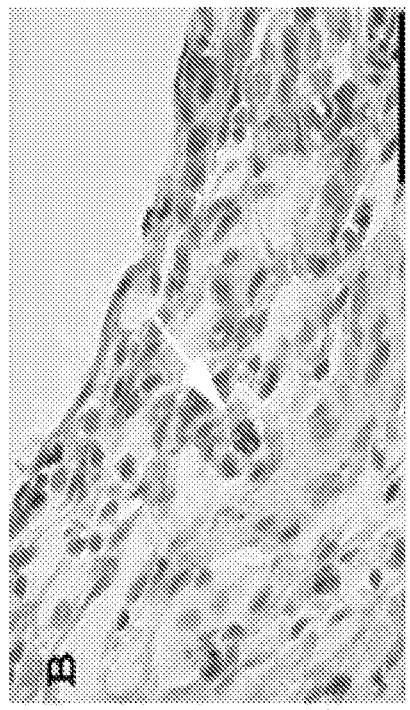
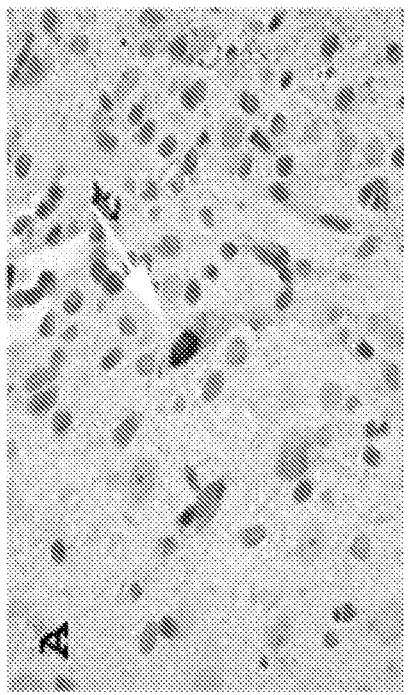
FIG. 25B
FIG. 25A
E5204 positive cells (white arrow) in UTC (A) and MSCs (B) treated animals.
Scale bar = 50μm

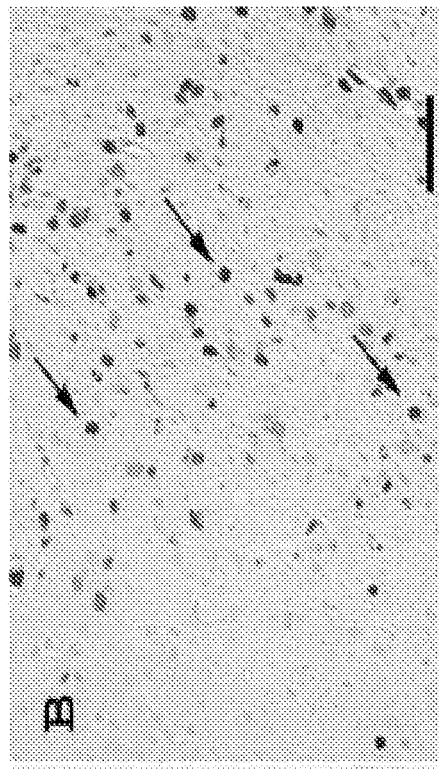
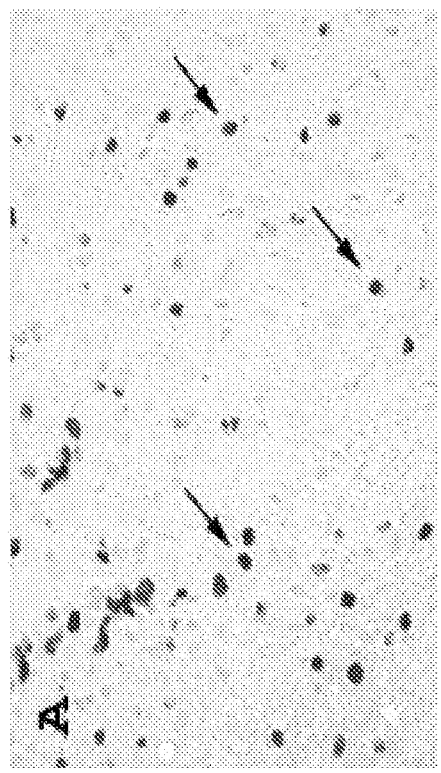
FIG. 26B
FIG. 26A
BrdU positive cells (black arrow) in the lesion boundary zone of UTC (A) and MSCs (B) treated animals.
Scale bar = 50μm vWF stained vessels (black arrow) seen in UTC (A) and MSCs (B) treated rats.
Scale bar = 50μm

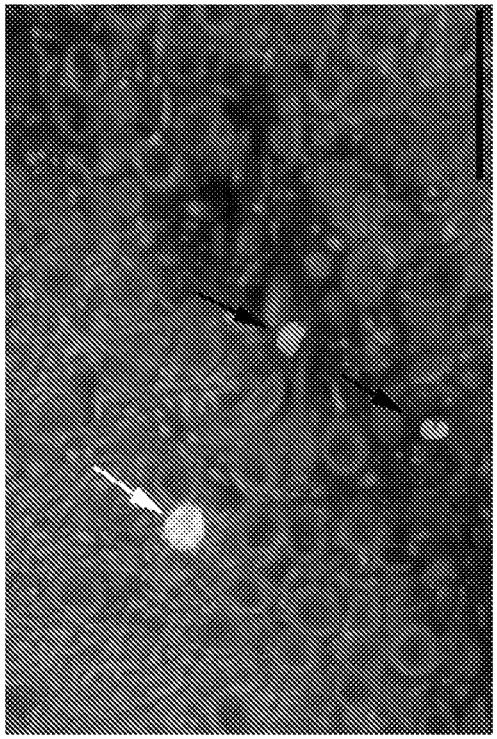

FIG. 32B

Immunohistochemistry is showing BrdU and Map-2 positive double stained cells (white arrow) in the dentate gyrus. BrdU only positive cells are indicated located by black arrows.

Scale bar = 50μm.

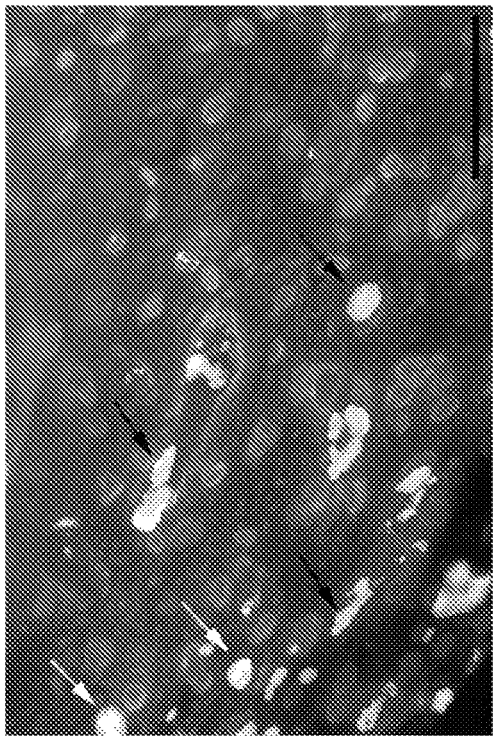

FIG. 32A

Immunohistochemistry is showing BrdU and Map-2 positive double stained cells (white arrows) in the lesion boundary zone. BrdU only positive cells are indicated by black arrows.

Scale bar = 50μm.

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagaaatcca aagagcaaat gg                                            22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agaatggaaa actggaatag g                                             21

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcttcgatgc ttcggattcc                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaattctcgg aatctctgtt g                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttacaagcag tgcagaaaac c                                                21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtaaacatt gaaaccacag cc                                               22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgcagctc tgtgtgaagg                                                  20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttcaaaaac ttctccacaa cc                                               22
```

```
<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccacgccac gctctcc                                                    17

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcctgtcagt tggtgctcc                                                  19
```

TREATMENT OF NEUROLOGICAL INJURY BY ADMINISTRATION OF HUMAN UMBILICAL CORD TISSUE-DERIVED CELLS

CROSS REFERENCE TO RELATED APPLICATIONS

This application is continuation-in-part application of U.S. patent application Ser. No. 12/642,773, filed Dec. 19, 2009, now abandoned, which claims benefit to U.S. Provisional Patent Application No. 61/139,305, filed Dec. 19, 2008, the contents of which are incorporated by reference herein in their entirety. This application is also a continuation-in-part application of U.S. patent application Ser. No. 14/152,649, filed Jan. 1, 2014, which is a continuation of U.S. application Ser. No. 13/605,716, filed Sept. 6, 2012, now U.S. Pat. No. 8,658,152, issued Feb. 25, 2014, which is a divisional of U.S. application Ser. No. 12/429,849, filed Apr. 24, 2009, now U.S. Pat. No. 8,277,796, issued Oct. 2, 2012, which is a continuation of U.S. application Ser. No. 10/877,269, filed Jun. 25, 2004, now U.S. Pat. No. 7,524,489, issued Apr. 28, 2009, which in turn claims benefit of U.S. Provisional Application No. 60/483,264, filed Jun. 27, 2003, the entire contents of which are incorporated by reference herein in their entirety.

FIELD OF THE INVENTION

This invention relates to the field of cell-based or regenerative therapy for neurological injury. In particular, the invention provides pharmaceutical compositions kits and methods for the regeneration or repair of neural tissue using cells.

BACKGROUND OF THE INVENTION

Various patents and other publications are referred to throughout the specification. Each of these publications is incorporated by reference herein, in its entirety.

Neurological diseases and other disorders of the central and peripheral nervous system are among the most debilitating that can be suffered by an individual, not only because of their physical effects, but also because of their permanence. In the past, a patient suffering from brain or spinal cord injury, or a neurodegenerative condition of the central or peripheral nervous system, such as Parkinson's disease, Alzheimer's disease or multiple sclerosis, to name a few, held little hope for recovery or cure.

Neurological damage and neurodegenerative diseases were long thought to be irreversible because of the inability of neurons and other cells of the nervous system to grow in the adult body. However, the adult mammalian brain retains some capacity for plasticity and neuronal regeneration following injury. (See, Kolb, B, *Can J Exp Psycho,* 1999; 53:62-76; Stroemer, R P, et al., *Stroke,* 1998; 29:2381-93; Walter, D H, et al., *Circulation,* 2002; 105(25):3017-24; Plate, K H, *J Neuropathol Exp Neurol,* 1999; 58(4):313-20; Szpak, G M, et al., *Folia Neuropathol,* 1999; 37(4):264-8; Jin, K, et al., *Proc Natl Acad Sci USA,* 2001; 98(8):4710-5; Parent, J M, et al., *Ann Neurol,* 2002; 52(6):802-13; Stroemer, R P, et al., *Stroke,* 1995; 26(11):2135-44; Keyvani, K, et al., *J Neuropathol Exp Neurol,* 2002; 61(10):831-40; Lois, C, et al., *Science,* 1996; 271(5251):978-81; and, Dutton, R, et al., *Dev Neurosci,* 2000; 22(1-2):96-105). For example, the subventricular zone (SVZ) contains a population of cells capable of undergoing differentiation into various cell types, including neurons, (See, Chen, J, et al., *Stroke,* 2001; 32:1005-1011; Evers, B M, et al., *J Am Coll Surg,* 2003; 197:458-478; Seyfried, D, et al., *J Neurosurg,* 2006; 104: 313-318) and experiments of ischemic injury and traumatic brain injury (TBI) suggest that cells in this region participate in the recovery process. Both clinical studies and animal models suggest that there are several mechanisms involved in cellular injury following intracranial hemorrhage (ICH). These include a traumatic or mechanical component, an ischemic component, and direct toxic effects of a blood clot. (See, Gong, C, et al., *Neurosurgery,* 2001; 48:875-883; Gong, C, et al., *Brain Res,* 2000; 871:57-65; Hua, Y, et al., *J Cereb Blood Flow Metab,* 2002; 22:55-61; Matsushita, K, et al., *J Cereb Blood Flow Metab,* 2000; 20:396-404; Xi, G, et al., *Stroke,* 2001; 32:2932-2938; and, Seyfried, D, et al., *J Neurosurg,* 2004; 101:104-107). Clinically, ICH occurs in close proximity to the ventricular system and therefore, recovery from injury after ICH may involve the SVZ.

Additionally, the recent advent of stem cell-based therapy for tissue repair and regeneration provides promising treatments for a number of neurodegenerative pathologies and other neurological disorders. Stem cells are capable of self-renewal and differentiation to generate a variety of mature neural cell lineages. Transplantation of such cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of biotherapeutic agents to a target location via exogenously supplied living cells or cellular components that produce or contain those agents.

Stem cells with neural potency have been isolated from adult tissues. For example, neural stem cells exist in the developing brain and in the adult nervous system. These cells can undergo expansion and can differentiate into neurons, astrocytes and oligodendrocytes. However, adult neural stem cells are rare, as well as being obtainable only by invasive procedures, and may have a more limited ability to expand in culture than do embryonic stem cells.

Other adult tissue may also yield progenitor cells useful for cell-based neural therapy. For instance, it has been reported recently that adult stem cells derived from bone marrow and skin can be expanded in culture and give rise to multiple lineages, including some neural lineages.

Postpartum tissues, such as the umbilical cord, have generated interest as an alternative source of stem cells. For example, methods for recovery of stem cells by perfusion of the placenta or collection from umbilical cord blood or tissue have been described. A limitation of stem cell procurement from these methods has been an inadequate volume of cord blood or quantity of cells obtained, as well as heterogeneity in, or lack of characterization of, the populations of cells obtained from those sources.

Additionally, neuroregeneration by mesencyhmal stem cells (MSC) after cerebral ischemia is associated with elevated levels of growth factors such as vascular endothelial growth factor (VEGF) and brain-derived neurotrophic factor (BDNF) localized to the area of the injury. In regions of the brain surrounding experimental infarction, it has been shown that there is increased microvessel formation and evidence of cells migrating along the microvessels, particularly cells from the SVZ. (See, Evers, B M, et al., *J Am Coll Surg,* 2003; 197:458-478). Also, it has been shown that MSC are associated with increased synaptogenesis, so that newly formed, or recovering cells exhibit more connections, which is consistent with the observation of improved functional recovery. (See, Seyfried, D, et al., *J Neurosurg,* 2006;

104:313-318). The cellular recovery process may be aided by the removal of debris and/or secretion of growth factors, thereby creating an environment inducive to neuronal cell regeneration. Given the debilitating nature of neurological injury there is a need to develop cellular regenerative therapies to aid in recovery.

SUMMARY OF THE INVENTION

This invention provides compositions, kits, and methods applicable to cell-based regenerative therapy for neurological injury. In particular, the invention features pharmaceutical compositions, devices and methods for the regeneration or repair of neural tissue using umbilical cord tissue-derived cells.

One aspect of the invention features a method of treating a patient having a neurological injury, the method comprising administering to the patient umbilical cord tissue-derived cells (UTC), in an amount effective to treat the neurodegenerative condition. In certain embodiments, the neurological injury is cerebral ischemia, reperfusion following acute ischemia, perinatal hypoxic-ischemic injury, cardiac arrest, intracranial hemorrhage, intracranial lesions, whiplash or shaken infant syndrome.

Another aspect of the invention features a method of stimulating regeneration capacity of a SVZ of a patient comprising administering to the patient umbilical cord tissue-derived cells in an amount effective to increase neurogenesis, angiogenesis, or synaptogenesis in the SVZ.

Another aspect of the invention features a method of decreasing apoptosis in a damaged or injured part of a patient's brain comprising administering to the patient umbilical cord tissue-derived cells in an amount effective to decrease the number of apoptotic cells in the damaged or injured part of a patient's brain.

Another aspect of the invention features a method of improving neurological function of a patient having a neurological injury comprising administering to the patient umbilical cord tissue-derived cells in an amount effective to improve the neurological function.

Another aspect of the invention features a pharmaceutical composition for treating a patient having a neurological injury, comprising a pharmaceutically acceptable carrier and umbilical cord tissue-derived cells. The neurological injury to be treated may be cerebral ischemia, reperfusion following acute ischemia, perinatal hypoxic-ischemic injury, cardiac arrest, intracranial hemorrhage, intracranial lesions, whiplash or shaken infant syndrome.

In certain embodiments, the pharmaceutical composition comprises cells that have been induced in vitro to differentiate into a neural cell or other lineage prior to formulation of the composition, or cells that have been genetically engineered to produce a gene product that promotes treatment of the neurological injury.

In certain embodiments, the pharmaceutical composition comprises at least one other cell type, such as astrocyte, oligodendrocyte, neuron, neural progenitor, neural stem cell or other multipotent or pluripotent stem cell. In these or other embodiments, the pharmaceutical composition comprises at least one other agent, such as a drug for neural therapy, or another beneficial adjunctive agent such as an anti-inflammatory agent, anti-apoptotic agents, antioxidant or growth factor.

In certain embodiments, the pharmaceutical composition is formulated for administration by injection or infusion. Alternatively, it may comprise an implantable device in which the cells are encapsulated, or a matrix or scaffold containing the cells.

According to yet another aspect of the invention, a kit is provided for treating a patient having a neurological injury. The kit comprises a pharmaceutically acceptable carrier, a population of umbilical cord tissue-derived cells and instructions for using the kit in a method of treating the patient. The kit may further comprise at least one reagent and instructions for culturing the umbilical cord tissue-derived cells. It may also comprise a population of at least one other cell type, or at least one other agent for treating a neurological injury.

According to another aspect of the invention, a method is provided for treating a patient having a neurological injury, which comprises administering to the patient a preparation made from umbilical cord tissue-derived cells. Such a preparation may comprise a cell lysate (or fraction thereof) of the umbilical cord tissue-derived cells, an extracellular matrix of the umbilical cord tissue-derived cells, or a conditioned medium in which the umbilical cord tissue-derived cells were grown. In another aspect, the invention features a pharmaceutical composition comprising a pharmaceutically acceptable carrier and a preparation made from the umbilical cord tissue-derived cells, which may be a cell lysate (or fraction thereof) of the umbilical cord tissue-derived cells, an extracellular matrix of the umbilical cord tissue-derived cells or a conditioned medium in which the umbilical cord tissue-derived cells were grown. Kits for practicing this aspect of the invention are also provided. These may include one or more of a pharmaceutically acceptable carrier or other agent or reagent, one or more of a cell lysate or fraction thereof, an extracellular matrix or a conditioned medium from the umbilical cord tissue-derived cells, and instructions for use of the kit components.

In various embodiments, the umbilical cord tissue-derived cells are induced in vitro to differentiate into a neural cell or other lineage prior to administration. In some embodiments, the cells are genetically engineered to produce a gene product that promotes treatment of the neurological injury, improves neurological function, and/or promotes the regeneration capacity.

In various embodiments of the invention, the umbilical cord tissue-derived cells are administered with at least one other cell type, such as an astrocyte, oligodendrocyte, neuron, neural progenitor, neural stem cell or other multipotent or pluripotent stem cell. In these embodiments, the other cell type can be administered simultaneously with, or before, or after, the umbilical cord tissue-derived cells. Likewise, in these or other embodiments, the cells are administered with at least one other agent, such as a drug for neural therapy, or another beneficial adjunctive agent such as an anti-inflammatory agent, anti-apoptotic agents, antioxidant or growth factor. In these embodiments, the other agent can be administered simultaneously with, or before, or after, the umbilical cord tissue-derived cells.

In some embodiments, the cells are administered at a pre-determined site in the central or peripheral nervous system of the patient. They can be administered by injection or infusion, or encapsulated within an implantable device, or by implantation of a matrix or scaffold containing the cells.

In certain embodiments, the cells are administered at different time points following the neurological injury. For example, the cells may be administered at times ranging from about 24 hours to about 168 hours (from about 1 day to about 7 days) following the injury.

Other features and advantages of the invention will be apparent from the detailed description and examples that follow.

BRIEF DESCRIPTION OF THE DRAWINGS

FIG. 25A shows the E5204 antibody staining to identify UTC at 35 days after injury in rats treated with PBS or 4×10$^6$ UTC or MSC at 24 hours following the injury (n=8). No positively stained cells were found with the PBS control. FIG. 25B shows the E5204 antibody staining to identify MSC at 35 days after injury in rats treated with PBS or 4×10$^6$ UTC or MSC at 24 hours following the injury (n=8).

FIG. 26A shows BrdU positive UTC cells 35 days after injury in rats treated with PBS or 4×10$^6$ UTC or MSC at 24 hours following the injury. FIG. 26B shows BrdU positive MSC cells 35 days after injury in rats treated with PBS or 4×10$^6$ UTC or MSC at 24 hours following the injury.

FIG. 32A shows BrdU and Map-2 positive double stained cells and BrdU-only positive stained cells in the lesion boundary zone. FIG. 32B shows BrdU and Map-2 positive double stained cells and BrdU-only positive stained cells in the dentate gyms.

DETAILED DESCRIPTION OF THE INVENTION

Figure 1:
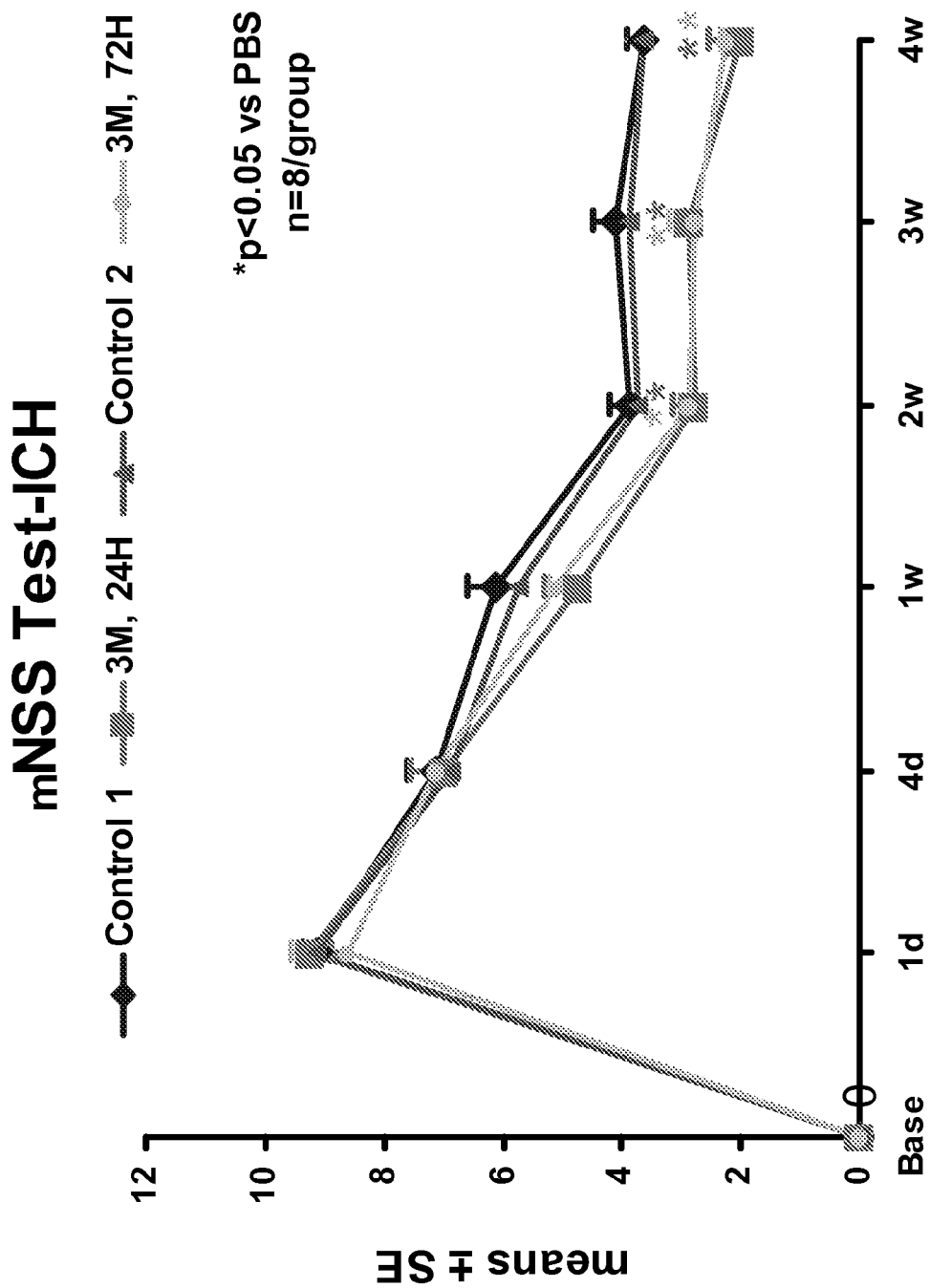
FIG. 1 shows the modified neurological severity score as determined by motor, sensory, balance and reflex tests on a graded scale of 0 to 18, with 0 being a normal score and 18 being maximal deficit, at 1 day, 4 days, 7 days, 14 days, 21 days and 28 days, after injury in rats treated with PBS or $3\times10^6$ UTC at either 24 hours or 72 hours following the injury (n=8).

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense.

Various terms used throughout the specification and claims are defined as set forth below.

The terms "individual," "patient" or "subject" as used herein generally refer to any form of animal, including mammals, such as humans and monkeys, who are treated with the pharmaceutical or therapeutic compositions or in accordance with the methods described.

"Stem cells" are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. "Totipotent" cells are able to give rise to all embryonic and extraembryonic cell types. "Pluripotent" cells are able to give rise to all embryonic cell types. "Multipotent" cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are "oligopotent" can give rise to a more restricted subset of cell lineages than multipotent stem cells, and cells that are "unipotent" are able to give rise to a single cell lineage (e.g., spermatogenic stem cells).

Stem cells are also categorized on the basis of the source from which they may be obtained. An "adult stem cell" is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An "embryonic stem cell" is a pluripotent cell from the inner cell mass of a blastocyst-stage embryo. A "fetal" stem cell is one that originates from fetal tissues or membranes. A "postpartum stem cell" is a multipotent or pluripotent cell that originates substantially from extraembryonic tissue available after birth, namely, the umbilical cord and the placenta. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Various terms are used to describe cells in culture. "Cell culture" refers generally to cells taken from a living organism and grown under controlled conditions ("in culture" or "cultured"). A "primary cell culture" is a culture of cells, tissues, or organs taken directly from an organism(s) before the first subculture. Cells are "expanded" in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time".

The term "mesenchymal stem cells" (MSCs) refers to cells from the immature embryonic connective tissue. A number of cell types come from mesenchymal stem cells, including chondrocytes, which produce cartilage.

The term "subventricular zone" (SVZ) refers to a paired brain structure situated throughout the lateral walls of the lateral ventricles. The lateral ventricles are part of the ventricular system of the brain. Classified as part of the telencephalon, they are the largest of the ventricles. The lateral ventricles connect to the central third ventricle through the interventricular foramina of Monro. Along with the subgranular zone of dentate gyrus, the subventricular zone serves as a source of neural stem cells in the process of adult neurogenesis.

The term "standard growth conditions" as used herein refers to culturing of cells at 37° C., in a standard atmosphere comprising 5% $CO_2$ and relative humidity maintained at about 100%. While the foregoing conditions are useful for culturing, it is to be understood that such conditions are capable of being varied by the skilled artisan who will appreciate the options available in the art for culturing cells.

The cells used in the present invention are generally referred to as "postpartum cells" or "postpartum-derived cells" (PPDC). The cells are more specifically "umbilicus-derived cells" or "umbilical cord-derived cells" (UDC), or "umbilical cord tissue-derived cells" (UTC). In addition, the cells may be described as being stem or progenitor cells, the latter term being used in the broad sense. The term "derived" is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below.

"Differentiation" is the process by which an unspecialized ("uncommitted") or less specialized cell acquires the features of a specialized cell, such as a nerve cell or a muscle cell, for example. A "differentiated" cell is one that has taken on a more specialized ("committed") position within the lineage of a cell. The term "committed," when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the "lineage" of a cell defines the heredity of the cell, i.e., which cells it came from and what cells it can give rise to. The lineage of a cell places the cell within a hereditary scheme of development and differentiation.

In a broad sense, a "progenitor cell" is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a "non-renewing progenitor cell" or as an "intermediate progenitor or precursor cell".

As used herein, the phrase "differentiates into a neural lineage or phenotype" refers to a cell that becomes partially or fully committed to a specific neural phenotype of the CNS or PNS, i.e., a neuron or a glial cell, the latter category including without limitation astrocytes, oligodendrocytes, Schwann cells and microglia.

The term "cell line" generally refers to a population of cells formed by one or more subcultivations of a primary cell culture. Each round of subculturing is referred to as a passage. When cells are subcultured, they are referred to as having been "passaged". A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore, the number of population doublings of a culture is greater than the passage number. The expansion of cells (i.e., the number of population doublings) during the period between passaging depends on many factors, including, but not limited to, the seeding density, substrate, medium, growth conditions, and time between passaging.

As used herein, the term "growth medium" generally refers to a medium sufficient for the culturing of umbilical cord tissue-derived cells. In particular, one medium for the culturing of the cells of the invention comprises Dulbecco's Modified Essential Media (DMEM). Particularly preferred is DMEM-low glucose (DMEM-LG) (Invitrogen, Carlsbad, Calif.). The DMEM-LG is preferably supplemented with serum, most preferably fetal bovine serum or human serum. Typically, 15% (v/v) fetal bovine serum (e.g. defined fetal bovine serum, Hyclone, Logan Utah) is added, along with antibiotics/antimycotics (preferably 100 Unit/milliliter penicillin, 100 milligrams/milliliter streptomycin, and 0.25 microgram/milliliter amphotericin B; Invitrogen, Carlsbad, Calif.), and 0.001% (v/v) 2-mercaptoethanol (Sigma, St. Louis Mo.). In some cases, different growth media are used or different supplementations are provided, and these are normally indicated in the text as supplementations to growth medium. In certain chemically-defined media the cells may be grown without serum present at all. In such cases, the cells may require certain growth factors, which can be added to the medium to support and sustain the cells. Presently preferred factors to be added for growth in serum-free media include one or more of bFGF, EGF, IGF-I, and PDGF. In more preferred embodiments, two, three or all four of the factors are added to serum free or chemically defined media. In other embodiments, LIF is added to serum-free medium to support or improve growth of the cells.

A "conditioned medium" is a medium in which a specific cell or population of cells has been cultured, and then removed. When cells are cultured in a medium, they may secrete cellular factors that can provide trophic support to other cells. Such trophic factors include, but are not limited to, hormones, cytokines, extracellular matrix (ECM), proteins, vesicles, antibodies, and granules. The medium containing the cellular factors is the conditioned medium.

Generally, a "trophic factor" is defined as a substance that promotes survival, growth, differentiation, proliferation and/or maturation of a cell, or stimulates increased activity of a cell.

When referring to cultured vertebrate cells, the term "senescence" (also "replicative senescence" or "cellular senescence") refers to a property attributable to finite cell cultures, namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells, they are actually resistant to programmed cell death (apoptosis) and have been maintained in their nondividing state for as long as three years. These cells are very much alive and metabolically active, but they do not divide. The nondividing state of senescent cells has not yet been found to be reversible by any biological, chemical, or viral agent.

The term "neurological injury" is an inclusive term encompassing conditions associated with neuronal cell death or compromise, including cerebrovascular insufficiency, focal or diffuse brain trauma, diffuse brain damage, and traumatic neuropathies (including, but not limited to, compression, crush, laceration and segmentation neuropathies). Examples of neurological injury are: cerebral ischemia or infarction including embolic occlusion, and thrombotic occlusion; reperfusion following acute ischemia; perinatal hypoxic-ischemic injury; cardiac arrest; intracranial hemorrhage of any type (such as epidural, subdural, subarachnoid and intracerebral); intracranial and intravertebral lesions (such as contusion, penetration, shear, compression and laceration); whiplash and shaken infant syndrome.

Other neurological injuries include tumors and other neoplastic conditions affecting the CNS and PNS. Though the underlying disease is considered proliferative (rather than an injury), surrounding tissues may be compromised. Furthermore, cell therapy may be utilized to deliver apoptotic or other antineoplastic molecules to the tumor site, e.g., via delivery of genetically modified cells producing such agents.

The term "treating (or treatment of) a neurological injury" refers to ameliorating the effects of, or delaying, halting or reversing the progress of, or delaying or preventing the onset of, a neurological injury as defined herein.

The term stimulating "regeneration capacity of a SVZ" refers to increasing the ability of the subventricular zone to reform or remake surrounding tissue, including neurological and endothelial tissue.

The term improving "neurological function" refers to making better a function, such as, for example, muscle strength, reflex response, or sensory perception. Determination that the neurological function has improved is assessed by various behavioral tests and motor, sensory, reflex and balance tests.

The term "decreasing apoptosis in a damaged or injured part of a patient's brain" refers to lowering the number of cells undergoing apoptosis, or programmed cell death, in a part of a patient's brain that has been subjected to some other injury or damage. The apoptosis can be determined by any methods known in the art, including but not limited to flow cytometry based apoptosis detection methods, immunohistochemistry methods, DNA fragmentation assays, caspase activity assays and the like. The apoptosis can also be determined by in vitro assays known in the art to model or predict the response in vivo.

The term "effective amount" refers to a concentration or amount of a compound, material or composition as described herein, that is effective to achieve a particular biological result. Such results include, but are not limited to cell growth and/or differentiation in vitro or in vivo, and treatment of a neurological injury as described herein. With respect to growth factors, an effective amount may range from about 1 nanogram/ml to about 1 microgram/ml. With respect to UTC as administered to a patient in vivo, an effective amount may range from as few as several hundred or fewer to as many as several million or more. In specific embodiments, an effective amount may range from about $10^3$ to about $10^{11}$ cells, more specifically at least about $10^4$ cells. It will be appreciated that the number of cells to be administered will vary depending on the specifics of the neurological injury to be treated, including but not limited to size or total volume/surface area to be treated, as well as proximity of the site of administration to the location of the region to be treated, among other factors familiar to the medicinal biologist.

The terms "effective period," "effective period of time" or "effective conditions" refer generally to a period of time or other controllable conditions (e.g., temperature, humidity for in vitro methods) necessary or preferred for an agent or pharmaceutical composition to achieve its intended result.

The terms "pharmaceutically acceptable carrier" or "pharmaceutically acceptable medium," which may be used interchangeably with the terms "biologically compatible carrier" or "biologically compatible medium," refer to reagents, cells, compounds, materials, compositions, and/or dosage forms that are not only compatible with the cells and other agents to be administered therapeutically, but also are suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes, sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Several terms are used herein with respect to cell or tissue transplantation or cell replacement therapy. The terms "autologous transfer," "autologous transplantation," "autograft" and the like refer to treatments wherein the cell or transplant donor is also the cell or transplant recipient. The terms "allogeneic transfer," "allogeneic transplantation," "allograft" and the like refer to treatments wherein the cell or transplant donor is of the same species as the recipient, but is not the same individual. A cell transfer in which the donor's cells have been histocompatibly matched with a recipient is sometimes referred to as a "syngeneic transfer". The terms "xenogeneic transfer," "xenogeneic transplantation," "xenograft" and the like refer to treatments wherein the cell or transplant donor is of a different species than the recipient.

The term "isolate" as used herein generally refers to a cell which has been separated from its natural environment. This term includes gross physical separation from its natural environment, e.g., removal from the donor animal. In preferred embodiments, an isolated cell is not present in a tissue, i.e., the cell is separated or dissociated from the neighboring cells with which it is normally in contact. Preferably, cells are administered as a cell suspension. As used herein, the phrase "cell suspension" includes cells which are in contact with a medium and which have been dissociated, e.g., by subjecting a piece to tissue to gentle trituration.

The term "matrix" as used herein generally refers to biodegradable and/or bioresorbable materials that are administered with the cells to a patient. The matrix may act as a temporary scaffold until replaced by newly grown cells. In some embodiments, the matrix may provide for the sustained release of factors or other agents used in conjunction with the cells and may provide a structure for developing tissue growth in the patient. In other embodiments, the matrix simply provides a temporary scaffold for the developing tissue. The matrix can be in particulate form (macroparticles greater than 10 microns in diameter or microparticles less than 10 micros in diameter), or it can be in the form of a structurally stable, three-dimensional implant (e.g., a scaffold). The matrix can be a slurry, hydrogel, or alternatively, a three dimensional structure such as a cube, cylinder, tube, block, film, sheet or an appropriate anatomical form.

The term "scaffold" as used herein generally refers to a three dimensional porous structure that provides a template for cell growth. A scaffold is made of biodegradable and/or bioresorbable materials that degrade over time within the body. The length of time taken for the scaffold to degrade may depend upon the molecular weight of the materials. Thus, higher molecular weight material may result in polymer scaffolds which retain their structural integrity for longer periods of time; while lower molecular weights results in both slower release and shorter scaffold lives. The scaffold may be made by any means known in the art. Examples of polymers which can be used to form the scaffold include natural and synthetic polymers.

Description

Neurological injuries, which encompass conditions associated with neuronal cell death or compromise, including cerebrovascular insufficiency, focal or diffuse brain trauma, diffuse brain damage, and traumatic neuropathies, have as a common feature the dysfunction or loss of a specific or vulnerable group of neural cells. This commonality enables development of similar therapeutic approaches for the repair and regeneration of vulnerable or damaged neural tissue, one of which is cell-based therapy. In its various embodiments described herein, the present invention features methods and pharmaceutical compositions for neural repair and regeneration that utilize progenitor cells and cell populations derived from postpartum umbilical cord tissues. The invention is applicable to any neurological injury, but is expected to be particularly suitable for a number of injuries including, without limitation, cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), and also whiplash and shaken infant syndrome.

As summarized above, the invention, in one of its aspects is generally directed to methods of treating neurological injuries using isolated umbilical cord tissue-derived cells (UTC), which are derived from umbilical cord tissue that has been rendered substantially free of blood. The UTC is capable of self-renewal and expansion in culture and has the potential to differentiate into cells of neural phenotypes. Certain embodiments feature populations comprising such cells, pharmaceutical compositions comprising the cells or components or products thereof, and methods of using the pharmaceutical compositions for treatment of patients with neurological injuries. The umbilical cord tissue-derived cells have been characterized by their growth properties in culture, by their cell surface markers, by their gene expression, by their ability to produce certain biochemical trophic factors, and by their immunological properties.

According to the methods described herein, mammalian umbilical cord tissue is digested and the UTC is isolated preferably in an aseptic environment. Blood and debris are preferably removed from the postpartum tissue prior to isolation of the UTC. For example, the postpartum tissue may be washed with buffer solution, such as but not limited to phosphate buffered saline. The wash buffer also may comprise one or more antimycotic and/or antibiotic agents, such as, but not limited to, penicillin, streptomycin, amphotericin B, gentamicin, and nystatin.

Whole tissue or a fragment or section thereof may be disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Ranging from weakly digestive (e.g. deoxyribonucleases and the neutral protease, dispase) to strongly digestive (e.g. papain and trypsin), such enzymes are available commercially. A nonexhaustive list of such enzymes includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with collagenase and dispase, or collagenase, dispase, and hyaluronidase. The skilled artisan will appreciate that many such enzyme treatments are known in the art for isolating cells from various tissue sources, and is well-equipped to assess new, or additional enzymes or enzyme combinations for their utility in isolating the cells of the invention. Preferred enzyme treatments can be from about 0.5 to 2 hours long or longer. In other preferred embodiments, the tissue in incubated at about 37° C. during the enzyme treatment of the dissociation step.

The isolated cells may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. The cells are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, mesenchymal stem cell growth medium (MSCGM), DMEM/F12, RPMI 1640, and CELL-GRO-FREE. The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises growth medium (e.g. DMEM-low glucose, serum, BME, and an antibiotic agent).

The cells are seeded in culture vessels at a density to allow cell growth. Preferably, the cells are cultured at about 0 to about 5 percent $CO_2$ by volume in air and at about 2 to about 25 percent $O_2$ by volume in air, preferably about 5 to about 20 percent $O_2$ in air. The cells preferably are cultured at about 25° C. to about 40° C. and more preferably are cultured at 37° C. The cells are preferably cultured in an incubator. The medium in the culture vessel can be static or agitated, for example, using a bioreactor. The UTC preferably is grown under low oxidative stress (e.g., with addition of glutathione, vitamin C, catalase, vitamin E, N-acetylcysteine). "Low oxidative stress," as used herein, refers to conditions of no or minimal free radical damage to the cultured cells.

In some embodiments of the invention, the UTC may be passaged or removed to a separate culture vessel containing fresh medium of the same or a different type as that used initially, where the population of cells can be mitotically expanded. Cells useful in the methods of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

Further, the different cell types present in postpartum tissue may be fractionated into subpopulations from which the UTC can be isolated. This may be accomplished using standard techniques for cell separation including, but not limited to, enzymatic treatment to dissociate postpartum tissue into its component cells, followed by cloning and selection of specific cell types, including, but not limited to: selection based on morphological and/or biochemical markers; selective growth of desired cells (positive selection); selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; counter-current distribution; electrophoresis; and fluorescence activated cell sorting (FACS).

The culture medium is changed as necessary. Incubation is continued until a sufficient number or density of cells accumulate in the dish. Thereafter, any original explanted tissue sections that exist may be removed, and the remaining cells separated from the dish by trypsinization using standard techniques or by using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be the UTC.

The UTC may be cryopreserved. Accordingly, UTC for autologous transfer (for either the mother or child) may be derived from appropriate postpartum tissues following the birth of a child, then cryopreserved so as to be available in the event they are later needed for transplantation.

The UTC may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of UTC-conditioned medium, for example, by Enzyme Linked ImmunoSorbent Assay (ELISA)), mixed lymphocyte reaction (e.g., as measure of stimulation of PBMCs), and/or other methods known in the art.

Examples of umbilicus tissue-derived cells were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

The UTC useful in the methods of the invention may possess one or more of the following growth features: (1) they require L-valine for growth in culture; (2) they are capable of growth in atmospheres containing oxygen from about 5% to about 20%; (3) they have the potential for at least about 40 doublings in culture before reaching senescence; and (4) they attach and expand on tissue culture vessels that are uncoated, or that are coated with gelatin, laminin, collagen, polyornithine, vitronectin or fibronectin.

Additionally, the UTC useful in the methods of the invention may possess a normal karyotype, which is maintained as the cells are passaged. Methods for karyotyping are available and known to those of skill in the art.

Also, the UTC useful in the methods of the invention may be characterized by production of certain proteins, including: (1) production of at least one of tissue factor, vimentin, and alpha-smooth muscle actin; and (2) production of at least one of: CD10, CD13, CD44, CD73, CD90, PDGFr-alpha, PD-L2 and HLA-A, B, C cell surface markers, as detected by flow cytometry. Additionally, the UTC useful in the methods of the invention may be characterized by lack of production of at least one of: CD31, CD34, CD45, CD80, CD86, CD117, CD141, CD178, B7-H2, HLA-G, and HLA-DR, DP, DQ cell surface markers, as detected by flow cytometry. UTC useful in the methods of the invention may produce at least two of: tissue factor; vimentin; and alpha-smooth muscle actin; or all three of the proteins tissue factor, vimentin, and alpha-smooth muscle actin.

Further, the UTC useful in the methods of the invention may be characterized by gene expression, which relative to a human cell that is a fibroblast, a mesenchymal stem cell, or an iliac crest bone marrow cell, is increased for a gene encoding at least one of: interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3.

Also, the UTC useful in the methods of the invention may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

Additionally, the UTC useful in the methods of the invention may be characterized by secretion of at least one of: MCP-1; IL-6; IL-8; GCP-2; HGF; KGF; FGF; HB-EGF; BDNF; TPO; MIPb; I309; MDC; RANTES; and TIMP1. Further, the UTC useful in the methods of the invention may be characterized by lack of secretion of at least one of: TGF-beta2; ANG2; PDGFbb; MIP1a; and VEGF, as detected by ELISA.

The UTC useful in the methods of the invention preferably comprise two or more of the above-listed growth, protein/surface marker production, gene expression or substance-secretion characteristics. The UTC useful in the methods of the invention may comprise three, four, five, six, seven, eight or more of the characteristics. The UTC useful in the methods of the invention may also comprise all of above characteristics.

Among the UTC useful in the methods of the invention in several of its aspects is the UTC having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A, B, C, wherein the cells produce the immunologically-detectable proteins which correspond to the listed markers. The UTC useful in the methods of the invention may also include, in addition to the foregoing, cells that do not produce proteins corresponding to any of the markers CD31, CD34, CD45, CD117, CD141, or HLA-DR, DP, DQ, as detected by flow cytometry.

Certain cells having the potential to differentiate along lines leading to various phenotypes are unstable and thus can spontaneously differentiate. The UTC useful in the methods of the invention are cells that do not spontaneously differentiate, for example, along neural lines. The UTC useful in the methods of the invention, when grown in growth medium, are substantially stable with respect to the cell markers produced on their surface, and with respect to the expression pattern of various genes, for example, as determined using an Affymetrix GENECHIP. The cells remain substantially constant, for example, in their surface marker characteristics over passaging, and through multiple population doublings.

However, one feature of the UTC useful in the methods of the invention is that they may be deliberately induced to differentiate into neural lineage phenotypes by subjecting them to differentiation-inducing cell culture conditions. This may be accomplished by one or more methods known in the art. For instance, as exemplified herein, the UTC may be plated on flasks coated with laminin in Neurobasal-A medium (Invitrogen, Carlsbad, Calif.) containing B27 (B27 supplement, Invitrogen), L-glutamine and Penicillin/Streptomycin, the combination of which is referred to herein as Neural Progenitor Expansion (NPE) medium. NPE media may be further supplemented with bFGF and/or EGF. Alternatively, the UTC useful in the methods of the invention may be induced to differentiate in vitro by (1) co-culturing the UTC with neural progenitor cells, or (2) growing the UTC in neural progenitor cell-conditioned medium.

Differentiation of the UTC may be demonstrated by a bipolar cell morphology with extended processes. The induced cell populations may stain positive for the presence of nestin. The differentiated UTC may be assessed by detection of nestin, TuJ1 (BIII tubulin), GFAP, tyrosine hydroxylase, GABA, O4 and/or MBP. Additionally, the UTC useful in the methods of the invention may exhibit the ability to form three-dimensional bodies characteristic of neuronal stem cell formation of neurospheres.

The UTC useful in the methods of the invention may include a cell population that is heterogeneous. A heterogeneous cell population useful in the methods of the invention may comprise at least about 5%, 10%, 20%, 30%, 40%, 50%, 60%, 70%, 80%, 90%, or 95% UTC as described above. The heterogeneous cell populations useful in the methods of the invention may further comprise stem cells or other progenitor cells, such as neural progenitor cells, or may further comprise fully differentiated neural cells. Additionally, the population may be substantially homogeneous, i.e., comprises substantially only the UTC (such as at least about 96%, 97%, 98%, 99% or more UTC). The homogeneous cell population useful in the methods of the invention may comprise umbilicus- or placenta-derived cells. Homogeneous populations of umbilicus-derived cells are preferably free of cells of maternal lineage. Homogeneous populations of placenta-derived cells may be of neonatal or maternal lineage. Homogeneity of a cell population may be achieved by any method known in the art, for example, by cell sorting (e.g., flow cytometry) or by clonal expansion in accordance with known methods. Thus, homogeneous UTC populations useful in the methods of the invention may comprise a clonal cell line of umbilical cord tissue-derived cells. Such populations are particularly useful when a cell clone with highly desirable functionality has been isolated.

Additionally, the UTC useful in the methods of the invention may include populations of cells incubated in the presence of one or more factors, or under conditions, that stimulate stem cell differentiation along a neurogenic pathway. Such factors are known in the art and the skilled artisan will appreciate that determination of suitable conditions for differentiation can be accomplished with routine experimentation. Optimization of such conditions can be accomplished by statistical experimental design and analysis, for example response surface methodology allows simultaneous optimization of multiple variables, for example in a biological culture. Exemplary factors include, but are not limited to factors, such as growth or trophic factors, demethylating agents, co-culture with neural lineage cells or culture in neural lineage cell-conditioned medium, as well other conditions known in the art to stimulate stem cell differentiation along a neurogenic pathway or lineage. (See, e.g., Lang, K J D, et al., *J. Neurosci. Res.*, 2004; 76:184-192; Johe, KK, et al., *Genes Devel.*, 1996; 10:3129-3140; Gottleib, D, *Ann. Rev. Neurosci.*, 2002; 25:381-407).

The UTC useful in the methods of the invention may also be genetically modified to produce neurotherapeutically useful gene products, or to produce antineoplastic agents for treatment of tumors, for example. Genetic modification may be accomplished using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells may be transformed or transfected with DNA controlled by, or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV 40, papillomavirus, Epstein-Barr virus or elastin gene promoter. Additionally, the control elements used to control expression of the gene of interest can allow for the regulated expression of the gene so that the product is synthesized only when needed in vivo. If transient expression is desired, constitutive promoters may be used in a non-integrating and/or replication-defective vector. Alternatively, inducible promoters could be used to drive the expression of the inserted gene when necessary. Inducible promoters include, but are not limited to, those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

The UTC useful in the methods of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a neuron or glial cell can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. (Mombaerts et al., *Proc. Nat. Acad. Sci. U.S.A.*, 1991; 88:3084). Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity. These techniques are described in detail by Davis, L G, et al., (eds), *Basic Methods in Molecular Biology*, 2nd ed., 1994, Appleton & Lange, Norwalk, Conn.

Additionally, cell lysates and cell soluble fractions prepared from the UTC, or heterogeneous or homogeneous cell populations comprising UTC, as well as the UTC or populations thereof that have been genetically modified or that have been stimulated to differentiate along a neurogenic pathway, which are useful in the methods of the invention, are provided. Use of the UTC lysate soluble fraction (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well-known in the art and include various means of mechanical disruption, enzymatic disruption, or chemical disruption, or combinations thereof. Such cell lysates may be prepared from cells directly in their growth medium, and thus contain secreted growth factors and the like, or they may be prepared from cells washed free of medium in, for example, PBS or other solution. Washed cells may be resuspended at concentrations greater than the original population density if preferred.

Whole cell lysates of the UTC useful in the methods of the invention may be prepared, e.g., by disrupting cells without subsequent separation of cell fractions. Alternatively, a cell membrane fraction may be separated from a soluble fraction of the cells by routine methods known in the art, e.g., centrifugation, filtration, or similar methods.

Cell lysates or cell soluble fractions prepared from populations of umbilical cord tissue-derived cells useful in the methods of the invention may be used as is, further concentrated by, for example, ultrafiltration or lyophilization, or even dried, partially purified, combined with pharmaceutically-acceptable carriers or diluents as are known in the art, or combined with other compounds such as biologicals, for example, pharmaceutically useful protein compositions. Cell lysates or fractions thereof may be used in vitro or in vivo, alone or, for example, with autologous or syngeneic live cells. The lysates, if introduced in vivo, may be introduced locally at a site of treatment, or remotely to provide, for example, needed cellular growth factors to a patient.

Additionally, the UTC useful in the methods of the invention may be cultured in vitro to produce biological products in high yield. For example, such cells, which either naturally produce a particular biological product of interest (e.g., a trophic factor), or that have been genetically engineered to produce a biological product, can be clonally expanded using the culture techniques described herein. Alternatively, cells may be expanded in a medium that induces differentiation to a neural lineage or other lineage. In either case, biological products produced by the cell and secreted into the medium can be readily isolated from the conditioned medium using standard separation techniques, e.g., such as differential protein precipitation, ion-exchange chromatography, gel filtration chromatography, electrophoresis, and HPLC, to name a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed, as described above. The biological product may then be purified using any one or more of the above-listed techniques.

Additionally, conditioned medium from the cultured UTC useful in the methods of the invention may be used in vitro and in vivo as described below. Use of the UTC conditioned medium allows the beneficial trophic factors secreted by the UTC to be used allogeneically in a patient without introducing intact cells that could trigger rejection, or other adverse immunological responses. Conditioned medium is prepared by culturing cells in a culture medium, then removing the cells from the medium.

Conditioned medium prepared from populations of the UTC useful in the methods of the invention may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Conditioned medium may be used in vitro or in vivo, alone or for example, with autologous or syngeneic live cells. The conditioned medium, if introduced in vivo, may be introduced locally at a site of treatment, or remotely to provide, for example needed cellular growth or trophic factors to a patient.

Additionally, an extracellular matrix (ECM) produced by culturing the UTC useful in the methods of the invention on liquid, solid or semi-solid substrates may be prepared, collected and utilized as an alternative to implanting live cells into a subject in need of tissue repair or replacement. The UTC is cultured in vitro, on a three dimensional framework as described elsewhere herein, under conditions such that a desired amount of ECM is secreted onto the framework. The cells comprising the new tissue are removed, and the ECM processed for further use, for example, as an injectable preparation. To accomplish this, cells on the framework are killed and any cellular debris is removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure.

Once the cells have been killed, the cellular membranes may be disrupted and cellular debris removed by treatment with a mild detergent rinse, such as EDTA, CHAPS or a zwitterionic detergent. Alternatively, the tissue can be enzymatically digested and/or extracted with reagents that break down cellular membranes and allow removal of cell contents. Examples of such enzymes include, but are not limited to, hyaluronidase, dispase, proteases, and nucleases. Examples of detergents include non-ionic detergents such as, for example, alkylaryl polyether alcohol (TRITON X-100), octylphenoxy polyethoxy-ethanol (Rohm and Haas Philadelphia, Pa.), BRIJ-35, a polyethoxyethanol lauryl ether (Atlas Chemical Co., San Diego, Calif.), polysorbate 20 (TWEEN 20), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending, for example, on whether the new tissue has been formed on a three-dimensional framework that is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM.

After it has been collected, the ECM may be processed further. For example, the ECM can be homogenized to fine particles using techniques well known in the art such as by sonication, so that it can pass through a surgical needle. The components of the ECM can be crosslinked, if desired, by gamma irradiation. For example, the ECM can be irradiated between 0.25 to 2 mega rads to sterilize and crosslink the ECM. Chemical crosslinking using agents that are toxic, such as glutaraldehyde, is possible but not generally preferred.

The amounts and/or ratios of proteins, such as the various types of collagen present in the ECM, may be adjusted by mixing the ECM produced by the UTC useful in the methods of the invention with ECM of one or more other cell types. In addition, biologically active substances such as proteins, growth factors and/or drugs, can be incorporated into the ECM. Exemplary biologically active substances include tissue growth factors, such as TGF-beta, and the like, which promote healing and tissue repair at the site of the injection. Such additional agents may be utilized with, for example, whole cell lysates, soluble cell fractions, or further purified components and products produced by the UTC.

In another aspect, the invention provides pharmaceutical compositions that utilize the UTC, UTC populations, components and products of the UTC in various methods for treating neurological injury, improving neurological function, stimulating the regenerative capacity of the SVZ or decreasing apoptosis in the SVZ. Some pharmaceutical compositions comprise live cells (UTC alone or admixed with other cell types). Other pharmaceutical compositions comprise UTC cellular components (e.g., cell lysates, soluble cell fractions, conditioned medium, ECM, or components of any of the foregoing) or products (e.g., trophic and other biological factors produced naturally by the UTC or through genetic modification, conditioned medium from UTC culture). In any case, the pharmaceutical composition may further comprise other active agents, such as anti-inflammatory agents, anti-apoptotic agents, antioxidants, growth factors, neurotrophic factors or neuroregenerative or neuroprotective drugs as known in the art.

Examples of other components that may be added to the UTC pharmaceutical compositions include, but are not limited to: (1) other neuroprotective or neurobeneficial drugs; (2) selected extracellular matrix components, such as one or more types of collagen known in the art, and/or growth factors, platelet-rich plasma, and drugs (alternatively, the UTC may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPOXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (7) local anesthetics, to name a few.

Pharmaceutical compositions encompassed by the invention comprise UTC, or components or products thereof, formulated with a pharmaceutically acceptable carrier or medium. Suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, and salts for influencing osmotic pressure, buffers, and coloring. Pharmaceutical carriers suitable for use in the present invention are known in the art and are described, for example, in Pharmaceutical Sciences (17th Ed., Mack Pub. Co., Easton, Pa.) and WO 96/05309.

Typically, but not exclusively, pharmaceutical compositions comprising UTC components or products, but not live cells, are formulated as liquids (or as solid tablets, capsules and the like, when oral delivery is appropriate). These may be formulated for administration by any acceptable route known in the art to achieve delivery of drugs and biological molecules to the target neural tissue, including, but not limited to, oral, nasal, ophthalmic and parenteral, including intravenous. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration by delivery via intracranial or intravertebral needles and/or catheters with or without pump devices.

Pharmaceutical compositions comprising the live UTC cells are typically formulated as liquids, semisolids (e.g., gels) or solids (e.g., matrices, scaffolds and the like, as appropriate for neural tissue engineering). Liquid compositions are formulated for administration by any acceptable route known in the art to achieve delivery of live cells to the target neural tissues. Typically, these include injection or infusion into the CNS or PNS, either in a diffuse fashion or targeted to the site of neurological injury or distress, by a route of administration including, but not limited to, intraocular, intracerebral, intraventricular, intracerebroventricular, intrathecal, intracisternal, intraspinal and/or peri-spinal routes of administration by delivery via intracranial or intravertebral needles and/or catheters with or without pump devices.

Pharmaceutical compositions comprising live cells in a semi-solid or solid carrier are typically formulated for surgical implantation at the site of neurological injury or distress. It will be appreciated that liquid compositions also may be administered by surgical procedures. Additionally, semi-solid or solid pharmaceutical compositions may comprise semi-permeable gels, lattices, cellular scaffolds and the like, which may be non-biodegradable or biodegradable. For example, it may be desirable or appropriate to sequester the exogenous cells from their surroundings, yet enable the cells to secrete and deliver biological molecules (e.g. neurotrophic factors) to surrounding neural cells. Cells, therefore, may be formulated as autonomous implants comprising living UTC or a cell population comprising UTC surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

Alternatively, different varieties of degradable gels and networks are utilized for the pharmaceutical compositions of the invention. For example, degradable materials particularly suitable for sustained release formulations include biocompatible polymers, such as poly(lactic acid), poly (lactic-co-glycolic acid), methylcellulose, hyaluronic acid, collagen, and the like.

Additionally, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established. (See, e.g., Tresco, P A, et al., *Adv. Drug Delivery Rev.,* 2000; 42:3-27; see also Hutmacher, D W, *J. Biomater. Sci. Polymer Edn.,* 2001; 12:107-174).

Examples of scaffold or matrix (sometimes referred to collectively as "framework") material that may be used in the present invention include nonwoven mats, porous foams, or self assembling peptides. Nonwoven mats may, for example, be formed using fibers comprised of a synthetic absorbable copolymer of glycolic and lactic acids (PGA/PLA), sold under the trade name VICRYL (Ethicon, Inc., Somerville, N.J.), Foams, composed of, for example, poly (epsilon-caprolactone)/poly(glycolic acid) (PCL/PGA) copolymer, formed by processes such as freeze-drying or lyophilizing, as discussed in U.S. Pat. No. 6,355,699 also may be utilized. Hydrogels such as self-assembling peptides (e.g., RAD16) may also be used. In situ-forming degradable networks are also suitable for use in the invention (see, e.g., Anseth, K S, et al., *J. Controlled Release,* 2002; 78:199-209; Wang, D, et al., *Biomaterials,* 2003; 24:3969-3980; U.S. Patent Publication 2002/0022676). These materials are formulated as fluids suitable for injection, then may be induced by a variety of means (e.g., change in temperature, pH, exposure to light) to form degradable hydrogel networks in situ or in vivo.

Also, the framework may be a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures.

Further, the framework may be molded into a useful shape, such as that of the spinal cord with segregated columns for nerve tract repair, for example (Friedman, J A, et al., *Neurosurgery,* 2002; 51:742-51). Furthermore, it will be appreciated that the UTC may be cultured on pre-formed, non-degradable surgical or implantable devices, e.g., in a manner corresponding to that used for preparing fibroblast-containing GDC endovascular coils, for instance (Marx, W F, et al., *Am. J. Neuroradiol.,* 2001; 22:323-333).

The matrix, scaffold or device may be treated prior to the inoculation of cells to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

The UTC-containing frameworks are prepared according to methods known in the art. For example, cells can be grown freely in a culture vessel to sub-confluency or confluency, lifted from the culture and inoculated onto the framework. Growth factors may be added to the culture medium prior to, during, or subsequent to inoculation of the cells to trigger differentiation and tissue formation, if desired. Alternatively, the frameworks themselves may be modified so that the growth of cells thereon is enhanced, or so that the risk of rejection of the implant is reduced. Thus, one or more biologically active compounds, including, but not limited to, anti-inflammatories, immunosuppressants or growth factors, may be added to the framework for local release.

The UTC, or cell populations comprising UTC, or components of or products produced by the UTC, may be used in a variety of ways to support and facilitate repair and regeneration of neural cells and tissues. Such utilities encompass in vitro, ex vivo and in vivo methods.

In Vitro and Ex Vivo Methods:

The UTC may be used in vitro to screen a wide variety of compounds for effectiveness and cytotoxicity of pharmaceutical agents, growth factors, regulatory factors, and the like. For example, such screening may be performed on substantially homogeneous populations of the UTC to assess the efficacy or toxicity of candidate compounds to be formulated with, or co-administered with, the UTC, for treatment of a neurological injury. Alternatively, such screening may be performed on the UTC that has been stimulated to differentiate into a neural cell or neural progenitor cell, for the purpose of evaluating the efficacy of new pharmaceutical drug candidates. In this embodiment, the UTC are maintained in vitro and exposed to the compound to be tested. The activity of a potentially cytotoxic compound can be measured by its ability to damage or kill cells in culture. This may readily be assessed by vital staining techniques. The effect of growth or regulatory factors may be assessed by analyzing the number or robustness of the cultured cells, as compared with cells not exposed to the factors. This may be accomplished using standard cytological and/or histological techniques, including the use of immunocytochemical techniques employing antibodies that define type-specific cellular antigens.

Additionally, as discussed above, the UTC can be cultured in vitro to produce biological products that are either naturally produced by the cells, or produced by the cells when induced to differentiate into neural or other lineages, or produced by the cells via genetic modification. For instance, TIMP1, TPO, KGF, HGF, FGF, HBEGF, BDNF, MIP1b, MCP1, RANTES, I309, TARC, MDC, and IL-8 were found to be secreted from UTC grown in growth medium. Some of these trophic factors, such as BDNF and IL-6, have important roles in neural regeneration. Other trophic factors, as yet undetected or unexamined, of use in neural repair and regeneration, are likely to be produced by the UTC and possibly secreted into the medium.

Also, the UTC may be used for production of conditioned medium, either from the undifferentiated UTC or from the UTC incubated under conditions that stimulate differentiation into a neural or other lineage. Such conditioned media are contemplated for use in in vitro or ex vivo culture of neurogenic precursor cells, or in vivo to support transplanted cells comprising homogeneous populations of the UTC or heterogeneous populations comprising UTC and neural progenitors, for example.

Additionally, UTC lysates, soluble cell fractions or components thereof, or ECM or components thereof, may be used for a variety of purposes. As mentioned above, some of these components may be used in pharmaceutical compositions. Also, a cell lysate or ECM may be used to coat or otherwise treat substances or devices to be used surgically, or for implantation, or for ex vivo purposes, to promote healing or survival of cells or tissues contacted in the course of such treatments.

Further, the UTC may be used in co-cultures in vitro to provide trophic support to other cells, in particular neural cells and neural progenitors. For co-culture, it may be desirable for the UTC and the desired other cells to be co-cultured under conditions in which the two cell types are in contact. This can be achieved, for example, by seeding the cells as a heterogeneous population of cells in culture medium or onto a suitable culture substrate. Alternatively, the UTC can first be grown to confluence, and then will serve as a substrate for the second desired cell type in culture. Additionally, the cells may further be physically separated, e.g., by a membrane or similar device, such that the other cell type may be removed and used separately, following the co-culture period. Use of the UTC in co-culture to promote expansion and differentiation of neural cell types may find applicability in research and in clinical/therapeutic areas. For instance, the UTC co-culture may be utilized to facilitate growth and differentiation of neural cells in culture, for basic research purposes or for use in drug screening assays, for example. The UTC co-culture may also be utilized for ex vivo expansion of neural progenitors for later administration for therapeutic purposes. For example, neural progenitor cells may be harvested from an individual, expanded ex vivo in co-culture with the UTC, then returned to that individual (autologous transfer) or another individual (syngeneic or allogeneic transfer). Following ex vivo expansion, the mixed population of cells comprising the UTC and neural progenitors may be administered to a patient in need of treatment. Alternatively, in situations where autologous transfer is appropriate or desirable, the co-cultured cell populations may be physically separated in culture, enabling removal of the autologous neural progenitors for administration to the patient.

In Vivo Methods:

As set forth in Examples 2-10, UTC have been shown to be effectively transplanted into the body, and to supply lost neural function in an animal model accepted for its predictability of efficacy in humans. Once transplanted into a targeted neural location in the body, the UTC may themselves differentiate into one or more neural phenotypes, or they may provide trophic support for neural progenitors and neural cells in situ, or they may exert a beneficial effect in both of those fashions, as well as others.

The UTC may be administered alone (e.g., as substantially homogeneous populations) or as admixtures with other cells. As described above, the UTC may be administered as formulated in a pharmaceutical preparation with a matrix or scaffold, or with conventional pharmaceutically acceptable carriers. Where the UTC are administered with other cells, they may be administered simultaneously or sequentially with the other cells (either before or after the other cells). Cells that may be administered in conjunction with the UTC include, but are not limited to, neurons, astrocytes, oligodendrocytes, neural progenitor cells, neural stem cells and/or other multipotent or pluripotent stem cells. The cells of different types may be admixed with the UTC immediately or shortly prior to administration, or they may be co-cultured together for a period of time prior to administration.

The UTC may be administered with other neuro-beneficial drugs or biological molecules, or other active agents, such as anti-inflammatory agents, anti-apoptotic agents, antioxidants, growth factors, neurotrophic factors or neuroregenerative or neuroprotective drugs as known in the art. When the UTC are administered with other agents, they may be administered together in a single pharmaceutical composition, or in separate pharmaceutical compositions, simultaneously or sequentially with the other agents (either before or after administration of the other agents).

Examples of other components that may be administered with the UTC include, but are not limited to: (1) other neuroprotective or neurobeneficial drugs; (2) selected extracellular matrix components, such as one or more types of collagen known in the art, and/or growth factors, platelet-rich plasma, and drugs (alternatively, UTC may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPOXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (6) local anesthetics, to name a few.

For example, the UTC may be administered as undifferentiated cells, i.e., as cultured in growth medium. Alternatively, the UTC may be administered following exposure in culture to conditions that stimulate differentiation toward a desired neural phenotype, e.g., astrocyte, oligodendrocyte or neuron, and more specifically, serotoninergic, dopaminergic, cholinergic, GABA-ergic or glutamatergic neurons (see, e.g., Isacson, O, *Lancet Neurology,* 2003; 2(7):417-424, or other lineage that supports neural regeneration or repair.

The UTC may be surgically implanted, injected, delivered (e.g., by way of a catheter or syringe), or otherwise administered directly or indirectly to the site of neurological damage or distress. Routes of administration of the UTC or compositions thereof include, but are not limited to, intravenous, intramuscular, subcutaneous, intranasal, intracerebral, intraventricular, intracerebroventricular, intrathecal, intracisternal, intraspinal and/or peri-spinal routes of administration by delivery via intracranial or intravertebral needles and/or catheters with or without pump devices.

When cells are administered in semi-solid or solid devices, surgical implantation into a precise location in the body is typically a suitable means of administration. Liquid or fluid pharmaceutical compositions, however, may be administered to a more general location in the CNS or PNS (e.g., throughout a diffusely affected area, such as would be the case in diffuse ischemic injury, for example), inasmuch as neural progenitor cells have been shown to be capable of extensive migration from a point of entry to the nervous system to a particular location, e.g., by following radial glia or by responding to chemical signals.

This migratory ability of neural stem cells has opened a new avenue for treatment of malignant brain tumors, i.e., use of progenitor cells for delivery of therapeutic genes/gene products for the treatment of these migratory tumors. For example, it has been reported that neural stem cells, when implanted into intracranial gliomas in vivo in adult rodents, distribute themselves quickly and extensively through the tumor bed and migrate in juxtaposition to expanding and advancing tumor cells, while continuing to stably express a foreign gene (Aboody, K, et al., *Proc. Natl. Acad. Sci. USA,* 2000; 97:12846-12851). The UTC are also expected to be suitable for this type of use, i.e., the UTC genetically modified to produce an apoptotic or other antineoplastic agent, e.g., IL-12 (Ehtesham, M, et al., *Cancer Research,* 2002; 62:5657-5663) or tumor necrosis factor-related apoptosis-inducing ligand (Ehtesham, M, et al., *Cancer Research,* 2002; 62:7170-7174) may be injected or otherwise administered to a general site of a malignant tumor (e.g., glioblastoma), whereafter the UTC can migrate to the tumor cells for local delivery of the therapeutic agent. The UTC can also facilitate neurological repair following tumor treatment, as described above, by differentiation into one or more neural phenotypes, or by providing trophic support for neural progenitors and neural cells.

Additionally, methods of treating neurological injury by administering pharmaceutical compositions comprising the UTC cellular components (e.g., cell lysates or components thereof) or products (e.g., trophic and other biological factors produced naturally by the UTC or through genetic modification, conditioned medium from the UTC culture) are provided by the invention. Again, these methods may further comprise administering other active agents, such as growth factors, neurotrophic factors or neuroregenerative or neuroprotective drugs as known in the art.

Dosage forms and regimes for administering the UTC or any of the other pharmaceutical compositions described herein are developed in accordance with good medical practice, taking into account the condition of the individual patient, e.g., nature and extent of the neurodegenerative condition, age, sex, body weight and general medical condition, and other factors known to medical practitioners. Thus, the effective amount of a pharmaceutical composition to be administered to a patient is determined by these considerations as known in the art.

Because the CNS is a somewhat immunoprivileged tissue, it may not be necessary or desirable to immunosuppress a patient prior to initiation of cell therapy with the UTC. Previously, it has been shown that UTC do not stimulate allogeneic PBMCs in a mixed lymphocyte reaction. (See, U.S. patent application Ser. No. 10/877,269, which issued as U.S. Pat. No. 7,524,489). Accordingly, transplantation with allogeneic, or even xenogeneic, UTC may be tolerated in some instances.

In other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above. These and other means for reducing or eliminating an immune response to the transplanted cells are known in the art. As an alternative, the UTC may be genetically modified to reduce their immunogenicity, as mentioned above.

Survival of transplanted UTC in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the neural tissue, and examining it visually or through a microscope. Alternatively, cells can be treated with stains that are specific for neural cells or products thereof, e.g., neurotransmitters. Transplanted cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

Functional integration of transplanted UTC into neural tissue of a subject can be assessed by examining restoration of the neural function that was damaged or diseased. Such functions include, but are not limited to motor, cognitive, sensory and endocrine functions, in accordance with procedures well known to neurobiologists and physicians. This restoration of neural function by the UTC can be used in methods to improve neurological function in patients following neurological injury.

Additionally, the UTC may be used in methods of stimulating the regenerative capacity of the SVZ in patients. For example, the regenerative capacity of the SVZ may be stimulated by showing that there is an increase in neurogenesis, angiogenesis or synaptogenesis. An increase in neurogenesis indicates that progenitor cells in the SVZ are proliferating in preparation to replace injured or damaged neural cells and that there are newly formed neuroblasts and other immature neurons. An increase in angiogenesis indicates that new blood vessel formation is occurring in the injured or damaged area to provide an oxygen supply to the injured or damaged tissue or to tissue that is being formed to replace the injured or damaged tissue. An increase in synaptogenesis indicates that new synapses are being formed, most likely in response to some stimulus that caused a decrease in the number of functioning synapses already present. The ability of the UTC to cause increases in neurogenesis, angiogenesis and synaptogenesis are set forth in Examples 3-10.

Further, the UTC may decrease the number of apoptotic cells in the injured or damaged part of the brain. Apoptosis may be a cause of secondary brain injury following traumatic brain injury and high rates of apoptosis may be associated with poorer prognosis after traumatic brain injury. (See, Minambres, et al., *Journal of Neurotrauma*, 2008; 25(6):581-591). A decrease in apoptosis in an area of the brain that has experienced injury or damage, therefore, may increase survival, improve neurological function and recovery from injury, and may act as an adjunct to other therapies, such as stimulating the regenerative capacity of the SVZ in patients following injury. Examples 7 and 9 demonstrate the ability of the UTC to decrease apoptosis in the damaged sections of brain tissue.

In another aspect, the invention provides kits that utilize the UTC, UTC populations, components and products of the UTC in various methods for neural regeneration and repair as described above. Where used for treatment of neurological injury, or other scheduled treatment, the kits may include one or more cell populations, including at least UTC and a pharmaceutically acceptable carrier (liquid, semi-solid or solid). The kits also optionally may include a means of administering the cells, for example by injection. The kits further may include instructions for use of the cells. Kits prepared for field hospital use, such as for military use may include full-procedure supplies including tissue scaffolds, surgical sutures, and the like, where the cells are to be used in conjunction with repair of acute injuries. Kits for assays and in vitro methods as described herein may contain one or more of (1) the UTC or components or products of the UTC, (2) reagents for practicing the in vitro method, (3) other cells or cell populations, as appropriate, and (4) instructions for conducting the in vitro method.

The following examples are provided to describe the invention in greater detail. They are intended to illustrate, not to limit, the invention.

The following abbreviations may appear in the examples and elsewhere in the specification and claims:
ANG2 (or Ang2) for angiopoietin 2
APC for antigen-presenting cells
BDNF for brain-derived neurotrophic factor
bFGF for basic fibroblast growth factor
bid (BID) for "bis in die" (twice per day)
CK18 for cytokeratin 18
CNS for central nervous system
CXC ligand 3 for chemokine receptor ligand 3
DMEM for Dulbecco's Minimal Essential Medium
DMEM:lg (or DMEM:Lg, DMEM:LG) for DMEM with low glucose
EDTA for ethylene diamine tetraacetic acid
EGF (or E) for epidermal growth factor
FACS for fluorescent activated cell sorting
FBS for fetal bovine serum
FGF (or F) for fibroblast growth factor
GCP-2 for granulocyte chemotactic protein-2
GFAP for glial fibrillary acidic protein
HB-EGF for heparin-binding epidermal growth factor
HCAEC for Human coronary artery endothelial cells
HGF for hepatocyte growth factor
hMSC for Human mesenchymal stem cells
HNF-1alpha for hepatocyte-specific transcription factor 1 alpha; HUVEC for Human umbilical vein endothelial cells
I309 for a chemokine and the ligand for the CCR8 receptor
IGF-1 for insulin-like growth factor 1
IL-6 for interleukin-6; IL-8 for interleukin 8
K19 for keratin 19; K8 for keratin 8
KGF for keratinocyte growth factor
LIF for leukemia inhibitory factor
MBP for myelin basic protein
MCP-1 for monocyte chemotactic protein 1
MDC for macrophage-derived chemokine
MIP1alpha for macrophage inflammatory protein 1 alpha
MIP1beta for macrophage inflammatory protein 1 beta
MMP for matrix metalloprotease (MMP)
MSC for mesenchymal stem cells
NHDF for Normal Human Dermal Fibroblasts
NPE for Neural Progenitor Expansion media
O4 for oligodendrocyte or glial differentiation marker O4
PBMC for Peripheral blood mononuclear cell
PBS for phosphate buffered saline
PDGFbb for platelet derived growth factor
PO for "per os" (by mouth)
PNS for peripheral nervous system
Rantes (or RANTES) for regulated on activation, normal T cell expressed and secreted
rhGDF-5 for recombinant human growth and differentiation factor 5
SC for subcutaneously
SDF-1alpha for stromal-derived factor 1 alpha
SHH for sonic hedgehog
SOP for standard operating procedure
TARC for thymus and activation-regulated chemokine
TCP for Tissue culture plastic
TCPS for tissue culture polystyrene
TGFbeta2 for transforming growth factor beta2
TGF beta-3 for transforming growth factor beta-3
TIMP1 for tissue inhibitor of matrix metalloproteinase 1
TPO for thrombopoietin
TuJ1 for BIII Tubulin
VEGF for vascular endothelial growth factor
vWF for von Willebrand factor
alphaFP for alpha-fetoprotein.

Additionally, as used in the following examples and elsewhere in the specification, the UTC useful in the methods of the invention may be isolated and characterized according to the disclosure of U.S. patent application Ser.

No. 10/877,269, which is incorporated by reference in its entirety as it relates to the description, isolation and characterization of UTC.

EXAMPLE 1

Lone-Term Neural Differentiation of Cells

The ability of umbilicus-derived cells to undergo long-term differentiation into neural lineage cells was evaluated. The UTC were isolated and expanded as described in Examples 13-15.

Frozen aliquots of UTC (umbilicus (022803) P11; (042203) P11; (071003) P12) previously grown in growth medium were thawed and plated at 5,000 cells/cm$^2$ in T-75 flasks coated with laminin (BD, Franklin Lakes, N.J.) in Neurobasal-A medium (Invitrogen, Carlsbad, Calif.) containing B27 (B27 supplement, Invitrogen), L-glutamine (4 mM), and Penicillin/Streptomycin (10 milliliters), the combination of which is herein referred to as Neural Progenitor Expansion (NPE) media. NPE media was further supplemented with bFGF (20 ng/ml, Peprotech, Rocky Hill, N.J.) and EGF (20 ng/ml, Peprotech, Rocky Hill, N.J.), herein referred to as NPE+bFGF+EGF.

In addition, adult human dermal fibroblasts (P11, Cambrex, Walkersville, Md.) and mesenchymal stem cells (P5, Cambrex) were thawed and plated at the same cell seeding density on laminin-coated T-75 flasks in NPE+bFGF+EGF. As a further control, fibroblasts, umbilicus, and placenta-derived cells were grown in growth medium for the period specified for all cultures.

Media from all cultures were replaced with fresh media once a week and cells observed for expansion. In general, each culture was passaged one time over a period of one month because of limited growth in NPE+bFGF+EGF.

After a period of one month, all flasks were fixed with cold 4% (w/v) paraformaldehyde (Sigma) for 10 minutes at room temperature. Immunocytochemistry was performed using antibodies directed against TuJ1 (BIII Tubulin; 1:500; Sigma, St. Louis, Mo.) and GFAP (glial fibrillary acidic protein; 1:2000; DakoCytomation, Carpinteria, Calif.). Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing block along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 1-1

Summary of Primary Antibodies Used

| Antibody | Concentration | Vendor |
|---|---|---|
| TuJ1 (BIII Tubulin) | 1:500 | Sigma, St. Louis, Mo. |
| GFAP | 1:2000 | DakoCytomation, Carpinteria, Ca. |

Immediately following plating, a subset of UTC attached to the culture flasks coated with laminin. This may have been due to cell death as a function of the freeze/thaw process or because of the new growth conditions. Cells that did attach adopted morphologies different from those observed in growth media.

Upon confluence, cultures were passaged and observed for growth. Very little expansion took place of those cells that survived passage. At this point, very small cells with no spread morphology and with phase-bright characteristics began to appear in cultures of umbilicus-derived cells. These areas of the flask were followed over time. From these small cells, bifurcating processes emerged with varicosities along their lengths, features very similar to previously described PSA-NCAM+ neuronal progenitors and TuJ1+ immature neurons derived from brain and spinal cord (Mayer-Proschel, M, et al. *Neuron*, 1997; 19(4):773-85; Yang, H, et al., *PNAS*, 2000; 97(24):13366-71). With time, these cells became more numerous, yet still were only found in clones. This indicates that NPE+bFGF+EGF media slows proliferation of PPDCs and alters their morphology.

Cultures were fixed at one month post-thawing/plating and stained for the neuronal protein TuJ1 and GFAP, an intermediate filament found in astrocytes. While all control cultures grown in growth medium and human fibroblasts and MSCs grown in NPE+bFGF+EGF medium were found to be TuJ1−/GFAP−, TuJ1 was detected in the umbilicus and placenta PPDCs. Expression was observed in cells with and without neuronal-like morphologies. No expression of GFAP was observed in either culture. The percentage of cells expressing TuJ1 with neuronal-like morphologies was less than or equal to 1% of the total population (n=3 umbilicus-derived cell isolates tested). While not quantified, the percentage of TuJ1+ cells without neuronal morphologies was higher in umbilicus-derived cell cultures than placenta-derived cell cultures. These results appeared specific as age-matched controls in growth medium did not express TuJ1. These results indicate that clones of UTC express neuronal proteins.

Methods for generating differentiated neurons (based on TuJ1 expression and neuronal morphology) from UTC were developed. While expression for TuJ1 was not examined earlier than one month in vitro, it is clear that at least a small population of UTC can give rise to neurons either through default differentiation or through long-term induction following one month's exposure to a minimal media supplemented with L-glutamine, basic FGF, and EGF.

EXAMPLE 2

Effect of Administration of Cells Following Brain Injury on Neurological Function. Intracerebral Hemorrhage (ICH) Model in Rat ICH was induced in male Wistar rats weighing 300-350 g by injecting 100 μl of autologous blood as essentially described by Seyfried, et al., *J. Neurosurg,* 2006; 104:313-318 (2006). Briefly, rats were anesthetized with xylazine (10 mg/kg) and ketamine (80 mg/kg). Once adequate anesthesia was achieved, the rats were maintained at 37° C. throughout the surgical procedure using a feedback regulated water heating pad. Under a dissecting scope, a 2 cm ventral skin incision was made along the crease formed by the abdomen and right thigh. Blunt dissection of the adductor muscles is used to visualize the right femoral artery. Five to ten millimeters of artery was carefully mobilized from the adjacent femoral vein and saphenous nerve. The artery was ligated at the distal end, and the proximal portion was temporarily blocked with a 4-0 suture. A PE50 catheter was then inserted into the vessel 1-2 cm through a small puncture and secured in place with a 4-0 suture. Then the rat was placed prone on a stereotactic frame (David Kopf Instruments, Tujunja, Calif.). A midline incision was made over the calvarium and carried down to the periosteum. A small periosteal elevator was used to expose the skull. Once this was accomplished, the stereotactic frame measurements were used to guide the site where the craniectomy took place. First identification of the bregma was performed and then a craniectomy was performed with the stereotactic drill (3.5 mm lateral to midline, 0.5 mm anterior to bregma, depth 5.5 mm below the surface to midline). 0.3 ml of autologous blood taken from the femoral artery was placed into a 1 cc syringe with a 26G½ needle that was loaded on the stereotactic frame. 0.1 ml of blood was then infused at a rate of 10 µl per minute with an infusion pump (600-910/920, Harvard Apparatus, Holliston, Mass.). To prevent blood from backing up, a piece of bone wax was used to close the craniectomy site and keep the blood in the brain. The skin was reapproximated with 4.0 silk suture, simple running.

At 24 hours or 72 hours after ICH, randomly selected animals underwent cell transplantation. Animals were anesthetized with 3.5% halothane in $N_2O:O_2$ (2:1) and maintained at 0.5% halothane using a facemask. UTC (see, U.S. patent application Ser. No. 10/877,269 for a description of isolation and characterization of UTCs useful in the methods of the invention) in 2 ml total fluid volume PBS or PBS alone (control) were injected into a tail vein of the animal. Experimental groups (n=8/group) consisted of PBS alone and UTC ($3\times10^6$). All rats were allowed to survive 28 days after surgery. In all animals, batteries of behavioral tests were measured one day, four days, and weekly thereafter.

mNSS is a composite of motor, sensory, balance and reflex tests. Neurological function, as assessed by mNSS (as described by Chen, J, et al., *Stroke,* 2001; 32:1005-1011) was graded on a scale of 0 to 18 (normal score 0; maximal deficit score 18). In the severity scores of injury, one point is awarded for the exhibition of certain abnormal behavior or for the lack of a tested reflex. Thus, the higher score, the more severe is the injury. The motor tests used were raising the rat by the tail, for which the following scores were given: flexion of forelimb (1), flexion of hindlimb (1), head moved more than 10° to the vertical axis within 30 seconds (1); and, walking on the floor, for which the following scores were given: normal walk (0), inability to walk straight (1), circling toward the paretic side (2), falling down to the paretic side (3). The sensory tests used were a placing test (visual and tactile test) and a proprioceptive test (deep sensation, pushing the paw against the table edge to stimulate limb muscles). The balance test used was a balance beam test, for which the following scores were given: balances with steady posture (0), grasps side of beam (1), hugs the beam and one limb falls down from the beam (2), hugs the beam and two limbs fall down from the beam, or spins on beam (>60 s) (3), attempts to balance on the beam but falls off (>40 s) (4), attempts to balance on the beam but falls off (>20 s) (5), and falls off, with no attempt to balance or hang on to the beam (<20 s) (6).

The corner test, as described by Zhang, L, et al., *J Neurosci Methods,* 2002; 117(2):207-14, was performed. Briefly, a rat was placed between two attached boards (dimensions of 30×20×1 cm3). The edges of the two boards were at a 30° angle with a small opening along the joint to encourage entry into the corner. The rat was placed facing and half way to the corner. When entering deep into the corner, both sides of the vibrissae were stimulated together. The rat then reared forward and upward, and then turned back to face the open end. A non-injured rat either turned left or right, but the injured rats preferentially turned toward the non-impaired side. The turns in one versus the other direction were recorded from ten trials for each test, and the fraction of the turns was used as the corner test score.

Figure 2:
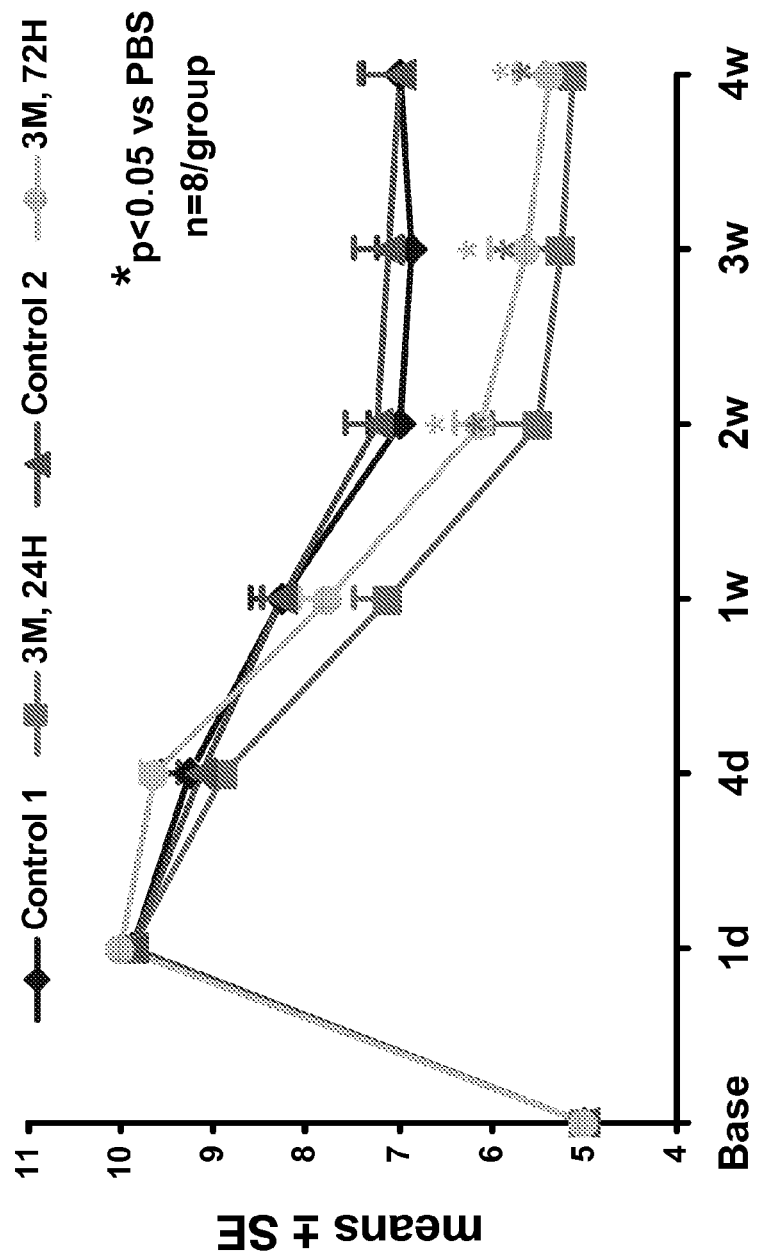
FIG. 2 shows the corner test score at 1 day, 4 days, 7 days, 14 days, 21 days and 28 days, after injury in rats treated with PBS or $3\times10^6$ UTC at either 24 hours or 72 hours following the injury (n=8).

Results from the functional tests indicated that rats treated 24 hours and 72 hours with UTC ($3\times10^6$) exhibited significant (p<0.05) improvement in the mNSS test and corner test. (See, FIGS. 1 and 2). mNSS total scores decreased significantly among rats treated at 24 hour and 72 hour with $3\times10^6$ UCT as compared to controls, at days 14, 21, and 28. (See, FIG. 1).

EXAMPLE 3

Effect of Administration of Cells Following Brain Injury on Cell Proliferation in the Subventricular Zone Bromodeoxyuridine (BrdU), a thymidine analog, can be incorporated into cells' genomic DNA during the S phase of cell cycle. BrdU positive cells in the subventricular zone (SVZ) are considered to be progenitor cells undergoing DNA synthesis in the S phase of the cell cycle. The number of BrdU cells in the SVZ is used as an indicator of neurogenesis.

The rats received daily intraperitoneal injections (IP) of 100 mg/Kg of BrdU starting at 24 hours after ICH and subsequently for the next 14 days. After 28 days, animals were reanesthetized with ketamine (80 mg/kg) and (xylazine 13 mg/kg) IP injection, and sacrificed (first by draining all of the blood from the body via a heart puncture and flushing the system with normal saline and then 4% paraformaldehyde). The skull was then removed with a rongeur and the brain removed and subsequently fixed in 4% paraformaldehyde and sliced/sectioned to grossly and histologically assess the region of the hemorrhage. Immunohistochemical staining was used for BrdU (mouse monoclonal antibody, 1:100; Boehringer Mannheim, Indianapolis, Ind.). Briefly, the brain tissue residing between +0.1 and 0.86 mm of the bregma on the third block was the most severely injured and therefore the third block was specifically selected for immunostaining. Every 40th coronal section from +0.1-0.86 mm of the bregma was used for immunochemical staining with the same antibody. Sections were blocked in a Tris-buffered saline containing 5% normal goat serum, 1% BSA and 0.05% TWEEN-20. Sections were then incubated with the primary antibodies following with the incubation with the appropriate secondary antibodies. Control experiments consisted of staining brain coronal tissue sections as outlined above, but omitted the primary antibodies. BrdU-positive cell numbers in the ipsilateral subventricular zone (SVZ) were counted with use of an Olympus BX40 microscope and a 3-CCD color video camera (Sony DXC-970MD) interfaced with an MCID image analysis system (Imaging Research, St. Catharines, Canada). The total numbers of BrdU-positive cells in the ipsilateral SVZ are reported.

Figure 3B:
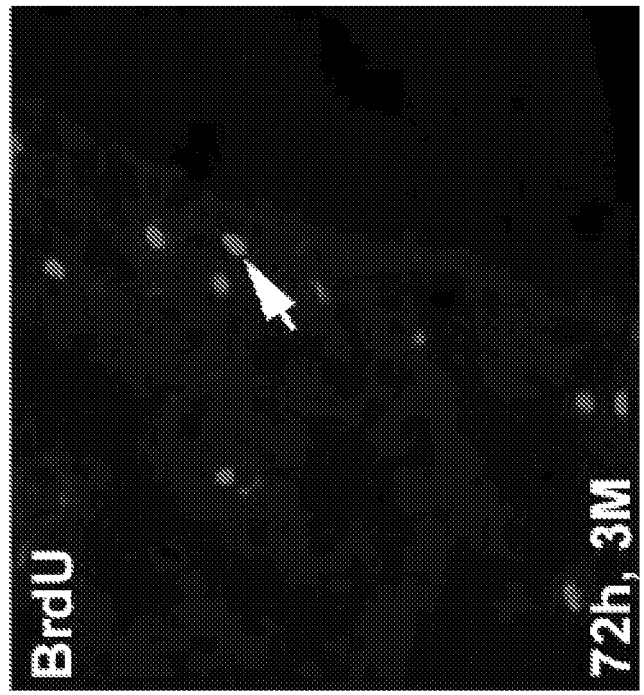
FIGS. 3A-3D show BrdU incorporation in cells of the SVZ in rats following injury and subsequent treatment with PBS at 72 hours post injury (FIG. 3A), with $3\times10^6$ UTC at 72 hours post injury (FIG. 3B), with PBS at 24 hours post injury (FIG. 3C), and with $3\times10^6$ UTC at 24 hours post injury (FIG. 3D).
Figure 3A:
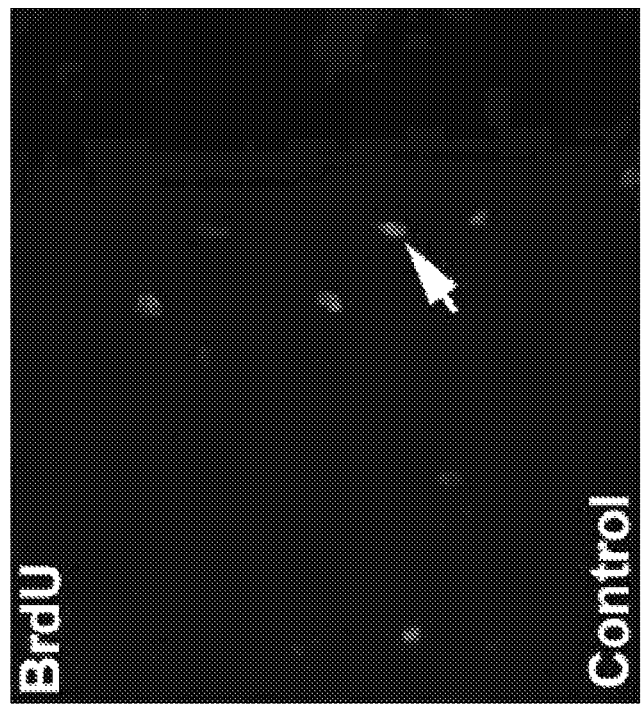
Figure 3D:
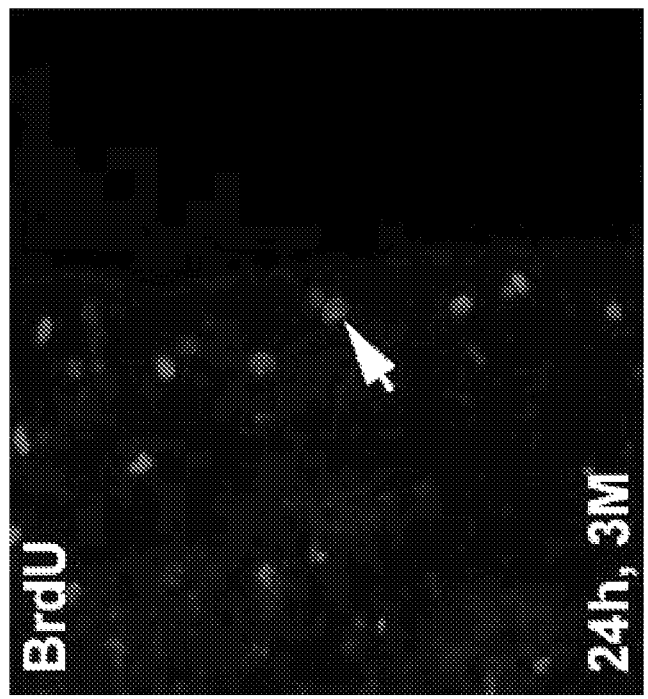
Figure 3C:
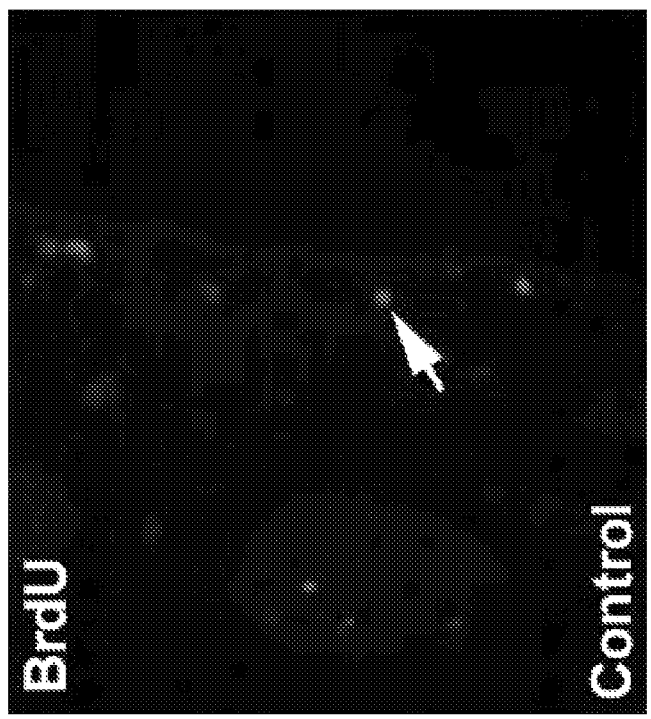
Figure 3F:
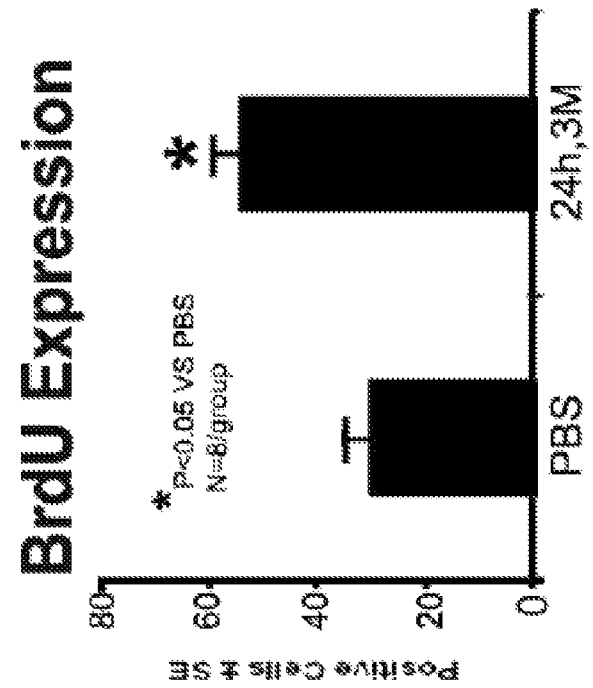
FIG. 3F shows the mean number with either PBS or $3\times10^6$ UTC at 24 hours post injury (n=8).
Figure 3E:
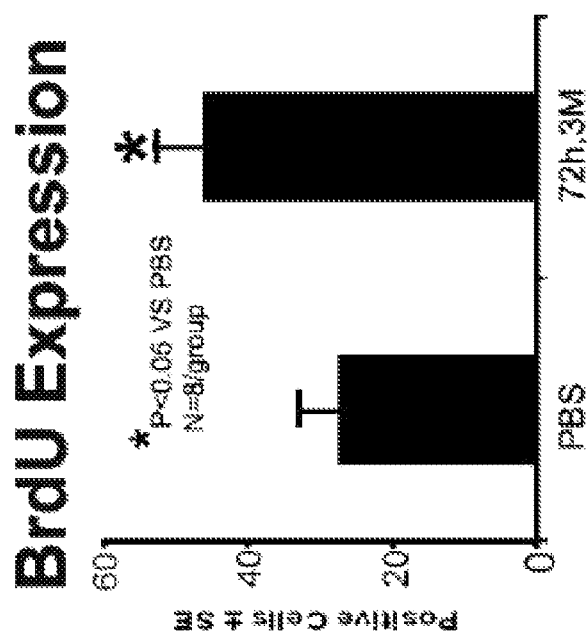
FIG. 3E shows the mean number of BrdU positive cells in the SVZ of rats following injury and subsequent treatment with either PBS or $3\times10^6$ UTC at 72 hours post injury (n=8)

The results show that the number of BrdU positive cells were significantly increased in the SVZ of the ipsilateral hemisphere of rats treated with $3\times10^6$ UTC at 24 hours or 72 hours after ICH compared with the control PBS group ($p<0.05$) (See FIGS. 3E and 3F).

EXAMPLE 4

Effect of Administration of Cells Following Brain Injury on Angiogenesis in the Damaged Area of the Brain Enlarged and thin-walled vessels in the boundary around the lesion are indicative of angiogenesis (Li, Y, et al., Neurology, 2002; 59:514-523). After 28 days, animals were reanesthetized, sacrificed and their brains removed as detailed in Example 3 for histological assessment. A monoclonal antibody against vWF (1:400, Dako, Carpinteria, Calif.) was used.

Figure 4B:
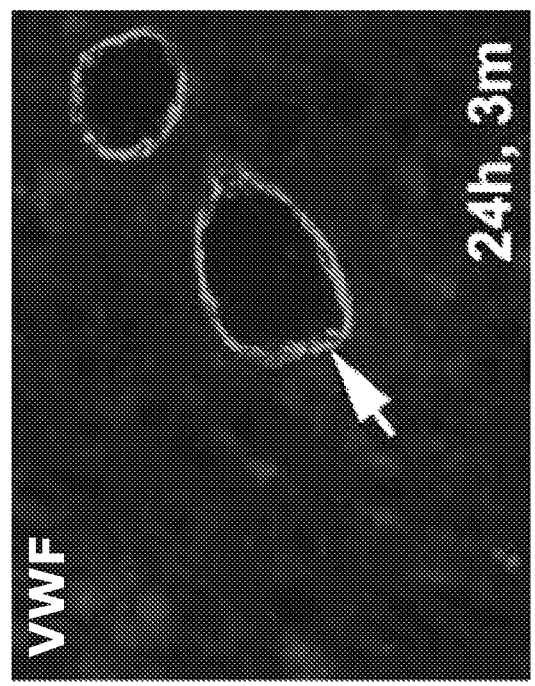
FIGS. 4A-D show VWF expression in blood vessels in damaged areas of the rat brains following injury and subsequent treatment with PBS at 24 hours post injury (FIG. 4A), with $3\times10^6$ UTC at 24 hours post injury (FIG. 4B), with PBS at 72 hours post injury (FIG. 4C), and with $3\times10^6$ UTC at 72 hours post injury (FIG. 4D).
Figure 4A:
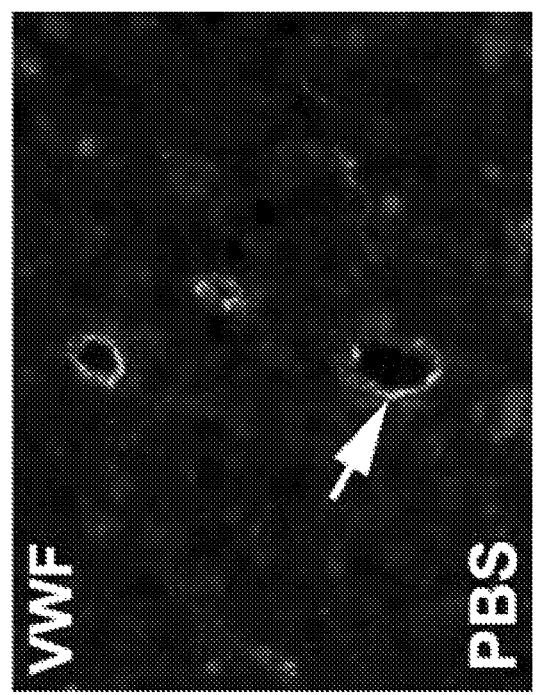
Figure 4D:
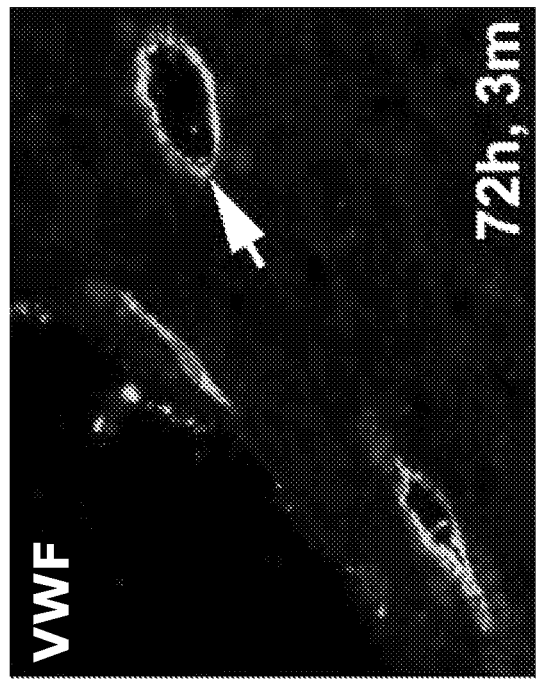
Figure 4C:
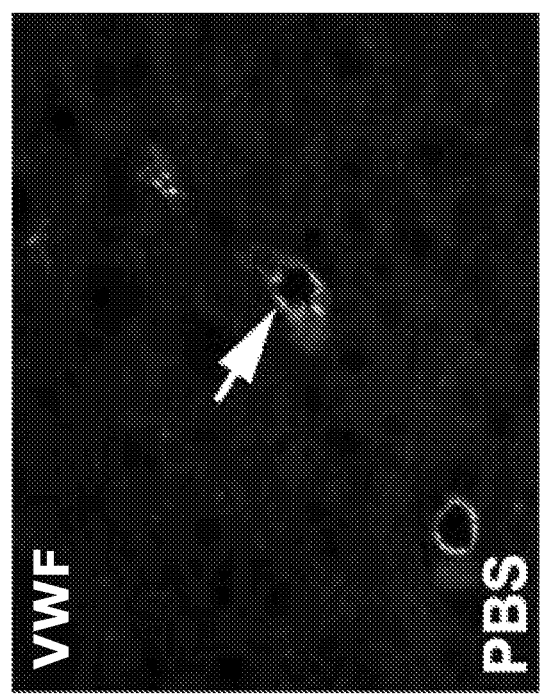
Figures 4E, 4F:
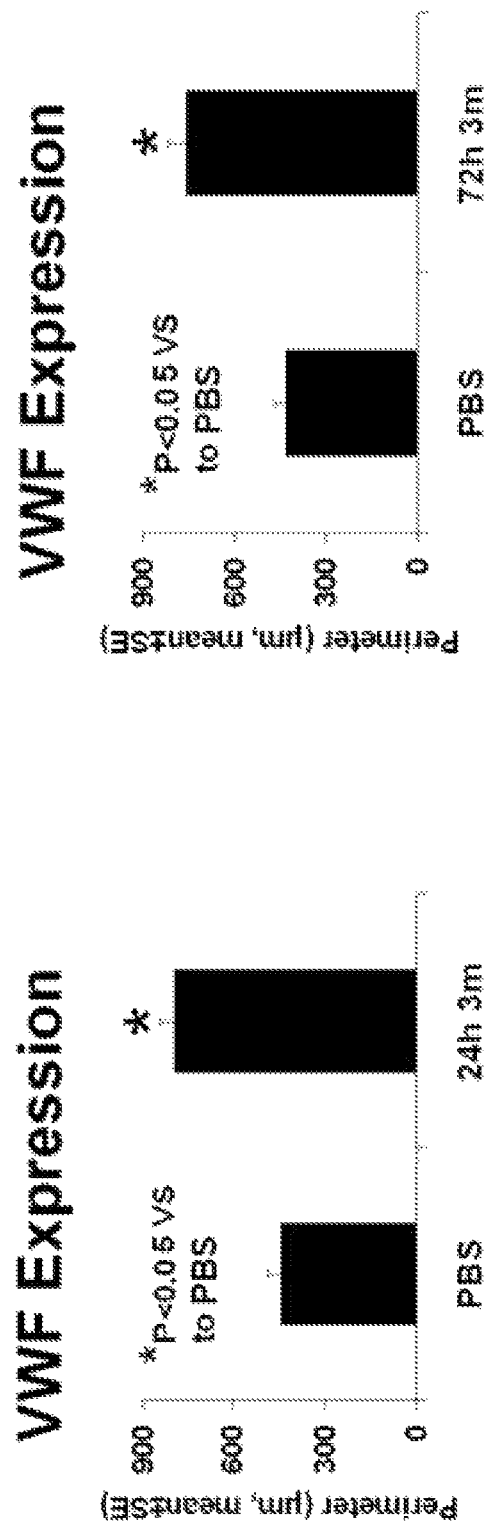
FIG. 4E shows the mean diameter (μm) of blood vessels in damaged areas of the rat brains following injury and subsequent treatment with either PBS or $3\times10^6$ UTC at 24 hours post injury (n=8)
FIG. 4F shows the mean diameter (μm) with either PBS or $3\times10^6$ UTC at 72 hours post injury (n=8).

The results show that the perimeters of vessels were significantly increased in treatment groups with $3\times10^6$ UTC at 24 hours or 72 hours after ICH compared with the control PBS group ($p<0.05$) (See FIGS. 4E and 4F).

Additionally, as noted in Example 3 above, BrdU can be incorporated into cells' genomic DNA during the S phase of cell cycle. By assessing the expression of Von Willebrand Factor in conjunction with BrdU incorporation it can be determined if actively dividing cells are contributing to the growth of new blood vessels at the ICH boundary (see protocol above).

Figure 5B:
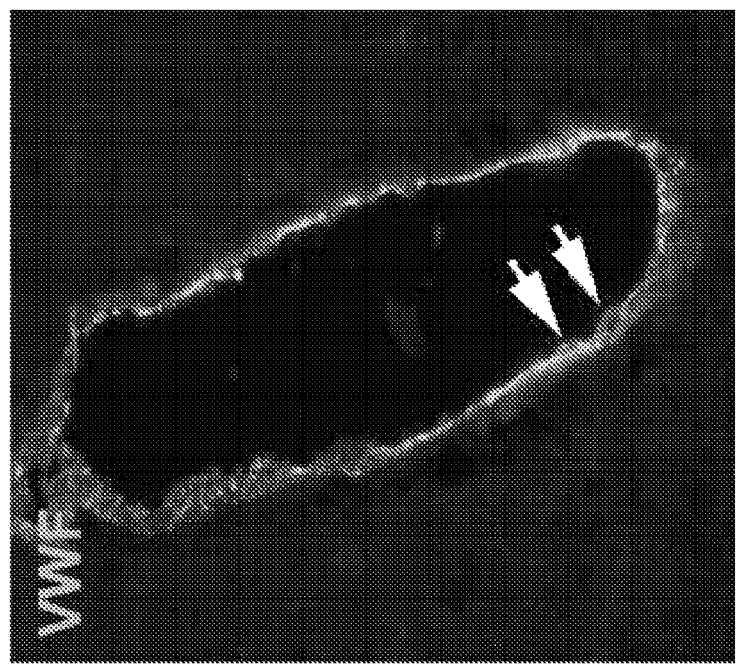
FIG. 5B shows VWF expression in blood vessels in damaged areas of the rat brains following injury.
Figure 5A:
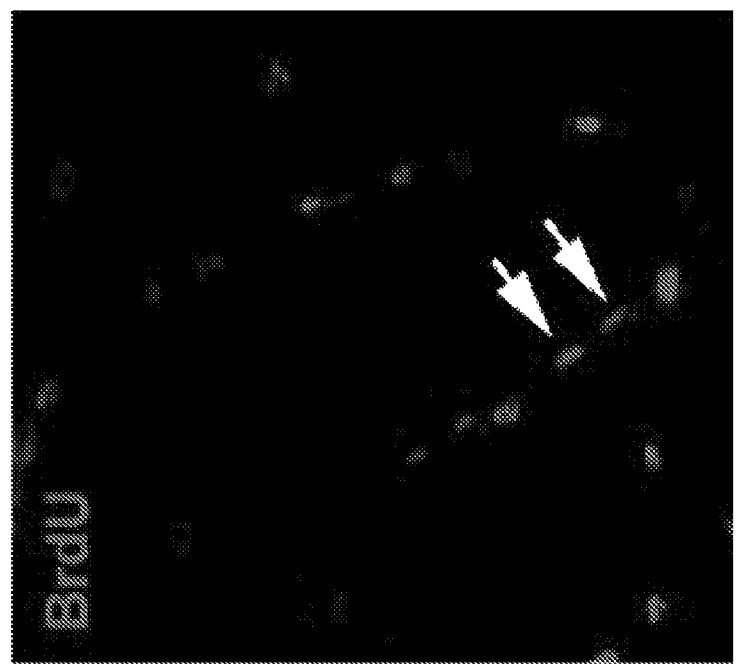
FIG. 5A shows BrdU incorporation in endothelial cells of blood vessels in damaged areas of the rat brains following injury.
Figure 5C:
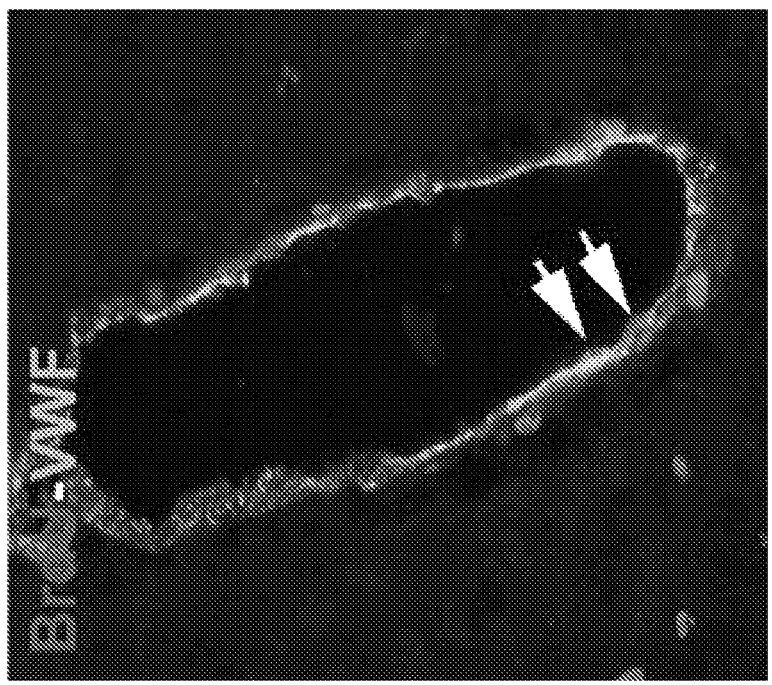
FIG. 5C shows BrdU incorporation in endothelial cells that are co-localized with VWF expressing tissue in blood vessels in damaged areas of the rat brains following injury.

Endothelial cells positive for BrdU are shown in FIG. 5A. Vessels positive for Von Willebrand Factor (vWF) are shown in FIG. 5B. FIG. 5C shows double immunostaining of BrdU reactive cells colocalized with vWF positively stained tissues in the vessel. Double staining revealed a subpopulation of cells that express a vascular marker while still dividing, suggesting that cells positive for vascular phenotype are newly formed during the recovery stage.

EXAMPLE 5

Effect of Administration of Cells Following Brain Injury on Neurogenesis in the Subventricular Zone Doublecortin (DCX) is a marker of neurogenesis, which is transiently expressed (during about 2-3 weeks) in newly formed neuroblasts. After 28 days, animals were reanesthetized, sacrificed and their brains removed as detailed in Example 3 for histological assessment. Goat anti-DCX (1:200; Santa Cruz Biotechnology, Santa Cruz, Calif.) was used.

Figure 6B:
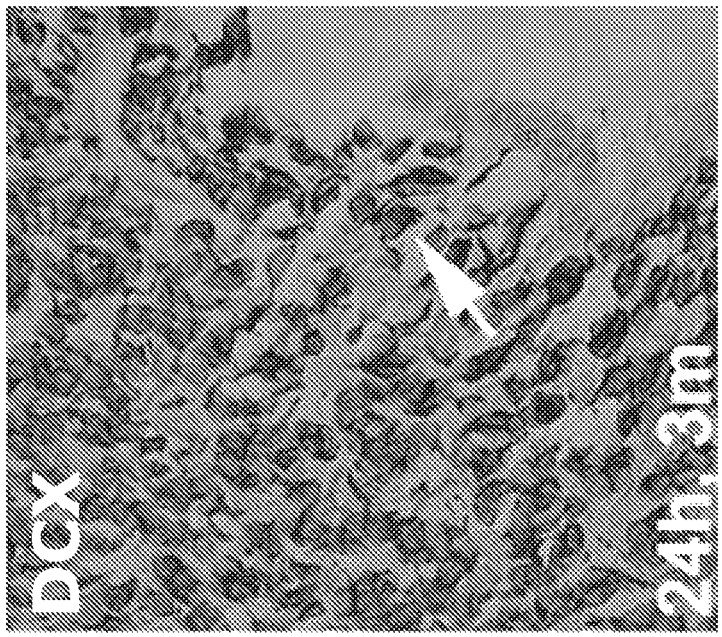
FIGS. 6A-D show Doublecortin (DCX) expression in the SVZ of the rat brains following injury and subsequent treatment with PBS at 24 hours post injury (FIG. 6A), with $3\times10^6$ UTC at 24 hours post injury (FIG. 6B), with PBS at 72 hours post injury (FIG. 6C), with $3\times10^6$ UTC at 72 hours post injury (FIG. 6D).
Figure 6A:
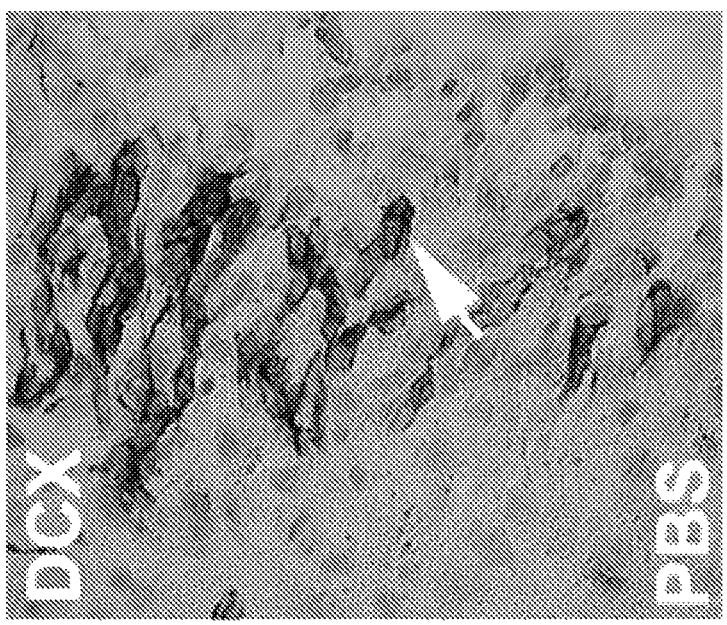
Figure 6D:
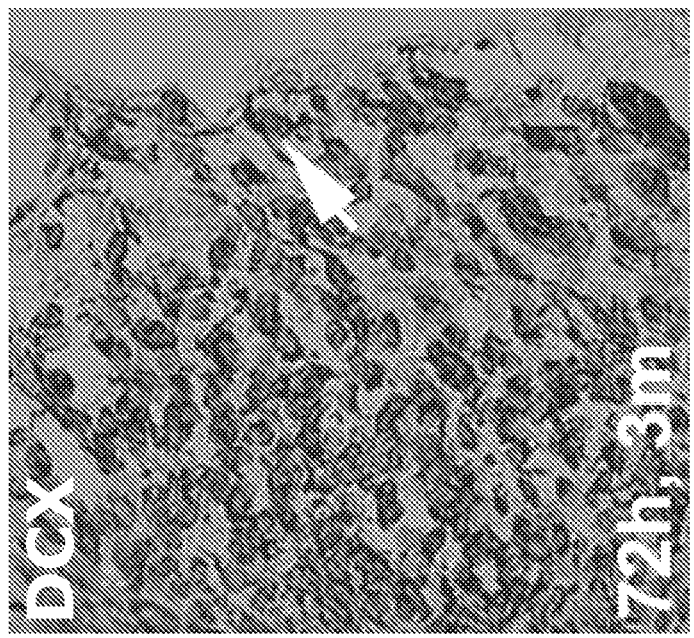
Figure 6C:
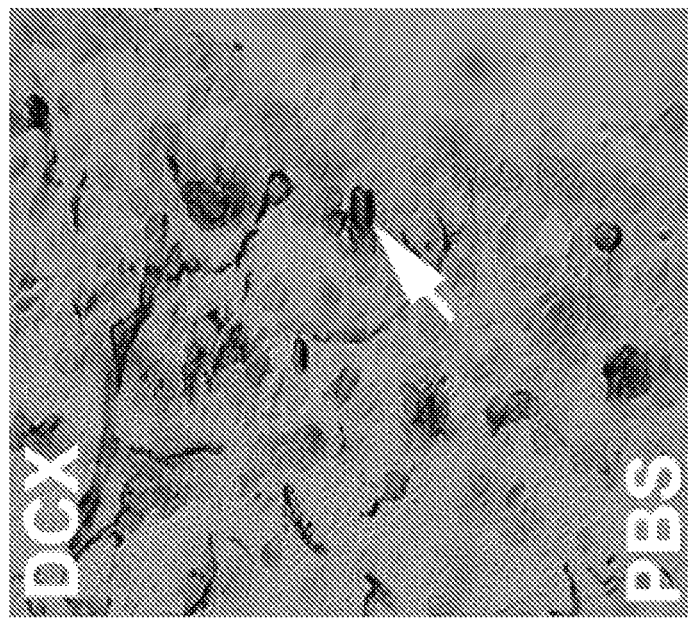
Figure 6F:
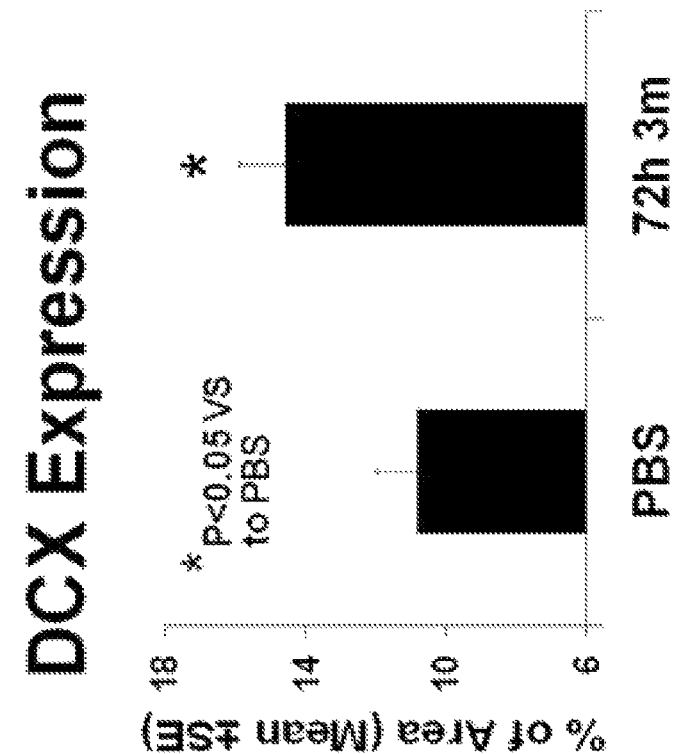
FIG. 6F shows the mean percentage of area with either PBS or $3\times10^6$ UTC at 72 hours post injury (n=8) that is positive for Doublecortin (DCX) expression.
Figure 6E:
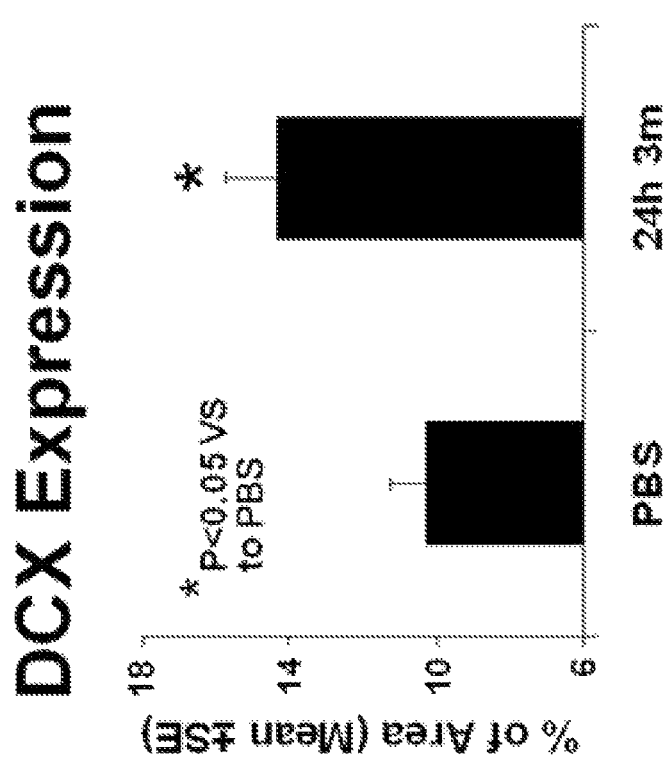
FIG. 6E shows the mean percentage of area of the SVZ of the rat brains following injury and subsequent treatment with either PBS or $3\times10^6$ UTC at 24 hours post injury (n=8) that is positive for Doublecortin (DCX) expression.

The results show immunoexpression for DCX in SVZ is significantly increased in treatment groups with $3\times10^6$ UTC at 24 hours or 72 hours after ICH compared with the control PBS group ($p<0.05$). (See FIGS. 6E and 6F).

Additionally, BIII Tubulin (TUJ1) is a neuron specific tubulin that is expressed during fetal and postnatal development and in putative neuronal cells of the SVZ. TUJ1 expression was assessed to detect any newly formed immature neurons. A mouse anti-TUJ1 (1:1000, Novus Biologicals Inc. Littleton, Colo.) was used.

Figure 7B:
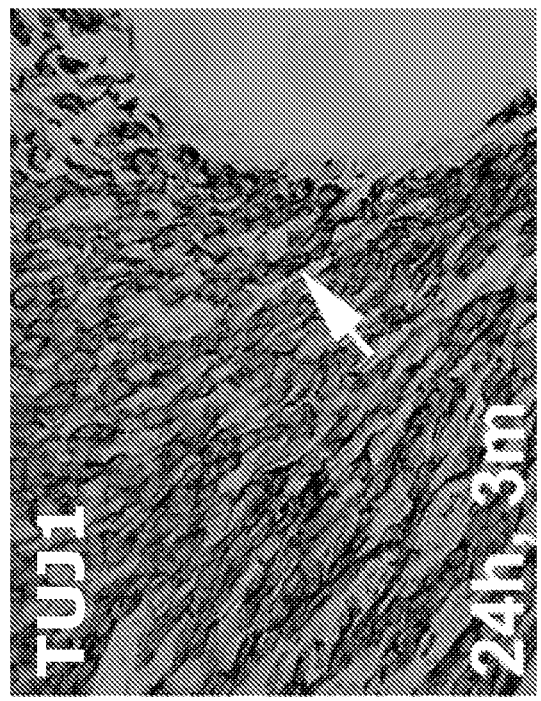
FIG. 7A-D show TUJ1 expression in the SVZ of the rat brains following injury and subsequent treatment with PBS at 24 hours post injury (FIG. 7A), with $3\times10^6$ UTC at 24 hours post injury (FIG. 7B), with PBS at 72 hours post injury (FIG. 7C), and with $3\times10^6$ UTC at 72 hours post injury (FIG. 7D).
Figure 7A:
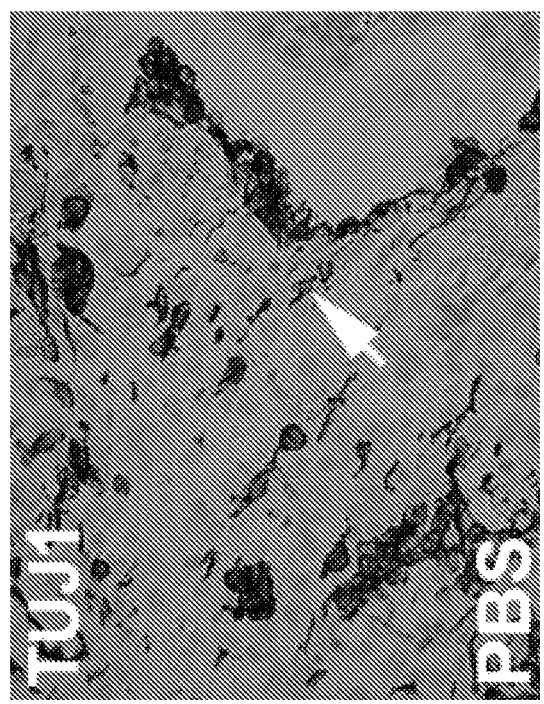
Figure 7D:
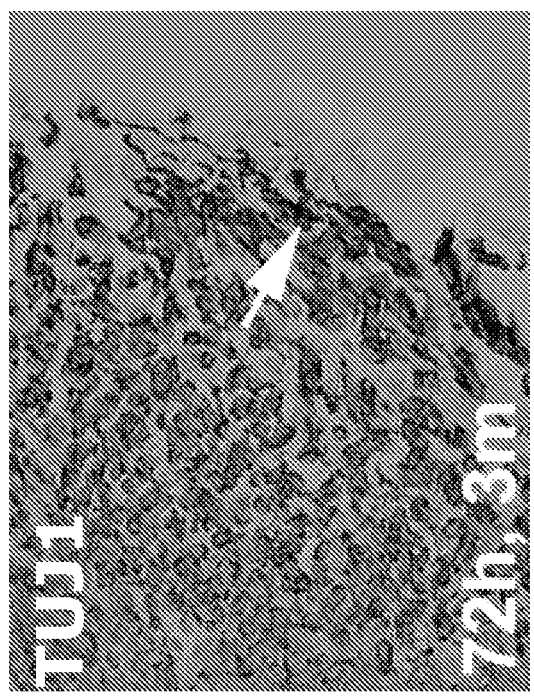
Figure 7C:
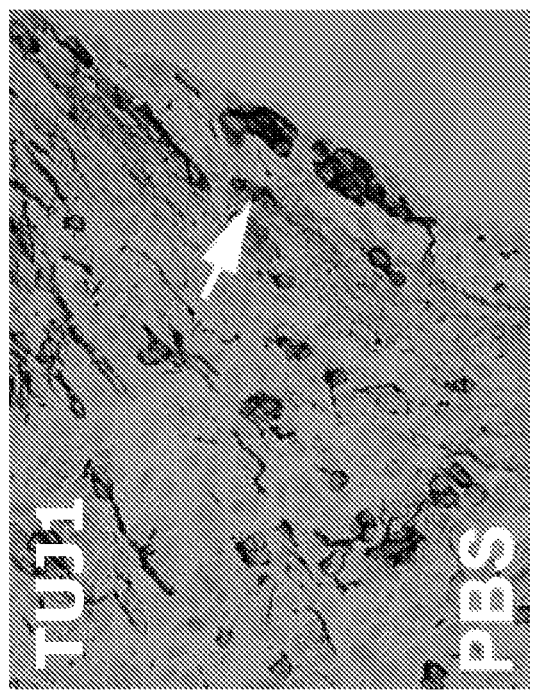
Figures 7E, 7F:
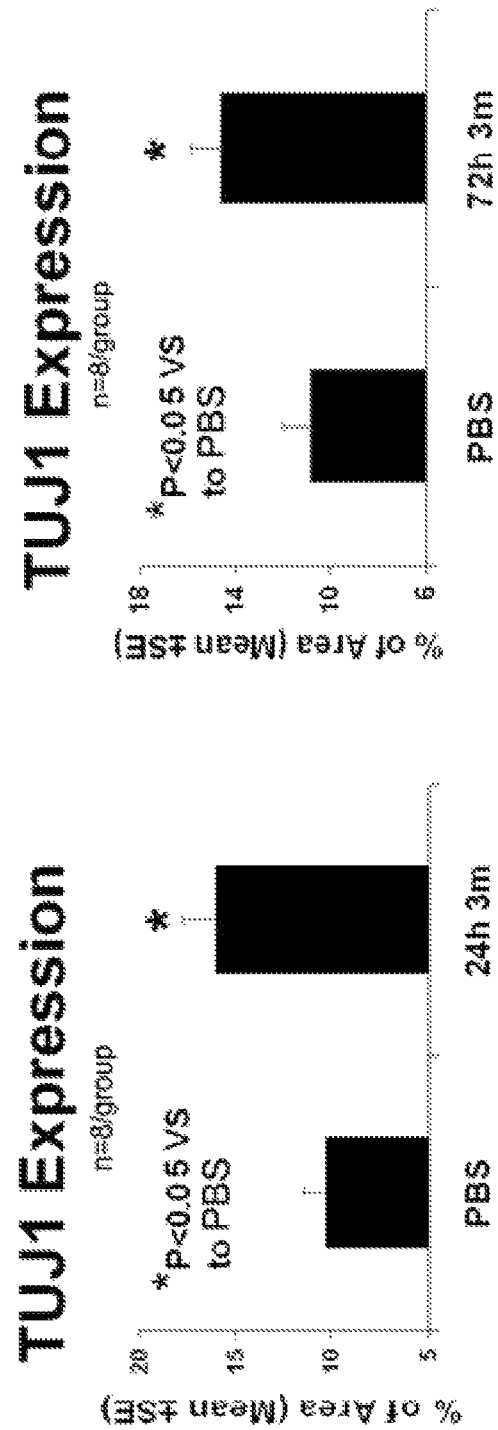
FIG. 7E shows the mean percentage of area of the SVZ of the rat brains following injury and subsequent treatment with either PBS or $3\times10^6$ UTC at 24 hours post injury (n=8) that is positive for TUJ1 expression.
FIG. 7F shows the mean percentage of area with either PBS or $3\times10^6$ UTC at 72 hours post injury (n=8) that is positive for TUJ1 expression.

The results show immunoexpression for TUJ1 in SVZ is significantly increased in treatment groups with $3\times10^6$ UTC at 24 hours or 72 hours after ICH compared with the control PBS group ($p<0.05$). (See FIGS. 7E and 7F).

EXAMPLE 6

Effect of Administration of Cells Following Brain Injury on Synaptogenesis in the Boundary Zone of Hematoma Synaptophysin, a presynaptic vesicle protein, is used as an indicator of synaptogenesis (Ujike, H, et al., Ann N Y Acad Sci., 2002; 965:55-67). After 28 days, animals were reanesthetized, sacrificed and their brains removed as detailed in Example 3 for histological assessment. Synaptophysin (1:40 mAb, Clone SY 38, Millipore, Billerica, Mass.) was used.

Figure 8B:
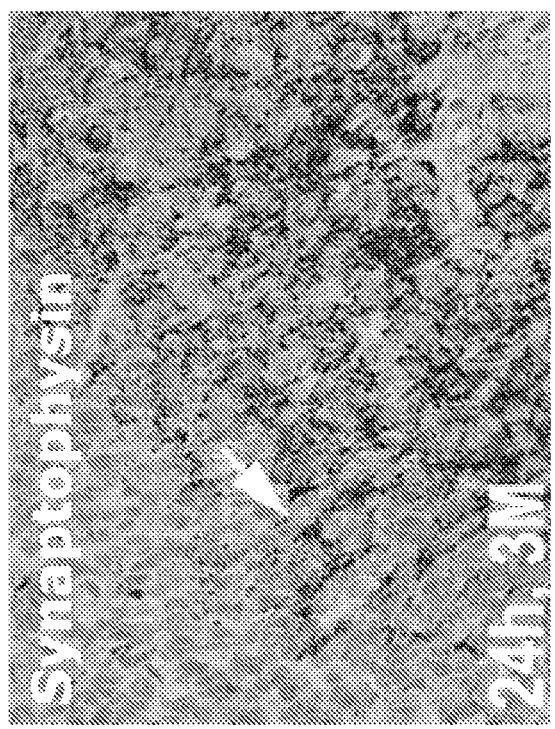
FIG. 8A-D show synaptophysin expression in the boundary zone of hematoma of the rat brains following injury and subsequent treatment with PBS at 24 hours post injury (FIG. 8A), with $3\times10^6$ UTC at 24 hours post injury (FIG. 8B), with PBS at 72 hours post injury (FIG. 8C), and with $3\times10^6$ UTC at 72 hours post injury (FIG. 8D).
Figure 8A:
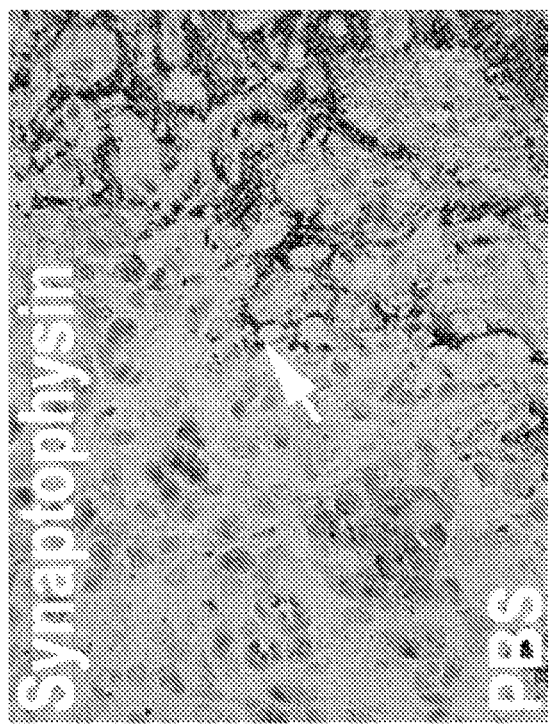
Figure 8D:
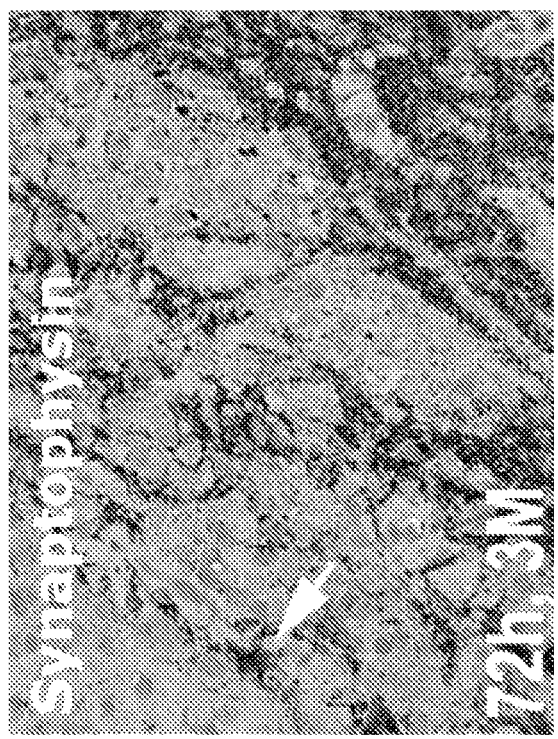
Figure 8C:
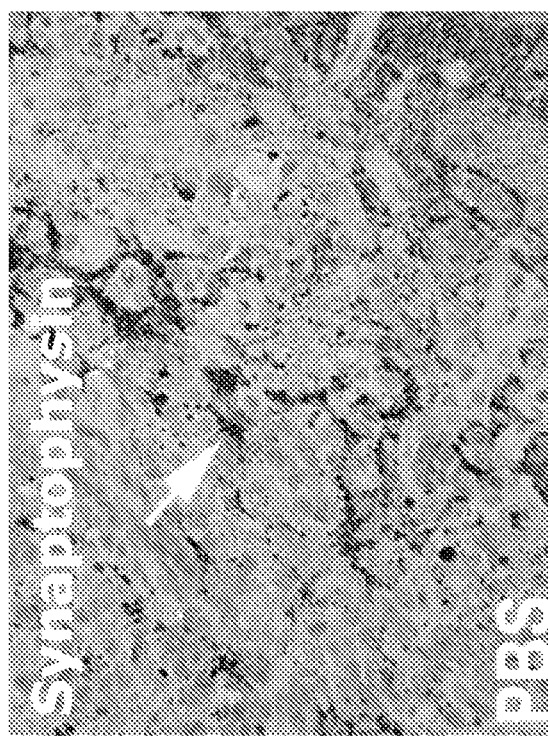
Figure 8F:
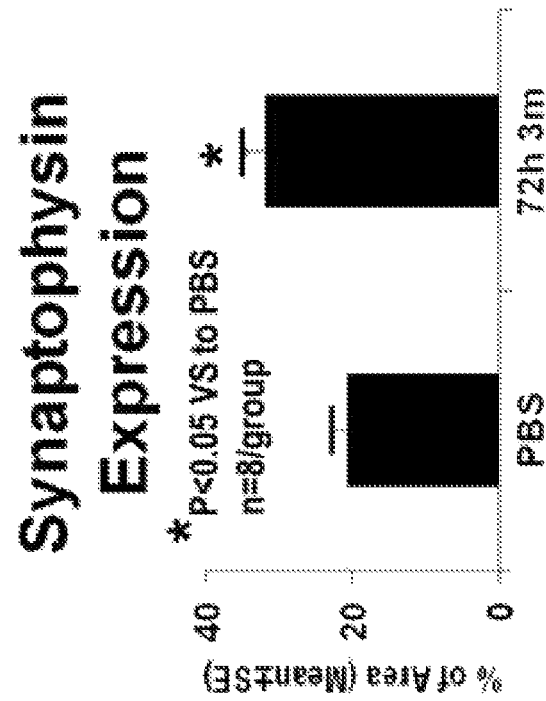
FIG. 8F shows the mean percentage of area with either PBS or $3\times10^6$ UTC at 72 hours post injury (n=8) that is positive for synaptophysin expression.
Figure 8E:
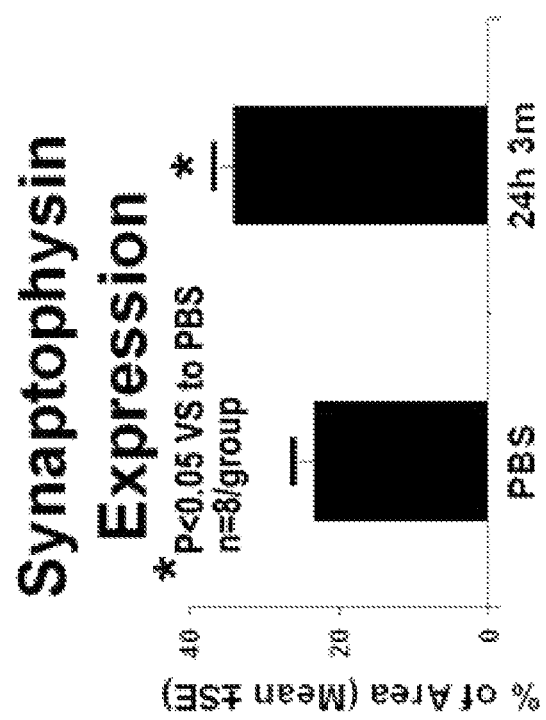
FIG. 8E shows the mean percentage of area of the boundary zone of hematoma of the rat brains following injury and subsequent treatment with either PBS or $3\times10^6$ UTC at 24 hours post injury (n=8) that is positive for synaptophysin expression.

The results show that the expression of synaptophysin increased significantly along the boundary zone of hematoma with $3\times10^6$ UTC at 24 hours or 72 hours after ICH compared with the control PBS group. ($p<0.05$.). (See FIGS. 8E and 8F).

EXAMPLE 7

Effect of Administration of Cells Following Brain Injury on Apoptosis in the Damaged Area of the Brain After 28 days, animals were reanesthetized, sacrificed and their brains removed as detailed in Example 3 for histological assessment. The terminal deoxynucleotidyltransferase (TdT)-mediated dUTP-biotin nick-end labeling (TUNEL) method (ApopTag Kit; Oncor, Gaithersburg, Md.) was used to assess in situ apoptotic detection according to manufacturer's specifications. The TUNEL method is based on the specific binding of TdT to 3'-OH ends of DNA and the ensuing synthesis of polydeoxynucleotide polymer cells. Briefly, after deparaffinizing brain sections and digesting protein using proteinase K and then quenching endogenous peroxidase activity with 2% $H_2O_2$ in PBS, the slides were placed in equilibration buffer and then in working-strength TdT enzyme, followed by working-strength stop/wash buffer. After two drops of antidigoxigenin-peroxidase were applied to the slides, peroxidase was detected with DAB. Negative controls were performed with distilled water for TdT enzyme in the preparation of working-strength TdT. The labeling target of the TUNEL method was the new 3'-OH DNA ends generated by DNA fragmentation, which were typically localized in morphologically identifiable nuclei and apoptotic bodies with dark brown, rounded or oval bodies.

Figure 9B:
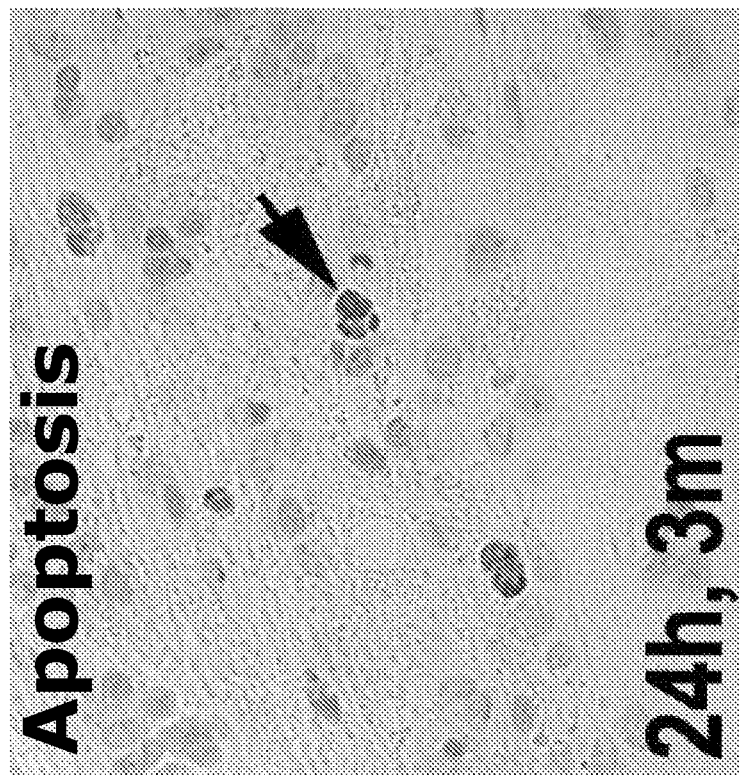
FIGS. 9A-D show TUNEL staining of apoptotic cells in the damaged area of the rat brains following injury and subsequent treatment with PBS at 24 hours post injury (FIG. 9A), with $3\times10^6$ UTC at 24 hours post injury (FIG. 9B), with PBS at 72 hours post injury (FIG. 9C), and with $3\times10^6$ UTC at 72 hours post injury (FIG. 9D).
Figure 9A:
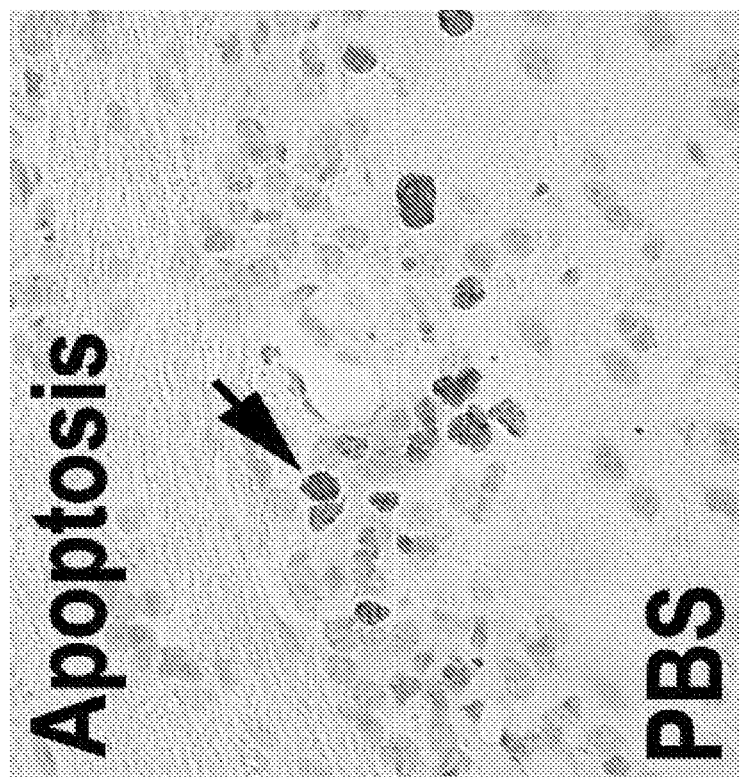
Figure 9D:
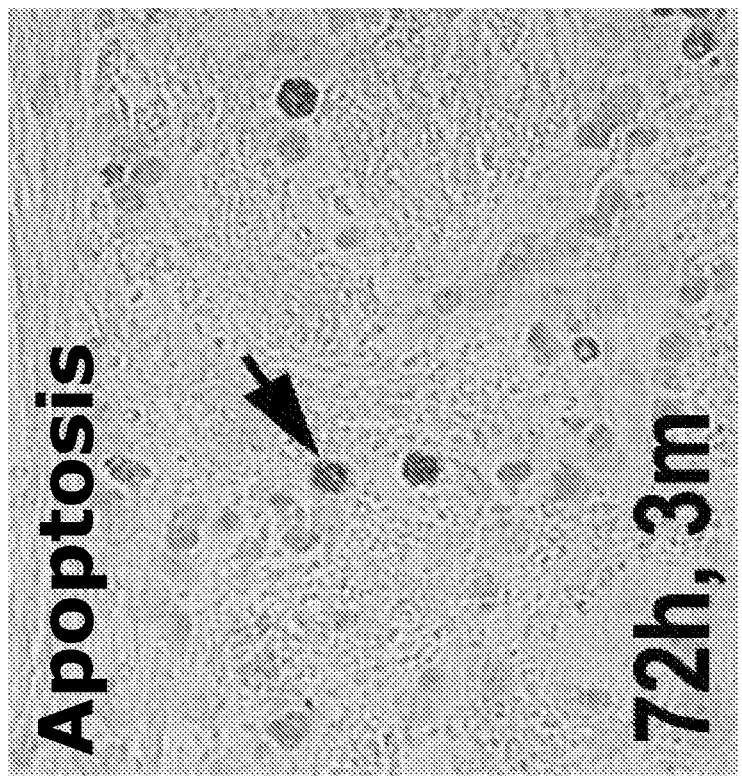
Figure 9C:
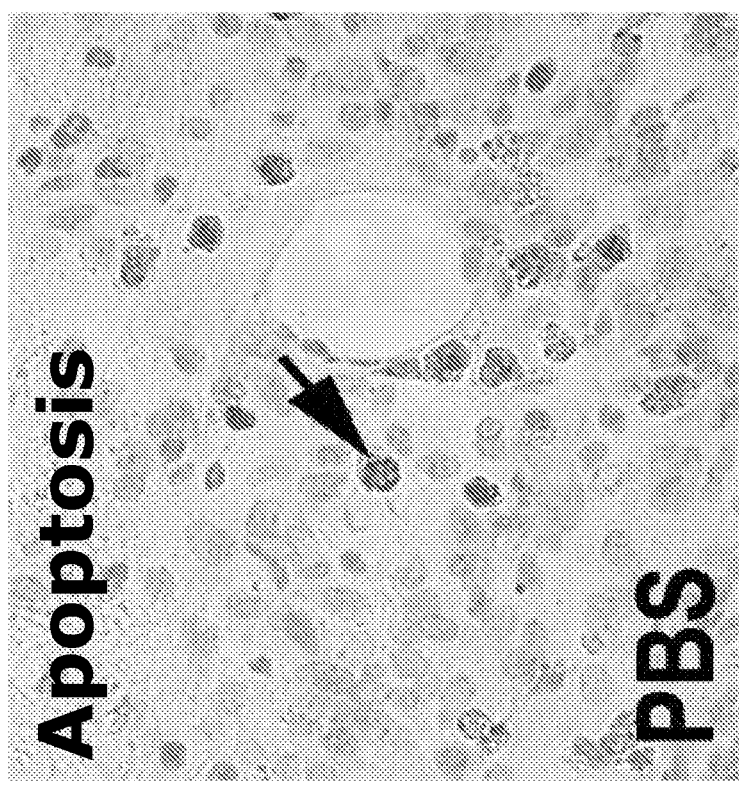
Figures 9E, 9F:
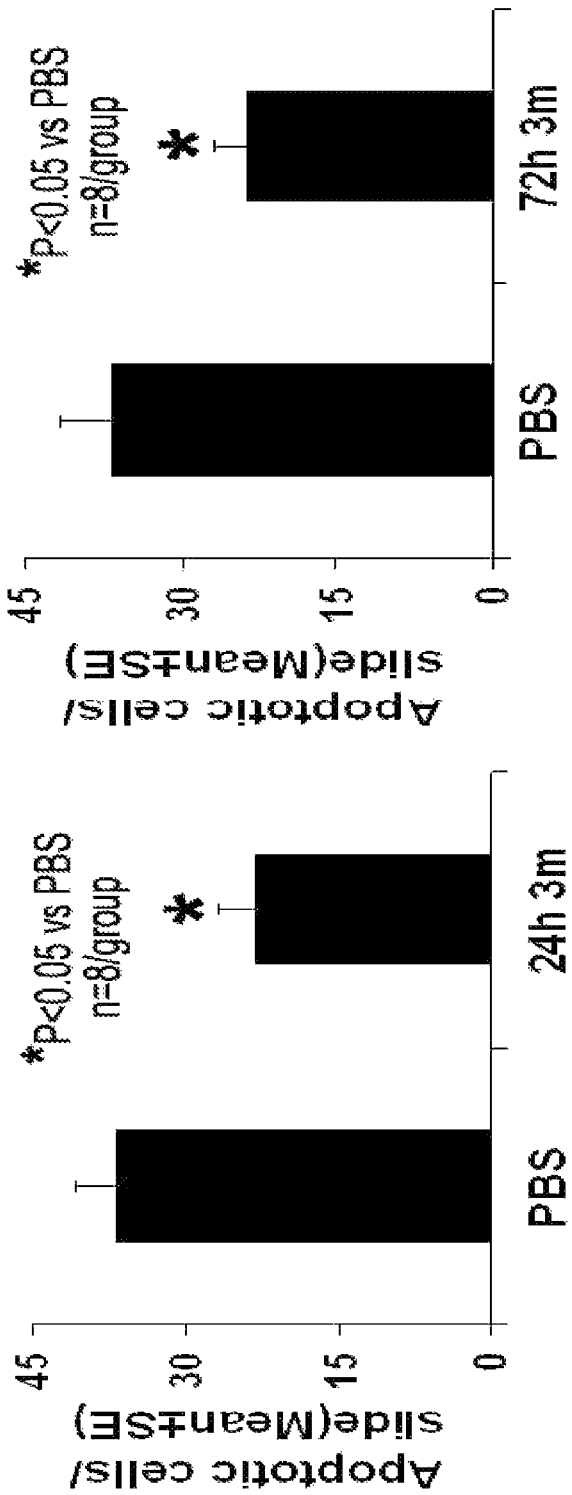
FIG. 9E shows the mean number of apoptotic cells per slide in the damaged area of the rat brains following injury and subsequent treatment with either PBS or $3\times10^6$ UTC at 24 hours post injury (n=8)
FIG. 9F shows the mean number with either PBS or $3\times10^6$ UTC at 72 hours post injury (n=8).

The TUNEL staining showed apoptotic cells with typical dark brown, rounded or oval apoptotic bodies. Scattered apoptotic cells were present throughout the damaged tissue, the vast majority of which was located in the boundary zone of hematoma. The results show that the number of apoptotic cells were significantly reduced in the ipsilateral hemisphere with $3\times10^6$ UTC at 24 hours or 72 hours after ICH compared with the control PBS group. ($p<0.05$). (See FIGS. 9E and 9F).

EXAMPLE 8

Figure 10A:
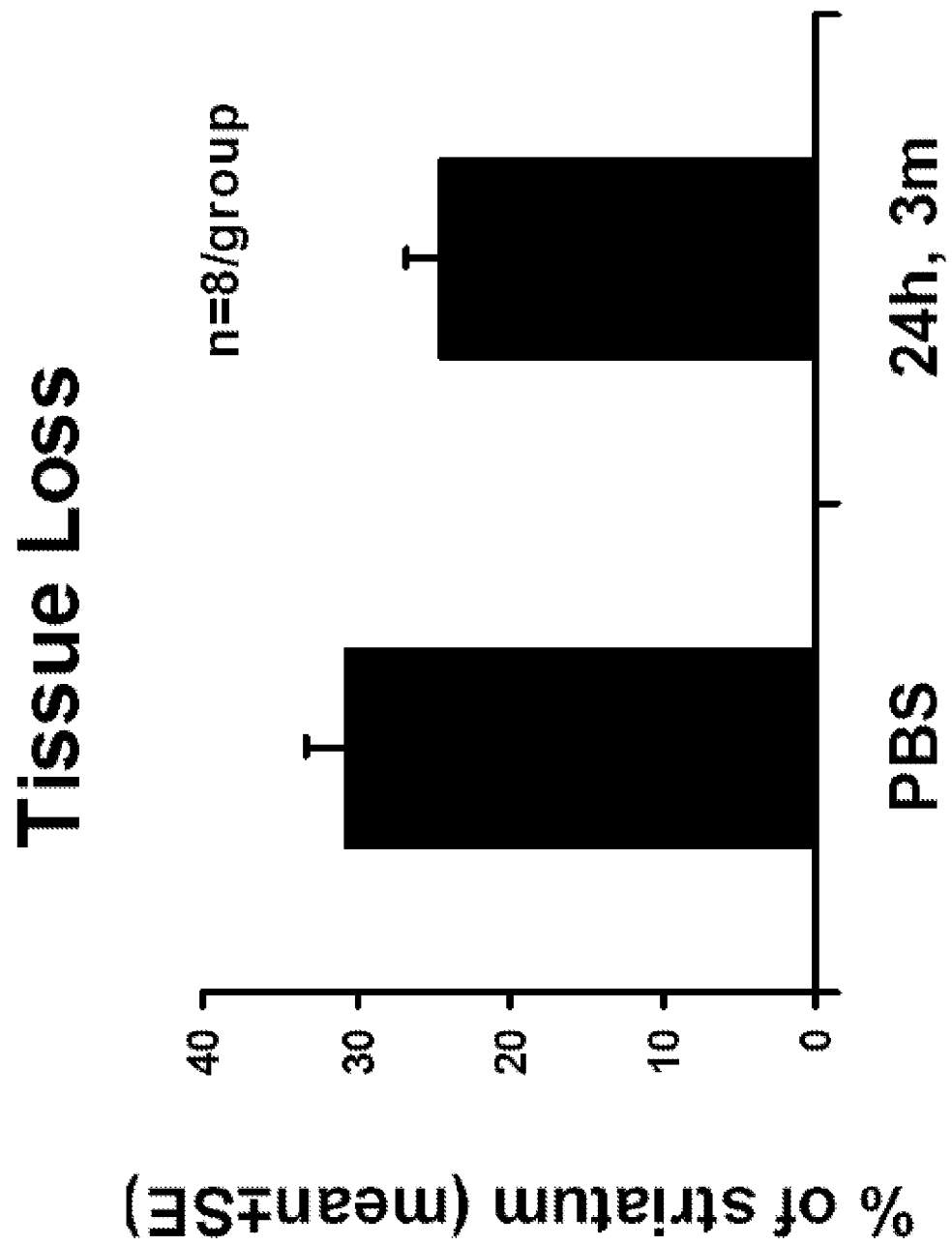
FIGS. 10A and 10B show the mean percentage of striatum lost in the rat brains following injury and subsequent treatment with either PBS or $3\times10^6$ UTC at 24 hours post injury (n=8) (FIG. 10A), and with either PBS or $3\times10^6$ UTC at 72 hours post injury (n=8) (FIG. 10B).
Figure 10B:
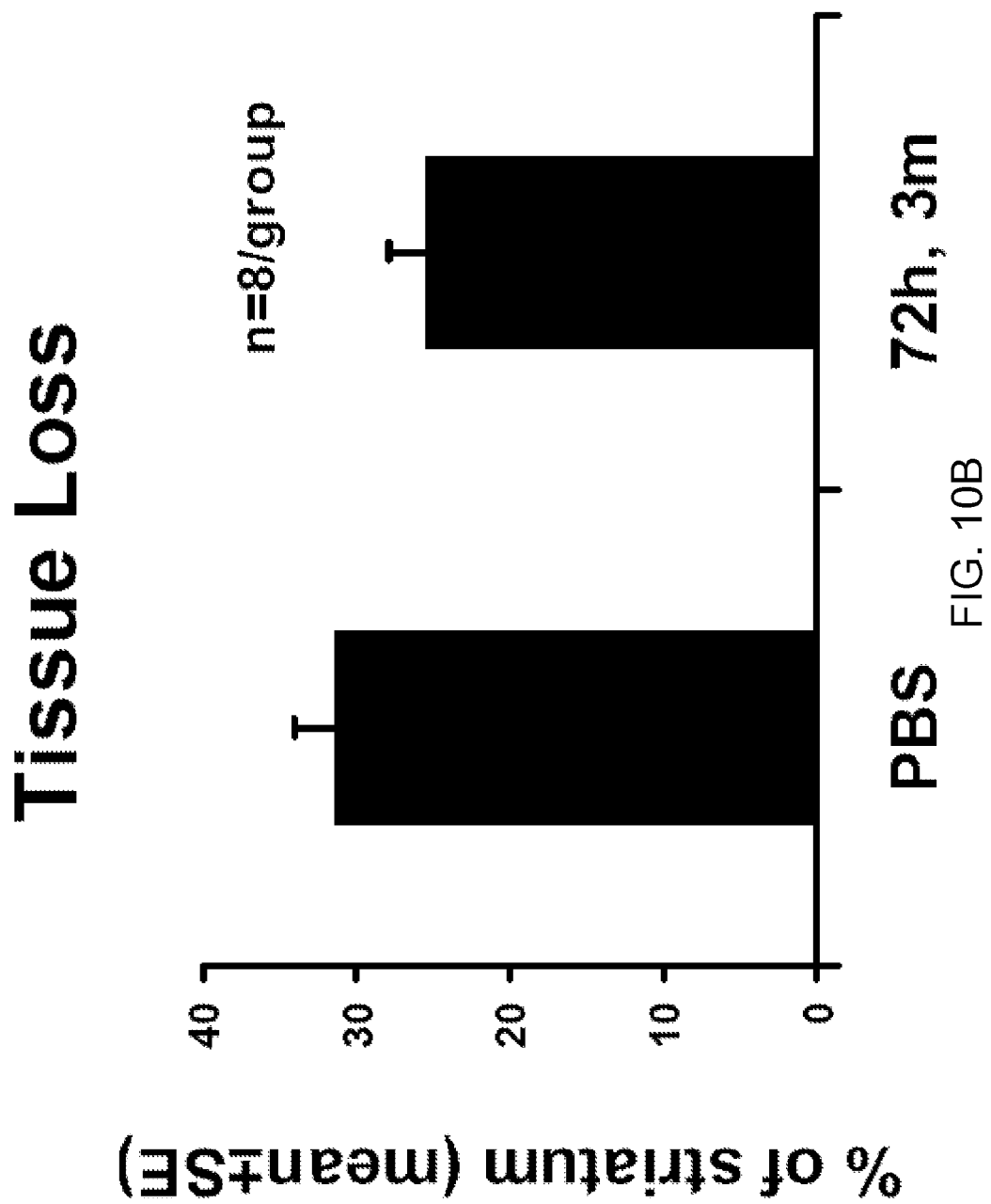

Effect of Administration of Cells Following Brain Injury on Tissue Loss in the Damaged Area of the Brain After 28 days, animals were reanesthetized, sacrificed and their brains removed as detailed in Example 3 for histological assessment. The cerebral tissues were cut into 7 equally spaced (2 mm) coronal blocks, and then processed for paraffin sectioning. A series of adjacent 6-µm-thick sections were cut from each block in the coronal plane and were stained with hematoxylin and eosin. The sections were traced by a Global Laboratory Image analysis system (Data Translation, Mariborn, Mass.). The area of preserved striatum on the side of the hemorrhage was subtracted from that of the contralateral side, thus determining the degree of tissue loss attributable to the ICH, and comparing treated to untreated animals. The results show that there is no significant difference in tissue loss with $3 \times 10^6$ UTC at 24 hours or 72 hours after ICH compared with the control PBS group. (See FIGS. 10A and 10B).

EXAMPLE 9

Effect of Administration of Cells at Different Time Points Following Brain Injury Examples 2-8 describe the effect of administration of UTC at 24 hours and 72 hours post-injury. In the present study, the therapeutic window was expanded by a delayed administration at 7 days, which better mimics the clinical situation (i.e., more patients will be able to be treated if the cells could be administered at 7 days).

ICH was induced in adult Wistar rats as described in Example 2 (See Seyfried, D, et al., *J Neurosurg*, 2006; 104:313-318), with a group of rats (n=40) divided into 4 groups of 10 animals each. At 72 hours or 1 week after ICH, randomly selected animals underwent cell transplantation. Animals were anesthetized with 3.5% halothane in $N_2O:O_2$ (2:1) and maintained at 0.5% halothane using a facemask. UTC in 2 ml total fluid volume PBS or PBS alone (control) were injected into a tail vein. Experimental groups (n=10/group) consisted of PBS alone and UTC (3 million). All rats were allowed to survive 28 days after cell transplantation.

In all animals, batteries of behavioral tests were measured one day, 4 days, 1 week, 2 weeks, 3 weeks, 4 weeks, 31 days and 35 days thereafter.

As described in Example 2, nMSS (See Chen, J, et al., *Stroke*, 2001; 32:1005-1011) and the Corner Test (see Zhang, L, et al., *J Neurosci Methods*, 2002; 117:207-214) indicate neurological function.

The Cylinder Test (see Zhang, L, et al., *J Neurosci Methods*, 2002; 117:207-214, and Hua, Y, et al., *Stroke*, 2002; 33:2478-2484) was adapted for use in rat to assess forelimb use and rotation asymmetry in a transparent cylinder (20 in cm diameter and 30 cm in height) for 3 to 10 minutes depending on the degree of activity during the trial. A mirror was placed to the side of the cylinder at an angle to enable the recording of forelimb movements even when the animal was turned away from the camera. Scoring was done by an experimenter blinded to the condition of the animal using a video cassette recorder with slow-motion and clear stop-frame capabilities. The behavior was scored according to the following criteria: (1) independent use of the left or right forelimb for contacting the wall during a full rear to initiate a weight-shifting movement or to regain center of gravity while moving laterally in a vertical posture and (2) simultaneous use of both the left and right forelimbs for contacting the cylinder wall during a full rear and for alternating lateral stepping movements along the wall.

For the Adhesive-Removal Somatosensory Test (see, Chen, J, et al., *Stroke*, 2001; 32:2682-2688) small pieces of adhesive-backed paper dots (of equal sizes, 56.55 mm²) were used as bilateral tactile stimuli occupying the distal-radial region on the wrist of each forelimb. The rat was then returned to its cage. The time to remove each stimulus from forelimbs was recorded on 5 trials per day. Before surgery, the animals were trained for 3 days. Once the rats were able to remove the dots within 10 seconds, they were subjected to ICH.

Results

1. Neurological Functional

Figure 11A:
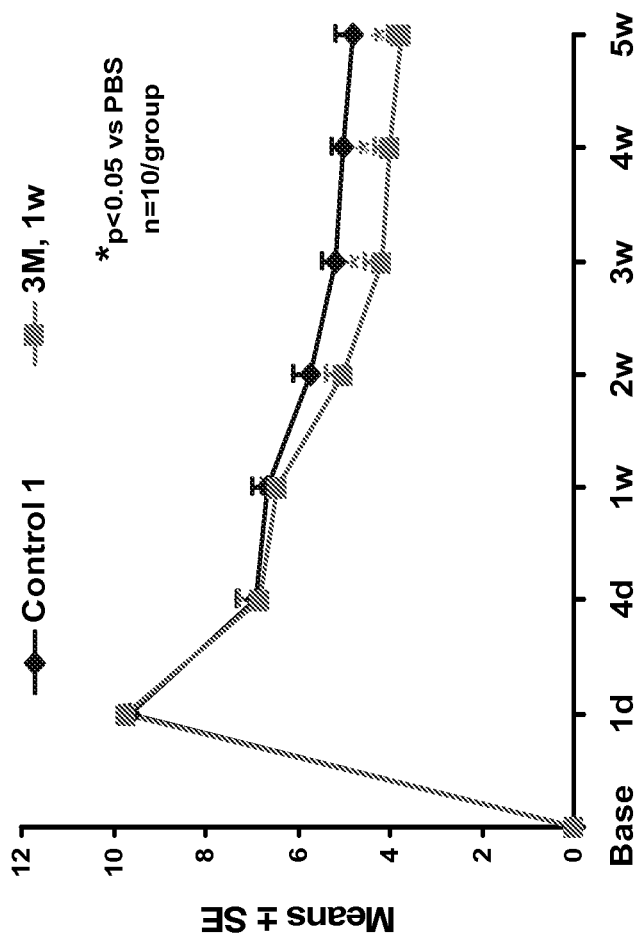
FIGS. 11A and 11B show the mNSS at 1 day, 4 days, 7 days, 14 days, 21 days, 28 days, 31 days and 35 days after injury in rats treated with PBS or $3\times10^6$ UTC at 7 days following the injury (n=10) (FIG. 11A), and with PBS or $3\times10^6$ UTC at 3 days following the injury (n=10) (FIG. 11B).
Figure 11B:
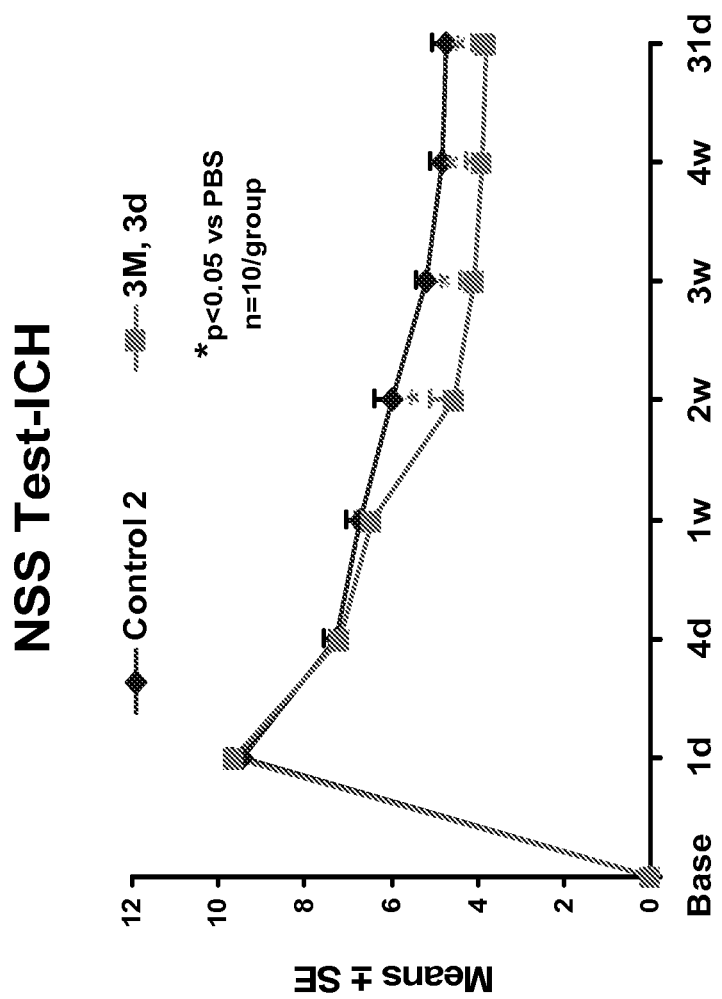

Results from the functional tests indicated that rats treated at day 7 or day 3 with $3 \times 10^6$ UTC exhibited significant ($p<0.05$) neurological functional improvement in the mNSS test, corner test, and cylinder test.

mNSS: mNSS total scores decreased significantly at days 21, 28, and 35 in rats receiving treatment at 7 days; and total scores decreased significantly at days 14, 21, 28 and 31 among rats treated at day 3 with $3 \times 10^6$ UTC compared to controls. (See, FIGS. 11A and 11B).

Figure 12A:
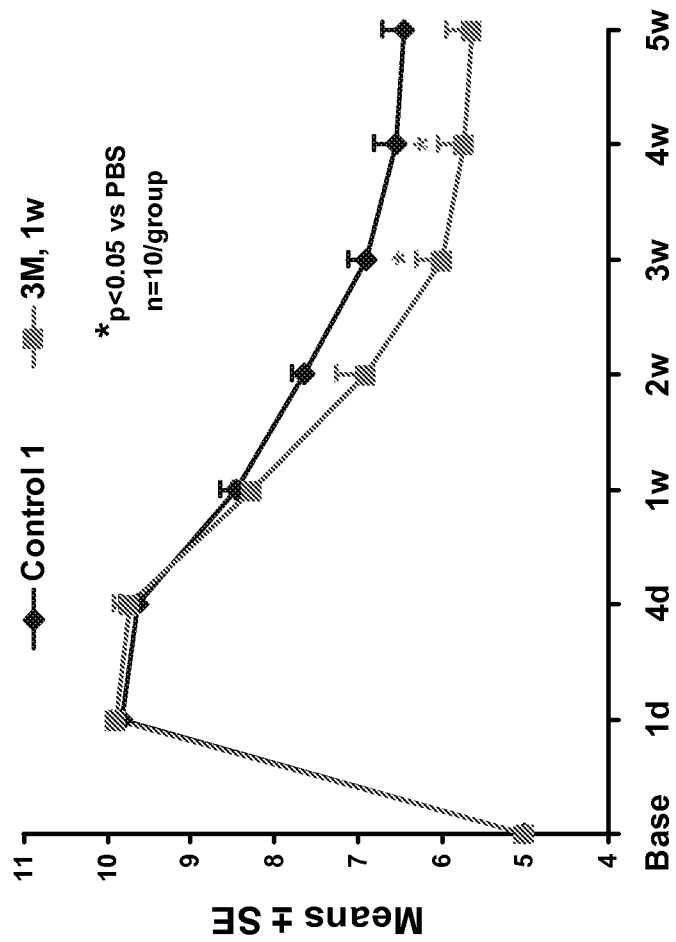
FIGS. 12A and 12B show the corner test score at 1 day, 4 days, 7 days, 14 days, 21 days, 28 days, 31 days and 35 days, after injury in rats treated with PBS or $3\times10^6$ UTC at 7 days following the injury (n=10) (FIG. 12A), and with PBS or $3\times10^6$ UTC at 3 days following the injury (n=10) (FIG. 12B).
Figure 12B:
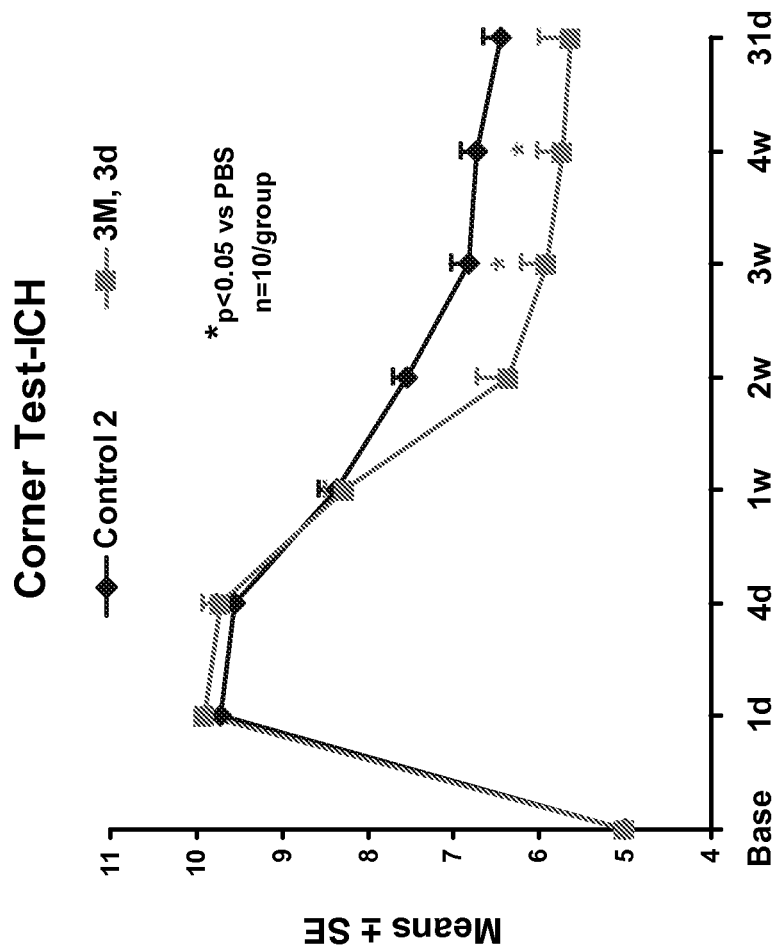

Corner Test: Corner test scores decreased significantly at days 21 and 28; and scores decreased but not significantly at days 31 and 35 among rats treated at day 7 or day 3 with $3 \times 10^6$ UTC compared to controls. (See, FIGS. 12A and 12B).

Figure 13A:
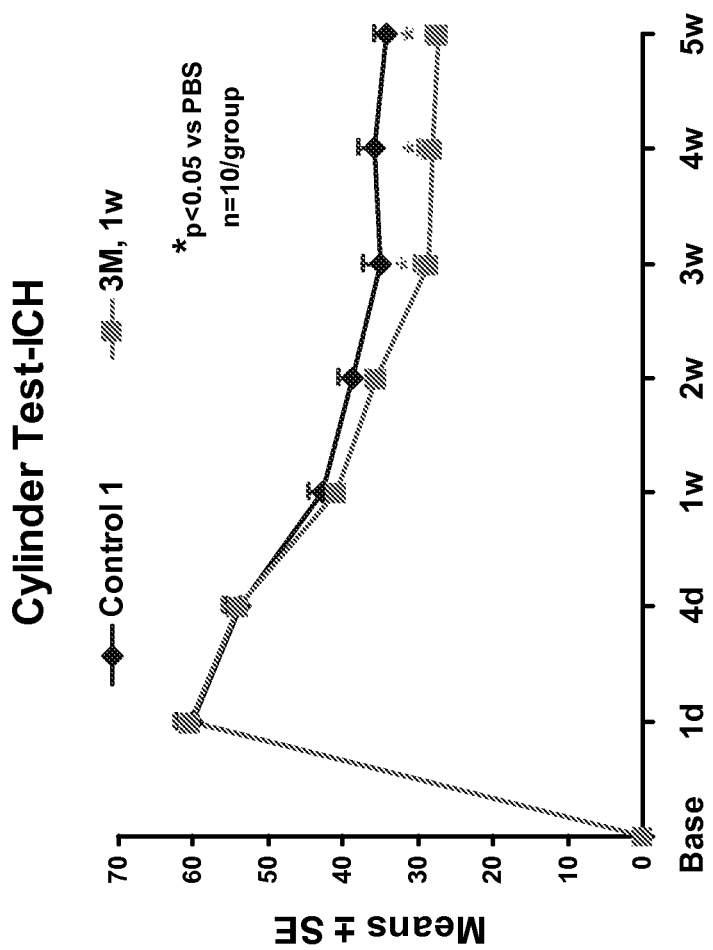
FIGS. 13A and 13B show the cylinder test score at 1 day, 4 days, 7 days, 14 days, 21 days, 28 days, 31 days and 35 days, after injury in rats treated with PBS or $3\times10^6$ UTC at 7 days following the injury (n=10) (FIG. 13A), and with PBS or $3\times10^6$ UTC at 3 days following the injury (n=10) (FIG. 13B).
Figure 13B:
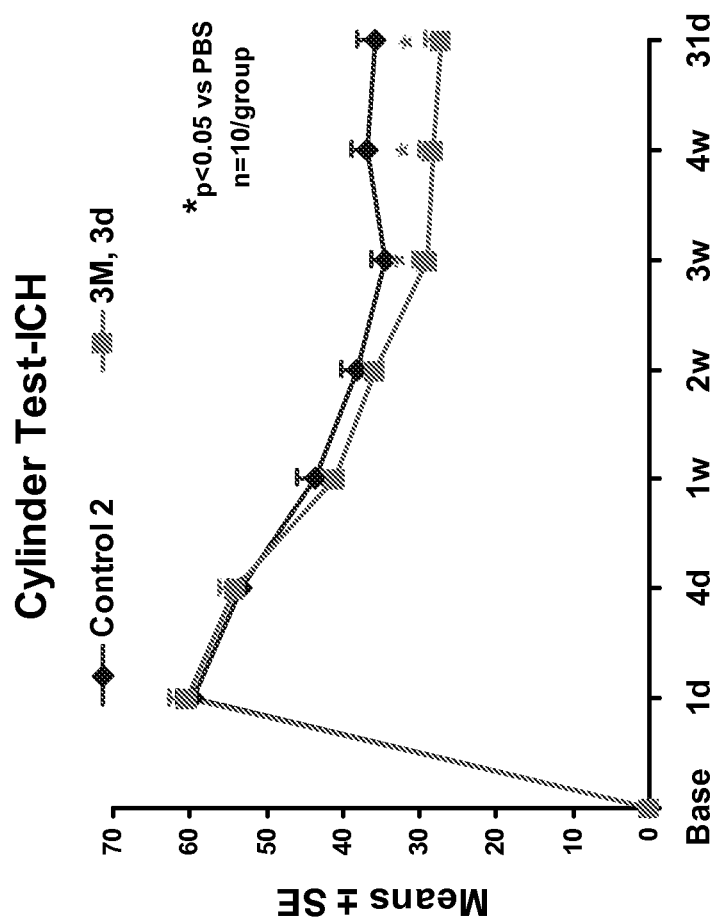

Cylinder Test: Cylinder scores decreased significantly at days 21, 28, 31 and 35, among rats treated at day 7 or day 3 with $3 \times 10^6$ UTC compared to controls. (See, FIGS. 13A and 13B).

Figure 14A:
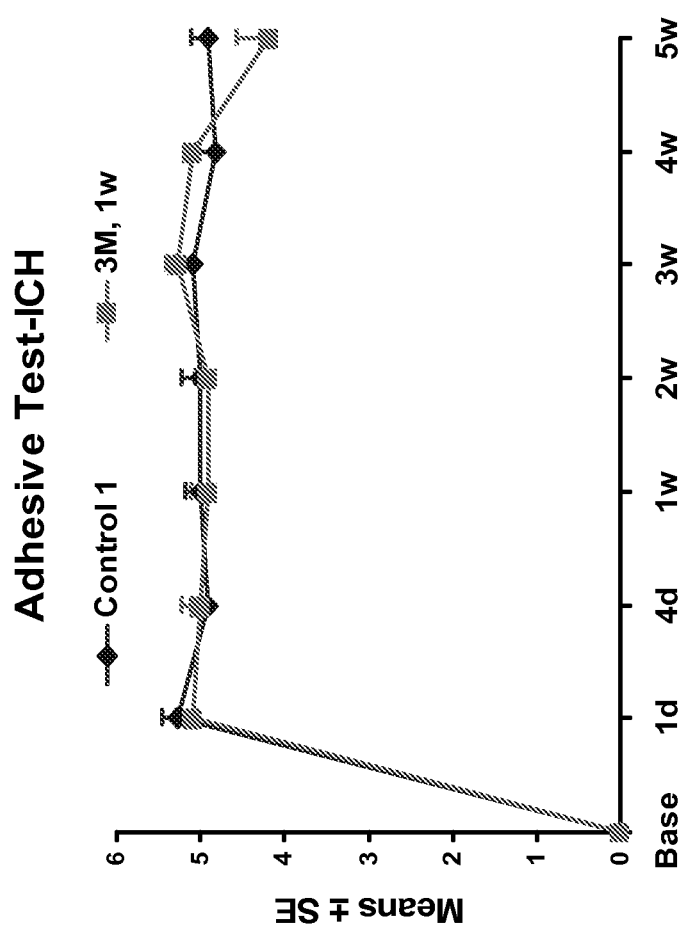
FIGS. 14A and 14B show the adhesive test score at 1 day, 4 days, 7 days, 14 days, 21 days, 28 days, 31 days and 35 days, after injury in rats treated with PBS or $3\times10^6$ UTC at 7 days following the injury (n=10) (FIG. 14A), and with PBS or $3\times10^6$ UTC at 3 days following the injury (n=10) (FIG. 14B).
Figure 14B:
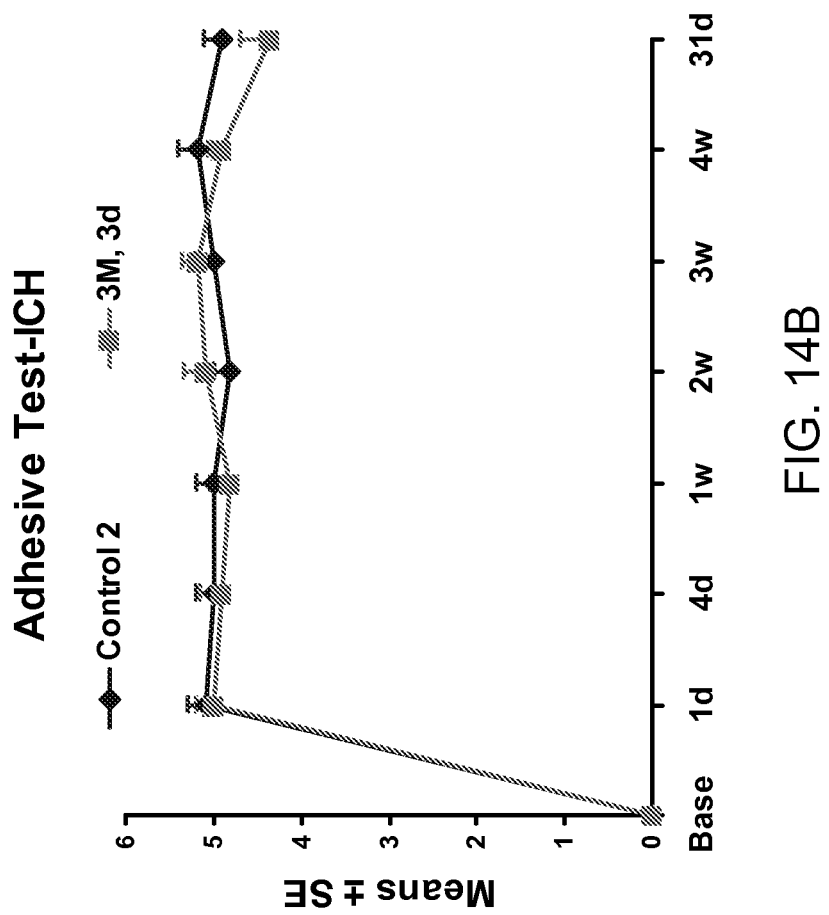
Figure 15A:
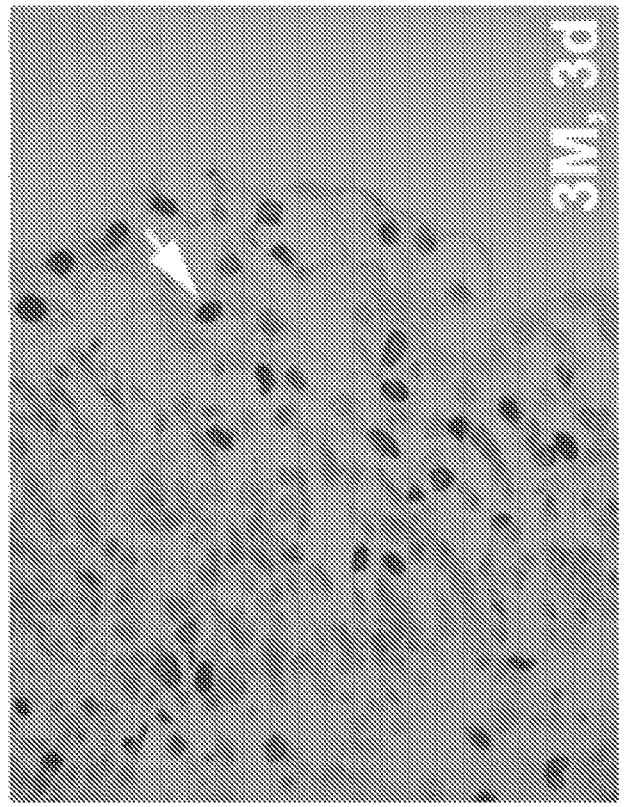
FIGS. 15A-15D show BrdU incorporation in cells of the SVZ in rats following injury and subsequent treatment with PBS at 72 hours post injury (FIG. 15A), with $3\times10^6$ UTC at 72 hours post injury (FIG. 15B), with PBS at 7 days post injury (FIG. 15C), and with $3\times10^6$ UTC at 7 days post injury (FIG. 15D).
Figure 15B:
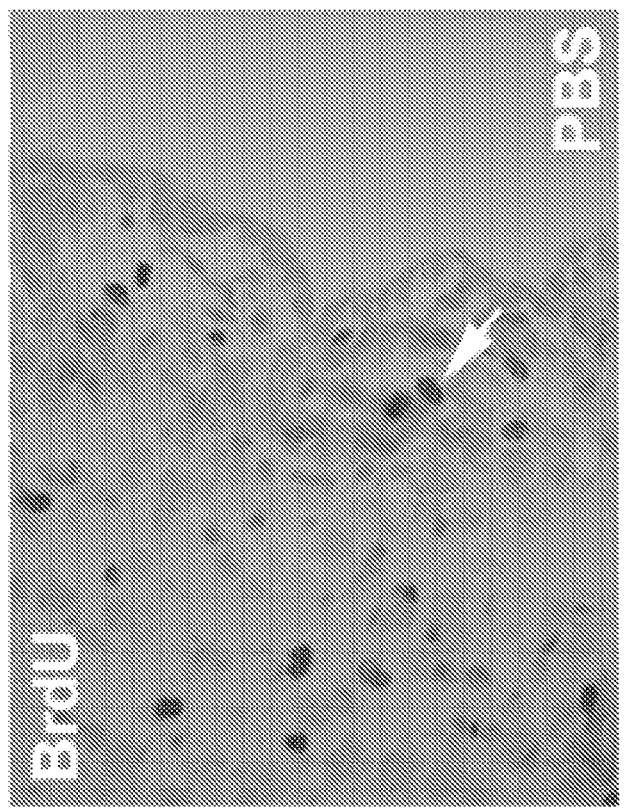
Figure 15D:
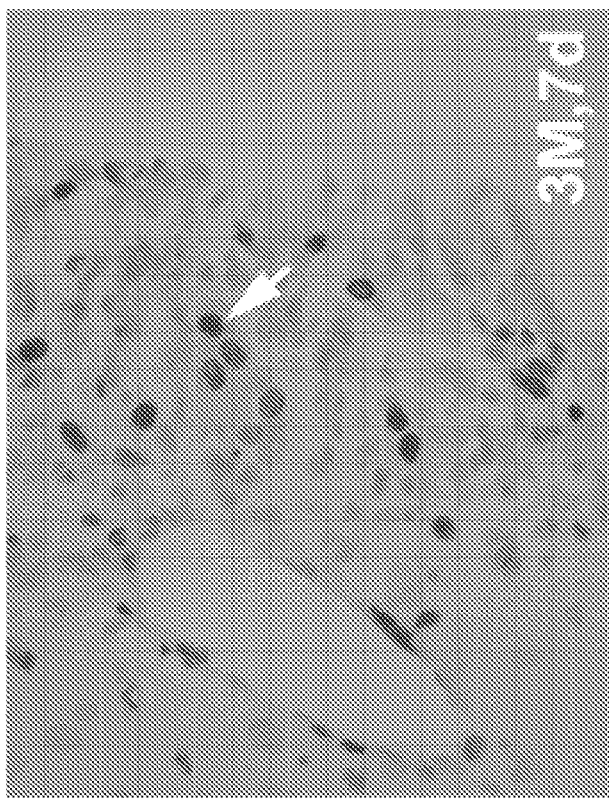
Figure 15C:
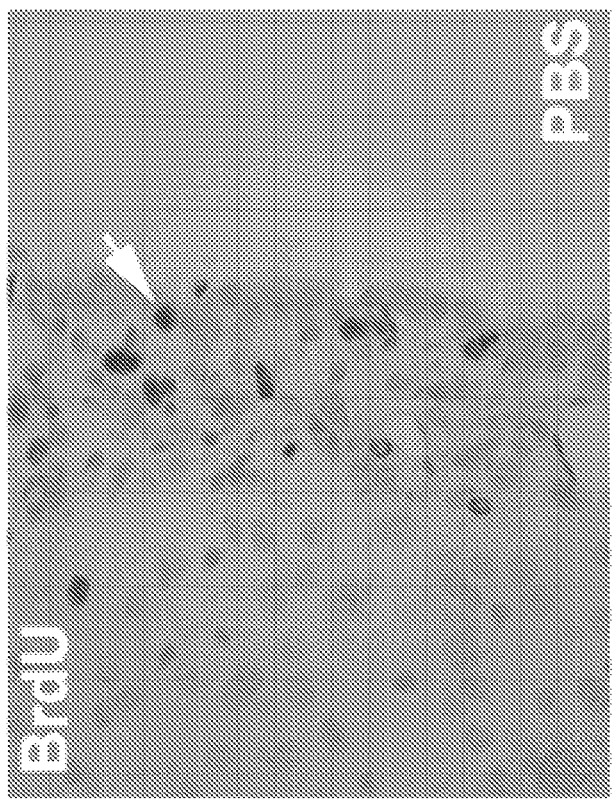
Figures 15E, 15F:
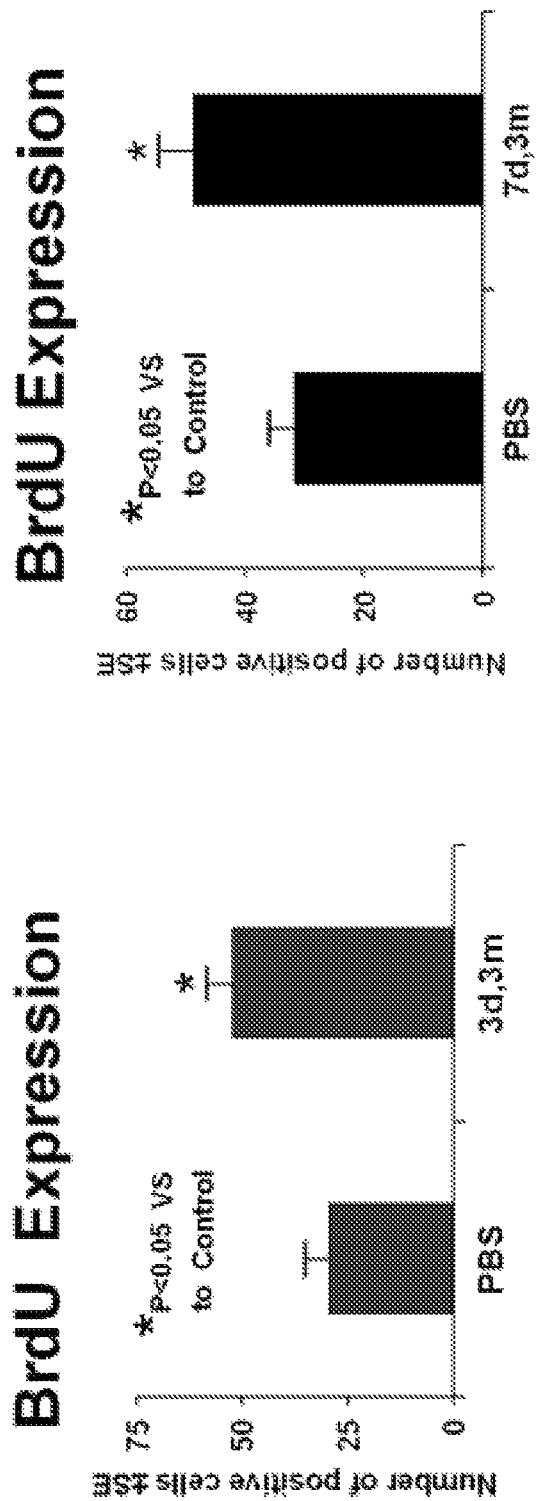
FIG. 15E shows the mean number of BrdU positive cells in the SVZ of rats following injury and subsequent treatment with either PBS or $3\times10^6$ UTC at 72 hours post injury (n=8)
FIG. 15F shows the mean number with either PBS or $3\times10^6$ UTC at 7 days post injury (n=8).
Figure 16B:
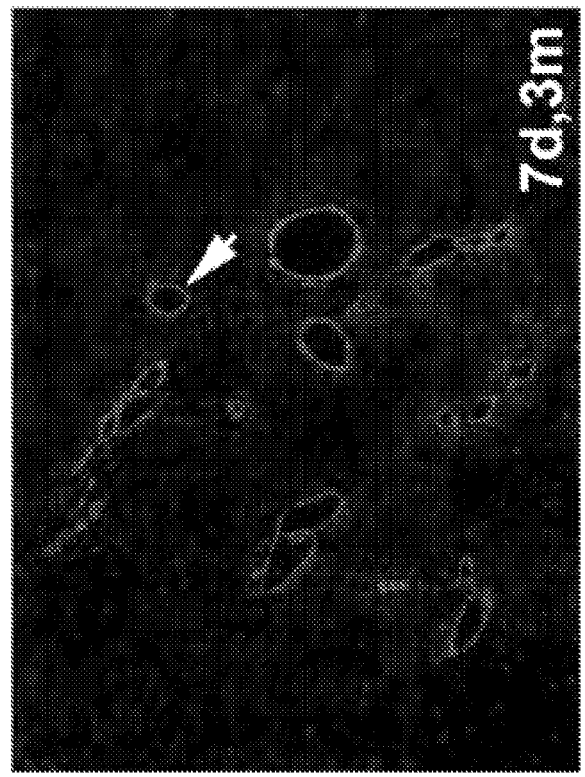
FIGS. 16A-D show VWF expression in blood vessels in damaged areas of the rat brains following injury and subsequent treatment with PBS at 7 days post injury (FIG. 16A), with 3×10$^6$ UTC at 7 days post injury (FIG. 16B), with PBS at 72 hours post injury (FIG. 16C), and with 3×10$^6$ UTC at 72 hours post injury (FIG. 16D).
Figure 16A:
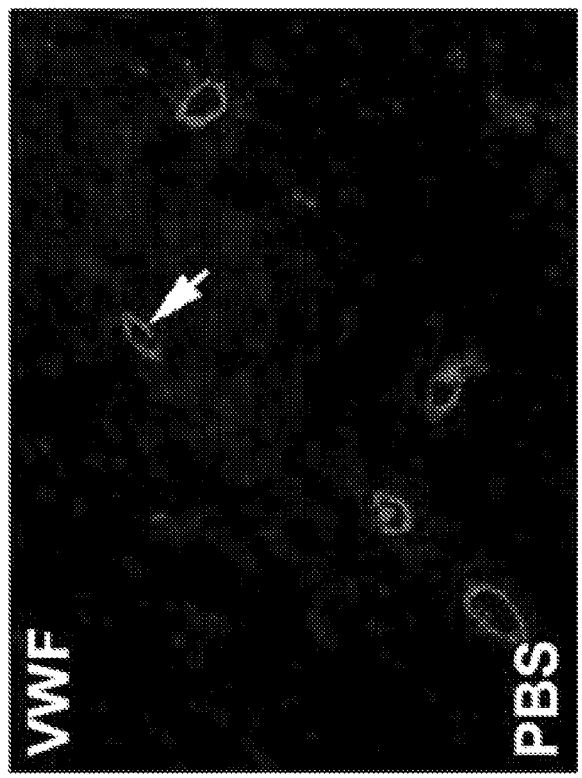
Figure 16D:
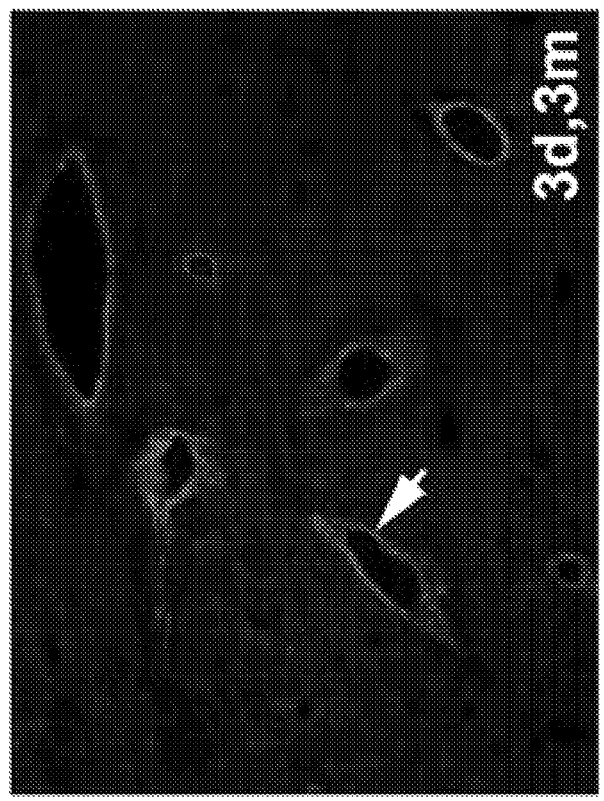
Figure 16C:
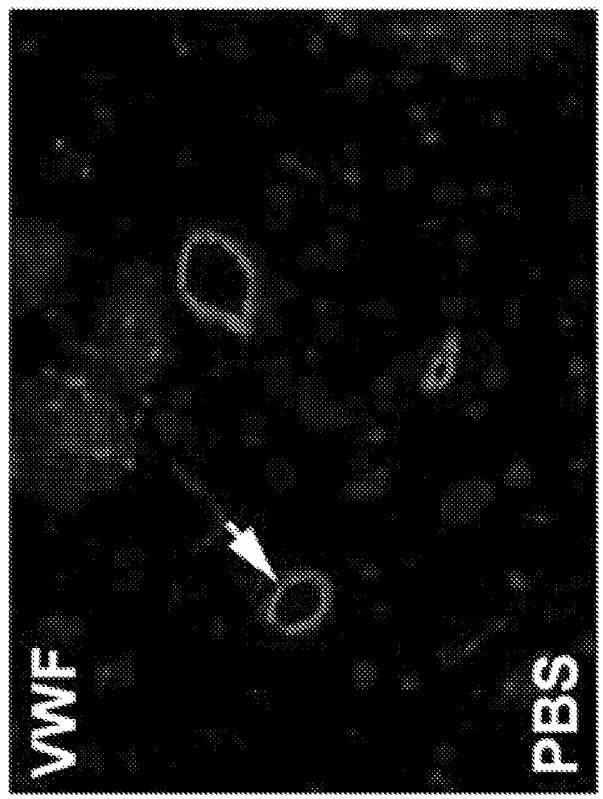
Figure 16F:
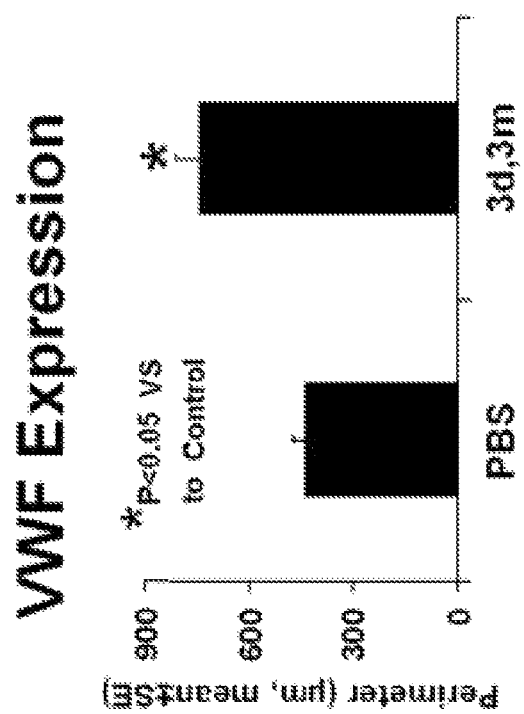
FIG. 16F shows the mean diameter (μm) with either PBS or 3×10$^6$ UTC at 72 hours post injury (n=10).
Figure 16E:
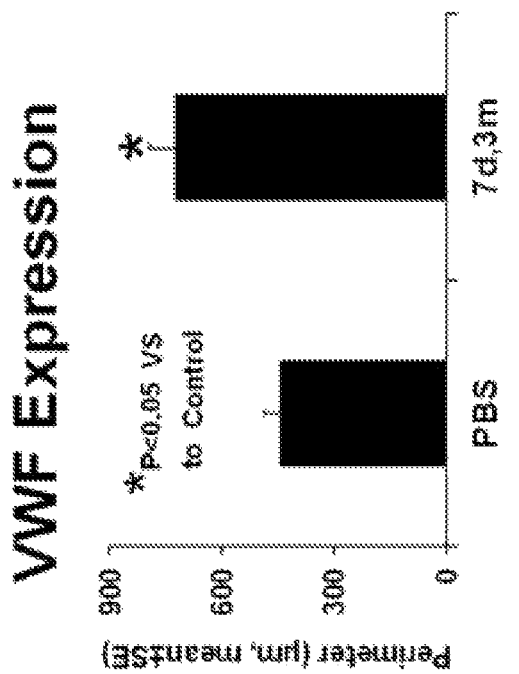
FIG. 16E shows the mean diameter (μm) of blood vessels in damaged areas of the rat brains following injury and subsequent treatment with either PBS or 3×10$^6$ UTC at 7 days post injury (n=10)

Adhesive Test: Adhesive test scores did not decrease significantly at any time point, among rats treated at day 7 or day 3 with $3 \times 10^6$ UTC compared to controls. (See, FIGS. 14A and 14B).

2. Histology

The number of BrdU positive cells were significantly increased in the SVZ of the ipsilateral hemisphere of rats treated with $3 \times 10^6$ UTC at day 3 or day 7 after ICH compared with the control PBS group ($p<0.05$). (See, FIGS. 15A-15F).

Enlarged and thin-walled vessels in the boundary around the lesion are indicative of angiogenesis (See, Li, Y, et al., *Neurology*, 2002; 59:514-523). Data showed that the perimeters of vessels were significantly increased in treatment groups with $3 \times 10^6$ UTC at day 7 or day 3 after ICH compared with the control PBS group ($p<0.05$). (See, FIGS. 16A-16F).

Figure 17B:
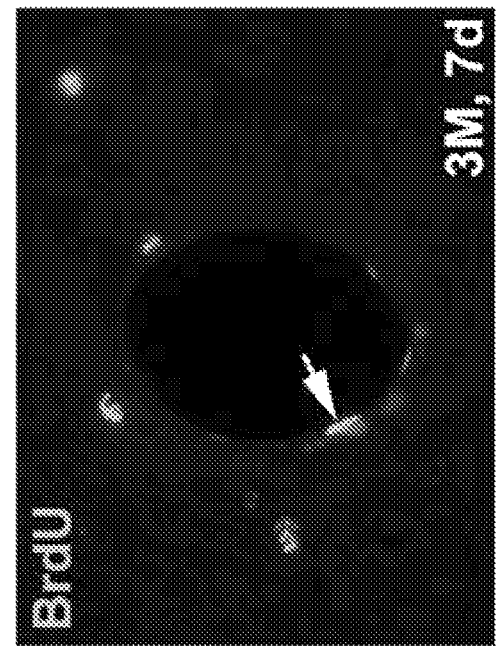
FIG. 17B shows BrdU incorporation in endothelial cells with 3×10$^6$ UTC at 7 days post injury (n=10).
Figure 17A:
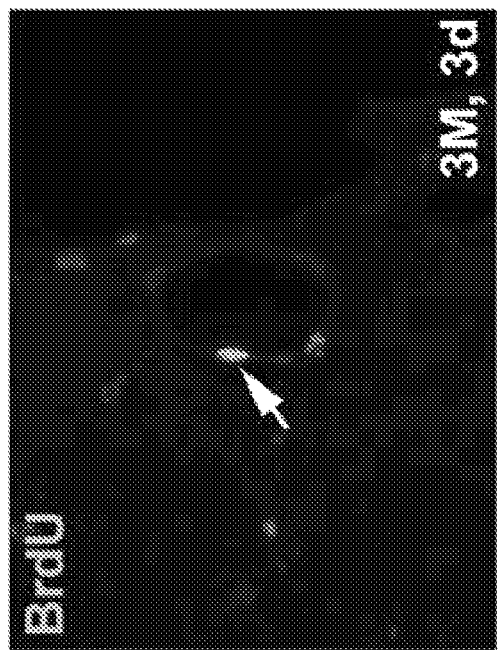
FIG. 17A shows BrdU incorporation in endothelial cells of blood vessels in damaged areas of the rat brains following injury and subsequent treatment with 3×10$^6$ UTC at 3 days post injury (n=10)
Figure 17D:
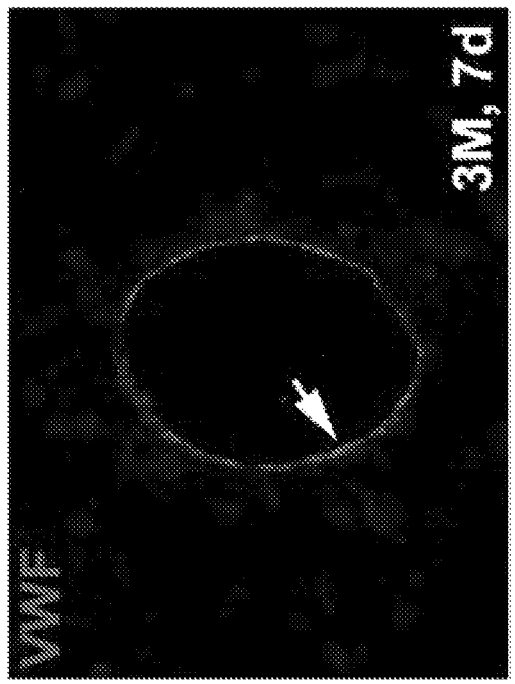
FIG. 17D shows VWF expression in blood vessels with 3×10$^6$ UTC at 3 days post injury (n=10).
Figure 17C:
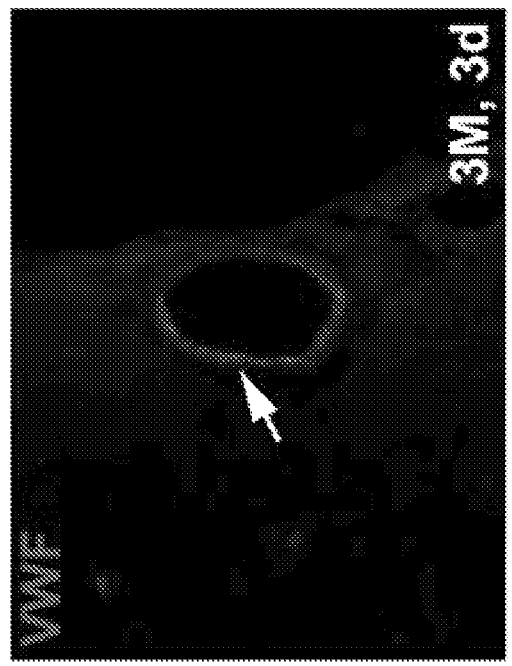
FIG. 17C shows VWF expression in blood vessels in damaged areas of the rat brains following injury and subsequent treatment with 3×10$^6$ UTC at 3 days post injury (n=10)
Figure 17F:
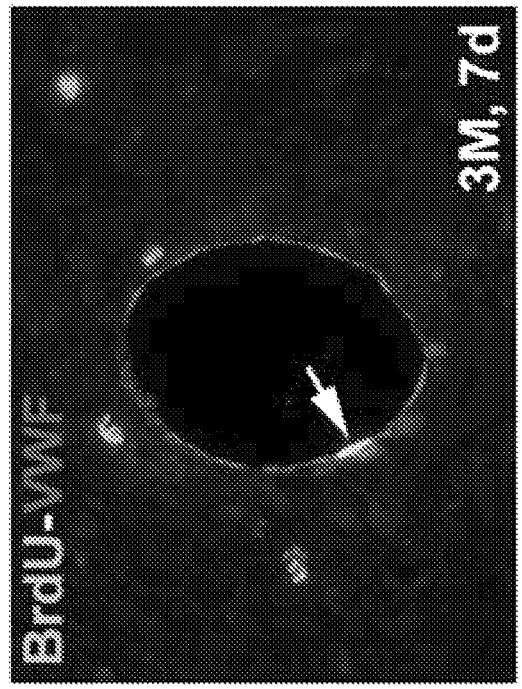
FIG. 17F shows BrdU incorporation in endothelial cells with 3×10$^6$ UTC at 7 days post injury (n=10).
Figure 17E:
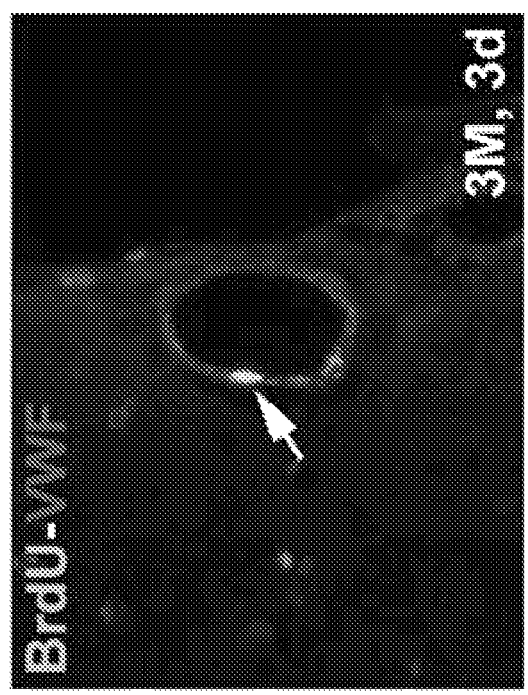
FIG. 17E shows BrdU incorporation in endothelial cells that are co-localized with VWF expressing tissue in blood vessels in damaged areas of the rat brains following injury and subsequent treatment with 3×10$^6$ UTC at 3 days post injury (n=10)
Figure 18B:
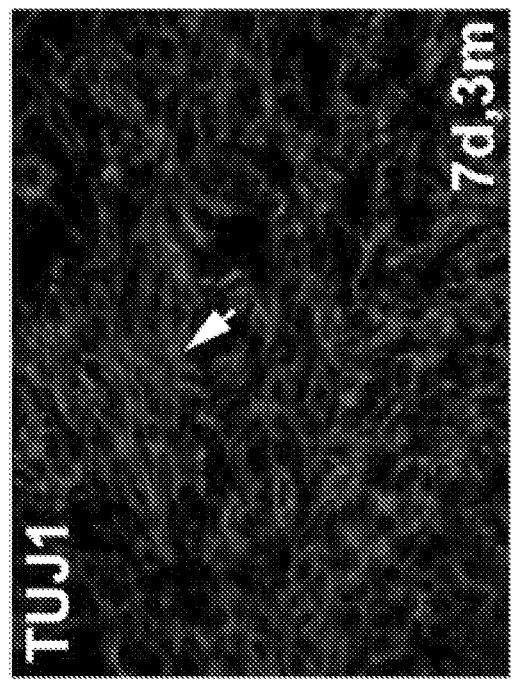
FIGS. 18A-D show TUJ1 expression in the SVZ of the rat brains following injury and subsequent treatment with PBS at 7 days post injury (FIG. 18A), with 3×10$^6$ UTC at 7 days post injury (FIG. 18B), with PBS at 3 days post injury (FIG. 18C), with 3×10$^6$ UTC at 3 days post injury (FIG. 18D).
Figure 18A:
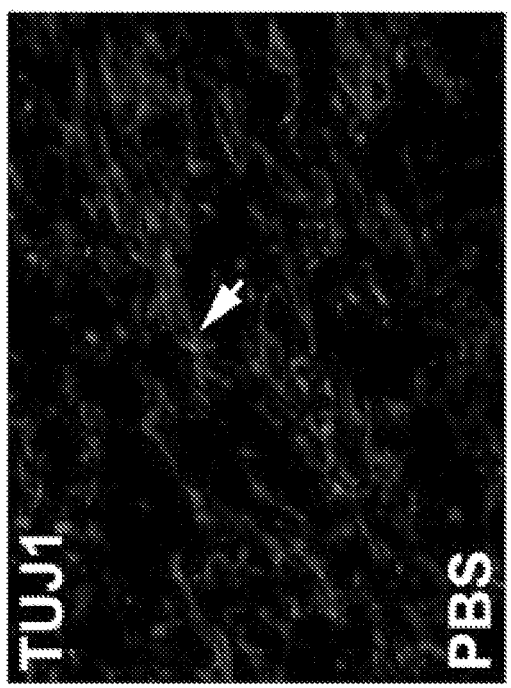
Figure 18D:
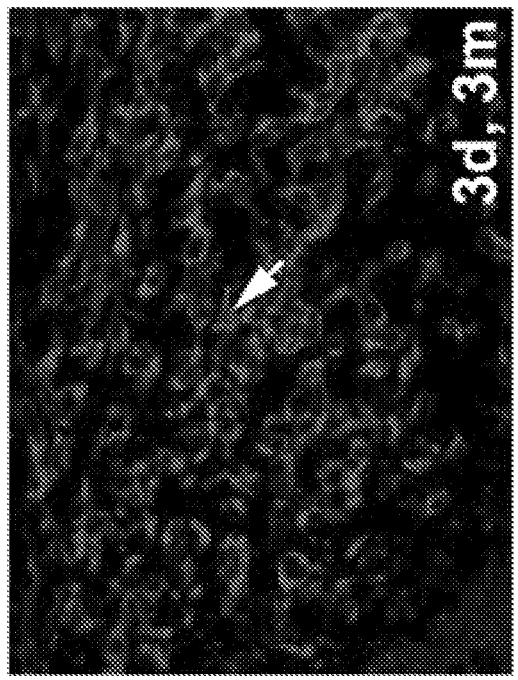
Figure 18C:
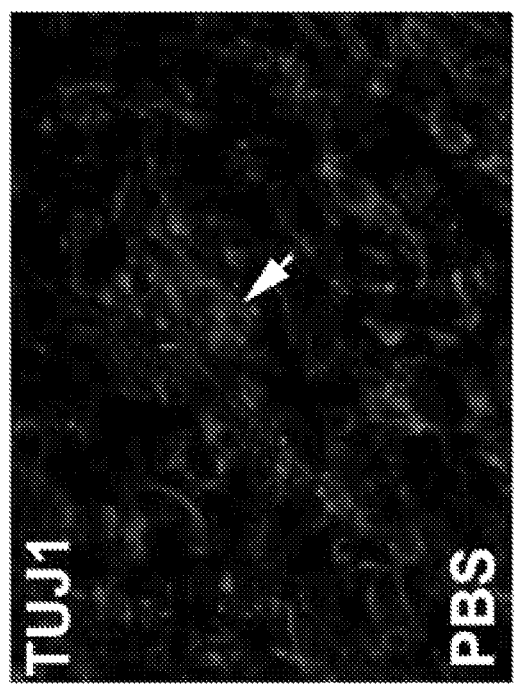
Figures 18E, 18F:
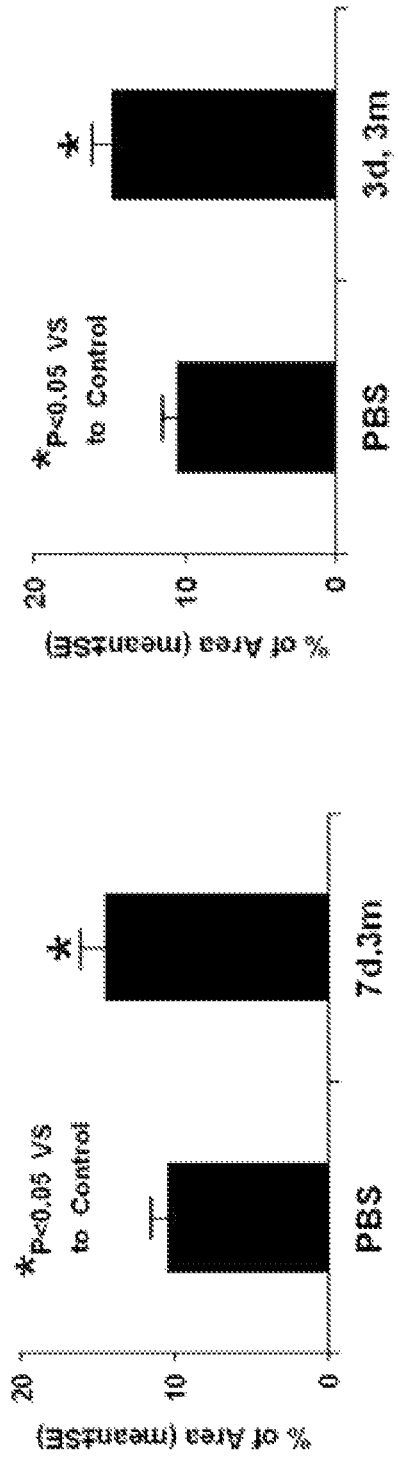
FIG. 18E shows the mean percentage of area of the SVZ of the rat brains following injury and subsequent treatment with either PBS or 3×10$^6$ UTC at 7 days post injury (n=10) that is positive for TUJ1 expression.
FIG. 18F shows the mean percentage of area with either PBS or 3×10$^6$ UTC at 72 hours post injury (n=10) that is positive for TUJ1 expression.
Figure 19B:
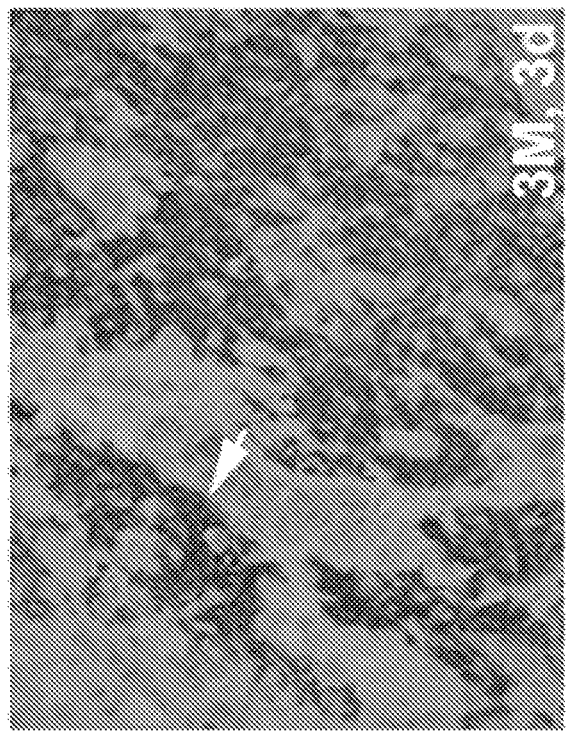
FIGS. 19A-D show synaptophysin expression in the boundary zone of hematoma of the rat brains following injury and subsequent treatment with PBS at 72 hours post injury (FIG. 19A), with 3×10$^6$ UTC at 72 hours post injury (FIG. 19B), with PBS at 7 days post injury (FIG. 19C), with 3×10$^6$ UTC at 7 days post injury (FIG. 19D).
Figure 19A:
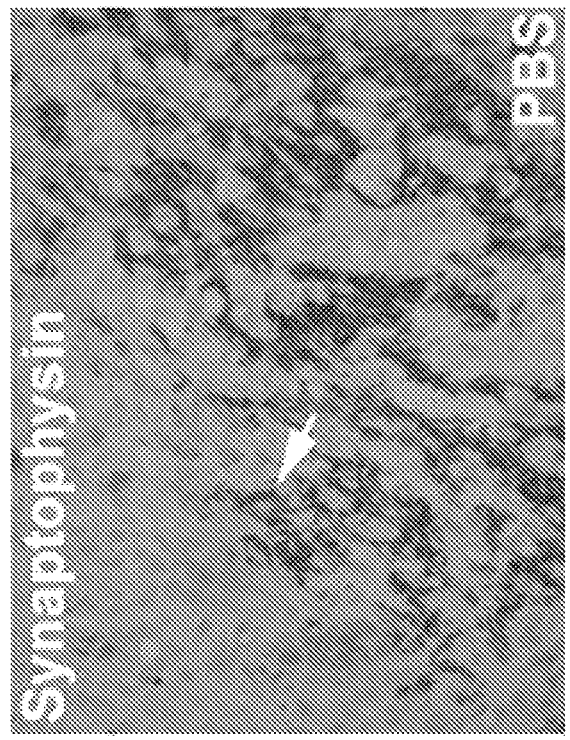
Figure 19D:
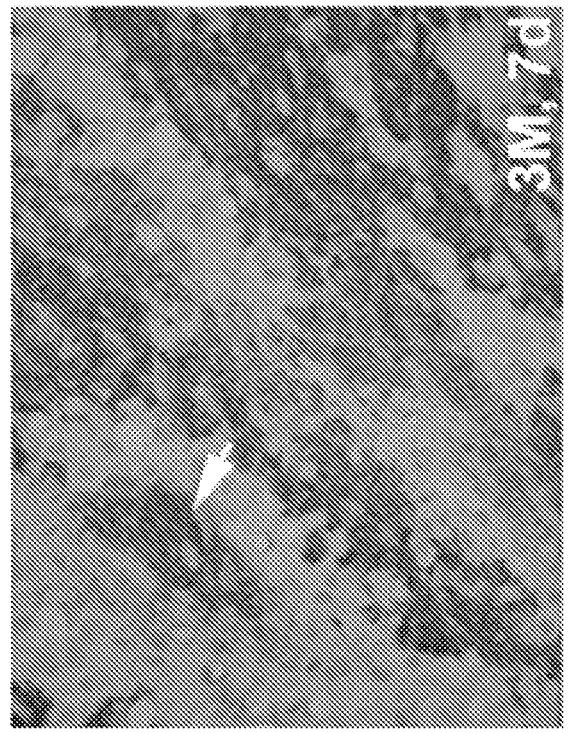
Figure 19C:
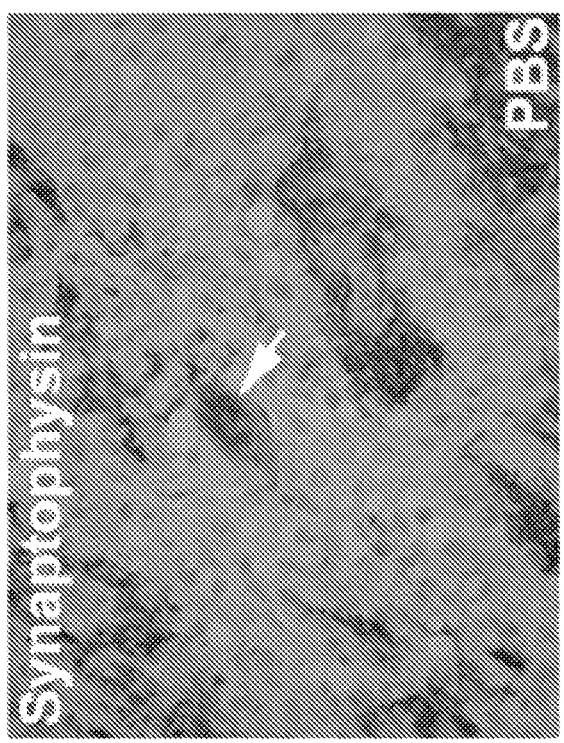
Figure 19F:
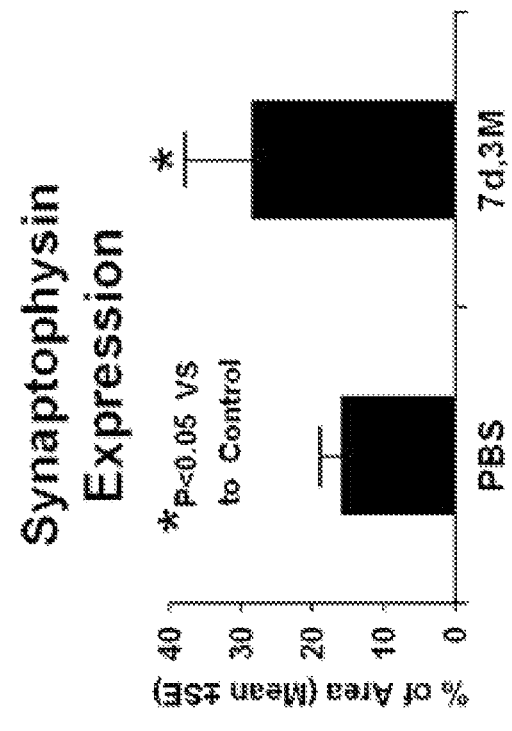
FIG. 19F shows the mean percentage of area with either PBS or 3×10$^6$ UTC at 7 days post injury (n=10) that is positive for synaptophysin expression.
Figure 19E:
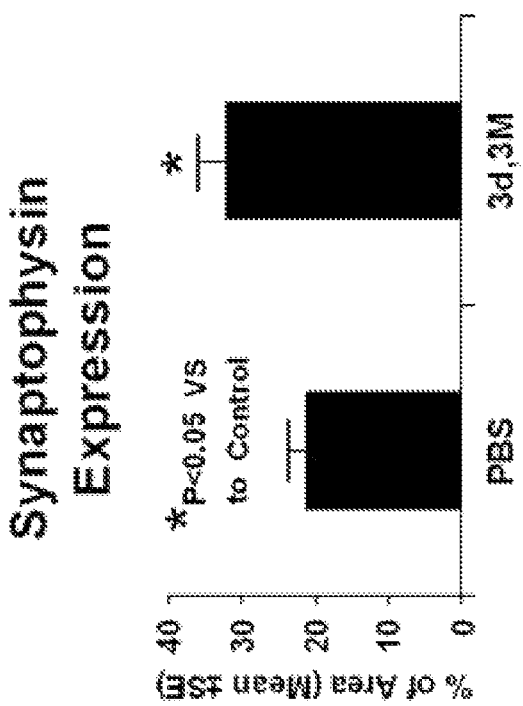
FIG. 19E shows the mean percentage of area of the boundary zone of hematoma of the rat brains following injury and subsequent treatment with either PBS or 3×10$^6$ UTC at 72 hours post injury (n=10) that is positive for synaptophysin expression.
Figure 20B:
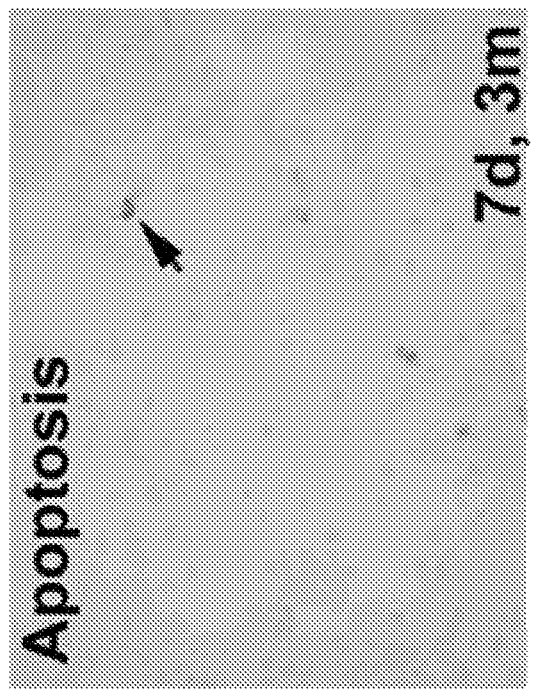
FIGS. 20A-D show TUNEL staining of apoptotic cells in the damaged area of the rat brains following injury and subsequent treatment with PBS at 7 days post injury (FIG. 20A), with 3×10$^6$ UTC at 7 days post injury (FIG. 20B), with PBS at 72 hours post injury (FIG. 20C), with 3×10$^6$ UTC at 72 hours post injury (FIG. 20D).
Figure 20A:
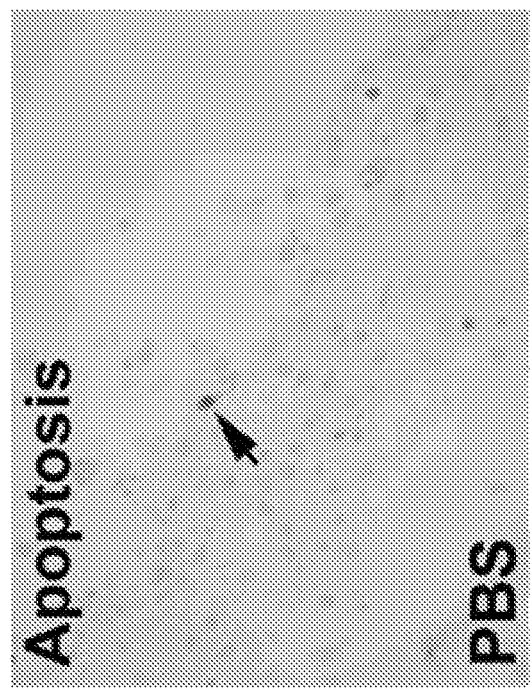
Figure 20D:
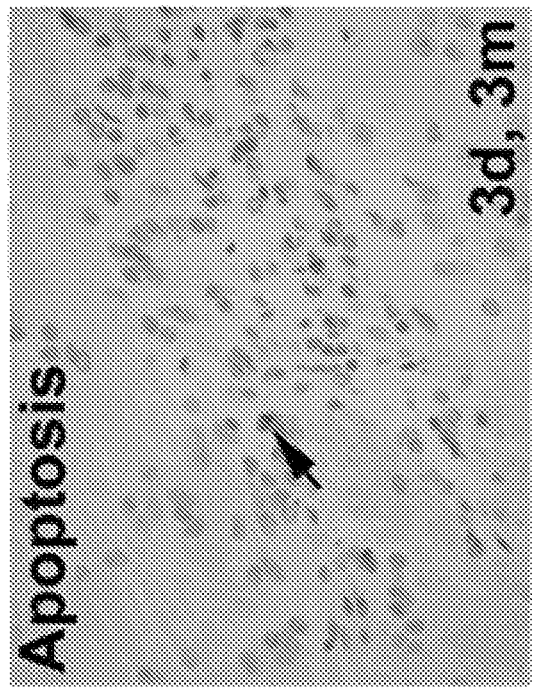
Figure 20C:
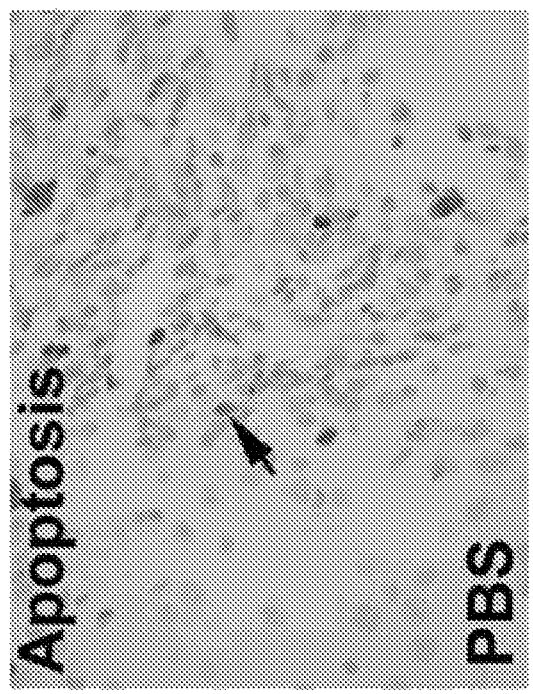
Figures 20E, 20F:
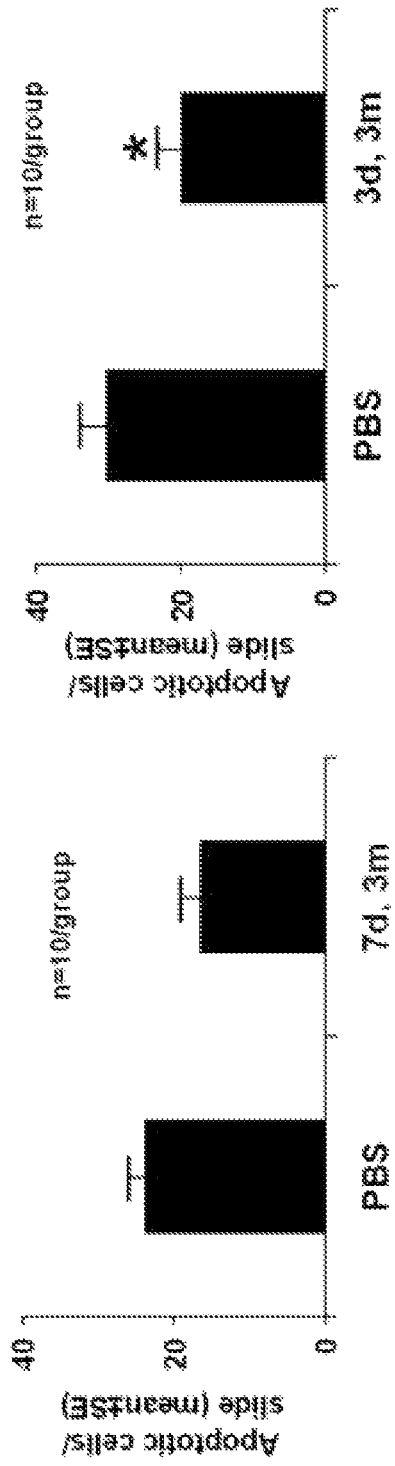
FIG. 20E shows the mean number of apoptotic cells per slide in the damaged area of the rat brains following injury and subsequent treatment with either PBS or 3×10$^6$ UTC at 7 days post injury (n=10)
FIG. 20F shows the mean number with either PBS or 3×10$^6$ UTC at 72 hours post injury (n=10).

BrdU-positive endothelial cells and vWF-positive vessels are shown at the ICH boundary in FIGS. 17A-17D. FIGS. 17E and 17F show double immunostaining of BrdU reactive cells colocalized with vWF positively stained tissues in the vessel. Double staining revealed a subpopulation of cells that express a vascular marker while still dividing, suggesting that cells positive for vascular phenotype are newly formed during the recovery stage. (See, FIGS. 17E-17F).

TUJ1 labeling was performed to detect any newly formed immature neurons. In this study, immunoexpression for TUJ1 in SVZ is significantly increased in treatment groups with $3 \times 10^6$ UTC cells at day 7 or day 3 after ICH compared with the control PBS group ($p<0.05$). (See, FIGS. 18A-18F).

Synaptophysin, a presynaptic vesicle protein, is used as an indicator of synaptogenesis (See, Ujike, H, et al., *Ann N Y Acad Sci.*, 2002; 965:55-67). Data demonstrated that the expression of synaptophysin increased significantly along the boundary zone of hematoma in the UTC cell treatment groups compared with the control PBS group ($p<0.05$). (See, FIGS. 19A-19F).

TUNEL staining showed apoptotic cells in the brain with typical dark brown, rounded or oval apoptotic bodies. Scattered apoptotic cells were present throughout the damaged tissue, the vast majority of which was located in the boundary zone of hematoma. Apoptotic cells are significantly reduced in the ipsilateral hemisphere in the UTC treatment groups at day 3 after ICH compared with the control PBS group (p<0.05). No significant differences of the total apoptotic cells number were detected among day 7 groups. (See, FIGS. 20A-20F).

Figure 21A:
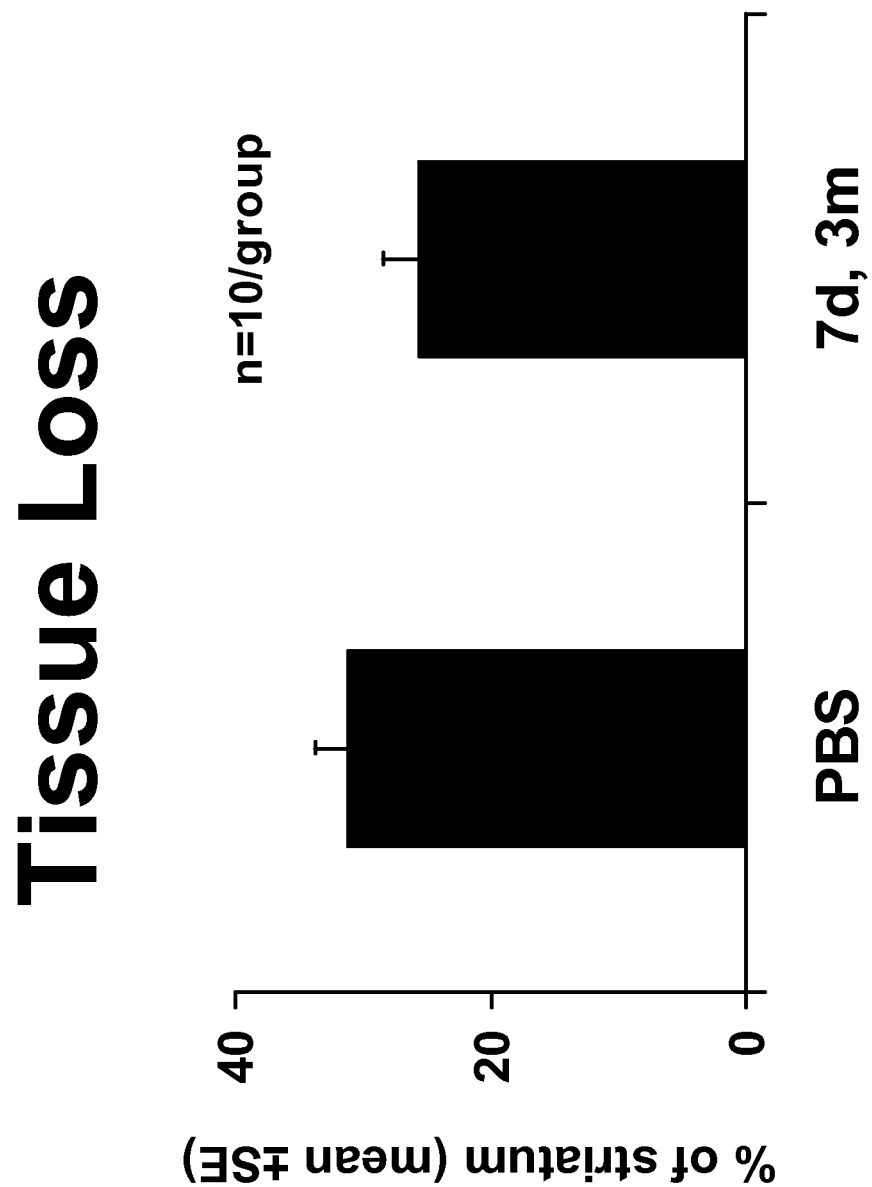
FIG. 21A shows the mean percentage of striatum lost in the rat brains following injury and subsequent treatment with either PBS or 3×10$^6$ UTC at 7 days post injury (n=10)
Figure 21B:
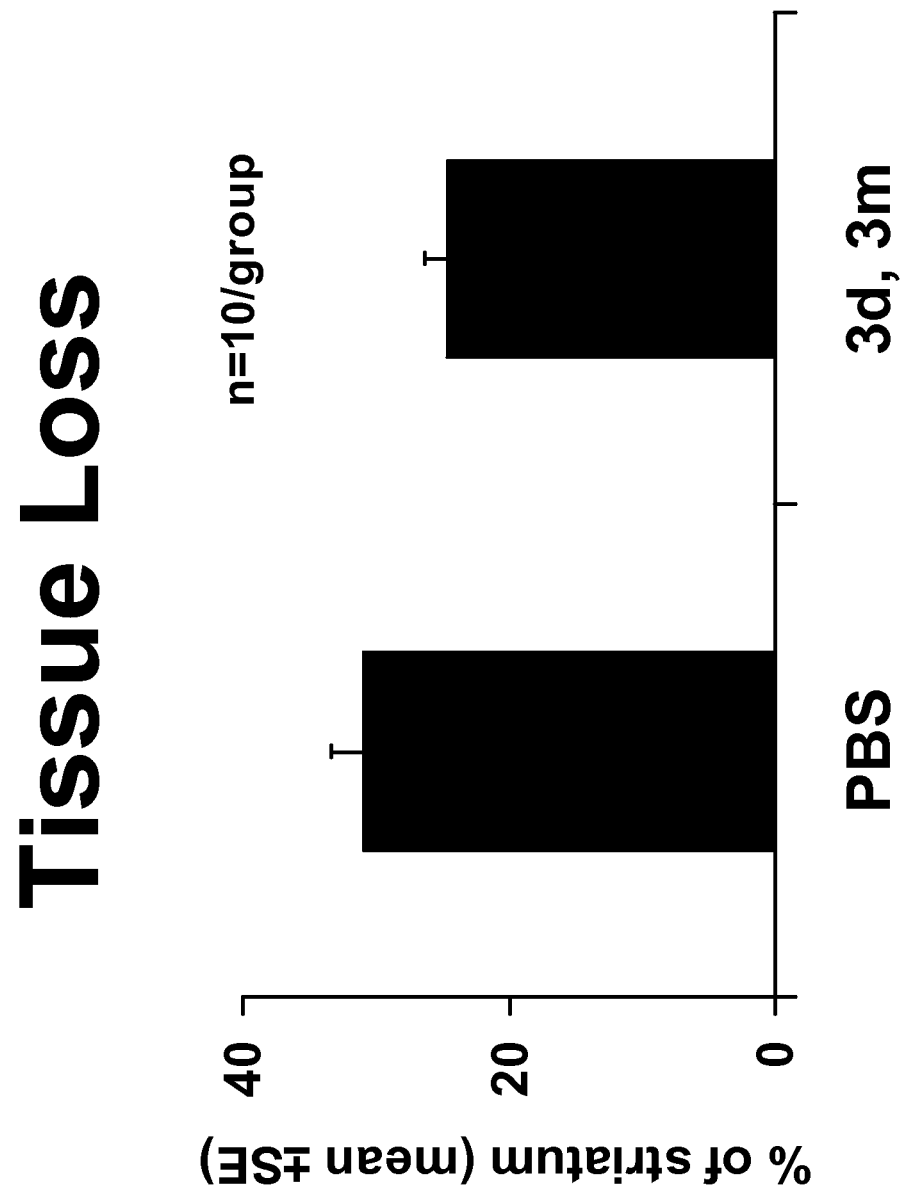
FIG. 21B shows the mean percentage with either PBS or 3×10$^6$ UTC at 72 hours post injury (n=10).

To determine tissue loss, cerebral tissues were cut into 7 equally spaced (2 mm) coronal blocks, and then processed for paraffin sectioning. A series of adjacent 6-um-thick sections were cut from each block in the coronal plane and were stained with hematoxylin and eosin. The sections were traced by the Global Laboratory Image analysis system (Data Translation, Marlboro, Mass.). The area of preserved striatum on the side of the hemorrhage was subtracted from that of the contralateral side, thus reckoning the degree of tissue loss from the ICH, and comparing treated to untreated animals. The results show that there is no significant difference in tissue loss with $3 \times 10^6$ UTC at 3 days or 7 days after ICH compared with the control PBS group. (See, FIGS. 21A and 21B).

For donor cell identification, the grafted human cells in the brain of rats were stained with three different antibodies: NuMa (Ab-2) Mouse mAb (107-7) (Anti-Nuclear Matrix, Catalog# NA09L, Calbiochem); Purified Mouse Anti-Human β2-Microglobulin (Catalog#555550, BD Biosciences); and Mouse anti-Human Mitochondria (Catalog#E5204, Spring Bioscience Corp). The immunostaining was performed at the same time with two negative controls (i.e., the omission of primary antibody and the use of pre-immune serum) and one positive control for quality control of the immunoassay procedure. The positive control was human cells that were transplanted into the brains of mice. The result showed that the positive control worked very well, but no positive stained cells were seen in our experimental slides and negative control slides. We suspect that there are factors either with the tissue processing or the batch of injected cells that caused no reaction with the antibodies.

The results show that the transplanted UTC administrated at day 7 or day 3 after ICH can significantly improve functional outcomes by mNSS test, the corner turn test and cylinder test in treatment groups compared with the control PBS group (P<0.05). The treatment effects became statistically significant at day 14 after ICH, and persisted at least until 28 days after surgery. In addition, significantly more BrdU positive cells and cells with TUJ1 expression are presented in the SVZ of ipsilateral hemisphere of rats in treatment groups with $3 \times 10^6$ UTC given at day 7 or day 3 after ICH compared with the control PBS group (p<0.05). Microvessels and synaptophysin expression were significantly increased in the boundary zone of the injured area; and significantly lower numbers of apoptotic cells were found in the treatment group with injected cells at day 3 after ICH compared with the control group. The beneficial effects of intravenous infusion of UTC were not significantly different between day 7 and day 3 administrations after ICH.

EXAMPLE 10

Effect of Administration of Cells Following Brain Injury to Enhance Tissue Repair UTC and MSCs were tested to treat rats with traumatic brain injury to seek a new way to enhance tissue repair. UTC or MSCs were administered to treat young adult male rats after TBI.

24 male Wistar rats, body weight 300-330 g were used for this experiment (Charles River Breeding Company). After an appropriate period of quarantine, each rat was anesthetized with chloral hydrate (400 mg/kg). Buprenex 0.05 mg/kg was given preoperatively to all animals. The rats were subjected to controlled cortical impact (CCI). Body temperature was maintained at 37° C. with a heated pad and K module.

24 rats were divided in three groups (8 per group). Two treatment groups received UTC or MSCs ($4 \times 10^6$ in 2 ml of PBS) administered through the tail vein 24 h after TBI. For this rats were anesthetized with chloral hydrate 400 mg/kg administered intraperitoneally (i.p). Control animals received only 2 ml PBS, i.v.

All rats were tested on modified neurological severity score (mNSS) test and Morris Water Maze test at different time points after TBI. For labeling proliferating cells, bromodeoxyuridine (BrdU, 200 mg/kg; Sigma Chemical) was injected (intraperitoneally) daily for 14 days into rats starting 1 day after TBI. All rats were euthanized 35 days after TBI by injecting ketamine (160 mg/kg) and xylazine (20 mg/kg) i.p. The brain tissue was processed for histological analysis (staining).

mNSS was performed 1 day before TBI and then on days 1, 4, 7, 14, 28 and 35 after TBI. Morris Water Maze tests were performed days 31-35 after TBI. Data collection was automated by the HVS Image 2020 Plus Tracking System (US HVS Image, San Diego, Calif.).

All brain samples were stained with standard H&E as well as immunohistochemistry. H&E staining was performed to calculate lesion volume. Immunohistochemistry was done for identification of UTC or MSCs using anti-human mitochondrial antibody (E 5204).

To identify newly proliferating cells BrdU immunohistochemistry was done. Double staining with MAP-2 and vWF was performed to identify the phenotype of newly proliferating cells.

Results

Figure 22:
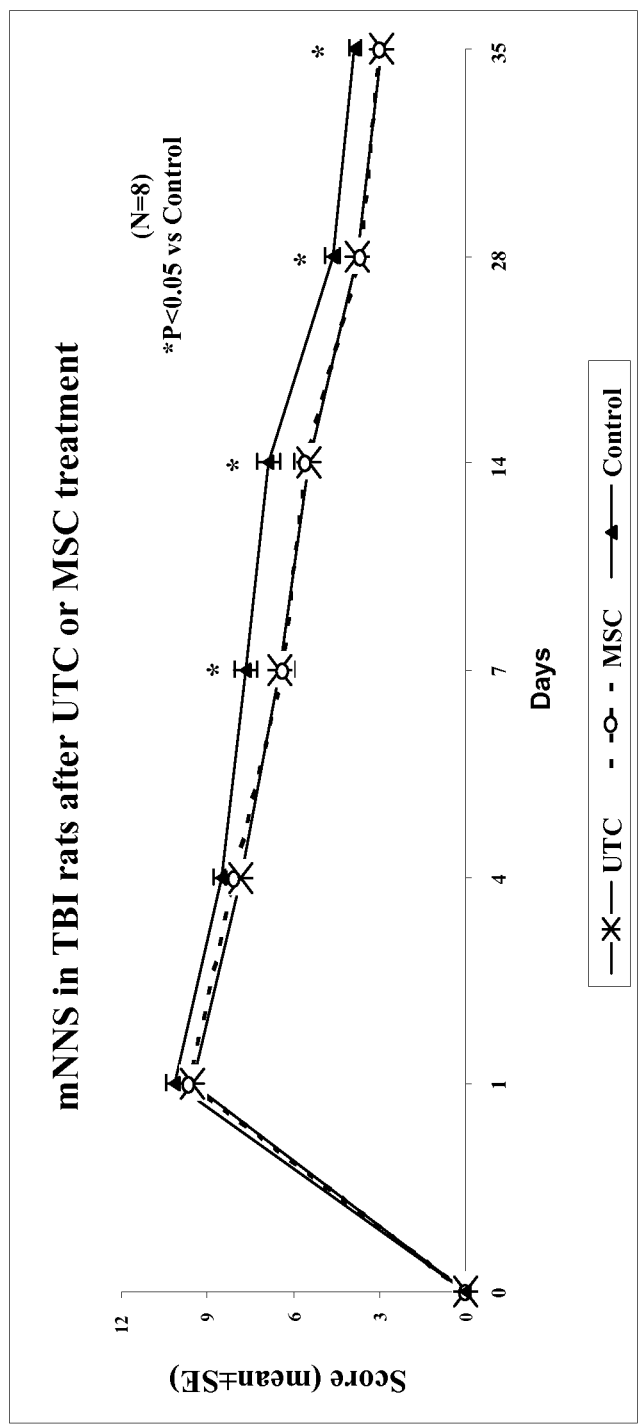
FIG. 22 shows the modified neurological severity score at 1 day, 4 days, 7 days, 14 days, 21 days, 28 days, and 35 days after injury in rats treated with PBS or 4×10$^6$ UTC or MSC at 24 hours following the injury (n=8).

There were significant differences in mNSS between both treated groups (UTC or MSCs treated rats) and the control group which was first visible at day 7 and persisted until the end of trial. (See, FIG. 22). There was no difference between the two treated groups.

Figure 23:
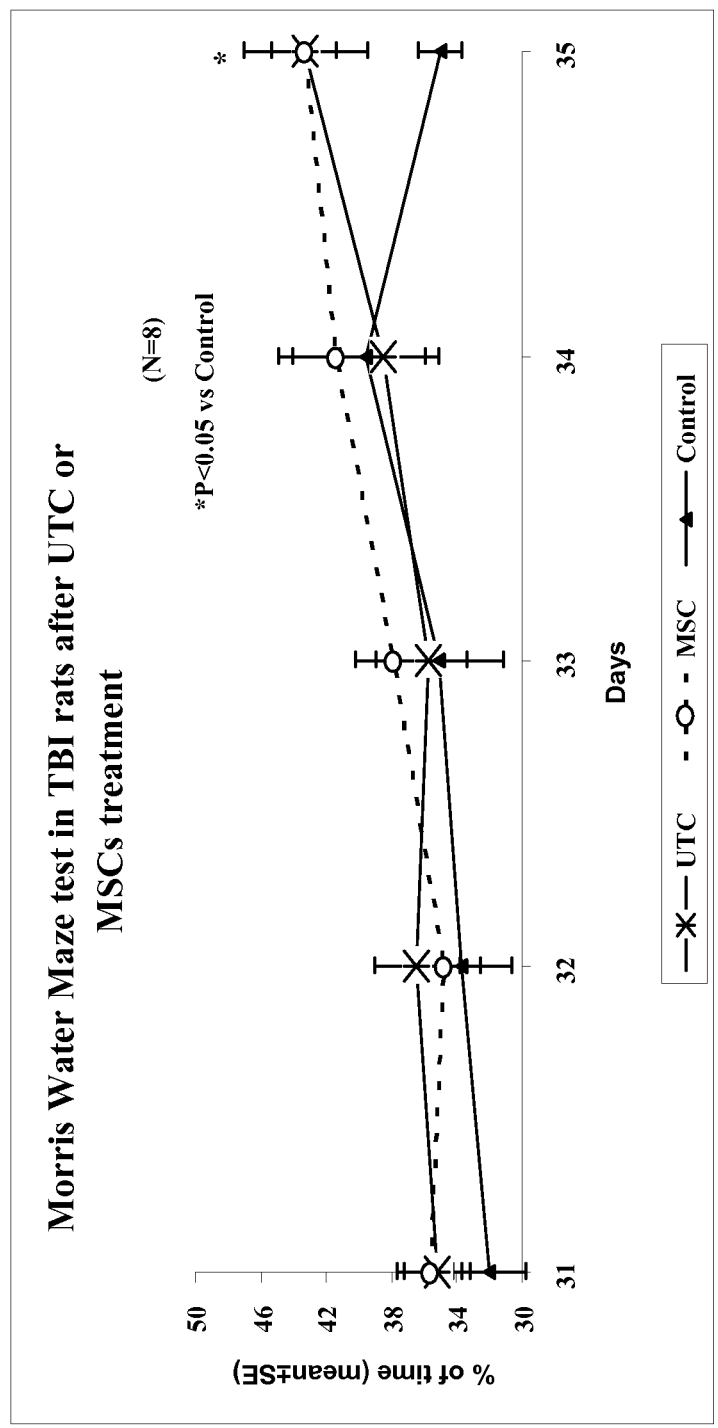
FIG. 23 shows the Morris Water Maze score at 31 days, 32 days, 33 days, 34 days and 35 days after injury in rats treated with PBS or 4×10$^6$ UTC or MSC at 24 hours following the injury (n=8).

There was improvement seen on day 35 in the UTC or MSCs treated groups compared to the control with Morris Water Maze test. (See, FIG. 23)

Figure 24:
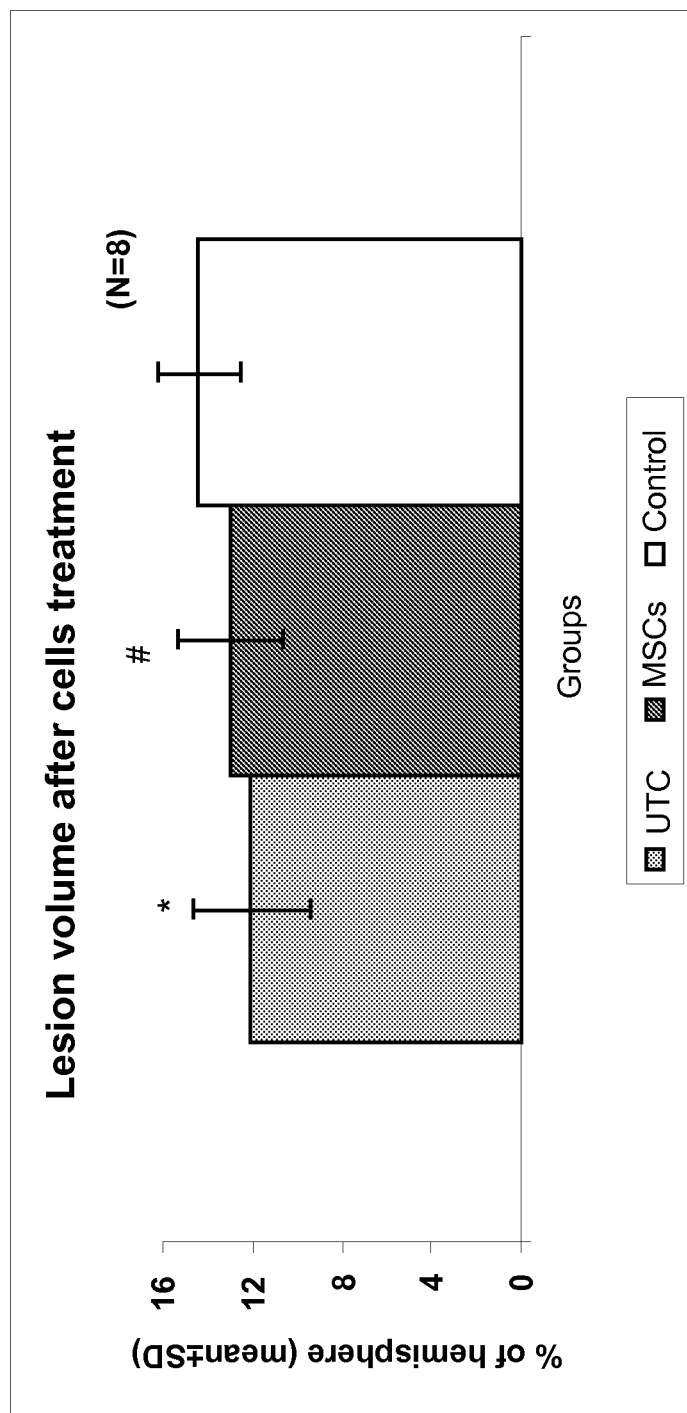
FIG. 24 shows the lesion volume as percent of brain hemisphere after injury in rats treated with PBS or 4×10$^6$ UTC or MSC at 24 hours following the injury (n=8).

For Lesion volume calculation, there was no significant difference in lesion volume between UTC or MSC treated rats and the control group of animals. (See, FIG. 24) (*P=0.07, #P=0.2)

To identify UTC or MSCs, immunohistochemistry was performed using E5204 antibody to identify donor UTC or MSCs. After 35 days we found E5204 positively stained cells in few brain sections of UTC and MSCs treated groups. The cells were seen primarily in the lesion boundary zone. No positively stained cells were found in control group. (See, FIGS. 25A and 25B)

Figure 27:
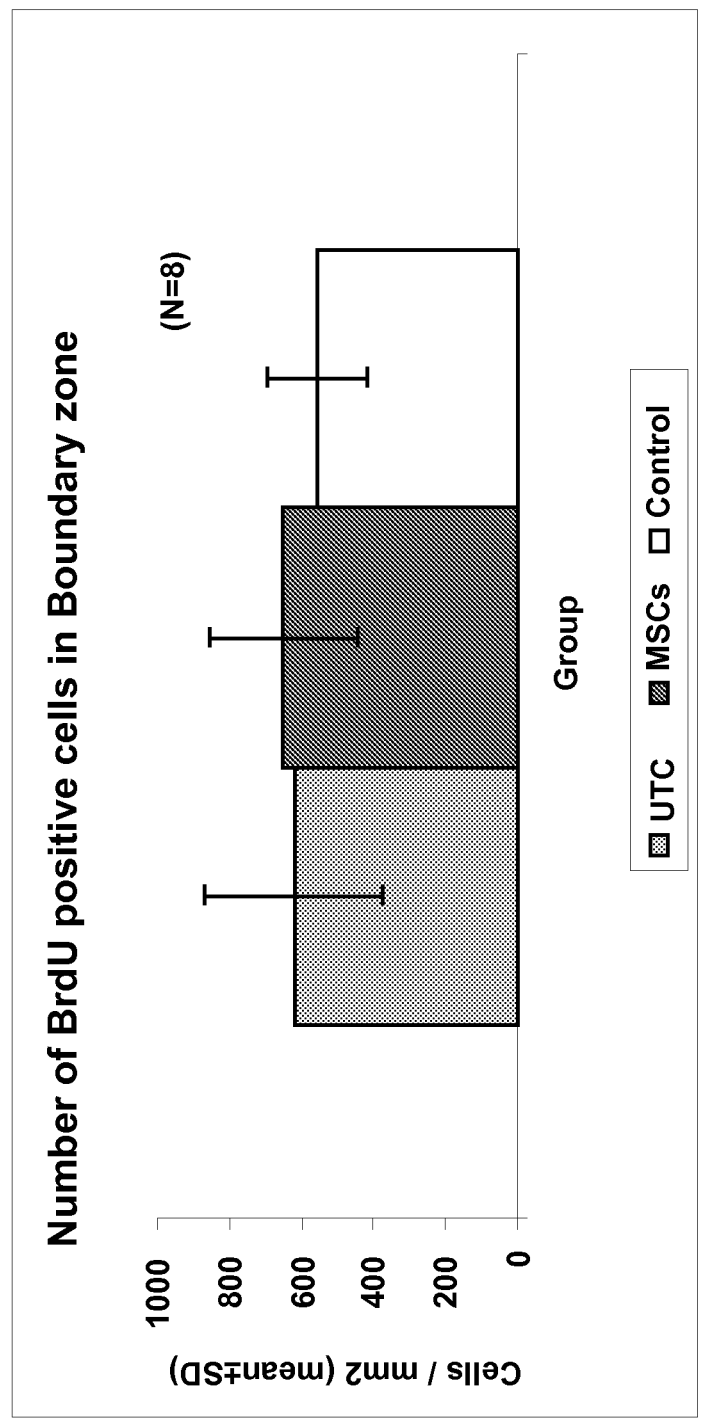
FIG. 27 shows the number of BrdU positive cells per mm$^2$ in the lesion boundary zone 35 days after injury in rats treated with PBS or 4×10$^6$ UTC or MSC at 24 hours following the injury (n=8).
Figure 28:
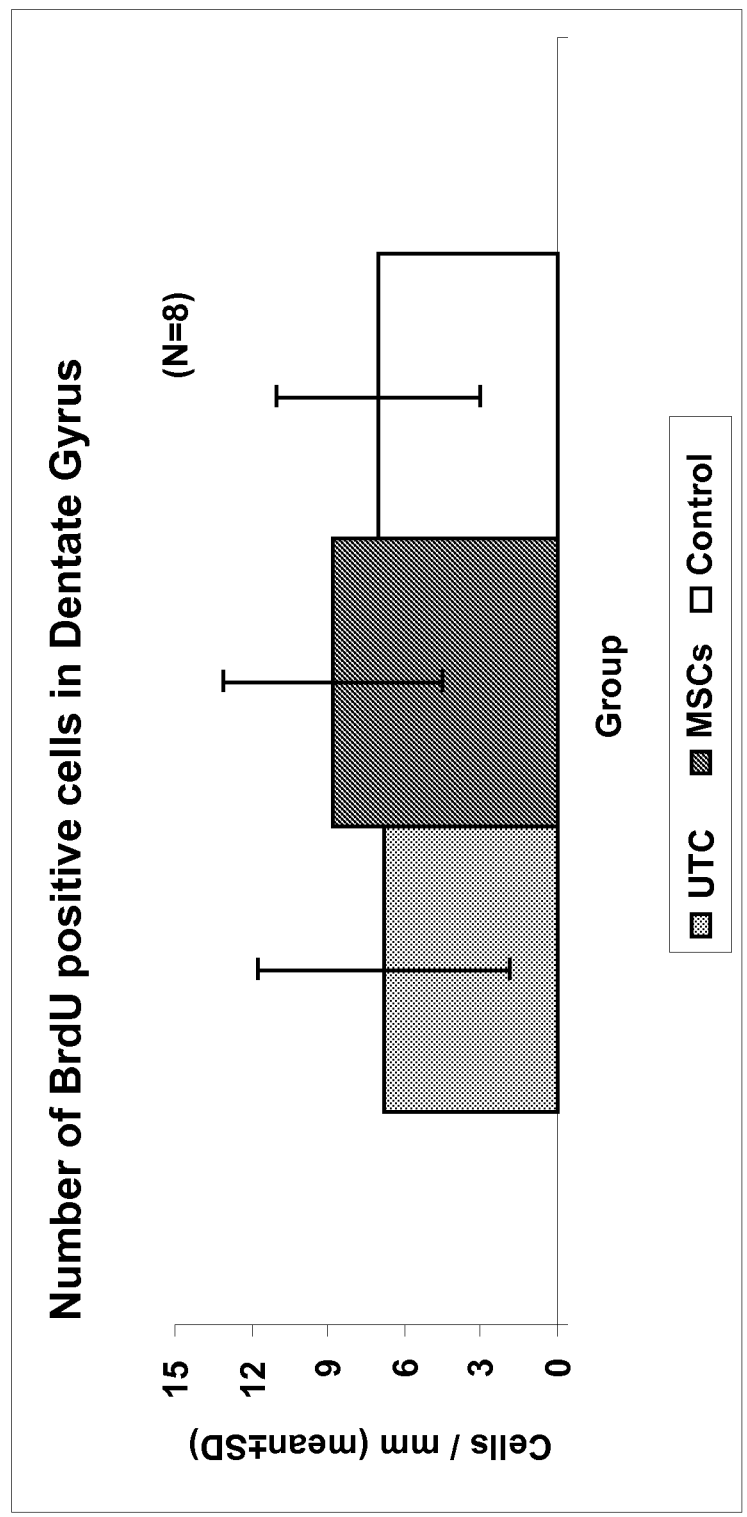
FIG. 28 shows the number of BrdU positive cells per mm$^2$ in the Dentate Gyrus 35 days after injury in rats treated with PBS or 4×10$^6$ UTC or MSC at 24 hours following the injury (n=8).
Figure 29A:
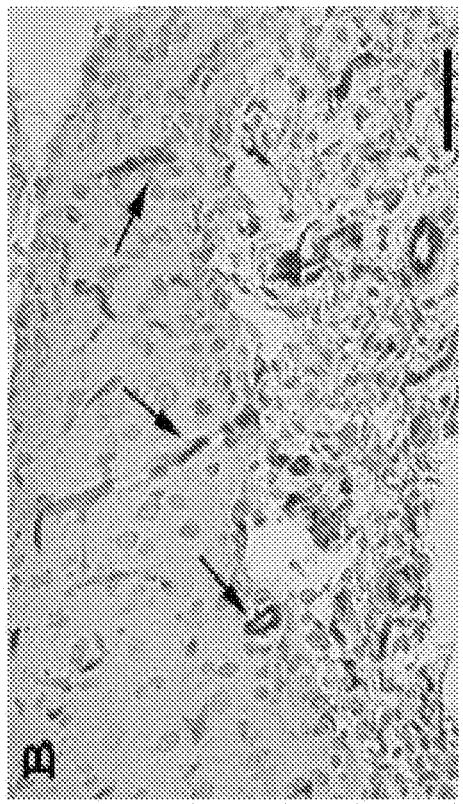
FIG. 29A shows vWF stained vessels 35 days after injury in rats treated with 4×10$^6$ UTC at 24 hours following the injury.
Figure 29B:
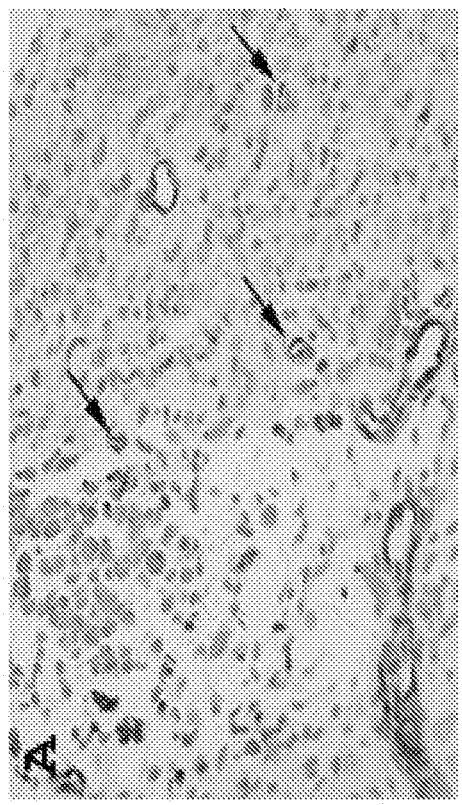
FIG. 29B shows vWF stained vessels 35 days after injury in rats treated with 4×10$^6$ MSC at 24 hours following the injury.
Figure 30:
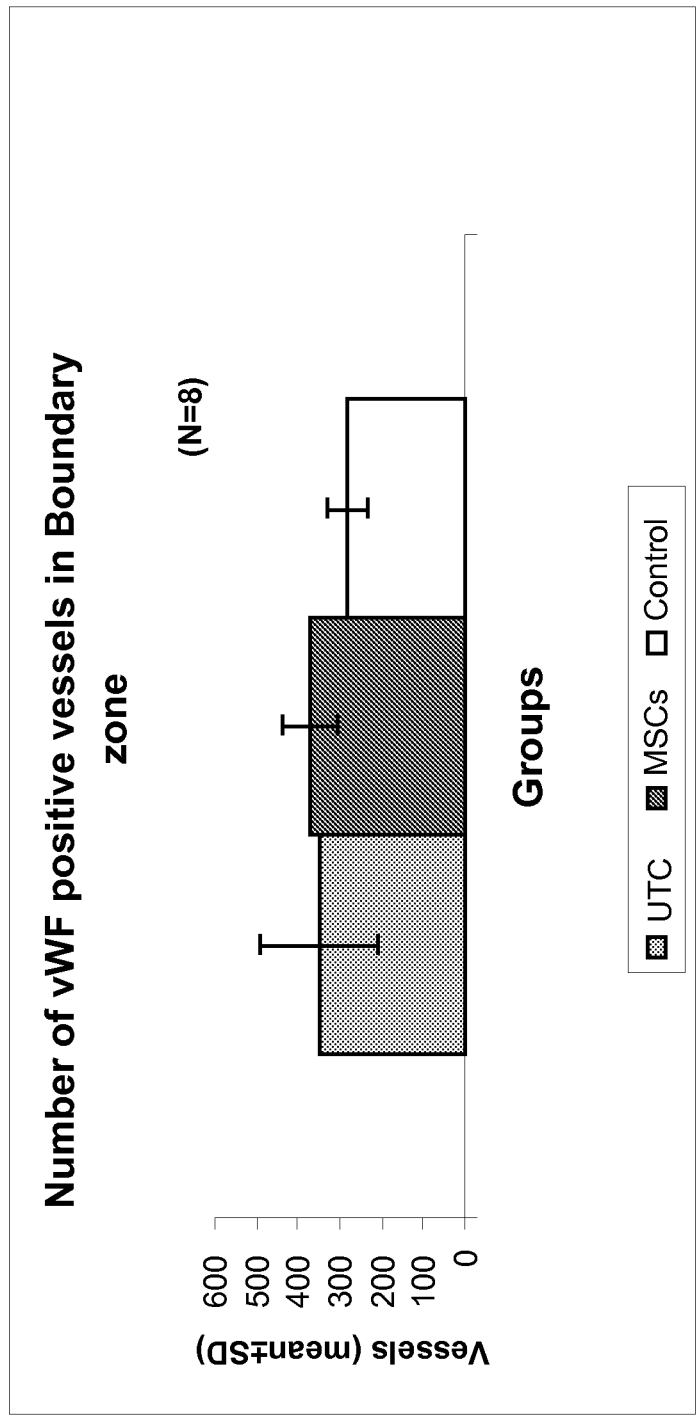
FIG. 30 shows the number of vWF positive vessels in the lesion boundary zone 35 days after injury in rats treated with PBS or 4×10$^6$ UTC or MSC at 24 hours following the injury (n=8).
Figure 31:
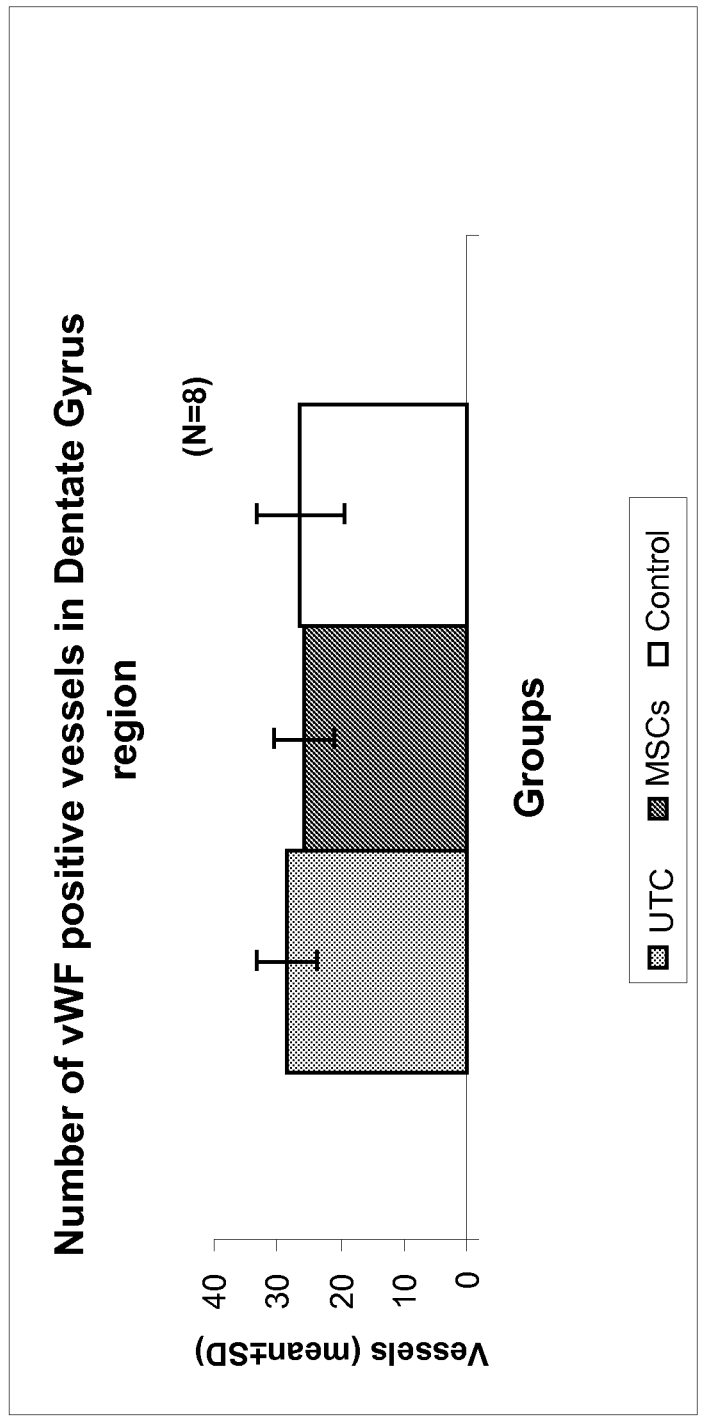
FIG. 31 shows the number of vWF positive vessels in the Dentate Gyrus 35 days after injury in rats treated with PBS or 4×10$^6$ UTC or MSC at 24 hours following the injury (n=8).

BrdU positive cells were seen in UTC (See, FIG. 26A) and MSC (See, FIG. 26B) primarily in the lesion boundary zone (See, FIG. 27), indicating neo-cellular proliferation. Very few cells were visible in the dentate gyms. (See, FIG. 28). There was, however, no difference between the treated and control groups of animals. (See, FIGS. 27 and 28)

vWF/DAB staining was performed to identify angiogenesis in UTC. (See, FIG. 29A) and MSC (See, FIG. 29B). There was no statistical difference in the number of positively stained vessels in treated versus control group of animals in either the boundary zone or dentate gyms. (See, FIG. 30 and FIG. 31)

For identification of phenotypes of newly generated cells, sections were stained with Map-2 (neuronal marker) and vWF (endothelial marker). Overlap was found between BrdU and Map-2 in some of the treated groups of animals. Positive overlap between BrdU and the Map-2 immunohistochemistry indicated that newly proliferating cells can differentiate into neurons (See, FIG. 32). No positive double staining was visible in control animals. Cells were also double stained with BrdU and vWF. No overlap was visible between them.

EXAMPLE 11

Trophic Factors for Neural Progenitor Support

The influence of UTC on adult neural stem and progenitor cell survival and differentiation through non-contact dependent (trophic) mechanisms was examined.

Fisher 344 adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (Paxinos, G, & Watson, C, 1997, The Rat Brain in Stereotaxic Coordinates). Tissue was washed in Neurobasal-A medium (Invitrogen, Carlsbad, Calif.) containing B27 (B27 supplement; Invitrogen), L-glutamine (4 mM; Invitrogen), and penicillin/streptomycin (Invitrogen), the combination of which is herein referred to as Neural Progenitor Expansion (NPE) medium. NPE medium was further supplemented with bFGF (20 ng/ml, Peprotech, Rocky Hill, N.J.) and EGF (20 ng/ml, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNAse (100 µl per 8 ml total volume, Sigma, St. Louis, Mo.) was also added. Next, the tissue/media was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250×g. Supernatant was removed, fresh NPE+bFGF+EGF was added and the pellet resuspended. The resultant cell suspension was passed through a 40 µm cell strainer (Becton Dickinson), plated on laminin-coated T-75 flasks (Becton Dickinson) or low cluster 24-well plates (Becton Dickinson), and grown in NPE+bFGF+EGF media until sufficient cell numbers were obtained for the studies outlined.

Umbilical cord tissue-derived cells (umbilicus (022803) P12, (042103) P12, (071003) P12) previously grown in growth medium were plated at 5,000 cells/transwell insert (sized for 24 well plate) and grown for a period of one week in growth medium in inserts to achieve confluence.

Neural progenitors, grown as neurospheres or as single cells, were seeded onto laminin-coated 24 well plates at an approximate density of 2,000 cells/well in NPE+bFGF+EGF for a period of one day to promote cellular attachment. One day later, transwell inserts containing UTC were added according to the following scheme:

(1) Transwell (umbilicus-derived cells in growth media, 200 µl)+neural progenitors (NPE+bFGF+EGF, 1 ml).
(2) Transwell (adult human dermal fibroblasts [1F1853]; Cambrex, Walkersville, Md.] P12 in Growth Media, 200 µl)+neural progenitors (NPE+bFGF+EGF, 1 ml).
(3) Control: neural progenitors alone (NPE+bFGF+EGF, 1 ml).
(4) Control: neural progenitors alone (NPE only, 1 ml).

After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 11-1. Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibody solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 µm DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 11-1

Primary Antibodies Used

| Antibody | Concentration | Vendor |
| --- | --- | --- |
| Rat 401 (nestin) | 1:200 | Chemicon, Temecula, Ca. |
| TuJ1 (BIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpinteria, Ca. |
| Myelin Basic Protein (MBP) | 1:400 | Chemicon |

Quantification of hippocampal neural progenitor differentiation was examined. A minimum of 1000 cells were counted per condition or if less, the total number of cells observed in that condition. The percentage of cells positive for a given stain was assessed by dividing the number of positive cells by the total number of cells as determined by DAPI (nuclear) staining.

To identify unique, secreted factors as a result of co-culture, conditioned media samples taken prior to culture fixation were frozen down at −80° C. overnight. Samples were then applied to ultrafiltration spin devices (MW cutoff 30 kD). Retentate was applied to immunoaffinity chromatography columns (anti-Hu-albumin; IgY) (immunoaffinity did not remove albumin from the samples). Filtrate was analyzed by MALDI. The pass through was applied to Cibachron Blue affinity chromatography columns. Samples were analyzed by SDS-PAGE and 2D gel electrophoresis.

Following culture with umbilicus-derived cells, co-cultured neural progenitor cells derived from adult rat hippocampus exhibited significant differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells.

The percentage of differentiated neural progenitors following co-culture with umbilicus-derived cells was quantified. Umbilicus-derived cells significantly enhanced the number of mature oligodendrocytes (MBP) (24.0% vs 0% in both control conditions). Furthermore, co-culture enhanced the number of GFAP+ astrocytes and TuJ1+ neurons in culture (47.2% and 8.7% respectively). These results were confirmed by nestin staining indicating that progenitor status was lost following co-culture (13.4% vs 71.4% in control condition 4).

Though differentiation also appeared to be influenced by adult human fibroblasts, such cells were not able to promote the differentiation of mature oligodendrocytes nor were they able to generate an appreciable quantity of neurons. Though not quantified, fibroblasts did, however, appear to enhance the survival of neural progenitors.

TABLE 11-2

Quantification of progenitor differentiation in control vs transwell co-culture with umbilical-derived cells (E = EGF, F = bFGF)

| Antibody | F + E/Umb [Cond.1] | F + E/F + E [Cond. 4] | F + E/removed [Cond. 5] |
| --- | --- | --- | --- |
| TuJ1 | 8.7% | 2.3% | 3.6% |
| GFAP | 47.2% | 30.2% | 10.9% |
| MBP | 23.0% | 0% | 0% |
| Nestin | 13.4% | 71.4% | 39.4% |

Conditioned media from umbilicus-derived co-cultures, along with the appropriate controls (NPE media ±1.7% serum, media from co-culture with fibroblasts), were examined for differences. Potentially unique compounds were identified and excised from their respective 2D gels.

Co-culture of adult neural progenitor cells with umbilicus-derived cells results in differentiation of those cells. Results presented in this example indicate that the differentiation of adult neural progenitor cells following co-culture with umbilicus-derived cells is particularly profound. Specifically, a significant percentage of mature oligodendrocytes was generated in co-cultures of umbilicus-derived cells. In view of the lack of contact between the umbilicus-derived cells and the neural progenitors, this result appears to be a function of soluble factors released from the umbilicus-derived cells (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+ (indicative of astrocytes). This may be due to the fact that such significant expansion occurred throughout the course of the procedure that contact between progenitors induced this differentiation (Song, H, et al., *Nature,* 2002; 417:29-32).

EXAMPLE 12

Short-Term Neural Differentiation of Cells

The ability of umbilicus-derived cells to differentiate into neural lineage cells was examined. Umbilical cord tissues were isolated and expanded as described in Example 12.

A modified Woodbury-Black protocol, which was originally performed to test the neural induction potential of bone marrow stromal cells, was used to assess the ability of UTC to differentiate into neural lineage cells (Woodbury, D, et al. *J Neurosci. Research,* 2000; 61(4):364-70). Briefly, UTC (022803) P4 were thawed and culture expanded in growth media at 5,000 cells/cm2 until sub-confluence (75%) was reached. Cells were then trypsinized and seeded at 6,000 cells per well of a Titretek II glass slide (VWR International, Bristol, Conn.). As controls, mesenchymal stem cells (P3; 1F2155; Cambrex, Walkersville, Md.), osteoblasts (P5; CC2538; Cambrex), adipose-derived cells (Artecel, U.S. Pat. No. 6,555,374B1) (P6; Donor 2) and neonatal human dermal fibroblasts (P6; CC2509; Cambrex) were also seeded under the same conditions.

All cells were initially expanded for 4 days in DMEM/F12 medium (Invitrogen, Carlsbad, Calif.) containing 15% (v/v) fetal bovine serum (FBS; Hyclone, Logan, Utah), basic fibroblast growth factor (bFGF; 20 ng/ml; Peprotech, Rocky Hill, N.J.), epidermal growth factor (EGF; 20 ng/ml; Peprotech) and penicillin/streptomycin (Invitrogen). After four days, cells were rinsed in phosphate-buffered saline (PBS; Invitrogen) and were subsequently cultured in DMEM/F12 medium+20% (v/v) FBS+penicillin/streptomycin for 24 hours. After 24 hours, cells were rinsed with PBS. Cells were then cultured for 1-6 hours in an induction medium which was comprised of DMEM/F12 (serum-free) containing 200 mM butylated hydroxyanisole, 10 µM □potassium chloride, 5 mg/ml insulin, 10 µM forskolin, 4 µM valproic acid, and 2 µM □hydrocortisone (all chemicals from Sigma, St. Louis, Mo.). Cells were then fixed in 100% ice-cold methanol and immunocytochemistry was performed (see methods below) to assess human nestin protein expression.

UTC (022803 P11) and adult human dermal fibroblasts (1F1853, P11) were thawed and culture expanded in growth medium at 5,000 cells/cm2 until sub-confluence (75%) was reached. Cells were then trypsinized and seeded at similar density as disclosed above, but onto (1) 24 well tissue culture-treated plates (TCP, Falcon brand, VWR International), (2) TCP wells+2% (w/v) gelatin adsorbed for 1 hour at room temperature, or (3) TCP wells+20 µg/milliliter adsorbed mouse laminin (adsorbed for a minimum of 2 hours at 37° C.; Invitrogen).

As disclosed above, cells were initially expanded and media switched at the aforementioned timeframes. One set of cultures was fixed, as before, at 5 days and six hours, this time with ice-cold 4% (w/v) paraformaldehyde (Sigma) for 10 minutes at room temperature. In the second set of cultures, medium was removed and switched to Neural Progenitor Expansion medium (NPE) consisting of Neurobasal-A medium (Invitrogen) containing B27 (B27 supplement; Invitrogen), L-glutamine (4 mM), and penicillin/streptomycin (Invitrogen). NPE medium was further supplemented with retinoic acid (RA; 1 μM; Sigma). This medium was removed 4 days later and cultures were fixed with ice-cold 4% (w/v) paraformaldehyde (Sigma) for 10 minutes at room temperature, and stained for nestin, GFAP, and TuJ1 protein expression (see Table 12-1).

TABLE 12-1

Summary of Primary Antibodies Used

| Antibody | Concentration | Vendor |
|---|---|---|
| Rat 401 (nestin) | 1:200 | Chemicon, Temecula, Ca. |
| Human Nestin | 1:100 | Chemicon |
| TuJ1 (BIII Tubulin) | 1:500 | Sigma, St. Louis, MO |
| GFAP | 1:2000 | DakoCytomation, Carpinteria, Ca. |
| Tyrosine hydroxylase (TH) | 1:1000 | Chemicon |
| GABA | 1:400 | Chemicon |
| Desmin (mouse) | 1:300 | Chemicon |
| alpha-alpha-smooth muscle actin | 1:400 | Sigma |
| Human nuclear protein (hNuc) | 1:150 | Chemicon |

Umbilicus-derived cells (042203; P11) adult human dermal fibroblasts (P11; 1F1853; Cambrex) were thawed and culture expanded in growth medium at 5,000 cells/cm2 until sub-confluence (75%) was reached. Cells were then trypsinized and seeded at 2,000 cells/cm2, but onto 24 well plates coated with laminin (BD Biosciences, Franklin Lakes, N.J.) in the presence of NPE media supplemented with bFGF (20 ng/ml; Peprotech, Rocky Hill, N.J.) and EGF (20 ng/ml; Peprotech) [whole media composition further referred to as NPE+F+E]. At the same time, adult rat neural progenitors isolated from hippocampus (P4; (062603) were also plated onto 24 well laminin-coated plates in NPE+F+E media. All cultures were maintained in such conditions for a period of 6 days (cells were fed once during that time) at which time media was switched to the differentiation conditions listed for an additional period of 7 days. Cultures were fixed with ice-cold 4% (w/v) paraformaldehyde (Sigma) for 10 minutes at room temperature, and stained for human or rat nestin, GFAP, and TuJ1 protein expression.

TABLE 12-2

Summary of Conditions for Two-Stage Differentiation Protocol

| COND. # | PRE-DIFFERENTIATION | $2^{nd}$ STAGE DIFF |
|---|---|---|
| 1 | NPE + F (20 ng/ml) + E (20 ng/ml) | NPE + SHH (200 ng/ml) + F8 (100 ng/ml) |
| 2 | NPE + F (20 ng/ml) + E (20 ng/ml) | NPE + SHH (200 ng/ml) + F8 (100 ng/ml) +RA (1 μM) |
| 3 | NPE + F (20 ng/ml) + E (20 ng/ml) | NPE + RA (1 μM) |
| 4 | NPE + F (20 ng/ml) + E (20 ng/ml) | NPE + F (20 ng/ml) + E (20 ng/ml) |
| 5 | NPE + F (20 ng/ml) + E (20 ng/ml) | Growth Medium |
| 6 | NPE + F (20 ng/ml) + E (20 ng/ml) | Condition 1B + MP52 (20 ng/ml) |
| 7 | NPE + F (20 ng/ml) + E (20 ng/ml) | Condition 1B + BMP7 (20 ng/ml) |
| 8 | NPE + F (20 ng/ml) + E (20 ng/ml) | Condition 1B + GDNF (20 ng/ml) |
| 9 | NPE + F (20 ng/ml) + E (20 ng/ml) | Condition 2B + MP52 (20 ng/ml) |
| 10 | NPE + F (20 ng/ml) + E (20 ng/ml) | Condition 2B + BMP7 (20 ng/ml) |
| 11 | NPE + F (20 ng/ml) + E (20 ng/ml) | Condition 2B + GDNF (20 ng/ml) |
| 12 | NPE + F (20 ng/ml) + E (20 ng/ml) | Condition 3B + MP52 (20 ng/ml) |
| 13 | NPE + F (20 ng/ml) + E (20 ng/ml) | Condition 3B + BMP7 (20 ng/ml) |
| 14 | NPE + F (20 ng/ml) + E (20 ng/ml) | Condition 3B + GDNF (20 ng/ml) |
| 15 | NPE + F (20 ng/ml) + E (20 ng/ml) | NPE + MP52 (20 ng/ml) |
| 16 | NPE + F (20 ng/ml) + E (20 ng/ml) | NPE + BMP7 (20 ng/ml) |
| 17 | NPE + F (20 ng/ml) + E (20 ng/ml) | NPE + GDNF (20 ng/ml) |

Umbilicus-derived cells (P11; (042203)) were thawed and culture expanded in growth medium at 5,000 cells/cm2 until sub-confluence (75%) was reached. Cells were then trypsinized and seeded at 2,000 cells/cm2, onto 24 well laminin-coated plates (BD Biosciences) in the presence of NPE+F (20 ng/ml)+E (20 ng/ml). In addition, some wells contained NPE+F+E+2% FBS or 10% FBS. After four days of "pre-differentiation" conditions, all media were removed and samples were switched to NPE medium supplemented with sonic hedgehog (SHH; 200 ng/ml; Sigma, St. Louis, Mo.), FGF8 (100 ng/ml; Peprotech), BDNF (40 ng/ml; Sigma), GDNF (20 ng/ml; Sigma), and retinoic acid (1 μM; Sigma). Seven days post medium change, cultures were fixed with ice-cold 4% (w/v) paraformaldehyde (Sigma) for 10 minutes at room temperature, and stained for human nestin, GFAP, TuJ1, desmin, and alpha-smooth muscle actin expression.

Adult rat hippocampal progenitors (062603) were plated as neurospheres or single cells (10,000 cells/well) onto laminin-coated 24 well dishes (BD Biosciences) in NPE+F (20 ng/ml)+E (20 ng/ml).

Separately, umbilicus-derived cells (042203) P11 were thawed and culture expanded in NPE+F (20 ng/ml)+E (20 ng/ml) at 5,000 cells/cm2 for a period of 48 hours. Cells were then trypsinized and seeded at 2,500 cells/well onto existing cultures of neural progenitors. At that time, existing medium was exchanged for fresh medium. Four days later, cultures were fixed with ice-cold 4% (w/v) paraformaldehyde (Sigma) for 10 minutes at room temperature, and stained for human nuclear protein (hNuc; Chemicon) (Table 11-1 above) to identify UTC.

Immunocytochemistry was performed using the antibodies listed in Table 11-1. Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Upon incubation in the first neural induction composition listed above, using glass slides, all cell types transformed into cells with bipolar morphologies and extended processes. Other larger non-bipolar morphologies were also observed. Furthermore, the induced cell populations stained positively for nestin, a marker of multipotent neural stem and progenitor cells.

When repeated on tissue culture plastic (TCP) dishes, as described in the second neural induction composition listed above, nestin expression was not observed unless laminin was pre-adsorbed to the culture surface. To further assess whether nestin-expressing cells could then go on to generate mature neurons, UTC and fibroblasts were exposed to NPE+RA (1 μM), a media composition known to induce the differentiation of neural stem and progenitor cells into such cells (Jang, Y K, et al., *J. Neurosci. Research*, 2004; 75(4):573-84; Jones-Villeneuve, E M, et al., *Mol Cel Biol.*, 1983; 3(12):2271-9; Mayer-Proschel, M, et al., *Neuron*, 1997; 19(4):773-85). Cells were stained for TuJ1, a marker for immature and mature neurons, GFAP, a marker of astrocytes, and nestin. Under no conditions was TuJ1 detected, nor were cells with neuronal morphology observed, suggesting that neurons were not generated in the short term. Furthermore, nestin and GFAP were no longer expressed by UTC, as determined by immunocytochemistry.

UTC isolates (as well as human fibroblasts and rodent neural progenitors as negative and positive control cell types, respectively) were plated on laminin (neural promoting)-coated dishes and exposed to 13 different growth conditions (and two control conditions) known to promote differentiation of neural progenitors into neurons and astrocytes. In addition, two conditions were added to examine the influence of GDF5, and BMP7 on PPDC differentiation. Generally, a two-step differentiation approach was taken, where the cells were first placed in neural progenitor expansion conditions for a period of 6 days, followed by full differentiation conditions for 7 days. Morphologically, both umbilicus- and placenta-derived cells exhibited fundamental changes in cell morphology throughout the time-course of this procedure. However, neuronal or astrocytic-shaped cells were not observed except for in control, neural progenitor-plated conditions. Immunocytochemistry, negative for human nestin, TuJ1, and GFAP confirmed the morphological observations.

Following one week's exposure to a variety of neural differentiation agents, cells were stained for markers indicative of neural progenitors (human nestin), neurons (TuJ1), and astrocytes (GFAP). Cells grown in the first stage in non-serum containing media had different morphologies than those cells in serum containing (2% or 10%) media, indicating potential neural differentiation. Specifically, following a two step procedure of exposing umbilicus-derived cells to EGF and bFGF, followed by SHH, FGF8, GDNF, BDNF, and retinoic acid, cells showed long extended processes similar to the morphology of cultured astrocytes. When 2% FBS or 10% FBS was included in the first stage of differentiation, cell number was increased and cell morphology was unchanged from control cultures at high density. Potential neural differentiation was not evidenced by immunocytochemical analysis for human nestin, TuJ1, or GFAP.

UTC were plated onto cultures of rat neural progenitors seeded two days earlier in neural expansion conditions (NPE+F+E). While visual confirmation of plated UTC proved that these cells were plated as single cells, human-specific nuclear staining (hNuc) 4 days post-plating (6 days total) showed that they tended to ball up and avoid contact with the neural progenitors. Furthermore, where UTC attached, these cells spread out and appeared to be innervated by differentiated neurons that were of rat origin, suggesting that the UTC may have differentiated into muscle cells. This observation was based upon morphology under phase contrast microscopy. Another observation was that typically large cell bodies (larger than neural progenitors) possessed morphologies resembling neural progenitors, with thin processes spanning out in multiple directions. HNuc staining (found in one half of the cell's nucleus) suggested that in some cases these human cells may have fused with rat progenitors and assumed their phenotype. Control wells containing only neural progenitors had fewer total progenitors and apparent differentiated cells than did co-culture wells containing umbilicus or placenta-derived cells, further indicating that both umbilicus- and placenta-derived cells influenced the differentiation and behavior of neural progenitors, either by release of chemokines and cytokines, or by contact-mediated effects.

Multiple protocols were conducted to determine the short term potential of UTC to differentiate into neural lineage cells. These included phase contrast imaging of morphology in combination with immunocytochemistry for nestin, TuJ1, and GFAP, proteins associated with multipotent neural stem and progenitor cells, immature and mature neurons, and astrocytes, respectively. Evidence was observed to suggest that neural differentiation occurred in certain instances in these short-term protocols.

Several notable observations were made in co-cultures of UTC with neural progenitors. This approach, using human UTC along with a xenogeneic cell type allowed for absolute determination of the origin of each cell in these cultures. First, some cells were observed in these cultures where the cell cytoplasm was enlarged, with neurite-like processes extending away from the cell body, yet only half of the body labeled with hNuc protein. Those cells may have been human UTC that had differentiated into neural lineage cells or they may have been UTC that had fused with neural progenitors. Second, it appeared that neural progenitors extended neurites to UTC in a way that indicates the progenitors differentiated into neurons and innervated the UTC. Third, cultures of neural progenitors and UTC had more cells of rat origin and larger amounts of differentiation than control cultures of neural progenitors alone, further indicating that plated UTC provided soluble factors and or contact-dependent mechanisms that stimulated neural progenitor survival, proliferation, and/or differentiation.

EXAMPLE 13

Isolation of Cells

Umbilical cords were obtained from National Disease Research Interchange (NDRI, Philadelphia, Pa.). The tissues were obtained following normal deliveries. The cell isolation protocols were performed aseptically in a laminar flow hood. To remove blood and debris, the cord was washed in phosphate buffered saline (PBS; Invitrogen, Carlsbad, Calif.) in the presence of penicillin at 100 Units/milliliter, streptomycin at 100 milligrams/milliliter and amphotericin B at 0.025 micrograms/milliliter (Invitrogen Carlsbad, Calif.). The tissues were then mechanically dissociated in 150 cm² tissue culture plates in the presence of 50 milliliters of medium (DMEM-low glucose or DMEM-high glucose; Invitrogen), until the tissue was minced into a fine pulp. The chopped tissues were transferred to 50 milliliter conical tubes (approximately 5 grams of tissue per tube).

The tissue was then digested in either DMEM-low glucose medium or DMEM-high glucose medium, each containing penicillin at 100 Units/milliliter, streptomycin at 100 milligrams/milliliter, amphotericin B at 0.25 micrograms/milliliter and the digestion enzymes. In some experiments an enzyme mixture of collagenase and dispase was used ("C: D") (collagenase (Sigma, St Louis, Mo.), 500 Units/milliliter; and dispase (Invitrogen), 50 Units/milliliter, in DMEM-Low glucose medium). In other experiments a mixture of collagenase, dispase and hyaluronidase ("C:D:H") was used (C:D:H=collagenase, 500 Units/milliliter; dispase, 50 Units/milliliter; and hyaluronidase (Sigma), 5 Units/milliliter, in DMEM-low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of growth medium (DMEM: low glucose (Invitrogen), 15 percent (v/v) fetal bovine serum (FBS; defined fetal bovine serum; Lot #AND18475; Hyclone, Logan, Utah), 0.001% (v/v) 2-mercaptoethanol (Sigma), penicillin at 100 Units per milliliter, streptomycin at 100 micrograms per milliliter, and amphotericin B at 0.25 micrograms per milliliter; (each from Invitrogen, Carlsbad, Calif.)). The cell suspension was filtered through a 70-micron nylon BD FALCON Cell Strainer (BD Biosciences, San Jose, Calif.). An additional 5 milliliters rinse comprising growth medium was passed through the strainer. The cell suspension was then passed through a 40-micrometer nylon cell strainer (BD Biosciences, San Jose, Calif.) and chased with a rinse of an additional 5 milliliters of growth medium.

The filtrate was resuspended in growth medium (total volume 50 milliliters) and centrifuged at 150×g for 5 minutes. The supernatant was aspirated and the cells were resuspended in 50 milliliters of fresh growth medium. This process was repeated twice more.

After the final centrifugation, supernatant was aspirated and the cell pellet was resuspended in 5 milliliters of fresh growth medium. The number of viable cells was determined using trypan blue staining. Cells were then cultured under standard conditions.

The cells isolated from umbilical cord tissues were seeded at 5,000 cells/cm² onto gelatin-coated T-75 flasks (Corning Inc., Corning, N.Y.) in growth medium. After two days, spent medium and unadhered cells were aspirated from the flasks. Adherent cells were washed with PBS three times to remove debris and blood-derived cells. Cells were then replenished with growth medium and allowed to grow to confluence (about 10 days from passage 0 to passage 1). On subsequent passages (from passage 1 to 2 etc), cells reached sub-confluence (75-85 percent confluence) in 4-5 days. For these subsequent passages, cells were seeded at 5,000 cells/cm². Cells were grown in a humidified incubator with 5 percent carbon dioxide at 37° C.

In some experiments, cells were isolated from umbilical cord tissues in DMEM-low glucose medium after digestion with LIBERASE (2.5 milligrams per milliliter, BLEND-ZYME 3; Roche Applied Sciences, Indianapolis, Ind.) and hyaluronidase (5 Units/milliliter, Sigma). Digestion of the tissue and isolation of the cells was as described for other protease digestions above, however, the LIBERASE/hyaluronidase mixture was used instead of the C:D or C:D:H enzyme mixture. Tissue digestion with LIBERASE resulted in the isolation of cell populations from postpartum tissues that expanded readily.

Procedures were compared for isolating cells from the umbilical cord using differing enzyme combinations. Enzymes compared for digestion included: i) collagenase; ii) dispase; iii) hyaluronidase; iv) collagenase:dispase mixture (C:D); v) collagenase:hyaluronidase mixture (C:H); vi) dispase:hyaluronidase mixture (D:H); and vii) collagenase: dispase:hyaluronidase mixture (C:D:H). Differences in cell isolation utilizing these different enzyme digestion conditions were observed (Table 13-1).

Other attempts were made to isolate pools of cells from umbilical cord by different approaches. In one instance, umbilical cord was sliced and washed with growth medium to dislodge the blood clots and gelatinous material. The mixture of blood, gelatinous material and growth medium was collected and centrifuged at 150×g. The pellet was resuspended and seeded onto gelatin coated flasks in growth medium. From these experiments a cell population was isolated that readily expanded.

Cells have also been isolated from cord blood samples obtained from NDRI. The isolation protocol used was that of International Patent Application PCT/US2002/029971 by Ho et al. Samples (50 milliliter and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in Complete Minimal Essential Medium (Gibco, Carlsbad Calif.) containing 10 percent fetal bovine serum (Hyclone, Logan Utah), 4 millimolar glutamine (Mediatech Herndon, Va.), penicillin at 100 Units per milliliter and streptomycin at 100 micrograms per milliliter (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

To determine whether cell populations could be isolated under different conditions and expanded under a variety of conditions immediately after isolation, cells were digested in growth medium with or without 0.001 percent (v/v) 2-mercaptoethanol (Sigma, St. Louis, Mo.), using the enzyme combination of C:D:H, according to the procedures provided above. All cells were grown in the presence of penicillin at 100 Units per milliliter and streptomycin at 100 micrograms per milliliter. Under all tested conditions cells attached and expanded well between passage 0 and 1 (Table 13-2). Cells in conditions 5-8 and 13-16 were demonstrated to proliferate well up to 4 passages after seeding, at which point they were cryopreserved.

The combination of C:D:H, provided the best cell yield following isolation, and generated cells that expanded for many more generations in culture than the other conditions (Table 13-1). An expandable cell population was not attained using collagenase or hyaluronidase alone. No attempt was made to determine if this result is specific to the collagenase that was tested.

TABLE 13-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success under conditions tested Cells attached and expanded well between passage 0 and 1 under all conditions tested for enzyme digestion and growth. Cells in experimental conditions 5-8 and 13-16 proliferated well up to 4 passages after seeding, at which point they were cryopreserved. All cells were cryopreserved for further analysis.

TABLE 13-2

Isolation and culture expansion of umbilical cord cells under varying conditions:

| Condition | Medium | 15% FBS | BME | Gelatin | 20% $O_2$ | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |
| 7 | DMEM-Lg | N (2%) | Y | N (Fibrone) | Y | PDGF/VEGF |
| 8 | DMEM-Lg | N (2%) | Y | N (Fibrone) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibrone) | Y | PDGF/VEGF |
| 16 | DMEM-Lg | N (2%) | N | N (Fibrone) | N (5%) | PDGF/VEGF |

Nucleated cells attached and grew rapidly. These cells were analyzed by flow cytometry and were similar to cells obtained by enzyme digestion.

The preparations contained red blood cells and platelets. No nucleated cells attached and divided during the first 3 weeks. The medium was changed 3 weeks after seeding and no cells were observed to attach and grow.

Populations of cells could be isolated from umbilical tissue efficiently using the enzyme combination collagenase (a metalloprotease), dispase (neutral protease) and hyaluronidase (mucolytic enzyme which breaks down hyaluronic acid). LIBERASE, which is a blend of collagenase and a neutral protease, may also be used. BLENDZYME 3, which is collagenase (4 Wunsch units/gram) and thermolysin (1714 casein Units/gram), was also used together with hyaluronidase to isolate cells. These cells expanded readily over many passages when cultured in growth expansion medium on gelatin coated plastic.

Cells were also isolated from residual blood in the cords, but not cord blood. The presence of cells in blood clots washed from the tissue, which adhere and grow under the conditions used, may be due to cells being released during the dissection process.

EXAMPLE 14

Growth Characteristics of Cells

The cell expansion potential of umbilical cord tissue-derived cells was compared to other populations of isolated stem cells. The process of cell expansion to senescence is referred to as Hayflick's limit (Hayflick, L, *J. Am. Geriatr. Soc.*, 1974; 22(1):1-12; Hayflick, L, *Gerontologist*, 1974; 14(1):37-45), 1974).

Tissue culture plastic flasks were coated by adding 20 milliliters 2% (w/v) gelatin (Type B: 225 Bloom; Sigma, St Louis, Mo.) to a T75 flask (Corning Inc., Corning, N.Y.) for 20 minutes at room temperature. After removing the gelatin solution, 10 milliliters of phosphate-buffered saline (PBS) (Invitrogen, Carlsbad, Calif.) was added and then aspirated.

For comparison of growth expansion potential the following cell populations were utilized; i) mesenchymal stem cells (MSC; Cambrex, Walkersville, Md.); ii) adipose-derived cells (U.S. Pat. No. 6,555,374 B1; U.S. Patent Application US20040058412); iii) normal dermal skin fibroblasts (cc-2509 lot #9F0844; Cambrex, Walkersville, Md.); and iv) umbilicus-derived cells. Cells were initially seeded at 5,000 cells/cm$^2$ on gelatin-coated T75 flasks in growth medium. For subsequent passages, cell cultures were treated as follows. After trypsinization, viable cells were counted after trypan blue staining. Cell suspension (50 microliters) was combined with trypan blue (50 microliters, Sigma, St. Louis Mo.). Viable cell numbers were estimated using a hemocytometer.

Following counting, cells were seeded at 5,000 cells/cm² onto gelatin-coated T 75 flasks in 25 milliliters of fresh growth medium. Cells were grown in a standard atmosphere (5 percent carbon dioxide (v/v)) at 37° C. The growth medium was changed twice per week. When cells reached about 85 percent confluence they were passaged; this process was repeated until the cells reached senescence.

At each passage, cells were trypsinized and counted. The viable cell yield, population doublings [ln (cells final/cells initial)/ln 2], and doubling time (time in culture/population doubling) were calculated. For the purposes of determining optimal cell expansion, the total cell yield per passage was determined by multiplying the total yield for the previous passage by the expansion factor for each passage (i.e., expansion factor=cells final/cells initial).

The expansion potential of cells banked at passage 10 was also tested. A different set of conditions was used. Normal dermal skin fibroblasts (cc-2509 lot #9F0844; Cambrex, Walkersville, Md.), umbilicus-derived cells were tested. These cell populations had been banked at passage 10 previously, having been cultured at 5,000 cells/cm² at each passage to that point. The effect of cell density on the cell populations following cell thaw at passage 10 was determined. Cells were thawed under standard conditions, and counted using trypan blue staining. Thawed cells were then seeded at 1,000 cells/cm² in growth medium. Cells were grown under standard atmospheric conditions at 37° C. growth medium was changed twice a week. Cells were passaged as they reached about 85% confluence. Cells were subsequently passaged until senescence, i.e., until they could not be expanded any further. Cells were trypsinized and counted at each passage. The cell yield, population doubling (ln (cells final/cells initial)/ln 2) and doubling time (time in culture/population doubling) were calculated. The total cell yield per passage was determined by multiplying total yield for the previous passage by the expansion factor for each passage (i.e., expansion factor=cells final/cells initial).

The expansion potential of freshly isolated umbilical cord tissue-derived cell cultures under low cell seeding conditions was tested in another experiment. Umbilicus-derived cells were isolated as described in Example 12. Cells were seeded at 1,000 cells/cm² and passaged as described above until senescence. Cells were grown under standard atmospheric conditions at 37° C. Growth medium was changed twice per week. Cells were passaged as they reached about 85% confluence. At each passage, cells were trypsinized and counted by trypan blue staining. The cell yield, population doubling (ln (cell final/cell initial)/ln 2) and doubling time (time in culture/population doubling) were calculated for each passage. The total cell yield per passage was determined by multiplying the total yield for the previous passage by the expansion factor for each passage (i.e., expansion factor=cell final/cell initial). Cells were grown on gelatin and non-gelatin coated flasks.

It has been demonstrated that low $O_2$ cell culture conditions can improve cell expansion in certain circumstances (United States Patent Application No. US20040005704). To determine if cell expansion of UTC could be improved by altering cell culture conditions, cultures of umbilicus-derived cells were grown in low oxygen conditions. Cells were seeded at 5,000 cells/cm² in growth medium on gelatin coated flasks. Cells were initially cultured under standard atmospheric conditions through passage 5, at which point they were transferred to low oxygen (5% $O_2$) culture conditions.

In other experiments cells were expanded on non-coated, collagen-coated, fibronectin-coated, laminin-coated and matrigel-coated plates. Cultures have been demonstrated to expand well on these different matrices.

Umbilicus-derived cells expanded for more than 40 passages generating cell yields of >1×10¹⁷ cells in 60 days. In contrast, MSCs and fibroblasts senesced after <25 days and <60 days, respectively. Although both adipose-derived and omental cells expanded for almost 60 days, they generated total cell yields of $4.5 \times 10^{12}$ and $4.24 \times 10^{13}$ respectively. Thus, when seeded at 5,000 cells/cm² under the experimental conditions utilized, umbilicus-derived cells expanded much better than the other cell types grown under the same conditions (Table 14-1).

TABLE 14-1

Growth characteristics for different cell populations grown to senescence

| Cell Type | Senescence | Total Population Doublings | Total Cell Yield |
|---|---|---|---|
| MSC | 24 days | 8 | $4.72 \times 10^7$ |
| Adipose | 57 days | 24 | $4.5 \times 10^{12}$ |
| Fibroblasts | 53 days | 26 | $2.82 \times 10^{13}$ |
| Umbilicus | 65 days | 42 | $6.15 \times 10^{17}$ |

Umbilicus-derived cells and fibroblast cells expanded for greater than 10 passages generating cell yields of $>1 \times 10^{11}$ cells in 60 days (Table 14-2). After 60 days under these conditions the fibroblasts became senescent whereas the umbilicus-derived cell populations senesced after 80 days, completing >40 population doublings.

TABLE 14-2

Growth characteristics for different cell populations using low density growth expansion from passage 10 till senescence

| Cell Type | Senescence | Total Population Doublings | Total Cell Yield |
|---|---|---|---|
| Fibroblast (P10) | 80 days | 43.68 | $2.59 \times 10^{11}$ |
| Umbilicus (P10) | 80 days | 53.6 | $1.25 \times 10^{14}$ |

Cells expanded well under the reduced oxygen conditions, however, culturing under low oxygen conditions does not appear to have a significant effect on cell expansion for umbilical cord tissue-derived cells. Standard atmospheric conditions have already proven successful for growing sufficient numbers of cells, and low oxygen culture is not required for the growth of umbilical cord tissue-derived cells.

The current cell expansion conditions of growing isolated umbilical cord tissue-derived cells at densities of about 5,000 cells/cm², in growth medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/cm²). Umbilical cord tissue derived cell expansion in low oxygen conditions also facilitates cell expansion, although no incremental improvement in cell expansion potential has yet been observed when utilizing these conditions for growth. Presently, culturing umbilical cord tissue-derived cells under standard atmospheric conditions is preferred for generating large pools of cells. When the culture conditions are altered, however, umbilical cord tissue-derived cell expansion can likewise be altered. This strategy may be used to enhance the proliferative and differentiative capacity of these cell populations.

Under the conditions utilized, while the expansion potential of MSC and adipose-derived cells is limited, UTC expand readily to large numbers.

EXAMPLE 15

Growth of Cells in Medium Containing D-Valine

It has been reported that medium containing D-valine instead of the normal L-valine isoform can be used to selectively inhibit the growth of fibroblast-like cells in culture (Hongpaisan J. *Cell Biol Int.*, 2000; 24:1-7; Sordillo L M, et al., *Cell Biol Int Rep.*, 1988; 12:355-64). Experiments were performed to determine whether umbilical cord tissue-derived cells could grow in medium containing D-valine.

Umbilicus-derived cells (P5) and fibroblasts (P9) were seeded at 5,000 cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a modified growth medium (DMEM with D-valine (special order Gibco), 15% (v/v) dialyzed fetal bovine serum (Hyclone, Logan, Utah), 0.001% (v/v) betamercaptoethanol (Sigma), penicillin at 50 Units/milliliter and streptomycin at 50 milligrams/milliliter (Gibco)).

Umbilicus-derived cells and fibroblast cells seeded in the D-valine-containing medium did not proliferate, unlike cells seeded in growth medium containing dialyzed serum. Fibroblasts cells changed morphologically, increasing in size and changing shape. All of the cells died and eventually detached from the flask surface after four weeks. Thus, it may be concluded that umbilical cord tissue-derived cells require L-valine for cell growth and to maintain long-term viability. L-valine is preferably not removed from the growth medium for umbilical cord tissue-derived cells.

EXAMPLE 16

Karyotype Analysis of Cells

Cell lines used in cell therapy are preferably homogeneous and free from any contaminating cell type. Human cells used in cell therapy should have a normal number (46) of chromosomes with normal structure. To identify umbilical cord tissue-derived cell lines that are homogeneous and free from cells of non-postpartum tissue origin, karyotypes of cell samples were analyzed.

Umbilical cord tissue-derived cells from postpartum tissue of a male neonate were cultured in growth media. Umbilical cord tissue from a male neonate (X,Y) was selected to allow distinction between neonatal-derived cells and maternal derived cells (X,X). Cells were seeded at 5,000 cells per square centimeter in growth medium in a T25 flask (Corning, Corning, N.Y.) and expanded to 80% confluence. A T25 flask containing cells was filled to the neck with growth media. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins. Each of the cell samples was characterized as homogeneous. (Table 16-1).

TABLE 16-1

Results of UTC karyotype analysis

| Tissue | Passage | Metaphase cells counted | Metaphase cells analyzed | Number of karyotypes | ISCN Karyotype |
|---|---|---|---|---|---|
| Umbilical | 23 | 20 | 5 | 2 | 46, XX |
| Umbilical | 6 | 20 | 5 | 2 | 46, XY |
| Umbilical | 3 | 20 | 5 | 2 | 46, XX |

Key:
N-Neonatal aspect;
V-villous region;
M-maternal aspect;
C-clone

Chromosome analysis identified umbilicus-derived cells whose karyotypes appear normal as interpreted by a clinical cytogenetic laboratory. Karyotype analysis also identified cell lines free from maternal cells, as determined by homogeneous karyotype.

EXAMPLE 17

Flow Cytometric Evaluation of Cell Surface Markers

Characterization of cell surface proteins or "markers" by flow cytometry can be used to determine a cell line's identity. The consistency of expression can be determined from multiple donors, and in cells exposed to different processing and culturing conditions. Cell lines isolated from umbilicus were characterized (by flow cytometry), providing a profile for the identification of these cell lines.

Cells were cultured in growth medium (Gibco Carlsbad, Calif.) with penicillin/streptomycin. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Adherent cells in flasks were washed in PBS and detached with Trypsin/EDTA. Cells were harvested, centrifuged, and resuspended in 3% (v/v) FBS in PBS at a cell concentration of 1×10$^7$ per ml. In accordance to the manufacture's specifications, antibody to the cell surface marker of interest (see below) was added to 100 μl of cell suspension and the mixture was incubated in the dark for 30 minutes at 4° C. After incubation, cells were washed with PBS and centrifuged to remove unbound antibody. Cells were resuspended in 500 μl PBS and analyzed by flow cytometry. Flow cytometry analysis was performed with a FACS calibur instrument (Becton Dickinson, San Jose, Calif.).

The following antibodies directed against cell surface markers were used.

| Antibody | Manufacture | Catalog Number |
|---|---|---|
| CD10 | BD Pharmingen (San Diego, Ca.) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, Mo.) | F-6522 |
| IgG- PE | Sigma | P-4685 |

Umbilical cord cells were analyzed at passages 8, 15, and 20.

To compare differences among donors, umbilical cord-derived cells from different donors were compared to each other.

Umbilical cord-derived cells cultured on gelatin-coated flasks were compared to umbilical cord-derived cells cultured on uncoated flasks.

Four treatments used for isolation and preparation of cells were compared. Cells derived from postpartum tissue by treatment with: 1) collagenase; 2) collagenase/dispase; 3) collagenase/hyaluronidase; and 4) collagenase/hyaluronidase/dispase were compared.

Umbilical cord-derived cells at passage 8, 15, and 20 analyzed by flow cytometry all expressed CD10, CD13, CD44, CD73, CD90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Umbilical cord-derived cells isolated from separate donors analyzed by flow cytometry each showed positive for production of CD10, CD13, CD44, CD73, CD90, PDGFr-alpha and HLA-A, B, C, reflected in the increased values of fluorescence relative to the IgG control. These cells were negative for production of CD31, CD34, CD45, CD117, CD141, and HLA-DR, DP, DQ with fluorescence values consistent with the IgG control.

Umbilical cord-derived cells expanded on gelatin-coated and uncoated flasks analyzed by flow cytometry were all positive for production of CD10, CD13, CD44, CD73, CD90, PDGFr-alpha and HLA-A, B, C, with increased values of fluorescence relative to the IgG control. These cells were negative for production of CD31, CD34, CD45, CD117, CD141, and HLA-DR, DP, DQ, with fluorescence values consistent with the IgG control.

Analysis of umbilical cord-derived cells by flow cytometry has established an identity of these cell lines. These umbilical cord-derived postpartum cells are positive for CD10, CD13, CD44, CD73, CD90, PDGFr-alpha, and HLA-A, B, C; and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

EXAMPLE 18

Analysis of Cells by Oligonucleotide Array

Oligonucleotide arrays were used to compare gene expression profiles of umbilicus-derived and placenta-derived cells with fibroblasts, human mesenchymal stem cells, and another cell line derived from human bone marrow. This analysis provided a characterization of the postpartum-derived cells and identified unique molecular markers for these cells.

Human umbilical cords and placenta were obtained from National Disease Research Interchange (NDRI, Philadelphia, Pa.) from normal full term deliveries with patient consent. The tissues were received and cells were isolated as described in Example 13 after digestion with a C:D:H mixture. Cells were cultured in growth medium on gelatin-coated plastic tissue culture flasks. The cultures were incubated at 37° C. with 5% $CO_2$.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen)). The cells were grown on standard tissue-treated plastic.

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan blue exclusion (Sigma, St. Louis, Mo.). The mononuclear cells were seeded in plastic tissue culture flasks at $5 \times 10^4$ cells/$cm^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with Affymetrix GENECHIP HG-U133A oligonucleotide arrays (Affymetrix, Santa Clara, Calif.). The hybridizations and data collection were performed according to the manufacturer's specifications. The hybridization and data collection was performed according to the manufacturer's specifications. Data analyses were performed using "Significance Analysis of Microarrays" (SAM) version 1.21 computer software (Tusher, V G, et al., *Proc. Natl. Acad. Sci. USA,* 2001; 98:5116-5121).

Fourteen different populations of cells were analyzed in this study. The cells along with passage information, culture substrate, and culture media are listed in Table 18-1.

TABLE 18-1

Cells analyzed by the microarray study. Cell lines are listed by identification code along with passage at time of analysis, cell growth substrate and growth medium.

| Cell Population | Passage | Substrate | Medium |
|---|---|---|---|
| Umbilicus (022803) | 2 | Gelatin | DMEM, 15% FBS, 2B-ME |
| Umbilicus (042103) | 3 | Gelatin | DMEM, 15% FBS, 2B-ME |
| Umbilicus (071003) | 4 | Gelatin | DMEM, 15% FBS, 2B-ME |
| Placenta (042203) | 12 | Gelatin | DMEM, 15% FBS, 2B-ME |
| Placenta (042903) | 4 | Gelatin | DMEM, 15% FBS, 2B-ME |
| Placenta (071003) | 3 | Gelatin | DMEM, 15% FBS, 2B-ME |
| ICBM (070203) (5% $O_2$) | 3 | Plastic | MEM, 10% FBS |
| ICBM (062703) (std. $O_2$) | 5 | Plastic | MEM, 10% FBS |
| ICBM (062703) (5% $O_2$) | 5 | Plastic | MEM, 10% FBS |
| hMSC (Lot 2F1655) | 3 | Plastic | MSCGM |
| hMSC (Lot 2F1656) | 3 | Plastic | MSCGM |
| hMSC (Lot 2F 1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by principle component analysis with SAM software as described above. Analysis revealed 290 genes that were expressed in different relative amounts in the cells tested. This analysis provided relative comparisons between the populations.

Table 18-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 18-2

The Euclidean Distances for the Cell Pairs. The Euclidean distance was calculated for the cell types using the 290 genes that were expressed differentially between the cell types. Similarity between the cells is inversely proportional to the Euclidean distance.

| Cell Pair | Euclidean Distance |
|---|---|
| ICBM-HMSC | 24.71 |
| PLACENTA-UMBILICAL | 25.52 |
| ICBM-FIBROBLAST | 36.44 |
| ICBM-PLACENTA | 37.09 |
| FIBROBLAST-MSC | 39.63 |
| ICBM-UMBILICAL | 40.15 |
| Fibroblast-Umbilical | 41.59 |
| MSC-PLACENTA | 42.84 |
| MSC-UMBILICAL | 46.86 |
| ICBM-PLACENTA | 48.41 |

Tables 18-3, 18-4, and 18-5 show the expression of genes increased in umbilical tissue-derived cells (Table 18-3), increased in placenta-derived cells (Table 18-4), and reduced in umbilicus- and placenta-derived cells (Table 18-5).

TABLE 18-3

Genes shown to have specifically increased expression in the UTC as compared to other cell lines assayed

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 18-4

Genes shown to have specifically increased expression in the placenta-derived cells as compared to other cell lines assayed

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | renin | NM_000537 |
| 210004_at | oxidized low density lipoprotein (lectin-like) receptor 1 | AF035776 |
| 214993_at | *Homo sapiens*, clone IMAGE:4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 18-5

Genes shown to have decreased expression in umbilicus-derived and placenta-derived cells as compared to other cell lines assayed

| Probe Set ID | Gene name | NCBI Accession Number |
|---|---|---|
| 210135_s_at | short stature homeobox 2 | AF022654.1 |
| 205824_at | heat shock 27kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeo box 2 (growth arrest-specific homeo box) | NM_005924.1 |
| 205817_at | sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (Drosophila) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | hephaestin | NM_014799.1 |
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeo box 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | biglycan | AA845258 |
| 201261_x_at | biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |
| 205422_s_at | integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36kDa | NM_000597.1 |

Tables 18-6, 18-7, and 18-8 show the expression of genes increased in human fibroblasts (Table 18-6), ICBM cells (Table 18-7), and MSCs (Table 18-8).

TABLE 18-6

Genes that were shown to have increased expression in fibroblasts as compared to the other cell lines assayed.

dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [*Homo sapiens*]
transforming growth factor, beta 2
hypothetical protein MGC29643
antigen identified by monoclonal antibody MRC OX-2
putative X-linked retinopathy protein

TABLE 18-7

Genes that were shown to have increased expression in the ICBM-derived cells as compared to the other cell lines assayed.

cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
Proteoglycan 1, secretory granule

TABLE 18-8

Genes that were shown to have increased expression in the MSC cells as compared to the other cell lines assayed.

interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1

TABLE 18-8-continued

Genes that were shown to have increased expression in the MSC cells as compared to the other cell lines assayed.

*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

The present example was performed to provide a molecular characterization of the cells derived from umbilical cord and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed on a GENECHIP oligonucleotide array that contained oligonucleotide probes for 22,000 genes.

The analysis revealed that transcripts for 290 genes were present in different amounts in these five different cell types. These genes include seven genes specifically increased in the umbilical tissue-derived cells and ten genes that are specifically increased in the placenta-derived cells. Fifty-four genes were found to have specifically lower expression levels in placenta-derived and umbilical cord-derived cells.

The expression of selected genes has been confirmed by PCR, as shown in Example 18. Postpartum-derived cells generally, and umbilical derived cells, in particular, have distinct gene expression profiles, for example, as compared to other human cells, such as the bone marrow-derived cells and fibroblasts tested here.

EXAMPLE 19

Cell Markers in Umbilical Cord Tissue-Derived Cells

Gene expression profiles of cells derived from umbilical cord were compared with those of cells derived from other sources using an Affymetrix GENECHIP. "Signature" genes were identified: interleukin-8 (IL-8), reticulon, chemokine receptor ligand 3 (CXC ligand 3), chemokine receptor (CXC motif) ligand 1, tumor necrosis factor, alpha-induced protein 3 and granulocyte chemotactic protein 2 (GCP-2). These "signature" genes were expressed at relatively high levels in umbilicus-derived cells.

The procedures described in this example were conducted to verify the microarray data and compare data for gene and protein expression, as well as to establish a series of reliable assays for detection of unique identifiers for umbilical cord tissue-derived cells.

Umbilicus-derived cells (four isolates), and normal human dermal fibroblasts (NHDF; neonatal and adult) were grown in growth medium in gelatin-coated T75 flasks. mesenchymal stem cells (MSCs) were grown in mesenchymal stem cell growth medium Bullet kit (MSCGM; Cambrex, Walkerville, Md.).

For IL-8 experiments, cells were thawed from liquid nitrogen and plated in gelatin-coated flasks at 5,000 cells/$cm^2$, grown for 48 hours in growth medium and then grown further for 8 hours in 10 milliliters of serum starvation medium [DMEM—low glucose (Gibco, Carlsbad, Calif.), penicillin (50 Units/milliliter), streptomycin (50 micrograms/milliliter)(Gibco) and 0.1% (w/v) Bovine Serum Albumin (BSA; Sigma, St. Louis, Mo.)]. RNA was then extracted and the supernatants were centrifuged at 150×g for 5 minutes to remove cellular debris. Supernatants were frozen at −80° C. until ELISA analysis.

The umbilical cord tissue-derived cells, as well as human fibroblasts derived from human neonatal foreskin, were cultured in growth medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliters culture medium and counted. Cells were grown in a 75 cm$^2$ flask containing 15 milliliters of growth medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of trypsin/EDTA (Gibco, Carlsbad, Calif.) were added to each flask. After cells detached from the flask, trypsin activity was neutralized with 8 milliliters of growth medium. Cells were transferred to a 15 milliliter centrifuge tube and centrifuged at 150×g for 5 minutes. Supernatant was removed and 1 milliliter growth medium was added to each tube to resuspend the cells. Cell number was determined with a hemocytometer.

The amount of IL-8 secreted by the cells into serum starvation medium was analyzed using ELISA assays (R&D Systems, Minneapolis, Minn.). All assays were conducted according to the instructions provided by the manufacturer.

RNA was extracted from confluent umbilical cord-derived cells and fibroblasts, or for IL-8 expression, from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 Units/sample) (Sigma St. Louis, Mo.). RNA was eluted with 50 microliters DEPC-treated water and stored at −80° C. RNA was also extracted from human umbilical cord. Tissue (30 milligrams) was suspended in 700 microliters of buffer RLT containing beta-mercaptoethanol. Samples were mechanically homogenized and the RNA extraction proceeded according to manufacturer's specification. RNA was extracted with 50 microliters of DEPC-treated water and stored at −80° C.

RNA was reverse-transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in umbilical cord cells (signature genes—including oxidized LDL receptor, interleukin-8, renin, and reticulon), were further investigated using real-time and conventional PCR.

PCR was performed on cDNA samples using gene expression products sold under the tradename Assays-On-Demand (Applied Biosystems) gene expression products. Oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems) using a 7000 sequence detection system with ABI Prism 7000 SDS software (Applied Biosystems). Thermal cycle conditions were initially 50° C. for 2 minutes and 95° C. for 10 minutes, followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Conventional PCR was performed using an ABI PRISM 7700 (Perkin Elmer Applied Biosystems, Boston, Mass.) to confirm the results from real-time PCR. PCR was performed using 2 microliters of cDNA solution (1×Taq polymerase (tradename AMPLITAQ GOLD) universal mix PCR reaction buffer (Applied Biosystems) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 19-1. Primer concentration in the final PCR reaction was 1 micromolar except for GAPDH which was 0.5 micromolar. GAPDH primers were the same as for real-time PCR, except that the manufacturer's TaqMan probe was not added to the final PCR reaction. Samples were separated on 2% (w/v) agarose gel and stained with ethidium bromide (Sigma, St. Louis, Mo.). Images were captured on 667 film (Universal Twinpack, VWR International, South Plainfield, N.J.) using a fixed focal-length POLAROID camera (VWR International, South Plainfield, N.J.).

TABLE 19-1

| Gene of Interest | Primers |
|---|---|
| Oxidized LDL receptor | S: 5'-GAGAAATCCAAAGAGCAAATGG-3' (SEQ ID NO: 1) <br> A: 5'-AGAATGGAAAACTGGAATAGG-3' (SEQ ID NO: 2) |
| Renin | S: 5'-TCTTCGATGCTTCGGATTCC-3' (SEQ ID NO: 3) <br> A: 5'-GAATTCTCGGAATCTCTGTTG-3' (SEQ ID NO: 4) |
| Reticulon | S: 5'- TTACAAGCAGTGCAGAAAACC-3' (SEQ ID NO: 5) <br> A: 5'- AGTAAACATTGAAACCACAGCC-3' (SEQ ID NO: 6) |
| Interleukin-8 | S: 5'- TCTGCAGCTCTGTGTGAAGG-3' (SEQ ID NO: 7) <br> A: 5'-CTTCAAAAACTTCTCCACAACC- 3' (SEQ ID NO: 8) |
| Chemokine (CXC) ligand 3 | S: 5'- CCCACGCCACGCTCTCC-3' (SEQ ID NO: 9) <br> A: 5'-TCCTGTCAGTTGGTGCTCC-3' (SEQ ID NO: 10) |

S = Sense, A = Anti-sense

Umbilical cord-derived cells were fixed with cold 4% (w/v) paraformaldehyde (Sigma-Aldrich, St. Louis, Mo.) for 10 minutes at room temperature. One isolate each of umbilical cord-derived cells at passage 0 (P0) (directly after isolation) and passage 11 (P11) (two isolates of Umbilical cord-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Ca.—raised against mouse), alpha-smooth muscle actin (SMA; 1:400; Sigma), cytokeratin 18 (CK18; 1:400; Sigma), von Willebrand Factor (vWF;

1:200; Sigma), and CD34 (human CD34 Class III; 1:100; DAKOCytomation, Carpinteria, Calif.). In addition, the following markers were tested on passage 11 umbilical cord-derived cells: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure to prevent epitope loss. Furthermore, in instances where the primary antibody was raised against goat (GCP-2, ox-LDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufacturer's specifications, and the cells were incubated for in the dark for 30 minutes at 4° C. After incubation, cells were washed with PBS and centrifuged to remove excess antibody. Cells requiring a secondary antibody were resuspended in 100 microliter of 3% FBS. Secondary antibody was added as per manufacturer's specification, and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), and Donkey against Goat IgG (sc-3743; Santa Cruz, Biotech.). Flow cytometry analysis was performed with FACScalibur (Becton Dickinson San Jose, Calif.).

Results of real-time PCR for selected "signature" genes performed on cDNA from cells derived from human umbilical cord, adult and neonatal fibroblasts, and Mesenchymal Stem Cells (MSCs) indicate that both reticulon and oxidized LDL receptor expression were higher in umbilicus-derived cells as compared to other cells. The data obtained from real-time PCR were analyzed by the $\Delta\Delta CT$ method and expressed on a logarithmic scale. No significant differences in the expression levels of CXC ligand 3 and GCP-2 were found between postpartum cells and controls. The results of real-time PCR were confirmed by conventional PCR. Sequencing of PCR products further validated these observations. No significant difference in the expression level of CXC ligand 3 was found between postpartum cells and controls using conventional PCR CXC ligand 3 primers listed in Table 19-1.

The expression of the cytokine, IL-8 in umbilical cord tissue-derived cells was elevated in both growth medium-cultured and serum-starved umbilical cord-derived cells. All real-time PCR data were validated with conventional PCR and by sequencing PCR products.

After growth in serum-free media, the conditioned media were examined for the presence of IL-8. The greatest amounts of IL-8 were detected in media in which umbilical cells had been grown (Table 19-2). No IL-8 was detected in medium in which human dermal fibroblasts had been grown.

TABLE 19-2

| IL-8 protein(pg/$10^6$ cells) measured by ELISA | |
|---|---|
| Cell type | IL-8 |
| Human fibroblasts | ND |
| Placenta Isolate 1 | ND |
| UMBC Isolate 1 | 2058.42 + 144.67 |
| Placenta Isolate 2 | ND |
| UMBC Isolate 2 | 2368.86 + 22.73 |
| Placenta Isolate3 (normal $O_2$) | 17.27 + 8.63 |
| Placenta Isolate 3 (low $O_2$, W/O BME) | 264.92 + 9.88 |

Results of the ELISA assay for interleukin-8 (IL-8) performed on placenta- and umbilical cord-derived cells as well as human skin fibroblasts. Values are presented here are picogram/million cells, n = 2, sem.
ND: Not Detected Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord-derived cells were positive for alpha-smooth muscle actin and vimentin, with the staining pattern consistent through passage 11.

The production of GROalpha, GCP-2, oxidized LDL receptor 1 and reticulon (NOGO-A) in umbilical cord-derived cells at passage 11 was investigated by immunocytochemistry. Umbilical cord-derived cells were GCP-2 positive, but GRO alpha production was not detected by this method. Furthermore, cells were NOGO-A positive.

Accordance between gene expression levels measured by microarray and PCR (both real-time and conventional) has been established for cells derived from umbilical cord tissue for two genes: reticulon, and IL-8. The expression of these genes was differentially regulated at the mRNA level in umbilical cord-derived cells, with IL-8 also differentially regulated at the protein level. Differential expression of GCP-2 and CXC ligand 3 was not confirmed at the mRNA level. Although this result does not support data originally obtained from the microarray experiment, this may be due to a difference in the sensitivity of the methodologies.

Cells derived from the human umbilical cord at passage 0 were probed for the expression of alpha-smooth muscle actin and vimentin, and were positive for both. The staining pattern was preserved through passage 11.

In conclusion, the complete mRNA data at least partially verifies the data obtained from the microarray experiments.

EXAMPLE 20

Immunohistochemical Characterization of Cellular Phenotypes

The phenotypes of cells found within human umbilical cord were analyzed by immunohistochemistry.

Human umbilical cord tissue was harvested and immersion fixed in 4% (w/v) paraformaldehyde overnight at 4° C. Immunohistochemistry was performed using antibodies directed against the following epitopes (See, Table 20-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 microns thick) using a standard cryostat (Leica Microsystems) and mounted onto glass slides for staining.

Immunohistochemistry was performed similar to previous studies (e.g., Messina, et al., *Exper. Neurol.*, 2003; 184:816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epifluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 20-1

Summary of Primary Antibodies Used

| Antibody | Concentration | Vendor |
|---|---|---|
| Vimentin | 1:500 | Sigma, St. Louis, Mo. |
| Desmin (rb) | 1:150 | Sigma |
| Desmin (m) | 1:300 | Chemicon, Temecula, Ca. |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, Ca. |
| GROalpha-PE | 1:100 | BD, Franklin Lakes, N.J. |
| GCP-2 | 1:100 | Santa Cruz Biotech |
| Ox-LDL R1 | 1:100 | Santa Cruz Biotech |
| NOGO-A | 1:100 | Santa Cruz Biotech |

Vimentin, desmin, SMA, CK18, vWF, and CD34 markers were expressed in a subset of the cells found within umbilical cord (data not shown). In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery and vein, but not contained within the vessels themselves. CK18 and desmin were observed within the vessels only, desmin being restricted to the middle and outer layers.

Vimentin, desmin, alpha-smooth muscle actin, cytokeratin 18, von Willebrand Factor, and CD34 are expressed in cells within human umbilical cord. Based on in vitro characterization studies showing that only vimentin and alpha-smooth muscle actin are expressed, the data suggests that the current process of umbilical cord-derived cell isolation harvests a subpopulation of cells or that the cells isolated change expression of markers to express vimentin and alpha-smooth muscle actin.

EXAMPLE 21

Secretion of Trophic Factors

The secretion of selected trophic factors from umbilicus-derived cells was measured. Factors selected for detection included: (1) those known to have angiogenic activity, such as hepatocyte growth factor (HGF) (Rosen et al., *Ciba Found. Symp.*, 1997; 212:215-26), monocyte chemotactic protein 1 (MCP-1) (Salcedo et al., *Blood*, 2000; 96:34-40), interleukin-8 (IL-8) (Li et al., *J. Immunol.*, 2003; 170:3369-76), keratinocyte growth factor (KGF), basic fibroblast growth factor (bFGF), vascular endothelial growth factor (VEGF) (Hughes et al., *Ann. Thorac. Surg.*, 2004; 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1alpha (SDF-1alpha); (2)

those known to have neurotrophic/neuroprotective activity, such as brain-derived neurotrophic factor (BDNF) (Cheng et al., Dev. Biol., 2003; 258; 319-33), interleukin-6 (IL-6), granulocyte chemotactic protein-2 (GCP-2), transforming growth factor beta2 (TGFbeta2); and (3) those known to have chemokine activity, such as macrophage inflammatory protein 1alpha (MIP1a), macrophage inflammatory protein 1beta (MIP1b), monocyte chemoattractant-1 (MCP-1), Rantes (regulated on activation, normal T cell expressed and secreted), I309, thymus and activation-regulated chemokine (TARC), Eotaxin, macrophage-derived chemokine (MDC), and IL-8.

Cells derived from umbilical cord, as well as human fibroblasts derived from human neonatal foreskin, were cultured in growth medium on gelatin-coated T75 flasks. Cells were cryopreserved at passage 11 and stored in liquid nitrogen. After thawing, growth medium was added to the cells, followed by transfer to a 15 milliliter centrifuge tube and centrifugation of the cells at 150xg for 5 minutes. The cell pellet was resuspended in 4 milliliters growth medium, and cells were counted. Cells were seeded at 5,000 cells/cm$^2$ in T75 flasks each containing 15 milliliters of growth medium, and cultured for 24 hours. The medium was changed to a serum-free medium (DMEM-low glucose (Gibco), 0.1% (w/v) bovine serum albumin (Sigma), penicillin (50 Units/milliliter) and streptomycin (50 micrograms/milliliter, Gibco)) for 8 hours. Conditioned serum-free medium was collected at the end of incubation by centrifugation at 14,000xg for 5 minutes and stored at −20° C.

To estimate the number of cells in each flask, cells were washed with phosphate-buffered saline (PBS) and detached using 2 milliliters trypsin/EDTA (Gibco). Trypsin activity was inhibited by addition of 8 milliliters growth medium. Cells were centrifuged at 150xg for 5 minutes. The supernatant was removed, and cells were resuspended in 1 milliliter growth medium. Cell number was estimated with a hemocytometer.

Cells were grown at 37° C. in 5% carbon dioxide and atmospheric oxygen. The amount of MCP-1, IL-6, VEGF, SDF-1alpha, GCP-2, IL-8, and TGF-beta2 produced by each cell sample was determined by ELISA (R&D Systems, Minneapolis, Minn.). All assays were performed according to the manufacturer's instructions. Values presented are picograms per milliliter per million cells (n=2, sem).

Chemokines (MIP1alpha, MIP1beta, MCP-1, Rantes, I309, TARC, Eotaxin, MDC, IL8), BDNF, and angiogenic factors (HGF, KGF, bFGF, VEGF, TIMP1, ANG2, PDGFbb, TPO, HB-EGF were measured using SEARCHLIGHT Proteome Arrays (Pierce Biotechnology Inc.). The Proteome Arrays are multiplexed sandwich ELISAs for the quantitative measurement of two to sixteen proteins per well. The arrays are produced by spotting a 2x2, 3x3, or 4x4 pattern of four to sixteen different capture antibodies into each well of a 96-well plate. Following a sandwich ELISA procedure, the entire plate is imaged to capture the chemiluminescent signal generated at each spot within each well of the plate. The signal generated at each spot is proportional to the amount of target protein in the original standard or sample.

MCP-1 and IL-6 were secreted by umbilicus-derived cells and dermal fibroblasts (Table 21-1). SDF-1alpha and GCP-2 were secreted by fibroblasts. GCP-2 and IL-8 were secreted by umbilicus-derived cells. TGF-beta2 was not detected from either cell type by ELISA.

TABLE 21-1

ELISA assay results
(values presented are picog/ml/million cells (n = 2, sem)

|  | MCP-1 | IL-6 | VEGF | SDF-1α | GCP-2 | IL-8 | TGF-beta2 |
|---|---|---|---|---|---|---|---|
| Fibroblast | 17 ± 1 | 61 ± 3 | 29 ± 2 | 19 ± 1 | 21 ± 1 | ND | ND |
| Umbilicus (022803) | 1150 ± 74 | 4234 ± 289 | ND | ND | 160 ± 11 | 2058 ± 145 | ND |
| Umbilicus (071003) | 2794 ± 84 | 1356 ± 43 | ND | ND | 2184 ± 98 | 2369 ± 23 | ND |

Key:
ND: Not Detected.

TIMP1, TPO, KGF, HGF, FGF, HBEGF, BDNF, MIP1b, MCP1, RANTES, I309, TARC, MDC, and IL-8 were secreted from umbilicus-derived cells (Tables 21-2 and 21-3). No Ang2, VEGF, or PDGF-bb were detected.

TABLE 21-2

SEARCHLIGHT Multiplexed ELISA assay results

|  | TIMP1 | ANG2 | PDGFbb | TPO | KGF | HGF | FGF | VEGF | HBEGF | BDNF |
|---|---|---|---|---|---|---|---|---|---|---|
| Hfb | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 |

Key:
hFB (human fibroblasts),
U1 (umbilicus-derived cells (022803)),
U3 (umbilicus-derived cells (071003)).
ND: Not Detected.

TABLE 21-3

SEARCHLIGHT Multiplexed ELISA assay results

|     | MIP1a | MIP1b | MCP1   | RANTES | I309 | TARC | Eotaxin | MDC  | IL8     |
|-----|-------|-------|--------|--------|------|------|---------|------|---------|
| hFB | ND    | ND    | 39.6   | ND     | ND   | 0.1  | ND      | ND   | 204.9   |
| U1  | ND    | 8.0   | 1694.2 | ND     | 22.4 | 37.6 | ND      | 18.9 | 51930.1 |
| U3  | ND    | 5.2   | 2018.7 | 41.5   | 11.6 | 21.4 | ND      | 4.8  | 10515.9 |

Key:
hFB (human fibroblasts),
U1 (umbilicus-derived PPDC (022803)),
U3 (umbilicus-derived PPDC (071003)).
ND: Not Detected.

Umbilicus-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

EXAMPLE 22

In Vitro Immunology

Umbilical cord cell lines were evaluated in vitro for their immunological characteristics in an effort to predict the immunological response, if any, these cells would elicit upon in vivo transplantation. Umbilical cord cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve CD4+ T cells (Abbas & Lichtman, Cellular and Molecular Immunology, 5th Ed. (2003) Saunders, Philadelphia, p. 171). The cell lines were also analyzed by flow cytometry for the expression of HLA-G (Abbas & Lichtman, Cellular and Molecular Immunology, 5th Ed. (2003) Saunders, Philadelphia, p. 171), CD178 (Coumans, et. al., Journal of Immunological Methods, 1999; 224:185-196), and PD-L2 (Abbas & Lichtman, Cellular and Molecular Immunology, 5th Ed. (2003) Saunders, Philadelphia, p. 171; Brown, et. al., The Journal of Immunology, 2003; 170:1257-1266). The expression of these proteins by cells residing in placental tissues is thought to mediate the immuno-privileged status of placental tissues in utero. To predict the extent to which umbilical cord tissue-derived cell lines elicit an immune response in vivo, the cell lines were tested in a one-way mixed lymphocyte reaction (MLR).

Cells were cultured in growth medium (DMEM-low glucose (Gibco, Carlsbad, Calif.), 15% (v/v) fetal bovine serum (FBS); (Hyclone, Logan, Utah.), 0.001% (v/v) beta-mercaptoethanol (Sigma, St. Louis, Mo.), 50 Units/milliliter penicillin, 50 micrograms/milliliter streptomycin (Gibco, Carlsbad, Calif.) until confluent in T75 flasks (Corning, Corning, N.Y.) coated with 2% gelatin (Sigma, St. Louis, Mo.).

Cells were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1\times10^7$ per milliliter. Antibody (Table 22-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACS calibur instrument (Becton Dickinson, San Jose, Calif.).

TABLE 22-1

Antibodies

| Antibody        | Manufacturer                  | Catalog Number |
|-----------------|-------------------------------|----------------|
| HLA-DRDPDQ      | BD Pharmingen (San Diego, Ca.) | 555558         |
| CD80            | BD Pharmingen (San Diego, Ca.) | 557227         |
| CD86            | BD Pharmingen (San Diego, Ca.) | 555665         |
| B7-H2           | BD Pharmingen (San Diego, Ca.) | 552502         |
| HLA-G           | Abcam (Cambridgeshire, UK)    | ab 7904-100    |
| CD178           | Santa Cruz (San Cruz, Ca.)    | sc-19681       |
| PD-L2           | BD Pharmingen (San Diego, Ca.) | 557846         |
| Mouse IgG2a     | Sigma (St. Louis, Mo)         | F-6522         |
| Mouse IgG1kappa | Sigma (St. Louis, Mo.)        | P-4685         |

Cryopreserved vials of passage 10 umbilical cord-derived cells labeled as cell line A were packaged on dry ice and sent to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and umbilical cord tissue-derived cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the umbilical cord-derived cells was calculated as the mean proliferation of the receiver plus mitomycin C-treated umbilical cord tissue-derived cell line divided by the baseline proliferation of the receiver.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilical cord-derived cell lines were mitomycin C-treated and cultured in a mixed lymphocyte reaction with the five individual allogeneic receivers. Reactions were performed in triplicate using two cell culture plates with three receivers per plate (Table 22-2). The average stimulation index ranged from 6.5 (plate 1) to 9 (plate 2) and the allogeneic donor positive controls ranged from 42.75 (plate 1) to 70 (plate 2) (Table 22-3).

TABLE 22-2

Mixed Lymphocyte Reaction Data-Cell Line A (Umbilical Cord)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| | SI (donor) | | | | 70 | | |
| | SI (cell line) | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| | SI (donor) | | | | 47 | | |
| | SI (cell line) | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| | SI (donor) | | | | 23 | | |
| | SI (cell line) | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| | SI (donor) | | | | 31 | | |
| | SI (cell line) | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| | SI (donor) | | | | 70 | | |
| | SI (cell line) | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 22-3

Average stimulation index of umbilical cord-derived cells and an allogeneic donor in a mixed lymphocyte reaction with five individual allogeneic receivers.

| | Recipient | Umbilical Cord |
|---|---|---|
| Plate 1 (receivers 1-4) | 42.75 | 6.5 |
| Plate 2 (receiver 5) | 70 | 9 |

Histograms of umbilical cord-derived cells analyzed by flow cytometry show negative expression of HLA-DR, DP, DQ, CD80, CD86, and B7-H2, as noted by fluorescence value consistent with the IgG control, indicating that umbilical cord-derived cell lines lack the cell surface molecules required to directly stimulate allogeneic PBMCs (e.g., CD4+ T cells).

Histograms of umbilical cord-derived cells analyzed by flow cytometry show positive expression of PD-L2, as noted by the increased value of fluorescence relative to the IgG control, and negative expression of CD178 and HLA-G, as noted by fluorescence value consistent with the IgG control.

In the mixed lymphocyte reactions conducted with umbilical cord-derived cell lines, the average stimulation index ranged from 6.5 to 9, and that of the allogeneic positive controls ranged from 42.75 to 70. Umbilical cord-derived cell lines were negative for the expression of the stimulating proteins HLA-DR, HLA-DP, HLA-DQ, CD80, CD86, and B7-H2, as measured by flow cytometry. Umbilical cord-derived cell lines were negative for the expression of immuno-modulating proteins HLA-G and CD178 and positive for the expression of PD-L2, as measured by flow cytometry. Allogeneic donor PBMCs contained antigen-presenting cells expressing HLA-DP, DR, DQ, CD80, CD86, and B7-H2, thereby allowing for the stimulation of allogeneic PBMCs (e.g., naïve CD4+ T cells). The absence of antigen-presenting cell surface molecules on umbilical cord-derived cells required for the direct stimulation of allogeneic PBMCs (e.g., naïve CD4+ T cells) and the presence of PD-L2, an immuno-modulating protein, may account for the low stimulation index exhibited by these cells in a MLR as compared to allogeneic controls.

EXAMPLE 23

Assay for Telomerase Activity

Telomerase functions to synthesize telomere repeats that serve to protect the integrity of chromosomes and to prolong the replicative life span of cells (Liu, K, et al., *PNAS,* 1999; 96:5147-5152). Telomerase consists of two components, telomerase RNA template (hTER) and telomerase reverse transcriptase (hTERT). Regulation of telomerase is determined by transcription of hTERT but not hTER. Real-time polymerase chain reaction (PCR) for hTERT mRNA thus is an accepted method for determining telomerase activity of cells.

Cell Isolation

Real-time PCR experiments were performed to determine telomerase production of human umbilical cord tissue-derived cells. Human umbilical cord tissue-derived cells were prepared in accordance with Examples 13-15 and the examples set forth in U.S. application Ser. No. 10/877,012 (the '012 application), which issued as U.S. Pat. No. 7,510,873. Generally, umbilical cords obtained from National Disease Research Interchange (Philadelphia, Pa.) following a normal delivery were washed to remove blood and debris and mechanically dissociated. The tissue was then incubated with digestion enzymes including collagenase, dispase and hyaluronidase in culture medium at 37° C. human umbilical cord tissue-derived cells were cultured according to the methods set forth in the examples of the '012 application. Mesenchymal stem cells and normal dermal skin fibroblasts (cc-2509 lot #9F0844) were obtained from Cambrex, Walkersville, Md. A pluripotent human testicular embryonal carcinoma (teratoma) cell line nTera-2 cells (NTERA-2 cl.D1), (see, Plaia et al., Stem Cells, 2006; 24(3):531-546) was purchased from ATCC (Manassas, Va.) and was cultured according to the methods set forth in the '012 application.

Total RNA Isolation

RNA was extracted from the cells using RNeasy® kit (Qiagen, Valencia, Calif.). RNA was eluted with 50 microliters DEPC-treated water and stored at −80° C. RNA was reverse transcribed using random hexamers with the TaqMan® reverse transcription reagents (Applied Biosystems, Foster City, Calif.) at 25° C. for 10 minutes, 37° C. for 60 minutes and 95° C. for 10 minutes. Samples were stored at −20° C.

Real-Time PCR

PCR was performed on cDNA samples using the Applied Biosystems Assays-On-Demand™ (also known as TaqMan® Gene Expression Assays) according to the manufacturer's specifications (Applied Biosystems). This commercial kit is widely used to assay for telomerase in human cells. Briefly, hTERT (human telomerase gene) (Hs00162669) and human GAPDH (an internal control) were mixed with cDNA and TaqMan® Universal PCR master mix using a 7000 sequence detection system with ABI prism 7000 SDS software (Applied Biosystems). Thermal cycle conditions were initially 50° C. for 2 min and 95° C. for 10 min followed by 40 cycles of 95° C. for 15 sec and 60° C. for 1 min. PCR data was analyzed according to the manufacturer's specifications.

Human umbilical cord tissue-derived cells (ATCC Accession No. PTA-6067), fibroblasts, and mesenchymal stem cells were assayed for hTERT and 18S RNA. As shown in Table 22-1, hTERT, and hence telomerase, was not detected in human umbilical cord tissue-derived cells.

TABLE 22-1

|  | hTERT | 18S RNA |
|---|---|---|
| Umbilical cells (022803) | ND | + |
| Fibroblasts | ND | + |

ND-not detected;
+ signal detected

Human umbilical cord tissue-derived cells (isolate 022803, ATCC Accession No. PTA-6067) and nTera-2 cells were assayed and the results showed no expression of the telomerase in two lots of hUTC while the teratoma cell line revealed high level of expression (Table 22-1).

TABLE 22-1

| Cell type | hTERT Exp.1 | Exp.2 | GAPDH Exp.1 | Exp.2 | hTERT norm |
|---|---|---|---|---|---|
| nTera2 | 22.85 | 27.31 | 16.41 | 16.31 | .61 |
| 022803 | — | — | 22.97 | 22.79 | — |

Therefore, it can be concluded that human umbilical tissue-derived cells do not express telomerase.

What is claimed:

1. A method of treating a patient having a neurological injury comprising administering to the patient isolated umbilical cord tissue-derived cells in an amount effective to treat the neurological injury, wherein the neurological injury is cerebral hemorrhage, cerebral ischemia or traumatic brain injury, and wherein the umbilical cord tissue-derived cells are derived from human umbilical cord tissue substantially free of blood, are capable of self-renewal and expansion in culture, have the potential to differentiate into cells of at least a neural phenotype, and do not express CD117.

2. The method of claim 1, wherein the cells are administered with at least one other cell type.

3. The method of claim 2, wherein the other cell type is an astrocyte, oligodendrocyte, neuron, neural progenitor, neural stem cell or other multipotent or pluripotent stem cell.

4. The method of claim 1, wherein the umbilical cord tissue-derived cells are administered at a pre-determined site in the central nervous system of the patient.

5. The method of claim 1, wherein the umbilical cord tissue-derived cells are administered by injection or infusion.

6. The method of claim 1, wherein the umbilical cord tissue-derived cells further express CD10, CD13, CD44, CD73, CD90, PDGFr-alpha and HLA-A, B, C.

7. The method of claim 1, wherein the umbilical cord tissue-derived cells further do not express CD31, CD34, CD45, CD141 and HLA-DR, DP, DQ.

8. The method of claim 1, wherein the neurological injury is cerebral hemorrhage.

9. The method of claim 1, wherein the neurological injury is cerebral ischemia.

10. The method of claim 1, wherein the neurological injury is traumatic brain injury.

11. A method of stimulating regeneration capacity of a subventricular zone of a patient following traumatic brain injury comprising administering to the patient isolated umbilical cord tissue-derived cells in an amount effective to increase neurogenesis, angiogenesis, or synaptogenesis, wherein the umbilical cord tissue-derived cells are derived from human umbilical cord tissue substantially free of blood, are capable of self-renewal and expansion in culture, have the potential to differentiate into cells of at least a neural phenotype, and do not express CD117.

12. The method of claim 11, wherein the umbilical cord tissue-derived cells are administered with at least one other cell type.

13. The method of claim 12, wherein the other cell type is an astrocyte, oligodendrocyte, neuron, neural progenitor, neural stem cell or other multipotent or pluripotent stem cell.

14. The method of claim 11, wherein the cells are administered at a pre-determined site in the central nervous system of the patient.

15. The method of claim 11, wherein the cells are administered by injection or infusion.

16. The method of claim 11, wherein the umbilical cord tissue-derived cells further express CD10, CD13, CD44, CD73, CD90, PDGFr-alpha and HLA-A, B, C.

17. The method of claim 11, wherein the umbilical cord tissue-derived cells further do not express CD31, CD34, CD45, CD141 and HLA-DR, DP, DQ.

* * * * *